US012662541B2

(12) United States Patent
Pasqualini et al.

(10) Patent No.: US 12,662,541 B2
(45) Date of Patent: Jun. 23, 2026

(54) ANTIBODY-DRUG CONJUGATES AGAINST THE RECEPTOR TYROSINE KINASE EphA5

(71) Applicants: Rutgers, The State University of New Jersey, New Brunswick, NJ (US); MBrace Therapeutics, Inc., San Diego, CA (US)

(72) Inventors: Renata Pasqualini, Newark, NJ (US); Wadih Arap, Newark, NJ (US); Fernanda I. Staquicini, Summit, NJ (US)

(73) Assignees: Rutgers, The State University of New Jersey, New Brunswick, NJ (US); MBrace Therapeutics, Inc., San Diego, CA (US)

( * ) Notice: Subject to any disclaimer, the term of this patent is extended or adjusted under 35 U.S.C. 154(b) by 794 days.

(21) Appl. No.: 18/052,479

(22) Filed: Nov. 3, 2022

(65) Prior Publication Data

US 2023/0293710 A1 Sep. 21, 2023

Related U.S. Application Data

(60) Provisional application No. 63/275,346, filed on Nov. 3, 2021.

(51) Int. Cl.
*C07K 16/28* (2006.01)
*A61K 47/68* (2017.01)

(52) U.S. Cl.
CPC .... *C07K 16/2866* (2013.01); *A61K 47/68031* (2023.08); *A61K 47/68037* (2023.08); *A61K 47/6811* (2017.08); *A61K 47/6889* (2017.08); *C07K 16/28* (2013.01); *C07K 2317/565* (2013.01)

(58) Field of Classification Search
CPC ................ C07K 16/2866; C07K 16/28; C07K 2317/565; A61K 47/6889; A61K 47/6811; A61K 47/68037; A61K 47/68031
See application file for complete search history.

(56) References Cited

U.S. PATENT DOCUMENTS

| 11,254,751 B2 | 2/2022 | Pasqualini et al. |
| 12,060,415 B2 | 8/2024 | Pasqualini et al. |
| 12,103,966 B2 | 10/2024 | Pasqualini et al. |
| 12,168,685 B2 | 12/2024 | Pasqualini et al. |
| 12,180,269 B2 | 12/2024 | Pasqualini et al. |
| 2006/0228349 A1 | 10/2006 | Acton et al. |
| 2010/0129917 A1 | 5/2010 | Panizza et al. |

(Continued)

FOREIGN PATENT DOCUMENTS

| JP | 2012-525854 | 5/2010 |
| WO | 2013040472 A2 | 3/2013 |
| WO | 2018057703 A1 | 3/2018 |

OTHER PUBLICATIONS

Chen, et al., "EphA5 protein, a potential marker for distinguishing histological grade and prognosis in ovarian serous carcinoma", J Ovarian Res, 9:83, Nov. 25, 2016, 7 pages.

(Continued)

*Primary Examiner* — Aurora M Fontainhas
*Assistant Examiner* — Selam Berhane
(74) *Attorney, Agent, or Firm* — Howson & Howson LLP; Cathy A. Kodroff

(57) ABSTRACT

The present invention relates in certain aspects to antibodies, binding polypeptides, and immunoconjugates specific for human EPH receptor A5 (EphA5).

114 Claims, 127 Drawing Sheets
Specification includes a Sequence Listing.

(56)          References Cited

U.S. PATENT DOCUMENTS

| 2010/0239571 A1 | 9/2010 | Mcdonagh et al. |
| 2010/0285036 A1 | 11/2010 | Smith et al. |
| 2014/0377288 A1 | 12/2014 | Staquicini et al. |
| 2019/0202922 A1 | 7/2019 | Pasqualini et al. |
| 2024/0115722 A1 | 4/2024 | Pasqualini et al. |
| 2024/0368258 A1 | 11/2024 | Pasqualini et al. |
| 2025/0302984 A1 | 10/2025 | Staquicini et al. |

OTHER PUBLICATIONS

D'Angelo, et al., "Selection of phage-displayed accessible recombinant targeted antibodies (SPARTA): methodology and applications", JCI Insight, 3(9), May 3, 2018, pp. e98305.

Giaginis, et al., "Clinical significance of ephrin (eph)-A1, -A2, -a4, -a5 and -a7 receptors in pancreatic ductal adenocarcinoma", Pathol Oncol Res, 16(2), 2010, pp. 267-276.

Staquicini, et al., "Receptor Tyrosine Kinase EphA5 is a Functional Molecular Target in Human Lung Cancer", J Biol Chem, 290(12), 2015, pp. 7345-7359.

Yang, et al., "Preclinical Studies of OBI-999: A Novel Globo H-Targeting Antibody-Drug Conjugate", Mol Cancer Ther, 20, 2021, pp. 1121-1132.

Zhang, et al., "Differential expression of EphA5 protein in gastric carcinoma and its clinical significance", Oncology letters, 17(6), 2019, pp. 5147-5153.

Zhang, et al., "EphA5 knockdown enhances the invasion and migration ability of esophageal squamous cell carcinoma via epithelial-mesenchymal transition through activating Wnt/beta-catenin pathway", Cancer Cell Int, 20:20, Jan. 13, 2020, 12 pages.

International Search Report & Written Opinion dated Apr. 7, 2023 for co-pending PCT International Application No. PCT/US2022/079232.

US 371 U.S. Appl. No. 18/707,250, filed May 3, 2024.

Office Action issued in corresponding Japanese Patent Application No. 2024-550122 (with agent provided English translation), dated Sep. 22, 2025.

Heavy Chain

| Predicted affinity MHC class II | VH0 | VH1 | VH2 | VH3 | VH4 | VH5 | VH6 |
|---|---|---|---|---|---|---|---|
| Number High | 6 | 4 | 4 | 4 | 3 | 2 | 2 |
| Number Moderate | 3 | 3 | 3 | 3 | 2 | 2 | 1 |

Light chain

| Predicted affinity MHC class II | VK0 | VK1 | VK2 | VK3 | VK4 | VK5 |
|---|---|---|---|---|---|---|
| Number High | 6 | 3 | 2 | 2 | 2 | 2 |
| Number Moderate | 2 | 1 | 1 | 1 | 1 | 1 |

FIG. 8

| Light Chain | Heavy Chain | | | | | | |
| --- | --- | --- | --- | --- | --- | --- | --- |
| | VH0 | VH1 | VH2 | VH3 | VH4 | VH5 | VH6 |
| VK0 | 2.53 | | | | | | |
| VK1 | 1.53 | 8.45 | | | | | |
| VK2 | | 7.38 | 8.60 | 10.18 | 8.64 | 10.09 | 8.02 |
| VK3 | | 9.65 | 9.49 | 10.12 | 8.79 | 8.40 | 9.80 |
| VK4 | | 9.48 | 12.45 | 13.00 | 10.38 | 9.54 | 9.92 |
| VK5 | | 8.56 | 9.60 | 12.90 | 8.31 | 9.31 | 7.71 |
| VK6 | | 8.36 | 11.60 | 10.93 | 8.58 | 9.68 | 8.88 |

FIG. 10

$$A + B \underset{k_d}{\overset{k_a}{\rightleftharpoons}} AB$$

$$K_D = \frac{k_d}{k_a}$$

$k_a$ = association rate constant $(M^{-1}s^{-1})$
$k_d$ = dissociation rate constant $(s^{-1})$ $$Chi\ square = \frac{\sum (r_f - r_x)^2}{n - p}$$

rf = fitted value at a given point
rx = experimental value at the same point
n = number of data points
p = number of fitted parameters

FIG. 12

| | Antibody | $k_a$ (1/Ms) | $k_d$ (1/s) | $K_D$ (M) | Relative $K_D$ | $R_{MAX}$ | $Chi^2$ $(RU^2)$ |
|---|---|---|---|---|---|---|---|
| | VH0/VK0 | $1.15 \times 10^{6}$ | $1.53 \times 10^{-3}$ | $1.33 \times 10^{-9}$ | 1.00 | 33.0 | 0.0651 |
| | VH0/VK1 | $1.22 \times 10^{-6}$ | $1.37 \times 10^{-3}$ | $1.12 \times 10^{-9}$ | 0.84 | 29.1 | 0.0286 |
| | VH1/VK0 | $1.22 \times 10^{-6}$ | $1.27 \times 10^{-3}$ | $1.04 \times 10^{-9}$ | 0.78 | 32.1 | 0.0425 |
| * | VH1/VK1 | $1.25 \times 10^{6}$ | $1.28 \times 10^{-3}$ | $1.02 \times 10^{-9}$ | 0.77 | 39.2 | 0.0125 |
| * | VH1/VK2 | $1.31 \times 10^{6}$ | $1.26 \times 10^{-3}$ | $9.68 \times 10^{-10}$ | 0.73 | 24.3 | 0.0118 |
| * | VH1/VK3 | $1.32 \times 10^{6}$ | $1.25 \times 10^{-3}$ | $9.48 \times 10^{-10}$ | 0.71 | 24.9 | 0.0120 |
| * | VH1/VK4 | $1.24 \times 10^{6}$ | $1.37 \times 10^{-3}$ | $1.10 \times 10^{-9}$ | 0.83 | 23.4 | 0.0059 |
| * | VH1/VK5 | $1.24 \times 10^{6}$ | $1.39 \times 10^{-3}$ | $1.12 \times 10^{-9}$ | 0.84 | 33.1 | 0.0121 |
| * | VH2/VK1 | $1.35 \times 10^{6}$ | $1.20 \times 10^{-3}$ | $8.90 \times 10^{-10}$ | 0.67 | 30.3 | 0.0119 |
| * | VH2/VK2 | $1.30 \times 10^{6}$ | $1.26 \times 10^{-3}$ | $9.71 \times 10^{-10}$ | 0.73 | 37.7 | 0.00878 |
| * | VH2/VK3 | $1.34 \times 10^{6}$ | $1.32 \times 10^{-3}$ | $9.85 \times 10^{-10}$ | 0.74 | 25.2 | 0.0066 |
| * | VH2/VK4 | $1.37 \times 10^{6}$ | $1.26 \times 10^{-3}$ | $9.17 \times 10^{-10}$ | 0.69 | 22.6 | 0.0063 |
| * | VH2/VK5 | $1.34 \times 10^{6}$ | $1.40 \times 10^{-3}$ | $1.05 \times 10^{-9}$ | 0.79 | 28.1 | 0.0076 |
| * | VH3/VK1 | $1.39 \times 10^{6}$ | $1.23 \times 10^{-3}$ | $8.84 \times 10^{-10}$ | 0.66 | 23.4 | 0.0072 |
| * | VH3/VK2 | $1.34 \times 10^{6}$ | $1.30 \times 10^{-3}$ | $9.68 \times 10^{-10}$ | 0.73 | 26.1 | 0.0049 |
| * | VH3/VK3 | $1.32 \times 10^{6}$ | $1.33 \times 10^{-3}$ | $1.01 \times 10^{-9}$ | 0.76 | 34.0 | 0.0068 |
| # | VH3/VK4 | $1.33 \times 10^{6}$ | $1.28E \times 10^{-3}$ | $9.56 \times 10^{-10}$ | 0.72 | 34.2 | 0.0119 |
| * | VH3/VK5 | $1.29 \times 10^{6}$ | $1.43 \times 10^{-3}$ | $1.10 \times 10^{-9}$ | 0.83 | 27.1 | 0.0060 |
| * | VH4/VK1 | $1.32 \times 10^{6}$ | $1.29 \times 10^{-3}$ | $9.75 \times 10^{-10}$ | 0.73 | 33.8 | 0.0074 |
| * | VH4/VK2 | $1.34 \times 10^{6}$ | $1.14 \times 10^{-3}$ | $8.54 \times 10^{-10}$ | 0.64 | 24.0 | 0.0044 |
| # | VH4/VK3 | $1.31 \times 10^{6}$ | $1.37 \times 10^{-3}$ | $1.04 \times 10^{-9}$ | 0.78 | 28.6 | 0.0055 |
| # | VH4/VK4 | $1.33 \times 10^{6}$ | $1.40 \times 10^{-3}$ | $1.05 \times 10^{-9}$ | 0.79 | 24.9 | 0.0045 |
| * | VH4/VK5 | $1.37 \times 10^{6}$ | $1.37 \times 10^{-3}$ | $9.96 \times 10^{-10}$ | 0.75 | 22.0 | 0.0066 |
| * | VH5/VK1 | $1.34 \times 10^{6}$ | $1.27 \times 10^{-3}$ | $9.47 \times 10^{-10}$ | 0.71 | 28.6 | 0.0085 |
| # | VH5/VK2 | $1.38 \times 10^{6}$ | $1.23 \times 10^{-3}$ | $8.92 \times 10^{-10}$ | 0.67 | 31.2 | 0.0169 |
| # | VH5/VK3 | $1.36 \times 10^{6}$ | $1.40 \times 10^{-3}$ | $1.03 \times 10^{-9}$ | 0.77 | 26.9 | 0.0093 |
| # | VH5/VK4 | $1.35 \times 10^{6}$ | $1.41 \times 10^{-3}$ | $1.04 \times 10^{-9}$ | 0.78 | 26.4 | 0.0096 |
| * | VH5/VK5 | $1.37 \times 10^{6}$ | $1.40 \times 10^{-3}$ | $1.03 \times 10^{-9}$ | 0.77 | 25.1 | 0.0092 |
| | VH6/VK1 | $1.65 \times 10^{-5}$ | $1.65 \times 10^{-1}$ | $1.00 \times 10^{-8}$ | 7.52 | 21.3 | 0.0525 |
| | VH6/VK2 | $1.74 \times 10^{-5}$ | $1.65 \times 10^{-1}$ | $9.49 \times 10^{-9}$ | 7.14 | 17.7 | 0.0349 |
| | VH6/VK3 | $5.22 \times 10^{-5}$ | $3.41 \times 10^{-1}$ | $6.52 \times 10^{-9}$ | 4.90 | 14.1 | 0.0651 |
| | VH6/VK4 | $2.15 \times 10^{-3}$ | $2.09 \times 10^{-1}$ | $9.76 \times 10^{-9}$ | 7.34 | 12.8 | 0.0544 |
| | VH6/VK5 | $4.01 \times 10^{-5}$ | $2.85 \times 10^{-1}$ | $7.10 \times 10^{-9}$ | 5.34 | 18.1 | 0.1130 |

FIG. 13

Heavy Chain

|  | VH0 | VH3 | VH4 | VH5 |
|---|---|---|---|---|
| VK0 | 61.0 |  |  |  |
| VK3 |  | - | 122.6 | 106.6 |
| VK4 |  | 150.4 | 112.3 | 143.1 |
| VK5 |  | - | - | 144.9 |

Light Chain

FIG. 15

| Antibody | Monomer % |
|----------|-----------|
| VH0/VK0 | 98.0 |
| VH3/VK4 | 98.0 |
| VH4/VK3 | 97.7 |
| VH4/VK4 | 97.7 |
| VH5/VK2 | 97.0 |
| VH5/VK3 | 97.0 |
| VH5/VK4 | 97.0 |

FIG. 18

| Antibody | $k_a$ (1/Ms) | $k_d$ (1/s) | $K_D$ (M) | Relative $K_D$ | $R_{MAX}$ | Chi² (RU²) |
|---|---|---|---|---|---|---|
| VH0/VK0 | $9.65 \times 10^{5}$ | $1.50 \times 10^{-3}$ | $1.56 \times 10^{-9}$ | 1.00 | 47.8 | 1.23 |
| VH3/VK4 | $1.31 \times 10^{-6}$ | $1.42 \times 10^{-3}$ | $1.08 \times 10^{-9}$ | 0.69 | 42.8 | 0.65 |
| VH4/VK3 | $1.49 \times 10^{-6}$ | $1.39 \times 10^{-3}$ | $9.37 \times 10^{-10}$ | 0.60 | 46.3 | 0.776 |
| VH4/VK4 | $1.27 \times 10^{-6}$ | $1.32 \times 10^{-3}$ | $1.04 \times 10^{-9}$ | 0.67 | 32.2 | 0.352 |
| VH5/VK2 | $1.34 \times 10^{-6}$ | $1.25 \times 10^{-3}$ | $9.34 \times 10^{-10}$ | 0.60 | 48.6 | 0.892 |
| VH5/VK3 | $1.21 \times 10^{-6}$ | $1.35 \times 10^{-3}$ | $1.11 \times 10^{-9}$ | 0.71 | 35.3 | 0.429 |
| VH5/VK4 | $1.23 \times 10^{-6}$ | $1.28 \times 10^{-3}$ | $1.04 \times 10^{-9}$ | 0.67 | 43.3 | 0.605 |

FIG. 19

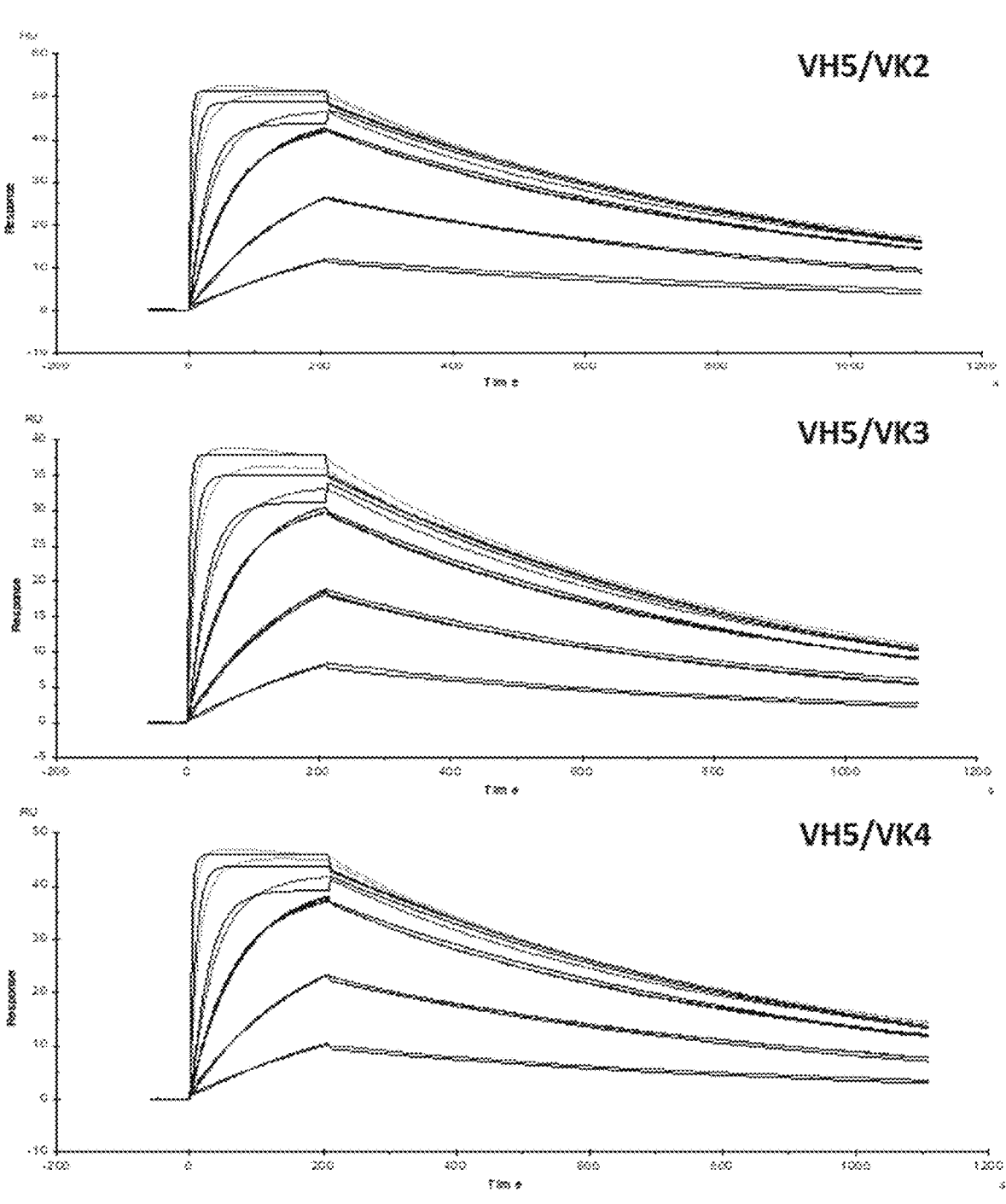
FIG. 20, continued

| Sample | Tm1 (°C) | Average Tm1 (°C) | Tm2 (°C) | Average Tm2 (°C) | Tonset (°C) | Average Tonset (°C) | Tagg 473 (°C) | Average Tagg 473 (°C) |
|---|---|---|---|---|---|---|---|---|
| VH0/VK0 | 57.83 | 57.9 | 65.83 | 65.83 | 54.92 | 55.1 | 65.72 | 65.6 |
|  | 57.87 |  | 65.83 |  | 55.23 |  | 65.60 |  |
| VH3/VK4 | 67.64 | 67.6 |  |  | 62.54 | 61.2 | 67.77 | 67.7 |
|  | 67.48 |  |  |  | 59.94 |  | 67.63 |  |
| VH4/VK3 | 69.14 | 69.6 |  |  | 65.69 | 65.2 | 69.82 | 69.8 |
|  | 69.99 |  |  |  | 64.80 |  | 69.69 |  |
| VH4/VK4 | 66.69 | 66.8 |  |  | 60.14 | 60.1 | 67.18 | 67.2 |
|  | 66.93 |  |  |  | 60.00 |  | 67.25 |  |
| VH5/VK2 | * | 67.5 |  |  | * | 60.9 | * | 68.1 |
|  | 67.54 |  |  |  | 60.95 |  | 68.08 |  |
| VH5/VK3 | * | 69.0 |  |  | * | 63.6 | * | 70.2 |
|  | 68.99 |  |  |  | 63.59 |  | 70.17 |  |
| VH5/VK4 | 66.00 | 66.2 |  |  | 61.33 | 60.9 | 68.05 | 68.1 |
|  | 66.46 |  |  |  | 60.52 |  | 68.25 |  |

FIG. 21

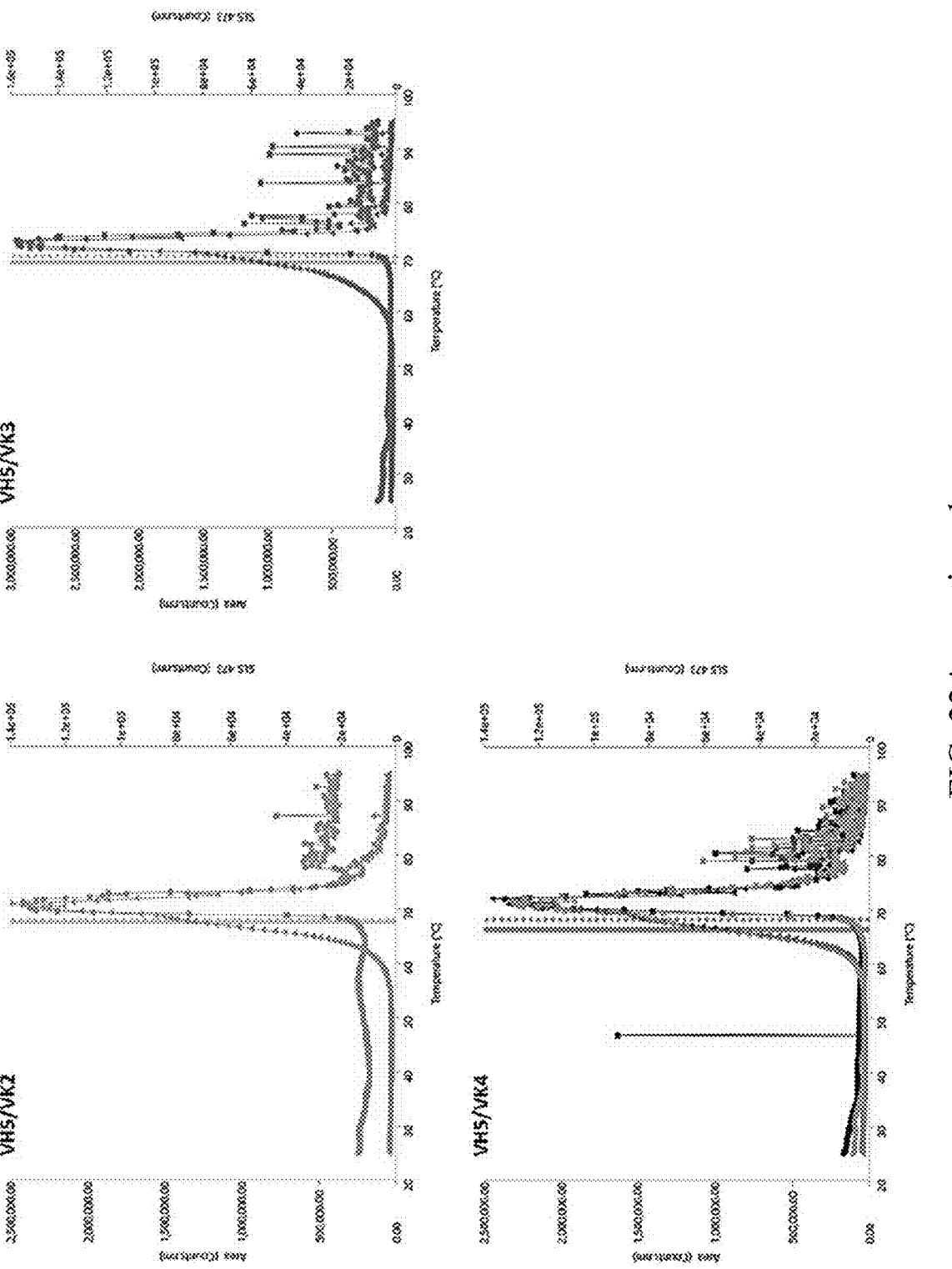
FIG. 22A, continued

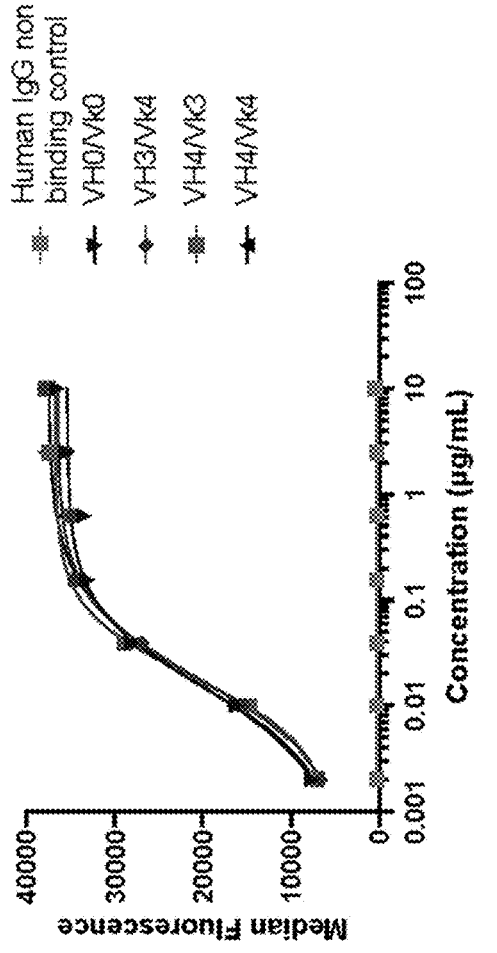
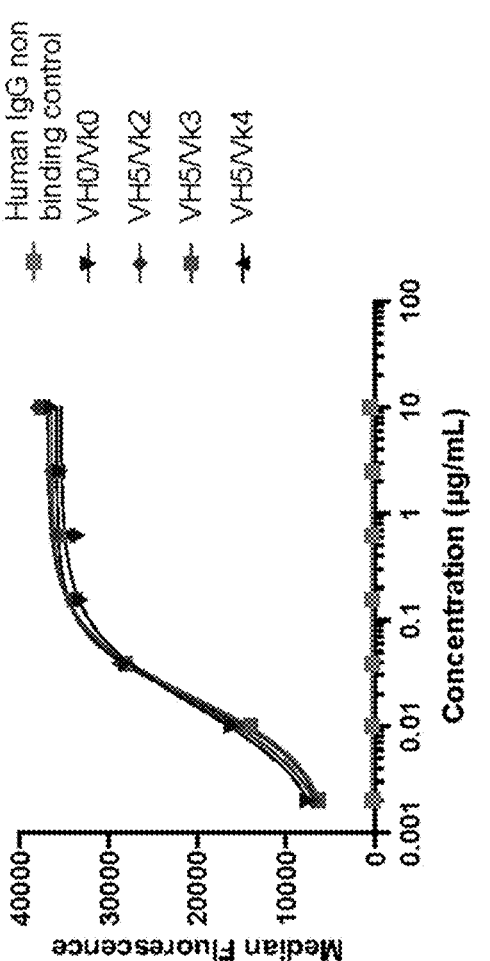
FIG. 24

| | Sample Details | | | H460 Cell Line | | H226 Cell Line | |
|---|---|---|---|---|---|---|---|
| Variant | Stock Concentration (mg/mL) | Starting Assay Concentration (µg/mL) | EC$_{50}$ (µg/ml) | Max. Binding (MFI) | EC$_{50}$ (µg/ml) | Max. Binding (MFI) |
| Mouse Anti-EphA5 | 1 | 10 | 0.025 | 27334 | N/A | N/A |
| Mouse IgG1 non-binding | 0.5 | 10 | N/A | N/A | N/A | N/A |
| Human IgG1 non-binding | 0.5 | 10 | N/A | N/A | N/A | N/A |
| VH0/VK0 | 3.06 | 10 | 0.015 | 35401 | N/A | N/A |
| VH3/VK4 | 3.15 | 10 | 0.018 | 36481 | N/A | N/A |
| VH4/VK3 | 3.67 | 10 | 0.018 | 36745 | N/A | N/A |
| VH4/VK4 | 3.02 | 10 | 0.017 | 37500 | N/A | N/A |
| VH5/VK2 | 3.31 | 10 | 0.017 | 36901 | N/A | N/A |
| VH5/VK3 | 3.44 | 10 | 0.019 | 36475 | N/A | N/A |
| VH5/VK4 | 2.92 | 10 | 0.018 | 35882 | N/A | N/A |

VH0/VK0
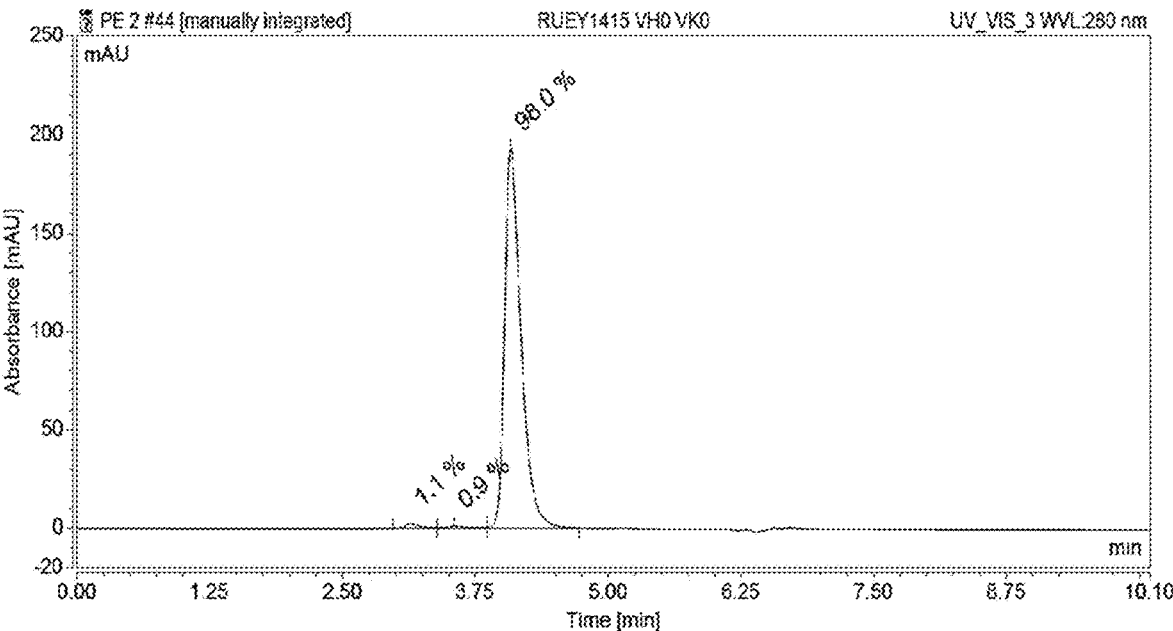
VH3/VK4
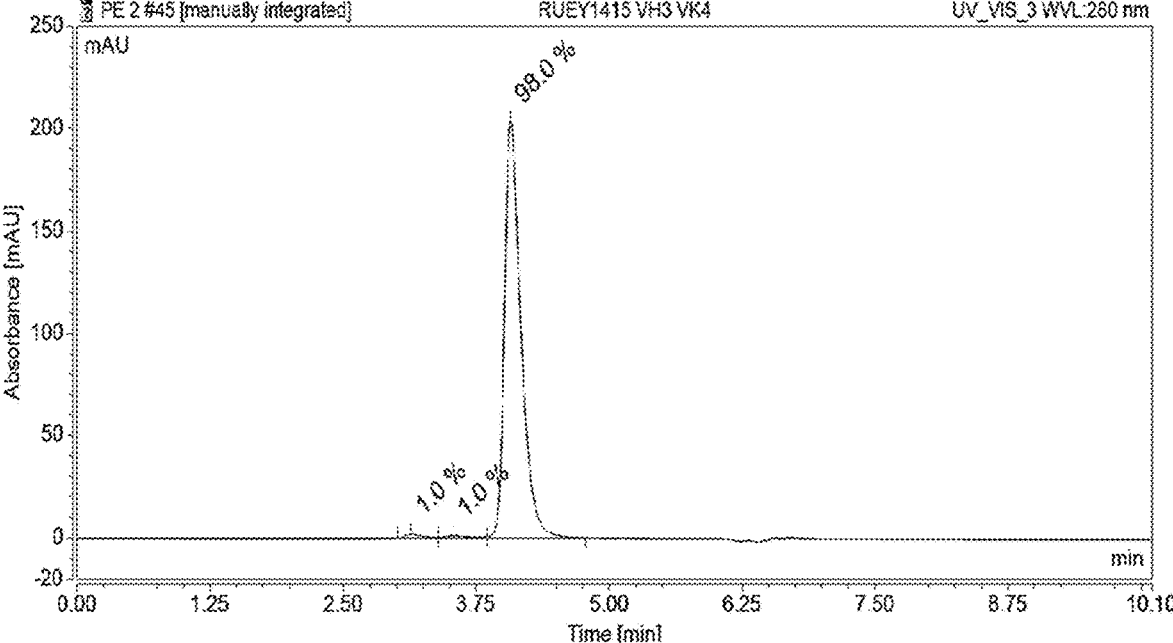
FIG. 31A

VH4/VK3
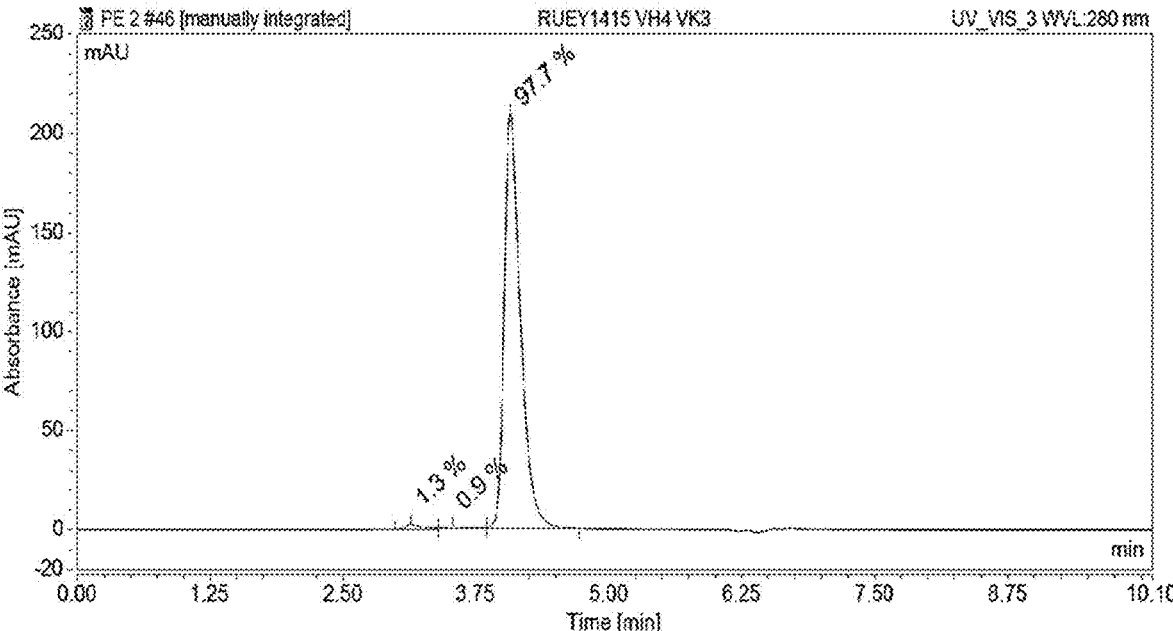
VH4/VK4
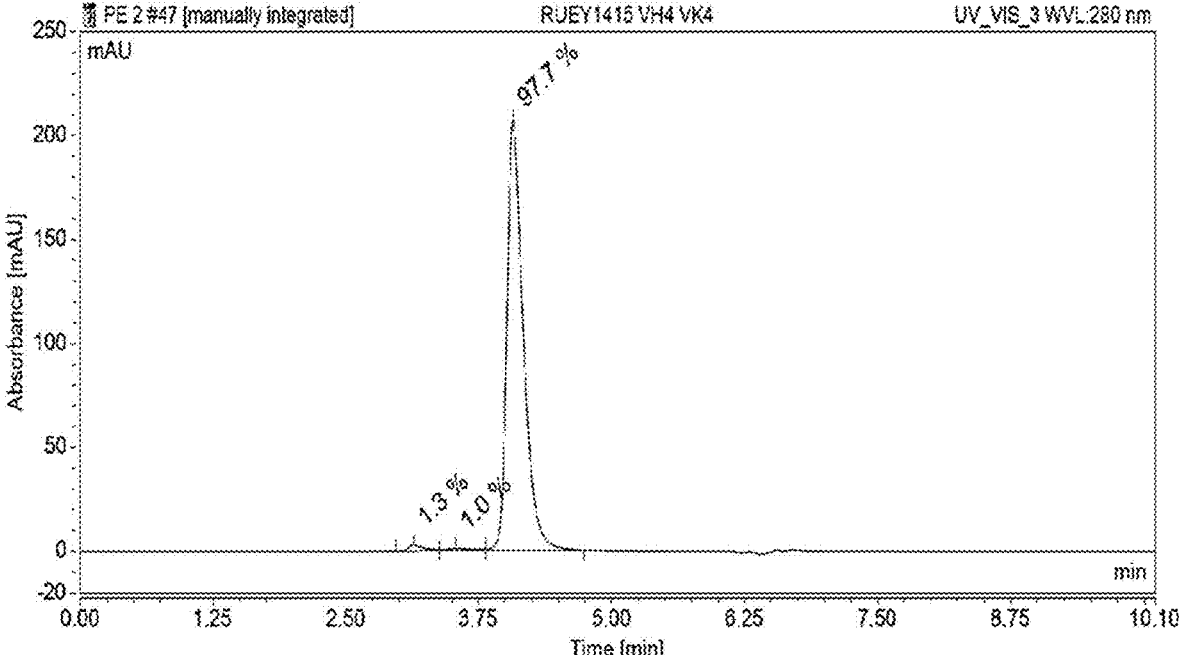
FIG. 31B

VH5/VK2
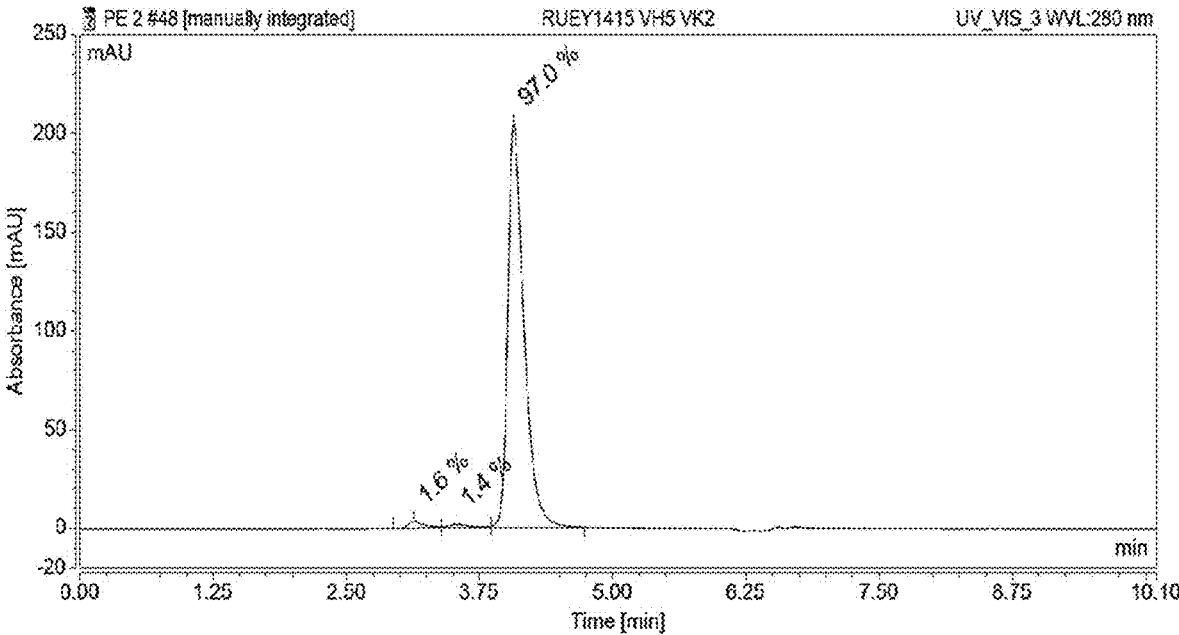
VH5/VK3
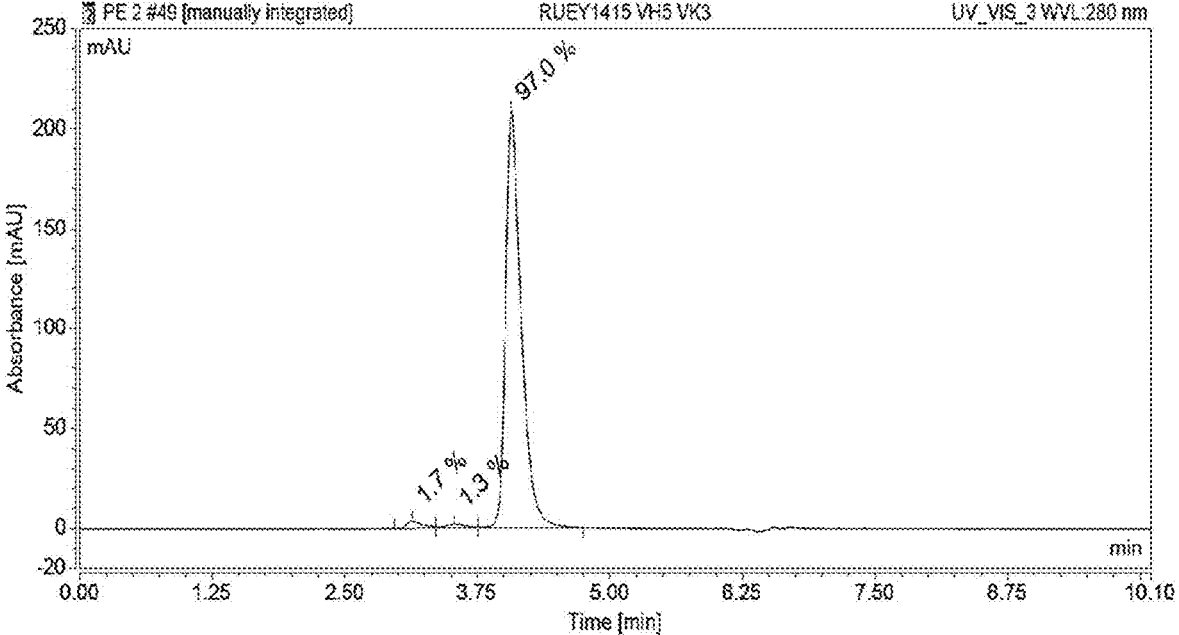
FIG. 31C

VH5/VK4
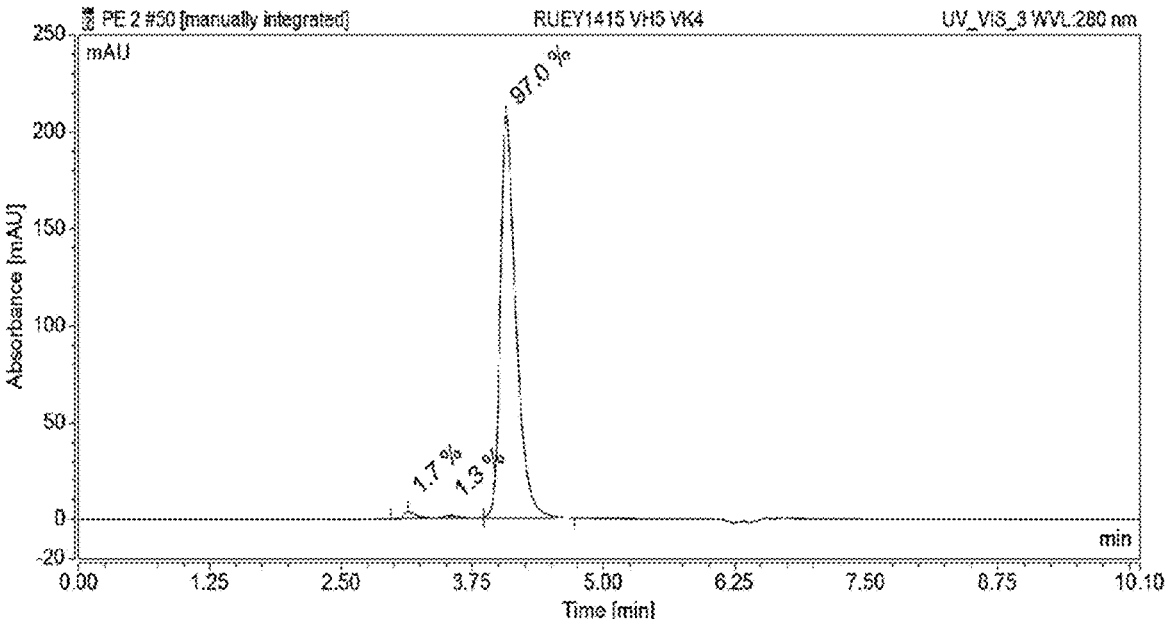
Overlays
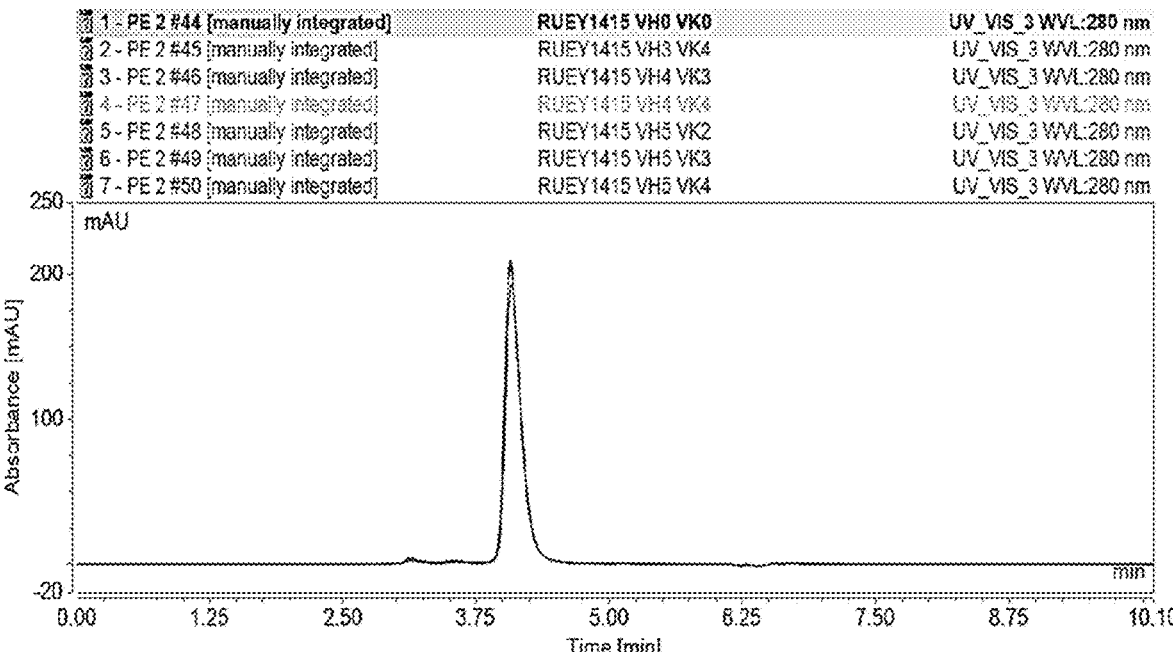
FIG. 31D

MC-VCP-MMAE

$$Average\ DAR_{non-reduced\ sample} = \frac{\sum_{i=0}^{n} SI_i \times i}{\sum_{i=0}^{n} SI_i}$$

$$Average\ DAR_{reduced\ sample} = 2 \times \frac{\sum_{i=0}^{n} LSI_i \times i}{\sum_{i=0}^{n} LSI_i} + 2 \times \frac{\sum_{i=0}^{n} HSI_i \times i}{\sum_{i=0}^{n} HSI_i}$$

FIG. 59A $$Average\ DAR = \frac{\sum_{i=0}^{n} AUC_i \times i}{\sum_{i=0}^{n} AUC_i}$$

$$MW_{ADC} = MW_{mAb} + DAR \times MW_{LP}$$

FIG. 59B

Assay Setup
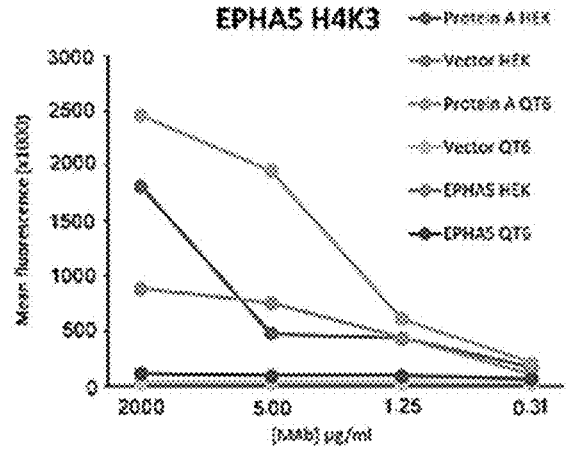
Membrane Proteome Array
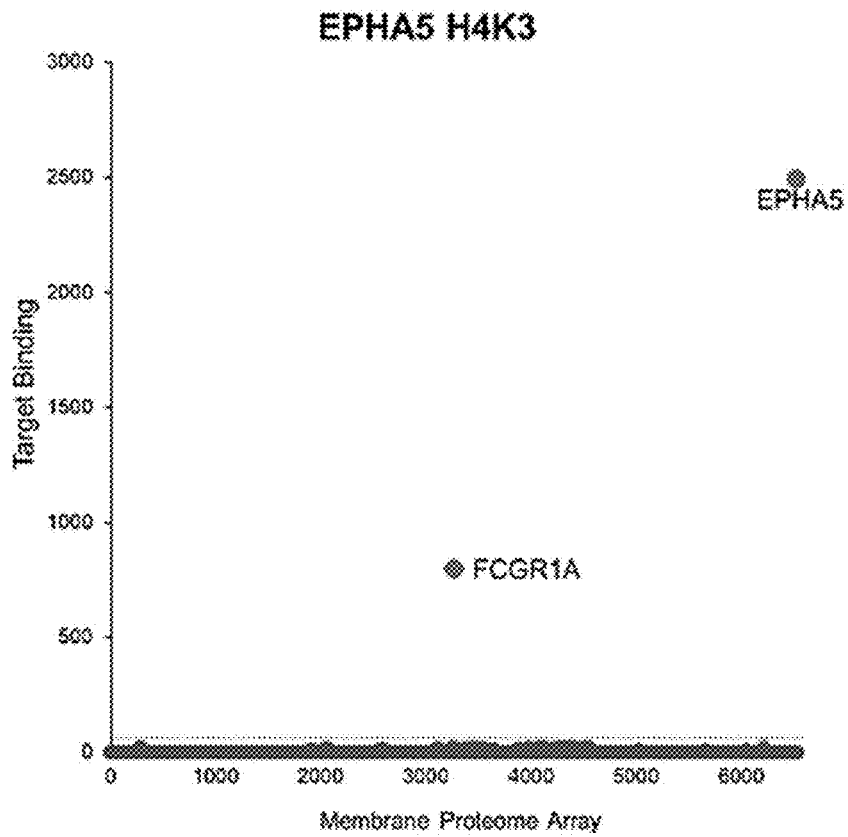
FIG. 60

Assay Setup
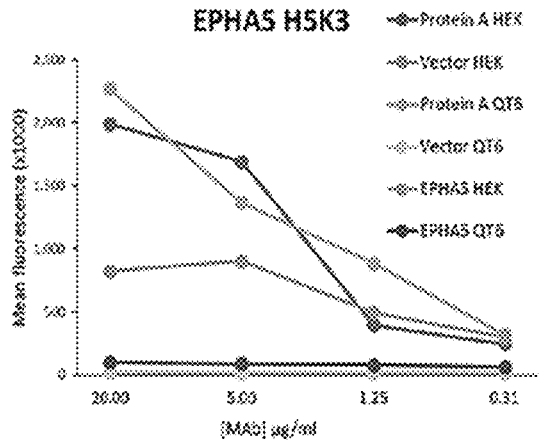
Membrane Proteome Array
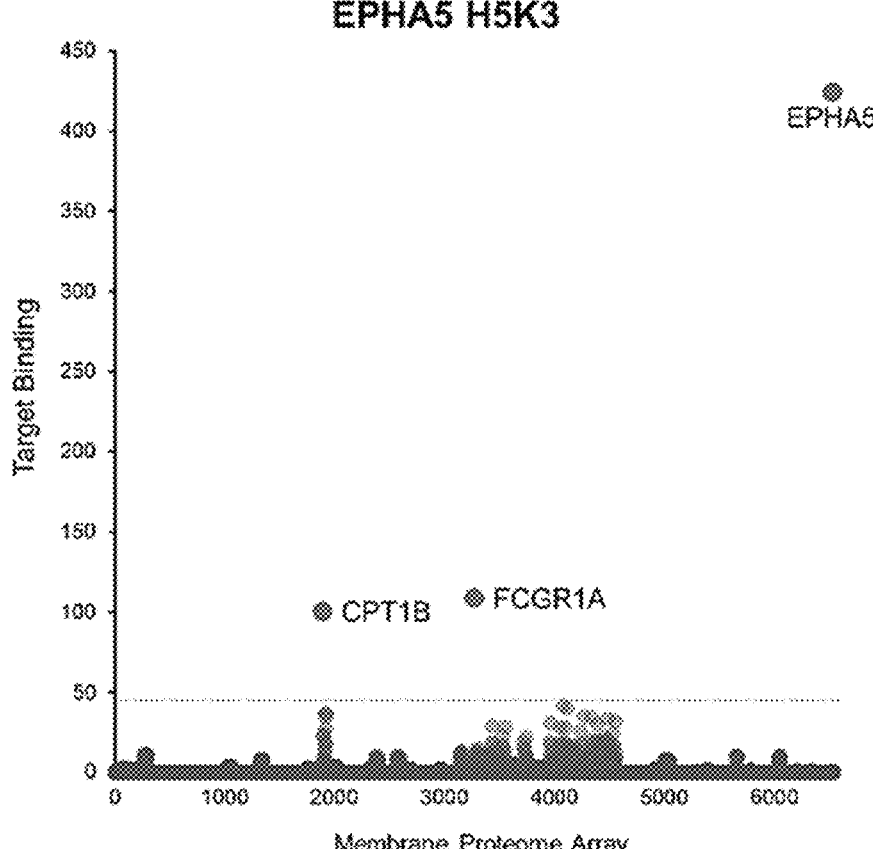
FIG. 61

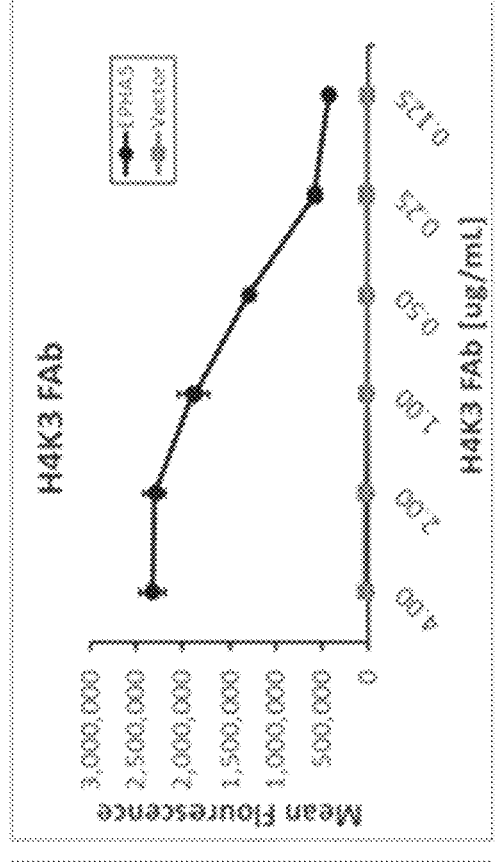
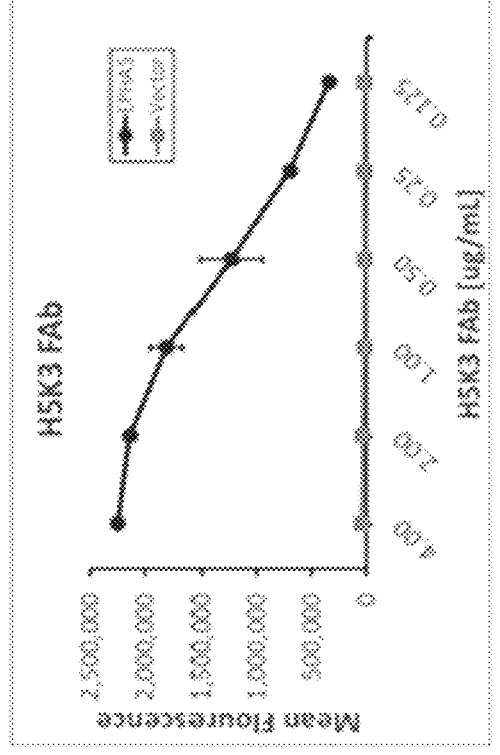
FIG. 62

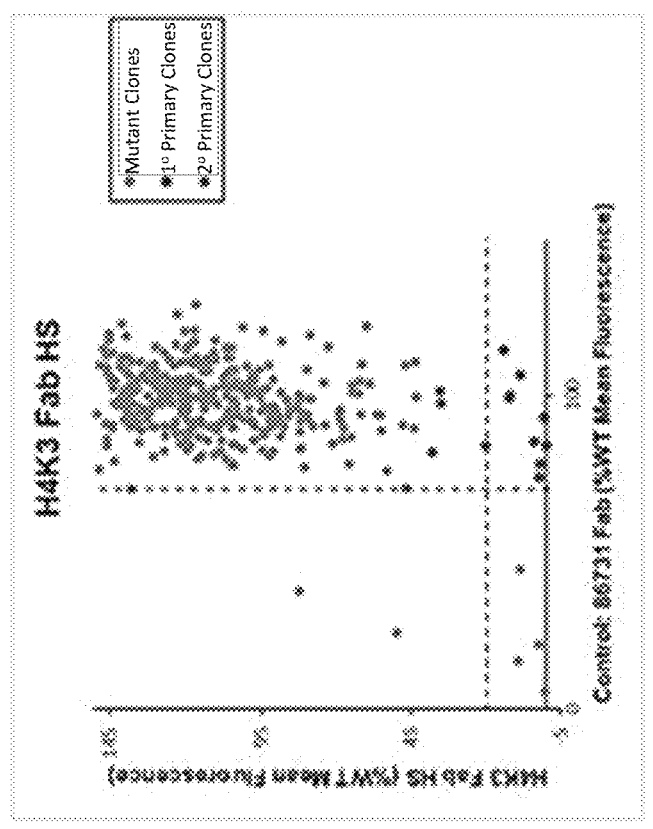
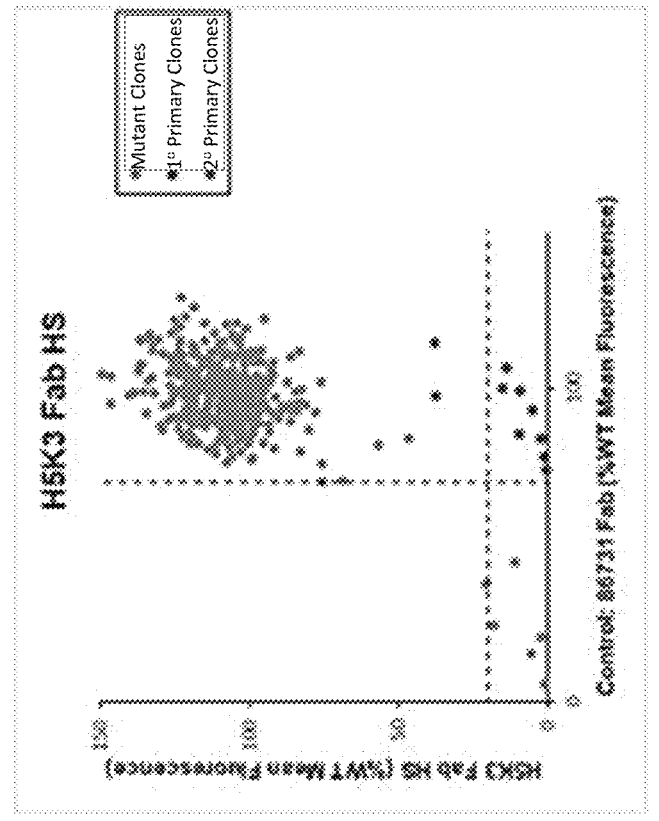
FIG. 63

| Antibody Name | Primary Residues |
|---|---|
| H5K3 Fab HS | R306, G308, F309, K321, T328 H329 E330 |
| H4K3 Fab HS | P306, G308, F309 K321, Y327, T328 H329 E330 |

FIG. 65

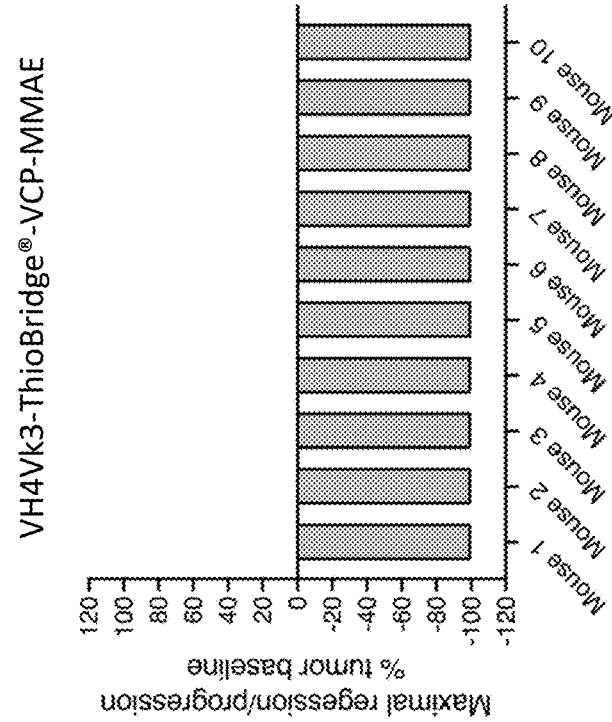
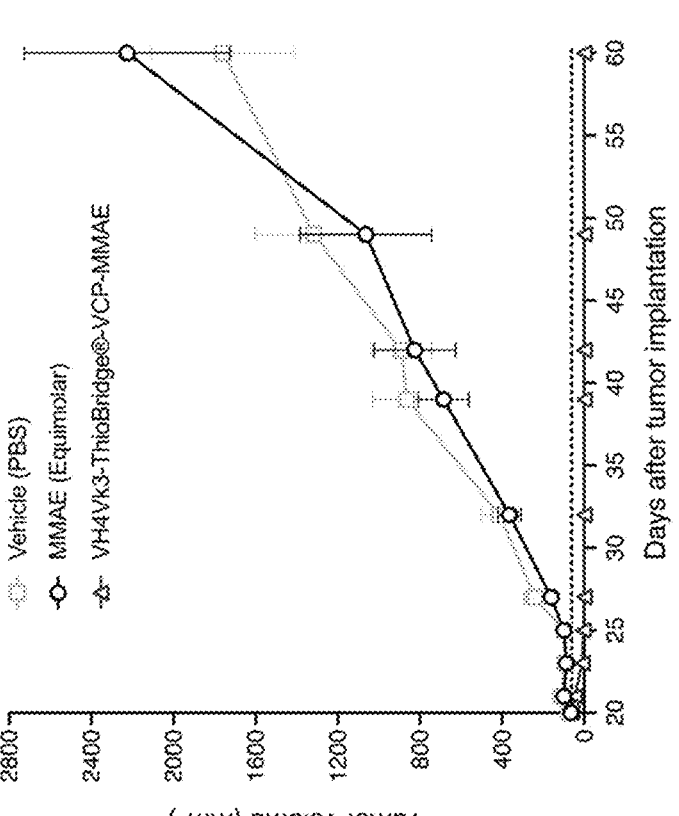
FIG. 72

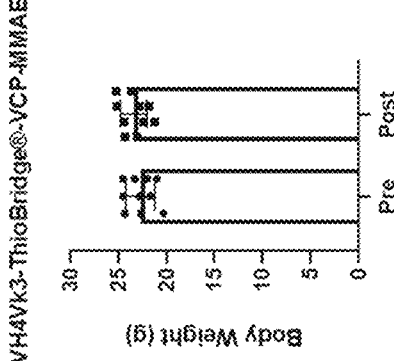
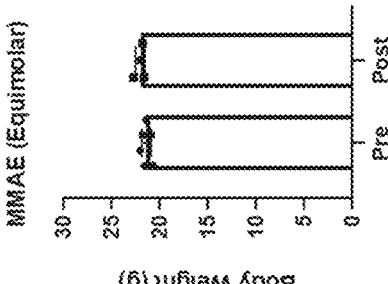
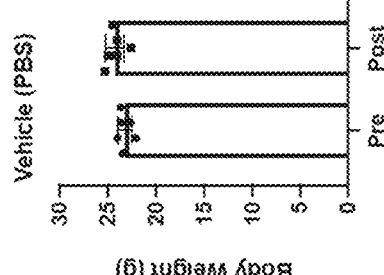
FIG. 73

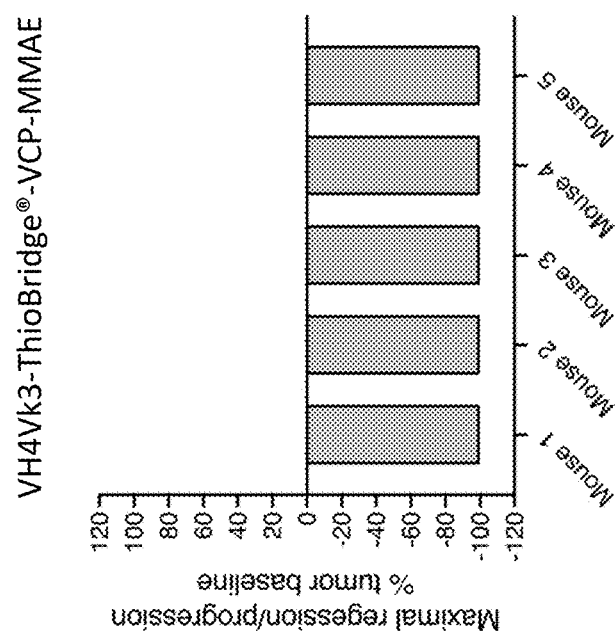
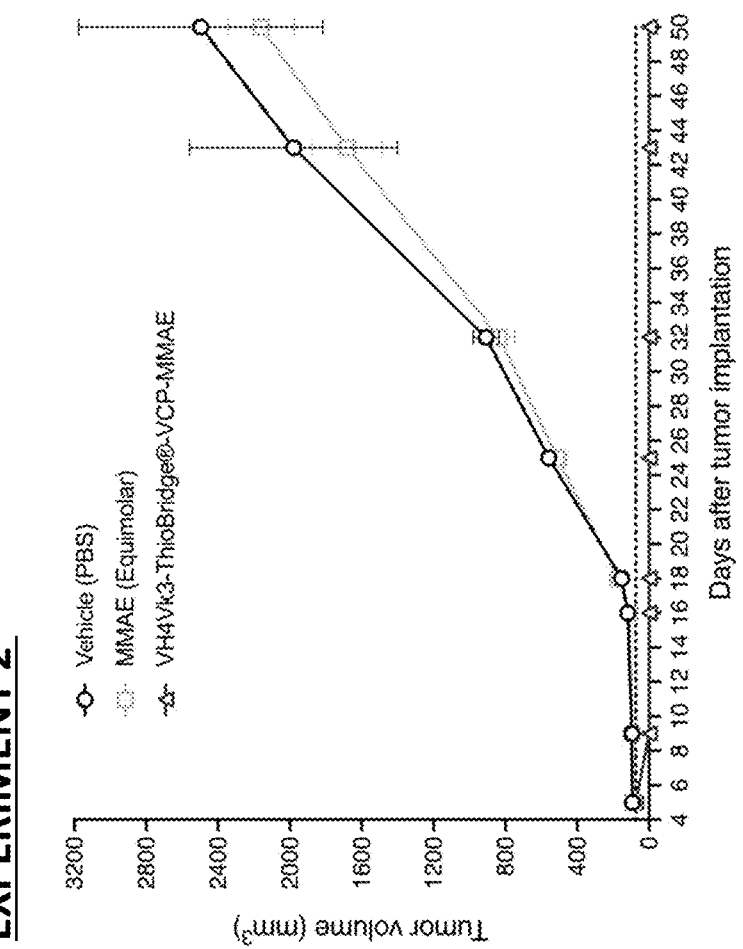
FIG. 74

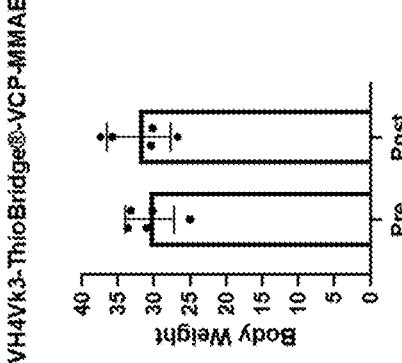
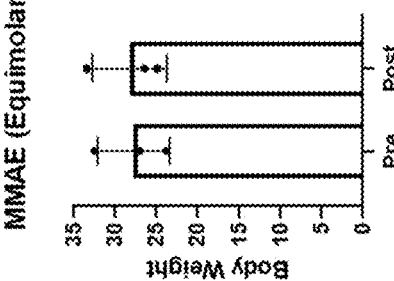
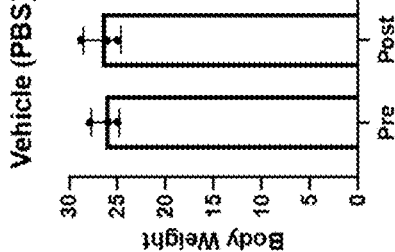
FIG. 75

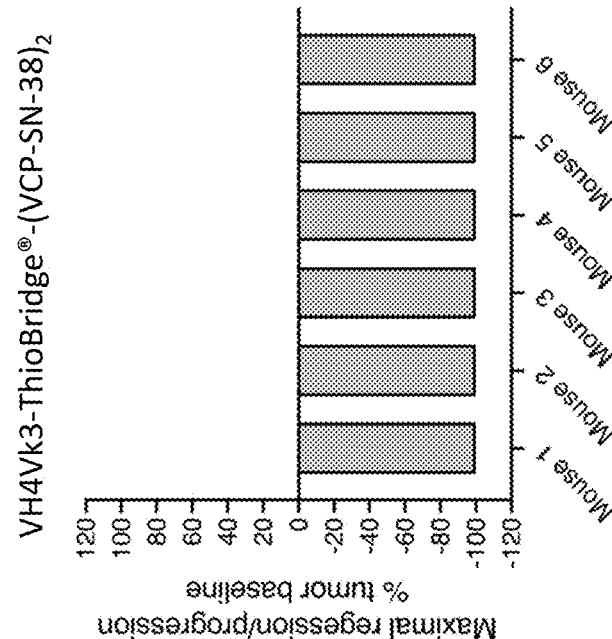
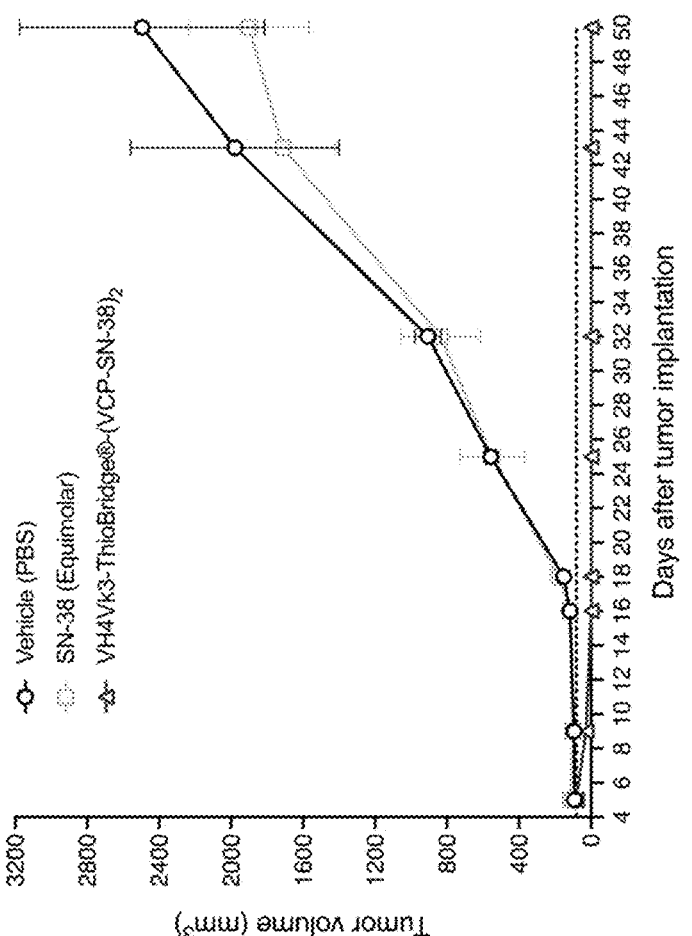
FIG. 76

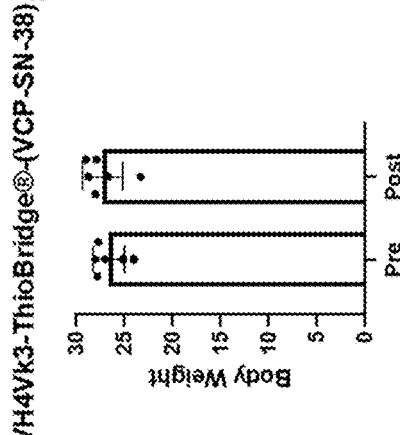
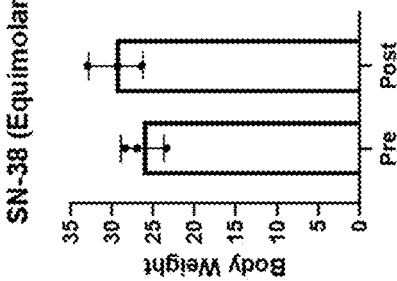
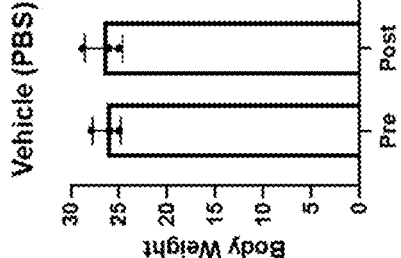
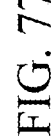
FIG. 77

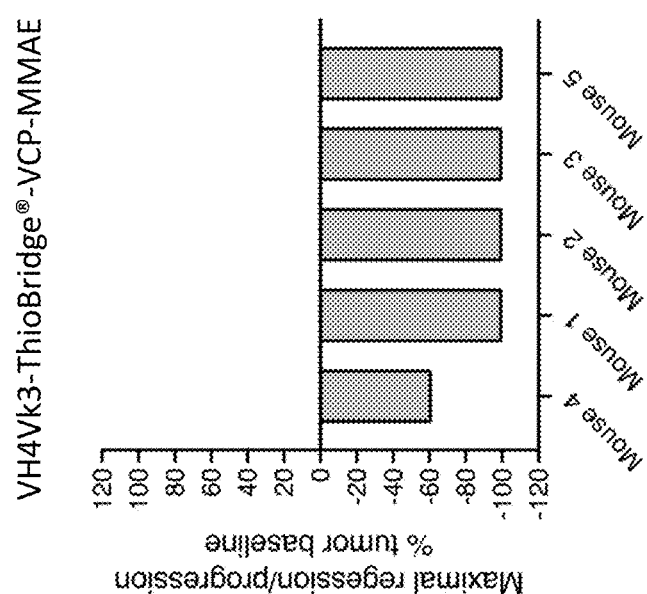
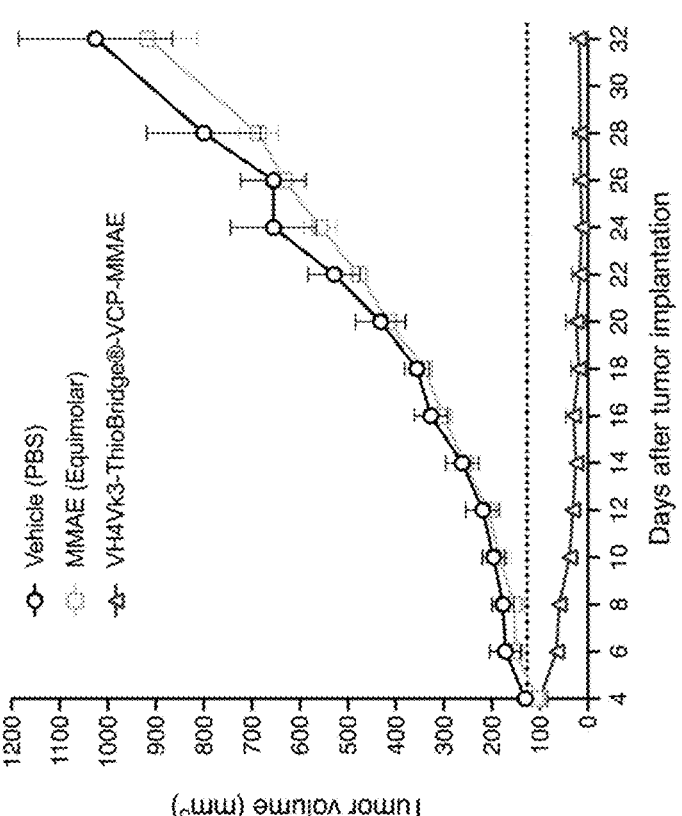
FIG. 78

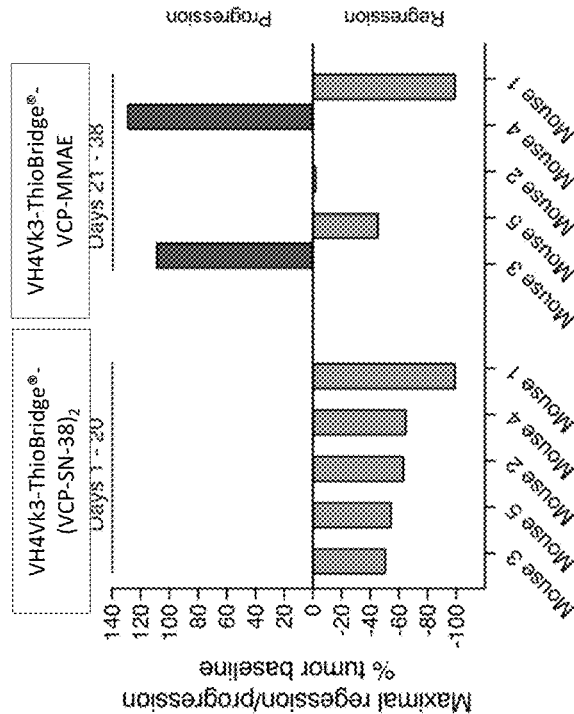
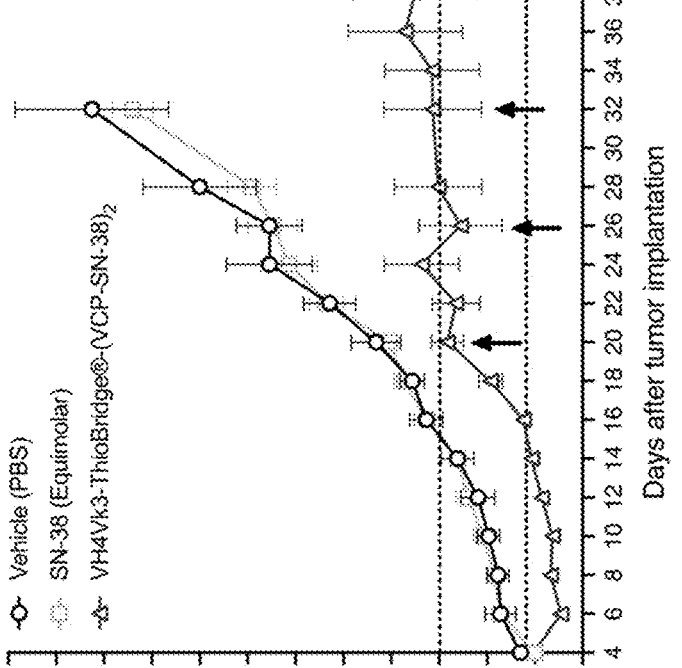
FIG. 80

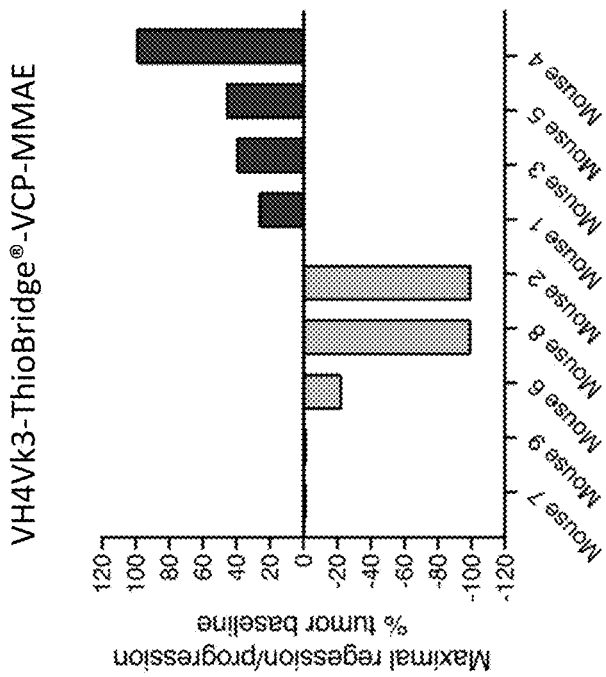
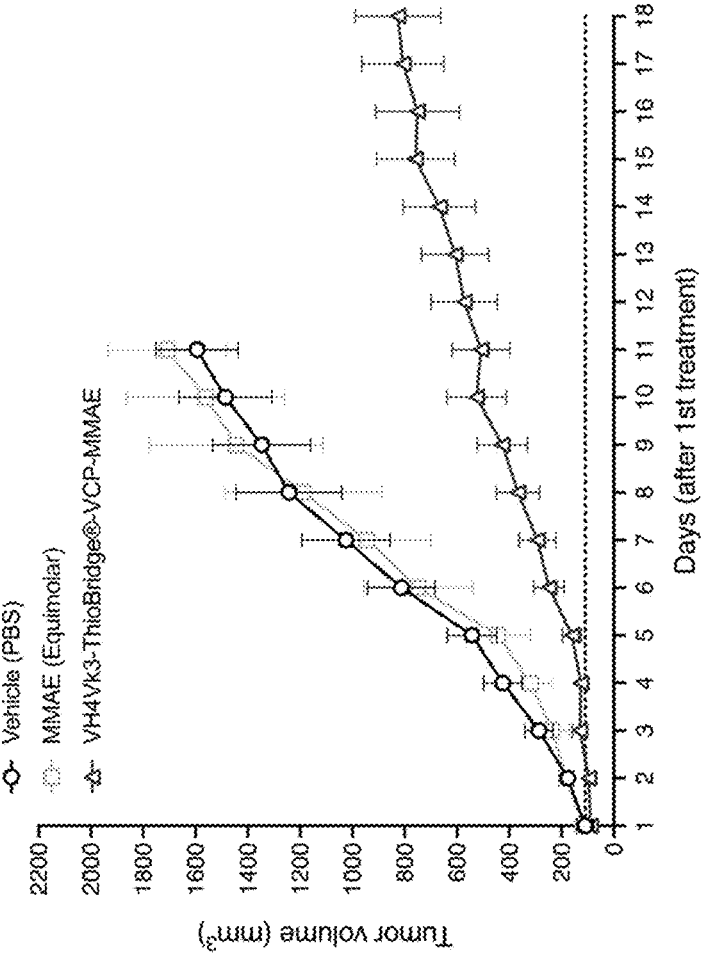
FIG. 82

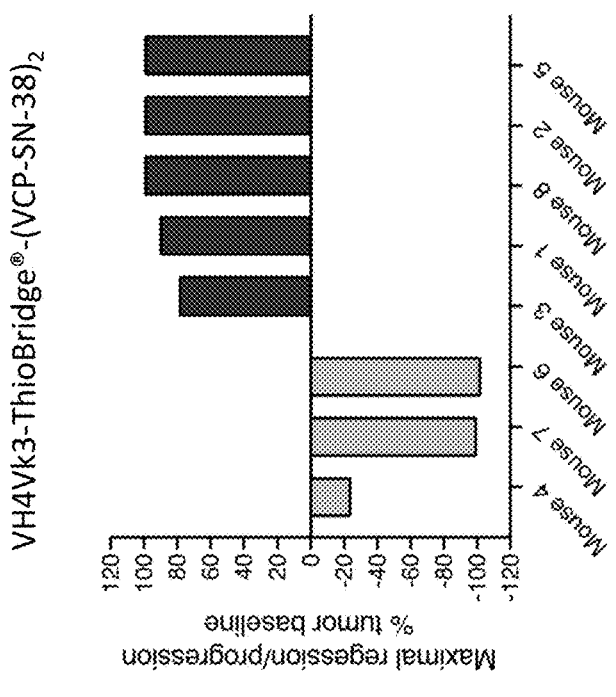
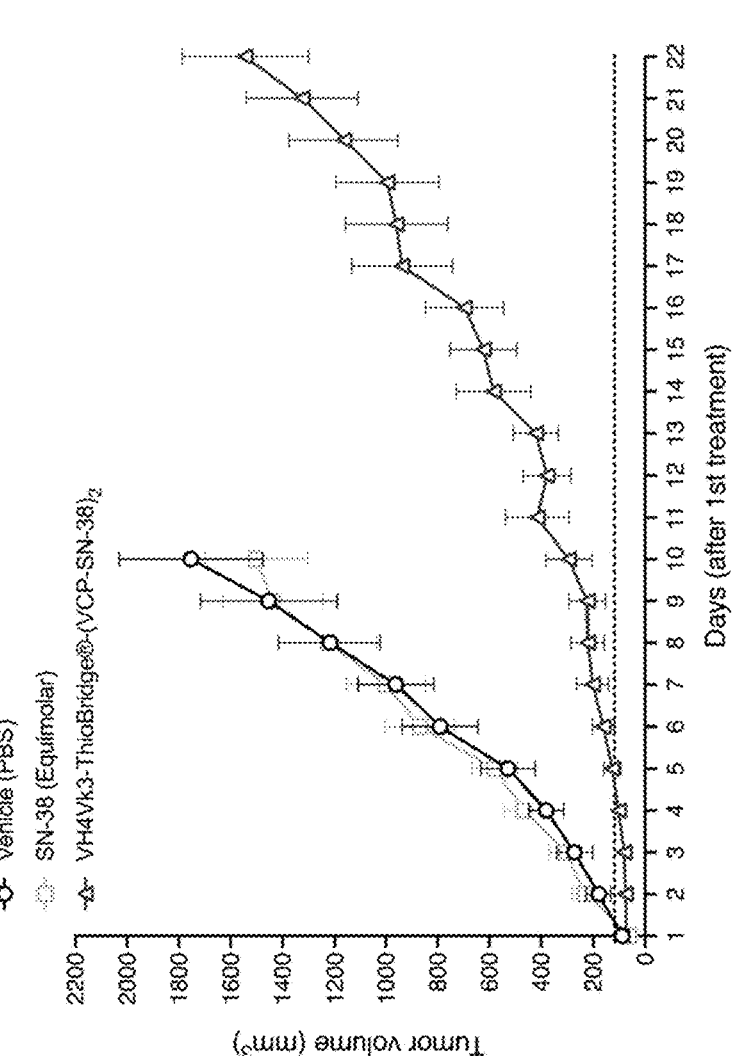
FIG. 84

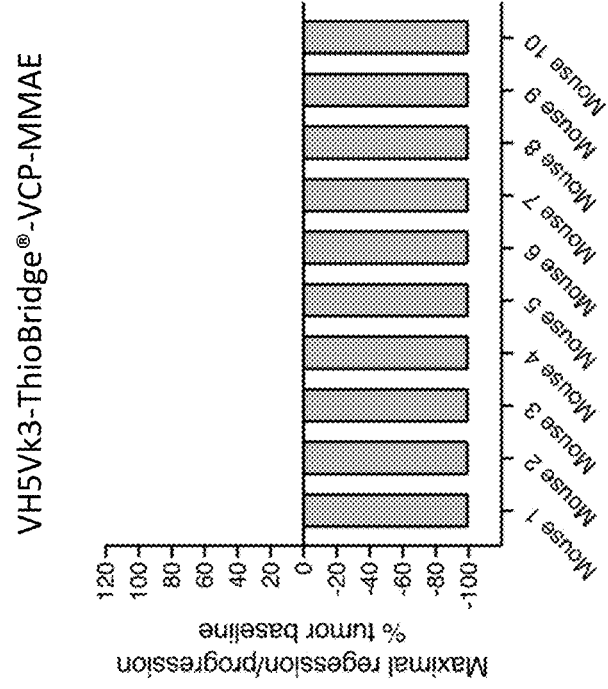
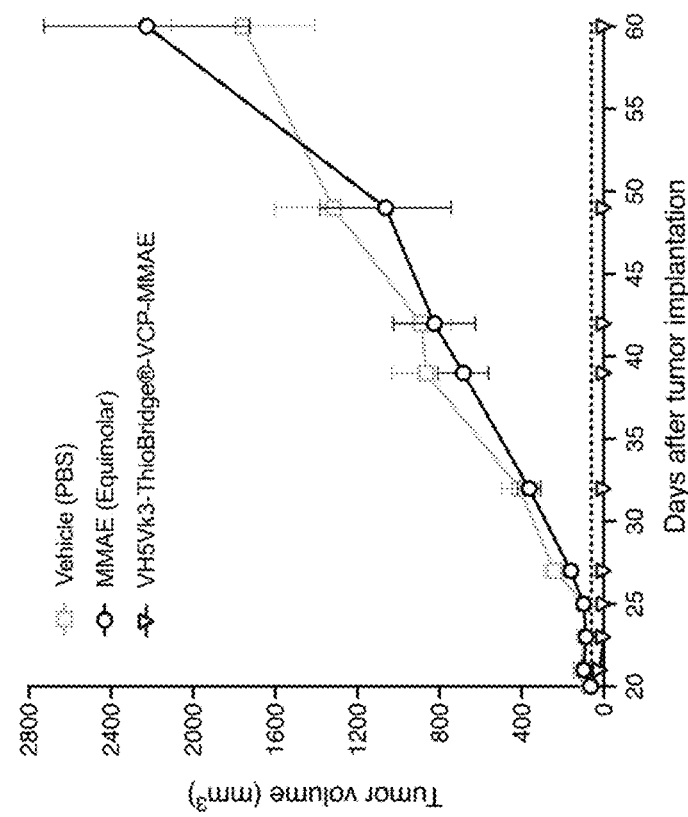
FIG. 86

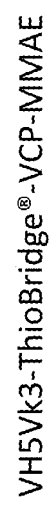
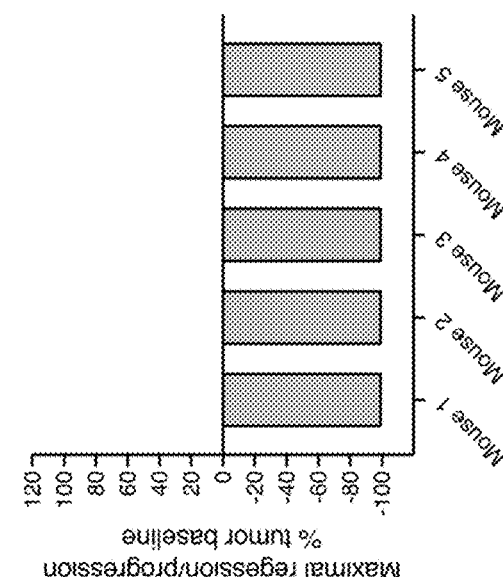
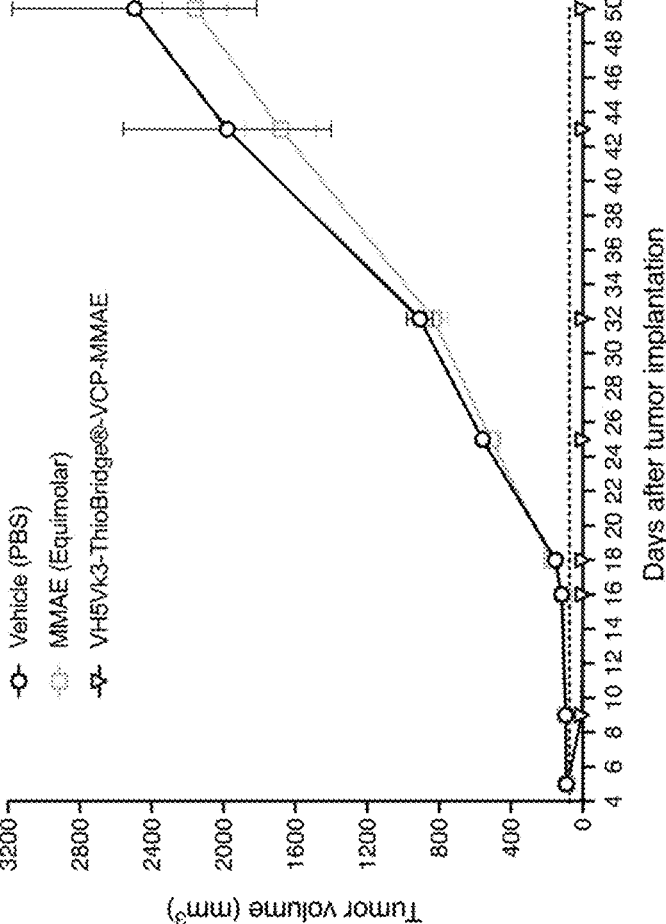
FIG. 88

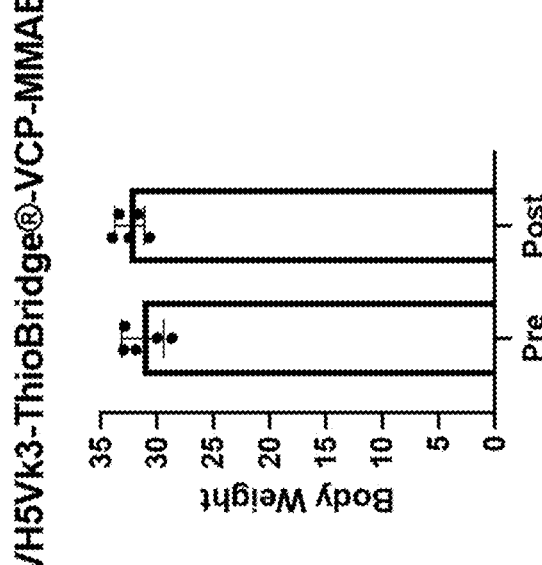
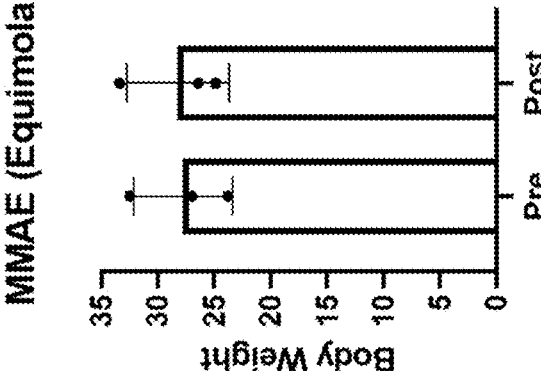
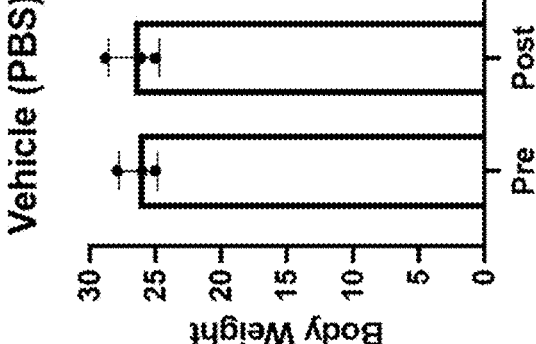
FIG. 89

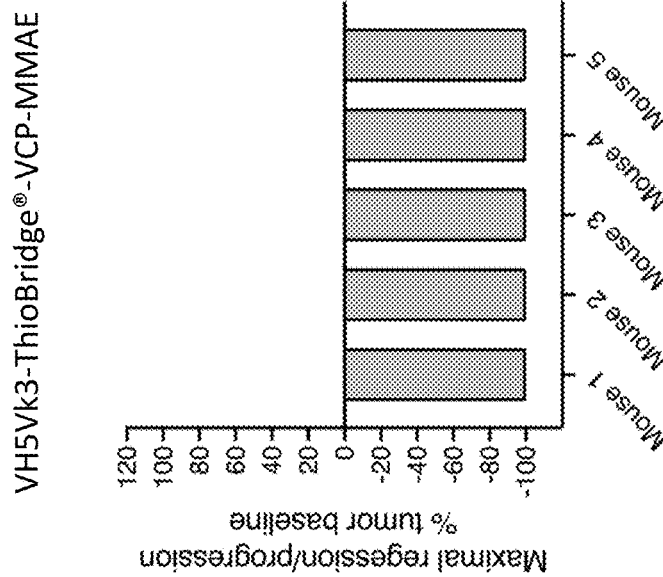
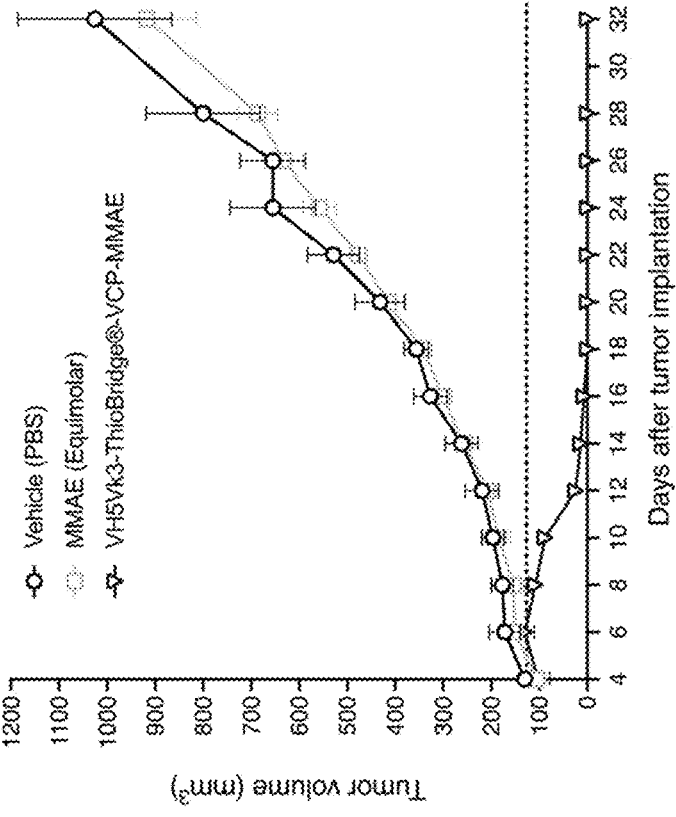
FIG. 90

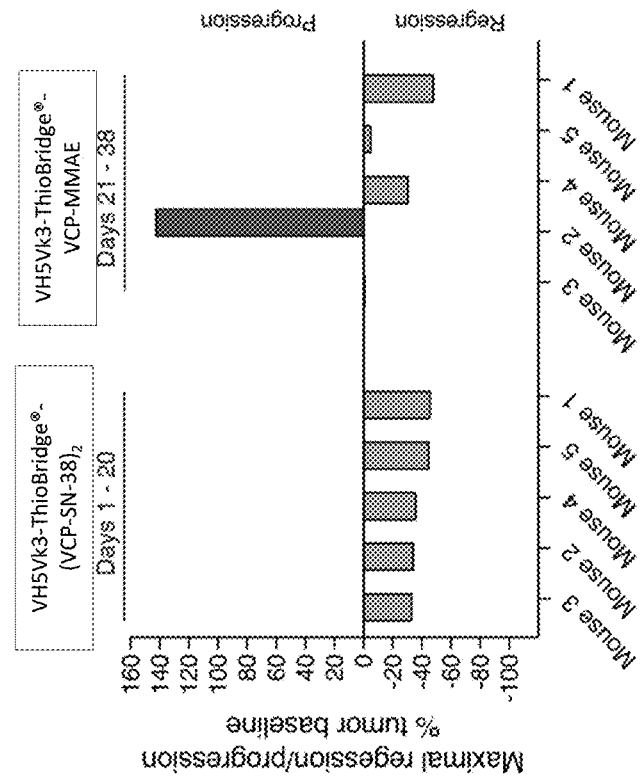
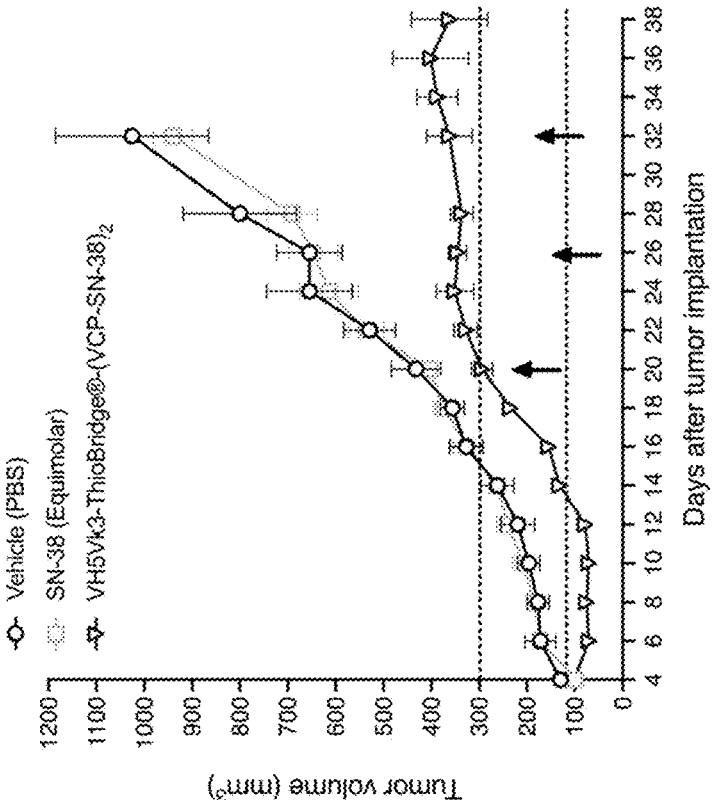
FIG. 92

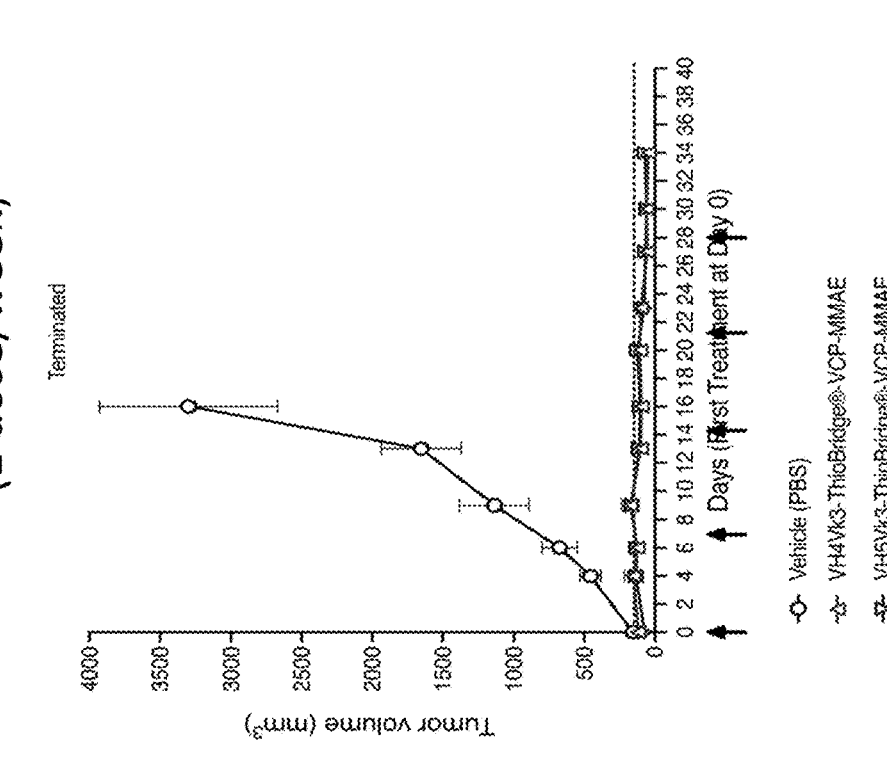
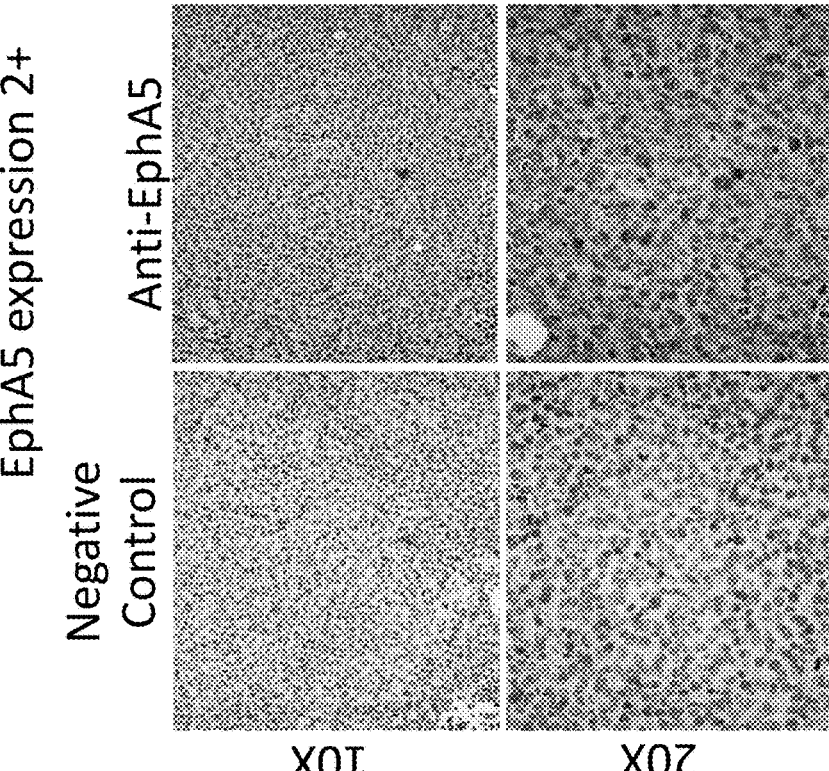
FIG. 98

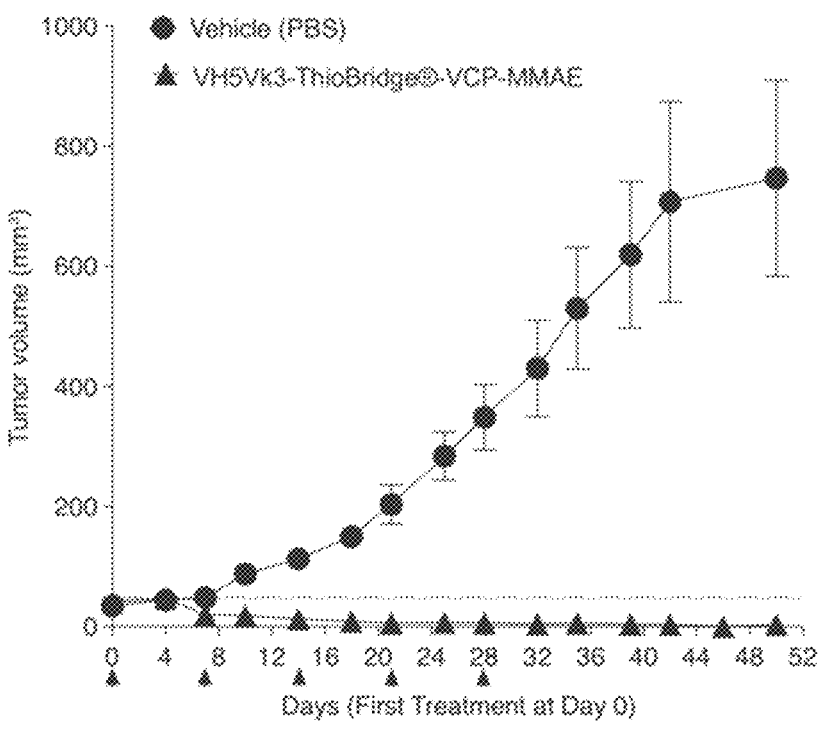
FIG. 108A
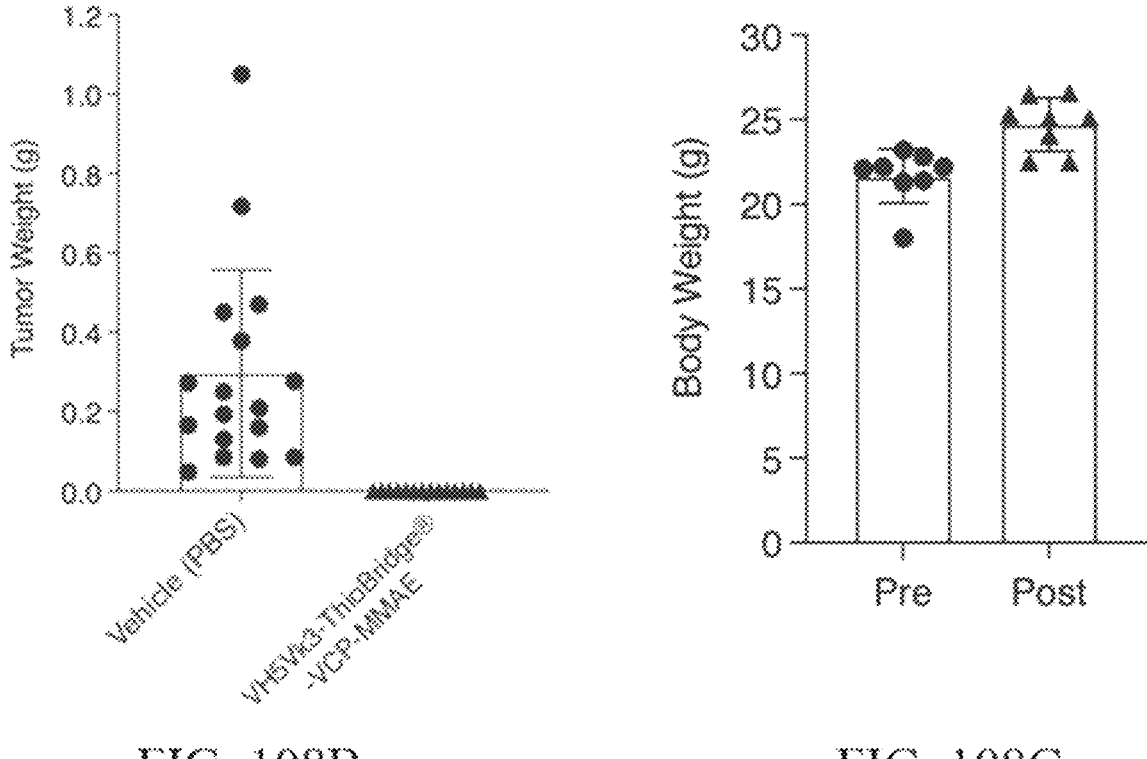
FIG. 108B
FIG. 108C

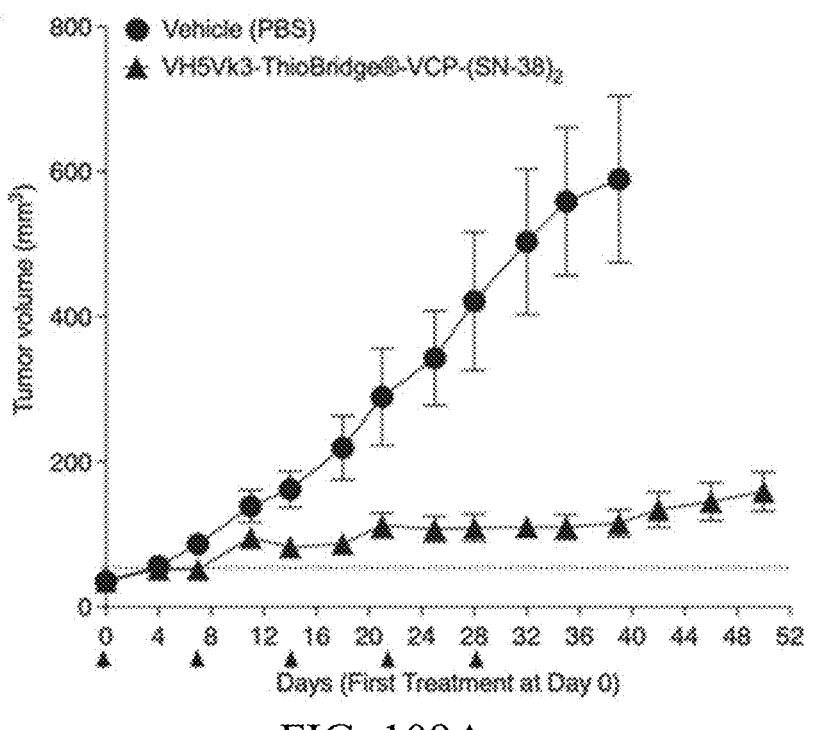
FIG. 109A
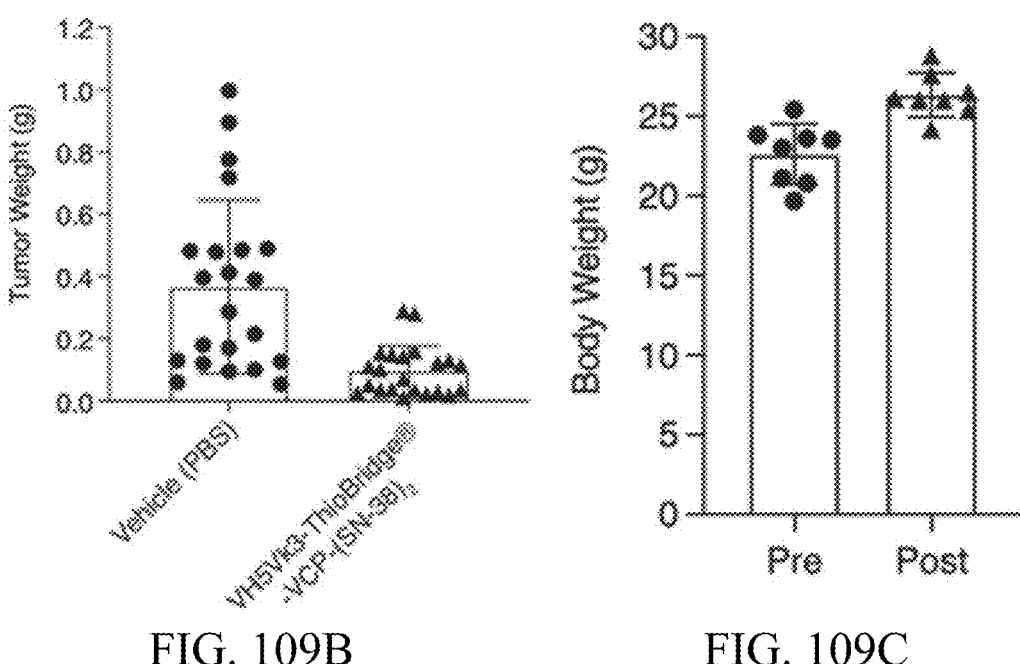
FIG. 109B                    FIG. 109C

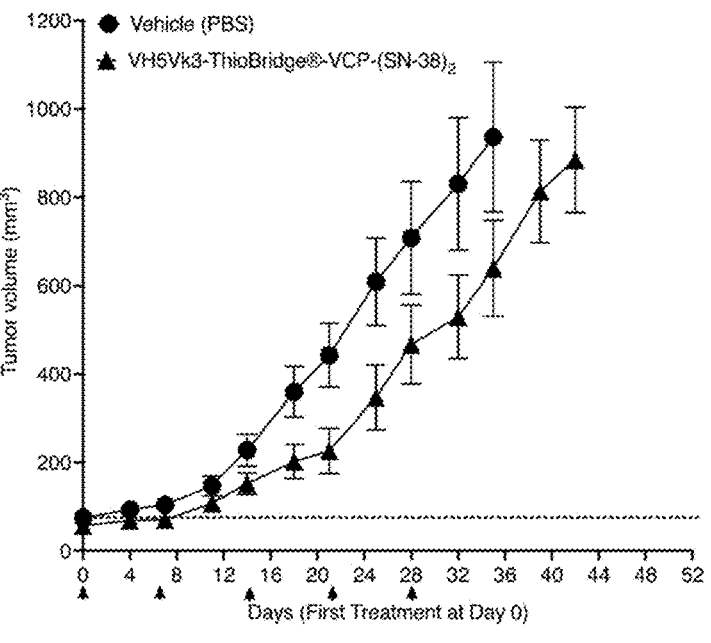
FIG. 112A
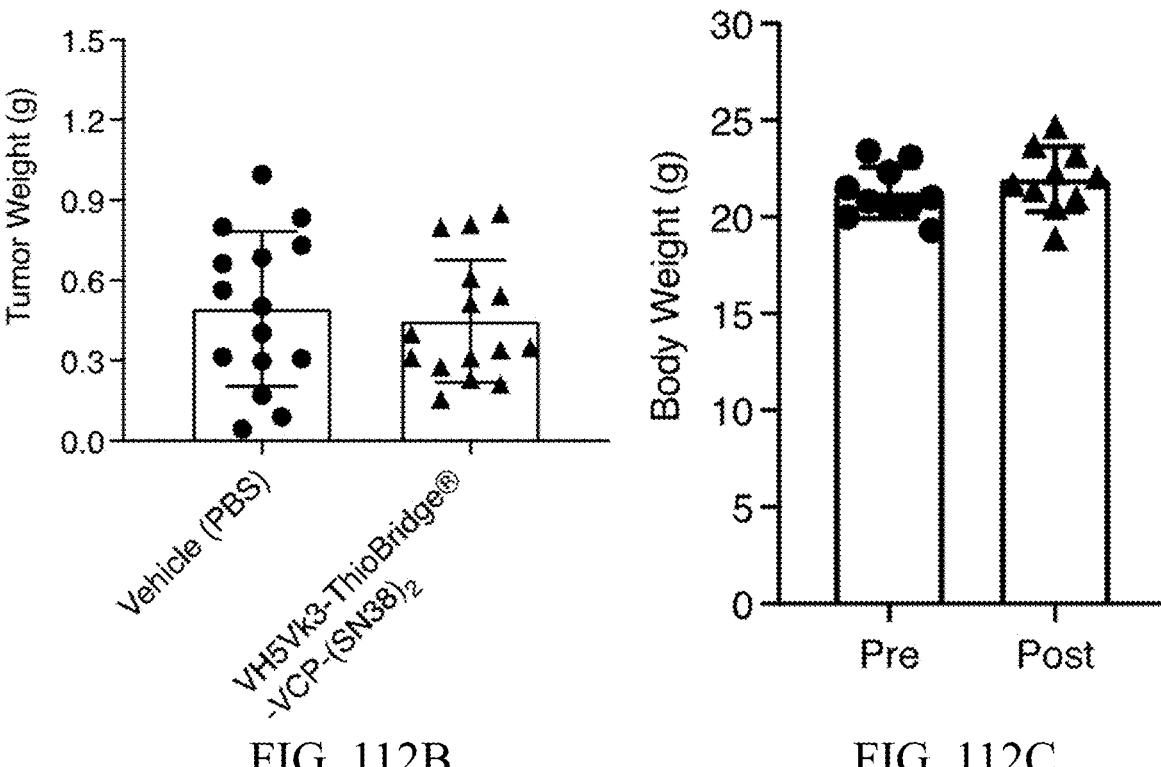
FIG. 112B                       FIG. 112C

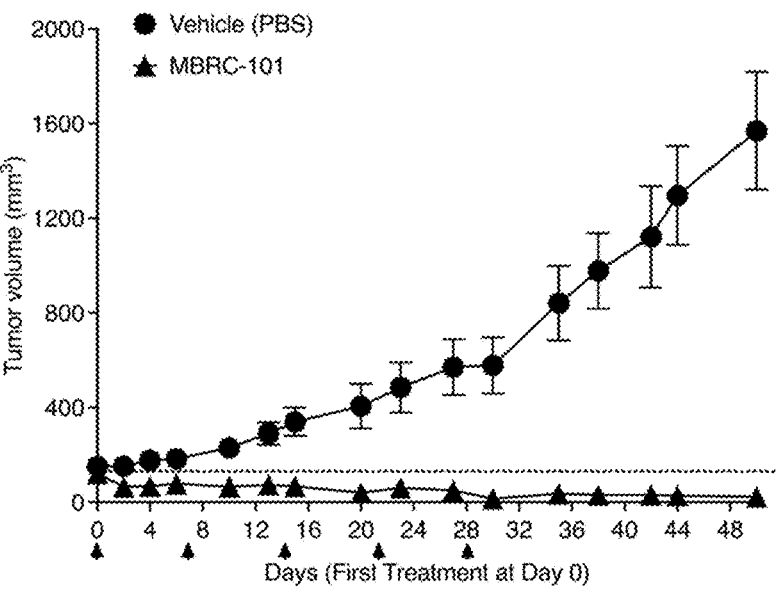
FIG. 117A
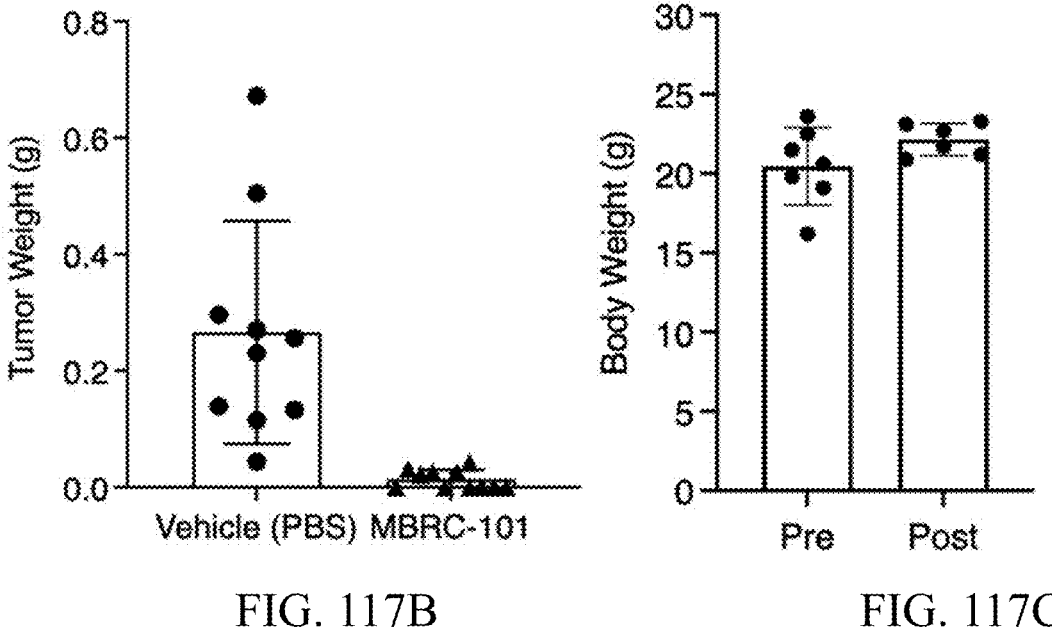
FIG. 117B
FIG. 117C

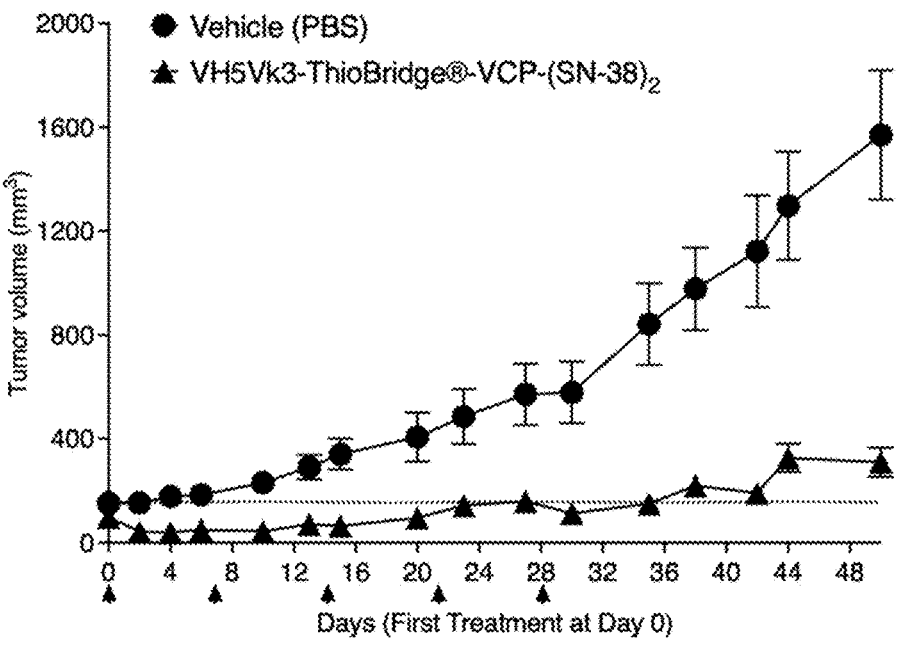
FIG. 118A
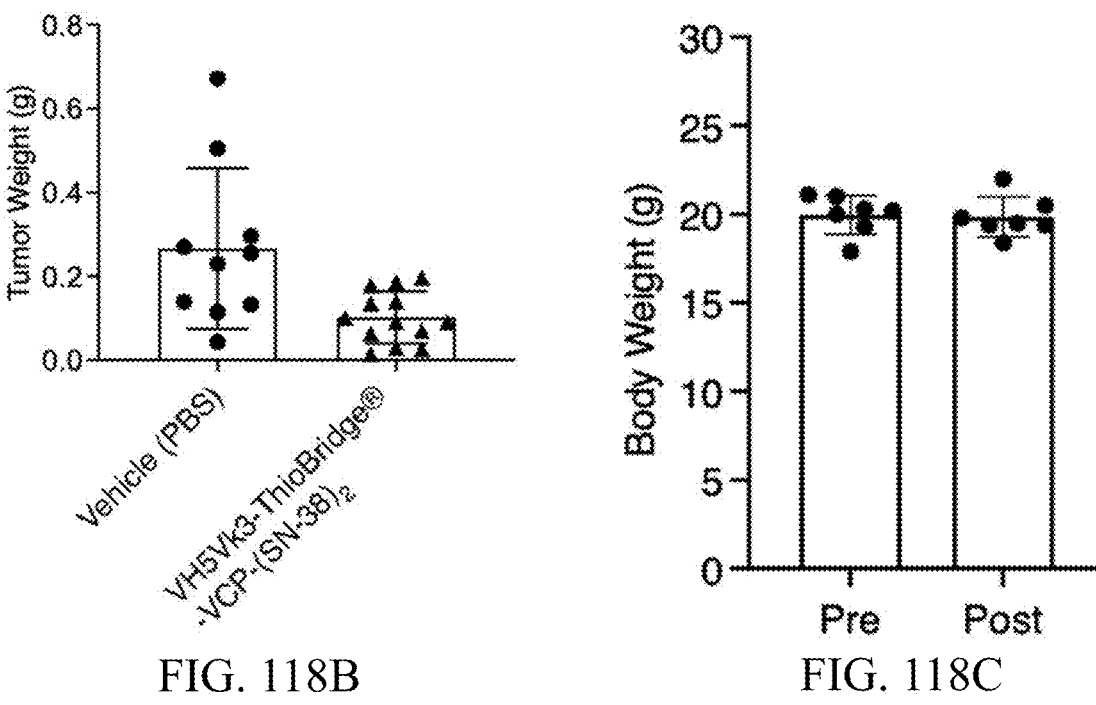
FIG. 118B
FIG. 118C

SEQUENCE LISTING

Sequence total quantity: 44
```
SEQ ID NO: 1                moltype = AA   length = 120
FEATURE                     Location/Qualifiers
source                      1..120
                            mol_type = protein
                            organism = synthetic construct
SEQUENCE: 1
EVTLKESGGG LVQPGGSRKL SCAASGFTFS TFGIHWVRQA PEKGLEWVAY ISGASTTIYY   60
ADTVKGRFTI SRDNPKNTLF LQMTSLRSED TAMYYCARYG TSFPYGLDYW GQGTSVTVSS  120

SEQ ID NO: 2                moltype = AA   length = 120
FEATURE                     Location/Qualifiers
source                      1..120
                            mol_type = protein
                            organism = synthetic construct
SEQUENCE: 2
EVTLVESGGG LVQPGGSRKL SCAASGFTFS TFGIHWVRQA PGKGLEWVAY ISGASTTIYY   60
ADTVKGRFTI SRDNSKNTLY LQMNSLRSED TAMYYCARYG TSFPYGLDYW GQGTSVTVSS  120

SEQ ID NO: 3                moltype = AA   length = 120
FEATURE                     Location/Qualifiers
source                      1..120
                            mol_type = protein
                            organism = synthetic construct
SEQUENCE: 3
EVTLVESGGG LVQPGGSLKL SCAASGFTFS TFGIHWVRQA PGKGLEWVAY ISGASTTIYY   60
ADTVKGRFTI SRDNSKNTLY LQMNSLRSED TAMYYCARYG TSFPYGLDYW GQGTLVTVSS  120

SEQ ID NO: 4                moltype = AA   length = 120
FEATURE                     Location/Qualifiers
source                      1..120
                            mol_type = protein
                            organism = synthetic construct
SEQUENCE: 4
EVQLVESGGG LVQPGGSLKL SCAASGFTFS TFGIHWVRQA PGKGLEWVAY ISGASTTIYY   60
ADTVKGRFTI SRDNSKNTLY LQMNSLRSED TAMYYCARYG TSFPYGLDYW GQGTLVTVSS  120

SEQ ID NO: 5                moltype = AA   length = 120
FEATURE                     Location/Qualifiers
source                      1..120
                            mol_type = protein
                            organism = synthetic construct
SEQUENCE: 5
EVQLVESGGG LVQPGGSLKL SCAASGFTFS TFGIHWVRQA PGKGLEWVAY ISGASTTIYY   60
ADTVKGRFTI SRDNSKNTLY LQMNSLRAED TAVYYCARYG TSFPYGLDYW GQGTLVTVSS  120

SEQ ID NO: 6                moltype = AA   length = 120
FEATURE                     Location/Qualifiers
source                      1..120
                            mol_type = protein
                            organism = synthetic construct
SEQUENCE: 6
EVQLVESGGG LVQPGGSLKL SCAASGFTFS TFGIHWVRQA PGKGLEWVAY ISGASTTIYY   60
ADSVKGRFTI SRDNSKNTLY LQMNSLRAED TAVYYCARYG TSFPYGLDYW GQGTLVTVSS  120

SEQ ID NO: 7                moltype = AA   length = 120
FEATURE                     Location/Qualifiers
source                      1..120
                            mol_type = protein
                            organism = synthetic construct
SEQUENCE: 7
EVQLVESGGG LVQPGGSLKL SCAASGFTFS TFGIHWVRQA PGKGLEWVAS ISGASTTIYY   60
ADSVKGRFTI SRDNSKNTLY LQMNSLRAED TAVYYCARYG TSFPYGLDYW GQGTLVTVSS  120

SEQ ID NO: 8                moltype = AA   length = 111
FEATURE                     Location/Qualifiers
source                      1..111
                            mol_type = protein
                            organism = synthetic construct
SEQUENCE: 8
DIVMTQSPGS LAVSLGQRAT ISCKASQSVD YDGDSYMNWY QQKPGQPPKL LIYGASNLES   60
GIPARFSGSG SGTDFTLNIH PVEEEDAASY YCQQSNEDPF TFGSGTKLEI K            111

SEQ ID NO: 9                moltype = AA   length = 111
FEATURE                     Location/Qualifiers
source                      1..111
                            mol_type = protein
                            organism = synthetic construct
```

-continued

```
SEQUENCE: 9
DIVMTQSPGS LAVSLGERAT INCKASQSVD YDGDSYMNWY QQKPGKAPKL LIYGASNLES   60
GIPDRFSGSG SGTDFTLTIS RLEEEDAASY YCQQSNEDPF TFGQGTKLEI K            111

SEQ ID NO: 10            moltype = AA   length = 111
FEATURE                  Location/Qualifiers
source                   1..111
                         mol_type = protein
                         organism = synthetic construct
SEQUENCE: 10
DIVMTQSPDS LAVSLGERAT INCKASQSVD YDGDSYMNWY QQKPGKAPKL LIYGASNLES   60
GIPDRFSGSG SGTDFTLTIS RLEPEDAASY YCQQSNEDPF TFGQGTKLEI K            111

SEQ ID NO: 11            moltype = AA   length = 111
FEATURE                  Location/Qualifiers
source                   1..111
                         mol_type = protein
                         organism = synthetic construct
SEQUENCE: 11
DIVMTQSPDS LAVSLGERAT INCKASQSVD YDGDSYMNWY QQKPGKAPKL LIYGASNLES   60
GIPDRFSGSG SGTDFTLTIS RLEPEDAAVY YCQQSNEDPF TFGQGTKLEI K            111

SEQ ID NO: 12            moltype = AA   length = 111
FEATURE                  Location/Qualifiers
source                   1..111
                         mol_type = protein
                         organism = synthetic construct
SEQUENCE: 12
DIVMTQSPDS LAVSLGERAT INCKSSQSVD YDGDSYMNWY QQKPGKAPKL LIYGASNLES   60
GIPDRFSGSG SGTDFTLTIS RLEPEDAASY YCQQSNEDPF TFGQGTKLEI K            111

SEQ ID NO: 13            moltype = AA   length = 111
FEATURE                  Location/Qualifiers
source                   1..111
                         mol_type = protein
                         organism = synthetic construct
SEQUENCE: 13
DIVMTQSPDS LAVSLGERAT INCKSSQSVD YDGDSYMNWY QQKPGKAPKL LIYGASNLES   60
GIPDRFSGSG SGTDFTLTIS RLEPEDAAVY YCQQSNEDPF TFGQGTKLEI K            111

SEQ ID NO: 14            moltype = AA   length = 330
FEATURE                  Location/Qualifiers
source                   1..330
                         mol_type = protein
                         organism = synthetic construct
SEQUENCE: 14
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 15            moltype = AA   length = 107
FEATURE                  Location/Qualifiers
source                   1..107
                         mol_type = protein
                         organism = synthetic construct
SEQUENCE: 15
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 16            moltype = AA   length = 5
FEATURE                  Location/Qualifiers
source                   1..5
                         mol_type = protein
                         organism = synthetic construct
SEQUENCE: 16
TFGIH                                                                5

SEQ ID NO: 17            moltype = AA   length = 17
FEATURE                  Location/Qualifiers
source                   1..17
                         mol_type = protein
                         organism = synthetic construct
SEQUENCE: 17
YISGASTTIY YADTVKG                                                  17

SEQ ID NO: 18            moltype = AA   length = 17
```

-continued

```
FEATURE           Location/Qualifiers
source            1..17
                  mol_type = protein
                  organism = synthetic construct
SEQUENCE: 18
YISGASTTIY YADSVKG                                                      17

SEQ ID NO: 19     moltype = AA  length = 17
FEATURE           Location/Qualifiers
source            1..17
                  mol_type = protein
                  organism = synthetic construct
SEQUENCE: 19
SISGASTTIY YADSVKG                                                      17

SEQ ID NO: 20     moltype = AA  length = 11
FEATURE           Location/Qualifiers
source            1..11
                  mol_type = protein
                  organism = synthetic construct
SEQUENCE: 20
YGTSFPYGLD Y                                                            11

SEQ ID NO: 21     moltype = AA  length = 15
FEATURE           Location/Qualifiers
source            1..15
                  mol_type = protein
                  organism = synthetic construct
SEQUENCE: 21
KASQSVDYDG DSYMN                                                        15

SEQ ID NO: 22     moltype = AA  length = 15
FEATURE           Location/Qualifiers
source            1..15
                  mol_type = protein
                  organism = synthetic construct
SEQUENCE: 22
KSSQSVDYDG DSYMN                                                        15

SEQ ID NO: 23     moltype = AA  length = 7
FEATURE           Location/Qualifiers
source            1..7
                  mol_type = protein
                  organism = synthetic construct
SEQUENCE: 23
GASNLES                                                                 7

SEQ ID NO: 24     moltype = AA  length = 9
FEATURE           Location/Qualifiers
source            1..9
                  mol_type = protein
                  organism = synthetic construct
SEQUENCE: 24
QQSNEDPFT                                                               9

SEQ ID NO: 25     moltype = DNA  length = 360
FEATURE           Location/Qualifiers
source            1..360
                  mol_type = other DNA
                  organism = synthetic construct
SEQUENCE: 25
gaagtgaccc tgaaagagtc tggcggagga ctggttcagc ctggcggatc tagaaagctg   60
tcttgtgccg cctccggctt caccttctct acctttggca tccactgggt ccgacaggcc  120
cctgagaaag gattggagtg ggtcgcctac atctccggcg cttccaccac catctactac  180
gccgataccg tgaagggcag attcaccatc agccgggaca accccaagaa caccctgttt  240
ctgcagatga ccagcctgcg gagcgaggac accgccatgt actactgtgc cagatacggc  300
accagctttc cctacggcct ggattattgg ggccagggaa cctccgttac agtctcctca  360

SEQ ID NO: 26     moltype = DNA  length = 360
FEATURE           Location/Qualifiers
source            1..360
                  mol_type = other DNA
                  organism = synthetic construct
SEQUENCE: 26
gaagtgaccc tggttgaatc tggcggagga ctggttcagc ctggcggctc tagaaagctg   60
tcttgtgccg cctctggctt caccttctcc acctttggca tccactgggt ccgacaggcc  120
cctggcaaag gattggagtg ggtcgcctat atctccggcg cctccaccac catctactac  180
gccgataccg tgaagggcag attcaccatc agccgggaca actccaagaa caccctgtac  240
ctgcagatga actccctgcg gagcgaggac accgccatgt actactgtgc cagatacggc  300
```

```
accagctttc cctacggcct ggattattgg ggccagggaa cctccgttac agtctcctca   360

SEQ ID NO: 27            moltype = DNA   length = 360
FEATURE                  Location/Qualifiers
source                   1..360
                         mol_type = other DNA
                         organism = synthetic construct
SEQUENCE: 27
gaagtgaccc tggttgaatc tggcggagga ctggttcagc ctggcggatc tctgaagctg   60
tcttgtgccg cctctggctt caccttctcc acctttggca tccactgggt ccgacaggcc   120
cctggcaaag gattggagtg ggtcgcctat atctccggcg cctccaccac catctactac   180
gccgataccg tgaagggcag attcaccatc agccgggaca actccaagaa caccctgtac   240
ctgcagatga actccctgcg gagcgaggac accgccatgt actactgtgc cagatacggc   300
accagctttc cctacggcct ggattattgg ggccagggaa ccctggttac agtctcctca   360

SEQ ID NO: 28            moltype = DNA   length = 360
FEATURE                  Location/Qualifiers
source                   1..360
                         mol_type = other DNA
                         organism = synthetic construct
SEQUENCE: 28
gaagtgcagc tggttgaatc tggcggagga ctggttcagc ctggcggatc tctgaagctg   60
tcttgtgccg cctctggctt caccttctcc acctttggca tccactgggt ccgacaggcc   120
cctggcaaag gattggagtg ggtcgcctat atctccggcg cctccaccac catctactac   180
gccgataccg tgaagggcag attcaccatc agccgggaca actccaagaa caccctgtac   240
ctgcagatga actccctgcg gagcgaggac accgccatgt actactgtgc cagatacggc   300
accagctttc cctacggcct ggattattgg ggccagggaa ccctggttac agtctcctca   360

SEQ ID NO: 29            moltype = DNA   length = 360
FEATURE                  Location/Qualifiers
source                   1..360
                         mol_type = other DNA
                         organism = synthetic construct
SEQUENCE: 29
gaagtgcagc tggttgaatc tggcggagga ctggttcagc ctggcggatc tctgaagctg   60
tcttgtgccg cctctggctt caccttctcc acctttggca tccactgggt ccgacaggcc   120
cctggcaaag gattggagtg ggtcgcctat atctccggcg cctccaccac catctactac   180
gccgataccg tgaagggcag attcaccatc agccgggaca actccaagaa caccctgtac   240
ctgcagatga actccctgag agccgaggac accgccgtgt actactgtgc cagatacggc   300
accagctttc cctacggcct ggattattgg ggccagggaa ccctggttac agtctcctca   360

SEQ ID NO: 30            moltype = DNA   length = 360
FEATURE                  Location/Qualifiers
source                   1..360
                         mol_type = other DNA
                         organism = synthetic construct
SEQUENCE: 30
gaagtgcagc tggttgaatc tggcggagga ctggttcagc ctggcggatc tctgaagctg   60
tcttgtgccg cctctggctt caccttctcc acctttggca tccactgggt ccgacaggcc   120
cctggcaaag gattggagtg ggtcgcctat atctccggcg cctccaccac catctactac   180
gccgattctg tgaagggcag attcaccatc agccgggaca actccaagaa caccctgtac   240
ctgcagatga actccctgag agccgaggac accgccgtgt actactgtgc cagatacggc   300
accagctttc cctacggcct ggattattgg ggccagggaa ccctggttac agtctcctca   360

SEQ ID NO: 31            moltype = DNA   length = 360
FEATURE                  Location/Qualifiers
source                   1..360
                         mol_type = other DNA
                         organism = synthetic construct
SEQUENCE: 31
gaagtgcagc tggttgaatc tggcggagga ctggttcagc ctggcggatc tctgaagctg   60
tcttgtgccg cctctggctt caccttctcc acctttggca tccactgggt ccgacaggcc   120
cctggcaaag gattggaatg ggtcgcctct atctccggcg cctccaccac catctactac   180
gccgattctg tgaagggcag attcaccatc agccgggaca actccaagaa caccctgtac   240
ctgcagatga actccctgag agccgaggac accgccgtgt actactgtgc cagatacggc   300
accagctttc cctacggcct ggattattgg ggccagggaa ccctggttac agtctcctca   360

SEQ ID NO: 32            moltype = DNA   length = 200
FEATURE                  Location/Qualifiers
source                   1..200
                         mol_type = other DNA
                         organism = synthetic construct
SEQUENCE: 32
gacatcgtga tgacacagtc tccaggcagc ctggctgtgt ccttgggaca gagagctacc   60
atctcctgca aggcctctca gtccgtggac tacgacggcg actcctacat gaactggtat   120
cagcagaagc ccgccagcc tcctaagctg ttgatctacg gcgcctccaa cctggaaagc   180
ggcatccctg ctagattctc                                               200

SEQ ID NO: 33            moltype = DNA   length = 333
```

-continued

```
FEATURE              Location/Qualifiers
source               1..333
                     mol_type = other DNA
                     organism = synthetic construct
SEQUENCE: 33
gacatcgtga tgacacagtc tccaggcagc ctggctgtgt ctctgggaga gagagccacc   60
atcaactgca aggcctctca gtccgtggac tacgacggcg actcctacat gaactggtat  120
cagcagaagc ccggcaaggc ccctaagctg ttgatctacg gcgcctccaa cctggaaagc  180
ggcatccctg atagattctc cggctctggc tctggcaccg acttcaccct gaccatctct  240
cggctggaag aggaagatgc cgcctcctac tactgccagc agtccaacga ggacccttc   300
acctttggcc agggcacaaa gttggagatc aaa                                333

SEQ ID NO: 34        moltype = DNA   length = 333
FEATURE              Location/Qualifiers
source               1..333
                     mol_type = other DNA
                     organism = synthetic construct
SEQUENCE: 34
gacatcgtga tgacccagtc tccagacagc ctggctgtgt ctctgggcga gagagccacc   60
atcaactgca aggcctctca gtccgtggac tacgacggcg actcctacat gaactggtat  120
cagcagaagc ccggcaaggc ccctaagctg ttgatctacg gcgcctccaa cctggaaagc  180
ggcatccctg atagattctc cggctctggc tctggcaccg acttcaccct gaccatcctt  240
agactggaac ctgaggacgc cgcctcctac tactgccagc agtctaacga ggacccttc   300
acctttggcc agggcacaaa gttggagatc aaa                                333

SEQ ID NO: 35        moltype = DNA   length = 333
FEATURE              Location/Qualifiers
source               1..333
                     mol_type = other DNA
                     organism = synthetic construct
SEQUENCE: 35
gacatcgtga tgacccagtc tccagacagc ctggctgtgt ctctgggcga gagagccacc   60
atcaactgca aggcctctca gtccgtggac tacgacggcg actcctacat gaactggtat  120
cagcagaagc ccggcaaggc ccctaagctg ttgatctacg gcgcctccaa cctggaaagc  180
ggcatccctg atagattctc cggctctggc tctggcaccg acttcaccct gaccatctct  240
agactggaac ctgaggatgc cgccgtgtac tactgccagc agtctaacga ggacccttc   300
acctttggcc agggcacaaa gttggagatc aaa                                333

SEQ ID NO: 36        moltype = DNA   length = 333
FEATURE              Location/Qualifiers
source               1..333
                     mol_type = other DNA
                     organism = synthetic construct
SEQUENCE: 36
gacatcgtga tgacccagtc tccagacagc ctggctgtgt ctctgggcga gagagccacc   60
atcaactgca agtcctctca gtccgtggac tacgacggcg actcctacat gaactggtat  120
cagcagaagc ccggcaaggc ccctaagctg ttgatctacg gcgcctccaa cctggaaagc  180
ggcatccctg atagattctc cggctctggc tctggcaccg acttcaccct gaccatctct  240
agactggaac ctgaggacgc cgcctcctac tactgccagc agtctaacga ggacccttc   300
acctttggcc agggcacaaa gttggagatc aaa                                333

SEQ ID NO: 37        moltype = DNA   length = 333
FEATURE              Location/Qualifiers
source               1..333
                     mol_type = other DNA
                     organism = synthetic construct
SEQUENCE: 37
gacatcgtga tgacccagtc tccagacagc ctggctgtgt ctctgggcga gagagccacc   60
atcaactgca agtcctctca gtccgtggac tacgacggcg actcctacat gaactggtat  120
cagcagaagc ccggcaaggc ccctaagctg ttgatctacg gcgcctccaa cctggaaagc  180
ggcatccctg atagattctc cggctctggc tctggcaccg acttcaccct gaccatctcc  240
agactggaac ctgaggatgc cgccgtgtac tactgccagc agtctaacga ggacccttc   300
acctttggcc agggcacaaa gttggagatc aaa                                333

SEQ ID NO: 38        moltype = AA   length = 450
FEATURE              Location/Qualifiers
source               1..450
                     mol_type = protein
                     organism = synthetic construct
SEQUENCE: 38
EVQLVESGGG LVQPGGSLKL SCAASGFTFS TFGIHWVRQA PGKGLEWVAY ISGASTTIYY   60
ADTVKGRFTI SRDNSKNTLY LQMNSLRAED TAVYYCARYG TSFPYGLDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                    450
```

-continued

```
SEQ ID NO: 39            moltype = AA  length = 450
FEATURE                  Location/Qualifiers
source                   1..450
                         mol_type = protein
                         organism = synthetic construct
SEQUENCE: 39
EVQLVESGGG LVQPGGSLKL SCAASGFTFS TFGIHWVRQA PGKGLEWVAY ISGASTTIYY   60
ADSVKGRFTI SRDNSKNTLY LQMNSLRAED TAVYYCARYG TSFPYGLDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 40            moltype = AA  length = 218
FEATURE                  Location/Qualifiers
source                   1..218
                         mol_type = protein
                         organism = synthetic construct
SEQUENCE: 40
DIVMTQSPDS LAVSLGERAT INCKASQSVD YDGDSYMNWY QQKPGKAPKL LIYGASNLES   60
GIPDRFSGSG SGTDFTLTIS RLEPEDAAVY YCQQSNEDPF TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 41            moltype = AA  length = 1037
FEATURE                  Location/Qualifiers
source                   1..1037
                         mol_type = protein
                         organism = synthetic construct
SEQUENCE: 41
MRGSGPRGAG RRRPPSGGGD TPITPASLAG CYSAPRRAPL WTCLLLCAAL RTLLASPSNE   60
VNLLDSRTVM GDLGWIAFPK NGWEEIGEVD ENYAPIHTYQ VCKVMEQNQN NWLLTSWISN  120
EGASRIFIEL KFTLRDCNSL PGGLGTCKET FNMYYFESDD QNGRNIKENQ YIKIDTIAAD  180
ESFTELDLGD RVMKLNTEVR DVGPLSKKGF YLAFQDVGAC IALVSVRVYY KKCPSVVRHL  240
AVFPDTITGA DSSQLLEVSG SCVNHSVTDE PPKMHCSAEG EWLVPIGKCM CKAGYEEKNG  300
TCQVCRPGFF KASPHIQSCG KCPPHSYTHE EASTSCVCEK DYFRRESDPP TMACTRPPSA  360
PRNAISNVNE TSVFLEWIPP ADTGGRKDVS YYIACKKCNS HAGVCEECGG HVRYLPRQSG  420
LKNTSVMMVD LLAHTNYTFE IEAVNGVSDL SPGARQYVSV NVTTNQAAPS PVTNVKKGKI  480
AKNSISLSWQ EPDRPNGIIL EYEIKYFEKD QETSYTIIKS KETTITAEGL KPASVYVFQI  540
RARTAAGYGV FSRRFEFETT PVFAASSDQS QIPVIAVSVT VGVILLAVVI GVLLSGSCCE  600
CGCGRASSLC AVAHPSLIWR CGYSKAKQDP EEEKMHFHNG HIKLPGVRTY IDPHTYEDPN  660
QAVHEFAKEI EASCITIERV IGAGEFGEVC SGRLKLPGKR ELPVAIKTLK VGYTEKQRRD  720
FLGEASIMGQ FDHPNIIHLE GVVTKSKPVM IVTEYMENGS LDTFLKKNDG QFTVIQLVGM  780
LRGISAGMKY LSDMGYVHRD LAARNILINS NLVCKVSDFG LSRVLEDDPE AAYTTRGGKI  840
PIRWTAPEAI AFRKFTSASD VWSYGIVMWE VVSYGERPYW EMTNQDVIKA VEEGYRLPSP  900
MDCPAALYQL MLDCWQKERN SRPKFDEIVN MLDKLIRNPS SLKTLVNASC RVSNLLAEHS  960
PLGSGAYRSV GEWLEAIKMG RYTEIFMENG YSSMDAVAQV TLEDLRRLGV TLVGHQKKIM 1020
NSLQEMKVQL VNGMVPL                                                1037

SEQ ID NO: 42            moltype = AA  length = 10
FEATURE                  Location/Qualifiers
source                   1..10
                         mol_type = protein
                         organism = synthetic construct
SEQUENCE: 42
GFTFSTFGIH                                                          10

SEQ ID NO: 43            moltype = AA  length = 25
FEATURE                  Location/Qualifiers
source                   1..25
                         mol_type = protein
                         organism = synthetic construct
```

```
SEQUENCE: 43
RPGFFKASPH IQSCGKCPPH SYTHE                                              25

SEQ ID NO: 44          moltype = DNA  length = 75
FEATURE                Location/Qualifiers
source                 1..75
                       mol_type = other DNA
                       organism = synthetic construct
SEQUENCE: 44
agacctgggt tcttcaaagc ctcacctcac atccagagct gcggcaaatg tccacctcac   60
agttataccc atgag                                                    75
```

ANTIBODY-DRUG CONJUGATES AGAINST THE RECEPTOR TYROSINE KINASE EphA5

CROSS-REFERENCE TO RELATED APPLICATION

The present application claims priority under 35 U.S.C. § 119(e) to U.S. Provisional Patent Application No. 63/275, 346, filed Nov. 3, 2021, which is hereby incorporated by reference in its entirety herein.

SEQUENCE LISTING

This disclosure contains one or more sequences in a computer readable format in an accompanying .xml file entitled "370602-7054US1_Sequence_Listing.XML", which is 47 KB in size and was created Nov. 3, 2022, the contents of which are incorporated herein by reference in their entirety.

STATEMENT REGARDING FEDERALLY SPONSORED RESEARCH OR DEVELOPMENT

This invention was developed with government support under grant number CA218853 awarded by the National Institutes of Health. The government has certain rights in the invention.

BACKGROUND OF THE INVENTION

Antibody-drug conjugates (ADC) has been proven to be a biologic that can deliver drug to targeted cells with high efficiency and minimized off-target effect. The receptor tyrosine kinase EphA5 is a surface molecule expressed in many types of human lung cancer cell lines and human lung cancer biopsies. As lung cancer becomes one of the most common and deadly human cancer types, effective therapies are urgently needed. As such, there is a need in the art for novel lung cancer therapies targeting tumor-specific targets like EphA5. The current invention addresses this need.

BRIEF SUMMARY OF THE INVENTION

The present invention relates in certain aspects to antibodies, binding polypeptides, and immunoconjugates specific for human EPH receptor A5 (EphA5).

In certain aspects, the invention provides an antibody or antigen-binding fragment thereof that specifically binds to an epitope of human EPH Receptor A5.

In certain embodiments of the above aspects or any other aspect or embodiment disclosed herein, the antibody or antigen-binding fragment comprises a heavy chain comprising a heavy chain variable region comprising an amino acid sequence having at least 85% sequence identity to SEQ ID NO:1.

In certain embodiments of the above aspects or any other aspect or embodiment disclosed herein, the antibody or antigen-binding fragment comprises a light chain comprising a light chain variable region comprising an amino acid sequence having at least 85% sequence identity to SEQ ID NO:8.

In certain embodiments of the above aspects or any other aspect or embodiment disclosed herein, the heavy chain variable region comprises three heavy chain complementarity-determining regions (HCDRs), wherein HCDR1 comprises the amino acid sequence set forth in SEQ ID NO:16, HCDR2 comprises the amino acid sequence selected from the group consisting of SEQ ID NOs:17-19, and HCDR3 comprises the amino acid sequence set forth in SEQ ID NO:20.

In certain embodiments of the above aspects or any other aspect or embodiment disclosed herein, the light chain variable region comprises three light chain complementarity-determining regions (LCDRs), wherein LCDR1 comprises the amino acid sequence selected from the group consisting of SEQ ID NOs:21 and 22, LCDR2 comprises the amino acid sequence set forth in SEQ ID NO:23, and LCDR3 comprises the amino acid sequence set forth in SEQ ID NO:24.

In certain aspects, the invention provides the antibody or antigen-binding fragment of the above aspect or any other aspect or embodiment disclosed herein.

In certain embodiments of the above aspects or any other aspect or embodiment disclosed herein, the heavy chain variable region comprises a HCDR1 comprising the amino acid sequence set forth in SEQ ID NO:16, a HCDR2 comprising the amino acid sequence set forth in SEQ ID NO:17, and a HCDR3 comprising the amino acid sequence set forth in SEQ ID NO:20; and the light chain variable region comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24.

In certain embodiments of the above aspects or any other aspect or embodiment disclosed herein, the heavy chain variable region comprises a HCDR1 comprising the amino acid sequence set forth in SEQ ID NO:16, a HCDR2 comprising the amino acid sequence set forth in SEQ ID NO:18, and a HCDR3 comprising the amino acid sequence set forth in SEQ ID NO:20; and the light chain variable region comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24.

In certain embodiments of the above aspects or any other aspect or embodiment disclosed herein, the heavy chain variable region comprises a HCDR1 comprising the amino acid sequence set forth in SEQ ID NO:16, a HCDR2 comprising the amino acid sequence set forth in SEQ ID NO:19, and a HCDR3 comprising the amino acid sequence set forth in SEQ ID NO:20; and the light chain variable region comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24.

In certain embodiments of the above aspects or any other aspect or embodiment disclosed herein, the heavy chain variable region comprises a HCDR1 comprising the amino acid sequence set forth in SEQ ID NO:16, a HCDR2 comprising the amino acid sequence set forth in SEQ ID NO:17, and a HCDR3 comprising the amino acid sequence set forth in SEQ ID NO:20; and the light chain variable region comprises a LCDR1 comprising the amino acid sequence set forth in SEQ ID NO:22, a LCDR2 comprising the amino acid sequence set forth in SEQ ID NO:23, and a LCDR3 comprising the amino acid sequence set forth in SEQ ID NO:24.

In certain embodiments of the above aspects or any other aspect or embodiment disclosed herein, the heavy chain variable region comprises a HCDR1 comprising the amino acid sequence set forth in SEQ ID NO:16, a HCDR2 comprising the amino acid sequence set forth in SEQ ID NO:18, and a HCDR3 comprising the amino acid sequence set forth in SEQ ID NO:20; and the light chain variable region comprises a LCDR1 comprising the amino acid sequence set forth in SEQ ID NO:22, a LCDR2 comprising the amino acid sequence set forth in SEQ ID NO:23, and a LCDR3 comprising the amino acid sequence set forth in SEQ ID NO:24.

In certain embodiments of the above aspects or any other aspect or embodiment disclosed herein, the heavy chain variable region comprises a HCDR1 comprising the amino acid sequence set forth in SEQ ID NO:16, a HCDR2 comprising the amino acid sequence set forth in SEQ ID NO:19, and a HCDR3 comprising the amino acid sequence set forth in SEQ ID NO:20; and the light chain variable region comprises a LCDR1 comprising the amino acid sequence set forth in SEQ ID NO:22, a LCDR2 comprising the amino acid sequence set forth in SEQ ID NO:23, and a LCDR3 comprising the amino acid sequence set forth in SEQ ID NO:24.

In certain embodiments of the above aspects or any other aspect or embodiment disclosed herein, the amino acid sequence of the heavy chain variable region has at least about 85%, 90%, 91%, 92%, 93%, 94%, 95%, 96%, 97%, 98%, or 99% sequence identity, and/or has 100% sequence identity, to the amino acid sequence selected from the group consisting of SEQ ID NOs:2-7.

In certain embodiments of the above aspects or any other aspect or embodiment disclosed herein, the heavy chain variable region comprises the amino acid sequence selected from the group consisting of SEQ ID NOs:2-7.

In certain embodiments of the above aspects or any other aspect or embodiment disclosed herein, the heavy chain variable region consists of the amino acid sequence selected from the group consisting of SEQ ID NOs:2-7.

In certain embodiments of the above aspects or any other aspect or embodiment disclosed herein, the heavy chain variable region is encoded by a nucleic acid sequence selected from the group consisting of SEQ ID NOs:26-31.

In certain embodiments of the above aspects or any other aspect or embodiment disclosed herein, the amino acid sequence of the light chain variable region has at least about 85%, 90%, 95%, 96%, 97%, 98%, or 99% sequence identity, and/or has 100% sequence identity, to the amino acid sequence selected from the group consisting of SEQ ID NOs:9-13.

In certain embodiments of the above aspects or any other aspect or embodiment disclosed herein, the light chain variable region comprises the amino acid sequence selected from the group consisting of SEQ ID NOs:9-13.

In certain embodiments of the above aspects or any other aspect or embodiment disclosed herein, the light chain variable region consists of the amino acid sequence selected from the group consisting of SEQ ID NOs:9-13.

In certain embodiments of the above aspects or any other aspect or embodiment disclosed herein, the light chain variable region is encoded by a nucleic acid sequence selected from the group consisting of SEQ ID NOs:33-37.

In certain embodiments of the above aspects or any other aspect or embodiment disclosed herein, the heavy chain variable region is set forth in SEQ ID NO:2 and the light chain variable region is set forth in SEQ ID NO:9.

In certain embodiments of the above aspects or any other aspect or embodiment disclosed herein, the heavy chain variable region is set forth in SEQ ID NO:2 and the light chain variable region is set forth in SEQ ID NO:10.

In certain embodiments of the above aspects or any other aspect or embodiment disclosed herein, the heavy chain variable region is set forth in SEQ ID NO:2 and the light chain variable region is set forth in SEQ ID NO:11.

In certain embodiments of the above aspects or any other aspect or embodiment disclosed herein, the heavy chain variable region is set forth in SEQ ID NO:2 and the light chain variable region is set forth in SEQ ID NO:12.

In certain embodiments of the above aspects or any other aspect or embodiment disclosed herein, the heavy chain variable region is set forth in SEQ ID NO:2 and the light chain variable region is set forth in SEQ ID NO:13.

In certain embodiments of the above aspects or any other aspect or embodiment disclosed herein, the heavy chain variable region is set forth in SEQ ID NO:3 and the light chain variable region is set forth in SEQ ID NO:9.

In certain embodiments of the above aspects or any other aspect or embodiment disclosed herein, the heavy chain variable region is set forth in SEQ ID NO:3 and the light chain variable region is set forth in SEQ ID NO:10.

In certain embodiments of the above aspects or any other aspect or embodiment disclosed herein, the heavy chain variable region is set forth in SEQ ID NO:3 and the light chain variable region is set forth in SEQ ID NO:11.

In certain embodiments of the above aspects or any other aspect or embodiment disclosed herein, the heavy chain variable region is set forth in SEQ ID NO:3 and the light chain variable region is set forth in SEQ ID NO:12.

In certain embodiments of the above aspects or any other aspect or embodiment disclosed herein, the heavy chain variable region is set forth in SEQ ID NO:3 and the light chain variable region is set forth in SEQ ID NO:13.

In certain embodiments of the above aspects or any other aspect or embodiment disclosed herein, the heavy chain variable region is set forth in SEQ ID NO:4 and the light chain variable region is set forth in SEQ ID NO:9.

In certain embodiments of the above aspects or any other aspect or embodiment disclosed herein, the heavy chain variable region is set forth in SEQ ID NO:4 and the light chain variable region is set forth in SEQ ID NO:10.

In certain embodiments of the above aspects or any other aspect or embodiment disclosed herein, the heavy chain variable region is set forth in SEQ ID NO:4 and the light chain variable region is set forth in SEQ ID NO:11.

In certain embodiments of the above aspects or any other aspect or embodiment disclosed herein, the heavy chain variable region is set forth in SEQ ID NO:4 and the light chain variable region is set forth in SEQ ID NO:12.

In certain embodiments of the above aspects or any other aspect or embodiment disclosed herein, the heavy chain variable region is set forth in SEQ ID NO:4 and the light chain variable region is set forth in SEQ ID NO:13.

In certain embodiments of the above aspects or any other aspect or embodiment disclosed herein, the heavy chain variable region is set forth in SEQ ID NO:5 and the light chain variable region is set forth in SEQ ID NO:9.

In certain embodiments of the above aspects or any other aspect or embodiment disclosed herein, the heavy chain variable region is set forth in SEQ ID NO:5 and the light chain variable region is set forth in SEQ ID NO:10.

In certain embodiments of the above aspects or any other aspect or embodiment disclosed herein, the heavy chain variable region is set forth in SEQ ID NO:5 and the light chain variable region is set forth in SEQ ID NO:11.

In certain embodiments of the above aspects or any other aspect or embodiment disclosed herein, the heavy chain variable region is set forth in SEQ ID NO:5 and the light chain variable region is set forth in SEQ ID NO:12.

In certain embodiments of the above aspects or any other aspect or embodiment disclosed herein, the heavy chain variable region is set forth in SEQ ID NO:5 and the light chain variable region is set forth in SEQ ID NO:13.

In certain embodiments of the above aspects or any other aspect or embodiment disclosed herein, the heavy chain variable region is set forth in SEQ ID NO:6 and the light chain variable region is set forth in SEQ ID NO:9.

In certain embodiments of the above aspects or any other aspect or embodiment disclosed herein, the heavy chain variable region is set forth in SEQ ID NO:6 and the light chain variable region is set forth in SEQ ID NO:10.

In certain embodiments of the above aspects or any other aspect or embodiment disclosed herein, the heavy chain variable region is set forth in SEQ ID NO:6 and the light chain variable region is set forth in SEQ ID NO:11.

In certain embodiments of the above aspects or any other aspect or embodiment disclosed herein, the heavy chain variable region is set forth in SEQ ID NO:6 and the light chain variable region is set forth in SEQ ID NO:12.

In certain embodiments of the above aspects or any other aspect or embodiment disclosed herein, the heavy chain variable region is set forth in SEQ ID NO:6 and the light chain variable region is set forth in SEQ ID NO:13.

In certain embodiments of the above aspects or any other aspect or embodiment disclosed herein, the heavy chain variable region is set forth in SEQ ID NO:7 and the light chain variable region is set forth in SEQ ID NO:9.

In certain embodiments of the above aspects or any other aspect or embodiment disclosed herein, the heavy chain variable region is set forth in SEQ ID NO:7 and the light chain variable region is set forth in SEQ ID NO:10.

In certain embodiments of the above aspects or any other aspect or embodiment disclosed herein, the heavy chain variable region is set forth in SEQ ID NO:7 and the light chain variable region is set forth in SEQ ID NO:11.

In certain embodiments of the above aspects or any other aspect or embodiment disclosed herein, the heavy chain variable region is set forth in SEQ ID NO:7 and the light chain variable region is set forth in SEQ ID NO:12.

In certain embodiments of the above aspects or any other aspect or embodiment disclosed herein, the heavy chain variable region is set forth in SEQ ID NO:7 and the light chain variable region is set forth in SEQ ID NO:13.

In certain embodiments of the above aspects or any other aspect or embodiment disclosed herein, the heavy chain variable region comprises a sequence that has at least 90% sequence identity to the sequence set forth in SEQ ID NO:2 and the light chain variable region comprises a sequence that has at least 90% sequence identity to the sequence set forth in SEQ ID NO:9.

In certain embodiments of the above aspects or any other aspect or embodiment disclosed herein, the heavy chain variable region comprises a sequence that has at least 90% sequence identity to the sequence set forth in SEQ ID NO:2 and the light chain variable region comprises a sequence that has at least 90% sequence identity to the sequence set forth in SEQ ID NO:10.

In certain embodiments of the above aspects or any other aspect or embodiment disclosed herein, the heavy chain variable region comprises a sequence that has at least 90% sequence identity to the sequence set forth in SEQ ID NO:2 and the light chain variable region comprises a sequence that has at least 90% sequence identity to the sequence set forth in SEQ ID NO:11.

In certain embodiments of the above aspects or any other aspect or embodiment disclosed herein, the heavy chain variable region comprises a sequence that has at least 90% sequence identity to the sequence set forth in SEQ ID NO:2 and the light chain variable region comprises a sequence that has at least 90% sequence identity to the sequence set forth in SEQ ID NO:12.

In certain embodiments of the above aspects or any other aspect or embodiment disclosed herein, the heavy chain variable region comprises a sequence that has at least 90% sequence identity to the sequence set forth in SEQ ID NO:2 and the light chain variable region comprises a sequence that has at least 90% sequence identity to the sequence set forth in SEQ ID NO:13.

In certain embodiments of the above aspects or any other aspect or embodiment disclosed herein, the heavy chain variable region comprises a sequence that has at least 90% sequence identity to the sequence set forth in SEQ ID NO:3 and the light chain variable region comprises a sequence that has at least 90% sequence identity to the sequence set forth in SEQ ID NO:9.

In certain embodiments of the above aspects or any other aspect or embodiment disclosed herein, the heavy chain variable region comprises a sequence that has at least 90% sequence identity to the sequence set forth in SEQ ID NO:3 and the light chain variable region comprises a sequence that has at least 90% sequence identity to the sequence set forth in SEQ ID NO:10.

In certain embodiments of the above aspects or any other aspect or embodiment disclosed herein, the heavy chain variable region comprises a sequence that has at least 90% sequence identity to the sequence set forth in SEQ ID NO:3 and the light chain variable region comprises a sequence that has at least 90% sequence identity to the sequence set forth in SEQ ID NO:11.

In certain embodiments of the above aspects or any other aspect or embodiment disclosed herein, the heavy chain variable region comprises a sequence that has at least 90% sequence identity to the sequence set forth in SEQ ID NO:3 and the light chain variable region comprises a sequence that has at least 90% sequence identity to the sequence set forth in SEQ ID NO:12.

In certain embodiments of the above aspects or any other aspect or embodiment disclosed herein, the heavy chain variable region comprises a sequence that has at least 90% sequence identity to the sequence set forth in SEQ ID NO:3 and the light chain variable region comprises a sequence that has at least 90% sequence identity to the sequence forth in SEQ ID NO:13.

In certain embodiments of the above aspects or any other aspect or embodiment disclosed herein, the heavy chain variable region comprises a sequence that has at least 90% sequence identity to the sequence set forth in SEQ ID NO:4 and the light chain variable region comprises a sequence that has at least 90% sequence identity to the sequence set forth in SEQ ID NO:9.

In certain embodiments of the above aspects or any other aspect or embodiment disclosed herein, the heavy chain variable region comprises a sequence that has at least 90% sequence identity to the sequence set forth in SEQ ID NO:4 and the light chain variable region comprises a sequence that has at least 90% sequence identity to the sequence set forth in SEQ ID NO:10.

In certain embodiments of the above aspects or any other aspect or embodiment disclosed herein, the heavy chain variable region comprises a sequence that has at least 90% sequence identity to the sequence set forth in SEQ ID NO:4 and the light chain variable region comprises a sequence that has at least 90% sequence identity to the sequence set forth in SEQ ID NO:11.

In certain embodiments of the above aspects or any other aspect or embodiment disclosed herein, the heavy chain variable region comprises a sequence that has at least 90% sequence identity to the sequence set forth in SEQ ID NO:4 and the light chain variable region comprises a sequence that has at least 90% sequence identity to the sequence set forth in SEQ ID NO:12.

In certain embodiments of the above aspects or any other aspect or embodiment disclosed herein, the heavy chain variable region comprises a sequence that has at least 90% sequence identity to the sequence set forth in SEQ ID NO:4 and the light chain variable region comprises a sequence that has at least 90% sequence identity to the sequence set forth in SEQ ID NO:13.

In certain embodiments of the above aspects or any other aspect or embodiment disclosed herein, the heavy chain variable region comprises a sequence that has at least 90% sequence identity to the sequence set forth in SEQ ID NO:5 and the light chain variable region comprises a sequence that has at least 90% sequence identity to the sequence set forth in SEQ ID NO:9.

In certain embodiments of the above aspects or any other aspect or embodiment disclosed herein, the heavy chain variable region comprises a sequence that has at least 90% sequence identity to the sequence set forth in SEQ ID NO:5 and the light chain variable region comprises a sequence that has at least 90% sequence identity to the sequence set forth in SEQ ID NO:10.

In certain embodiments of the above aspects or any other aspect or embodiment disclosed herein, the heavy chain variable region comprises a sequence that has at least 90% sequence identity to the sequence set forth in SEQ ID NO:5 and the light chain variable region comprises a sequence that has at least 90% sequence identity to the sequence set forth in SEQ ID NO:11.

In certain embodiments of the above aspects or any other aspect or embodiment disclosed herein, the heavy chain variable region comprises a sequence that has at least 90% sequence identity to the sequence set forth in SEQ ID NO:5 and the light chain variable region comprises a sequence that has at least 90% sequence identity to the sequence set forth in SEQ ID NO:12.

In certain embodiments of the above aspects or any other aspect or embodiment disclosed herein, the heavy chain variable region comprises a sequence that has at least 90% sequence identity to the sequence set forth in SEQ ID NO:5 and the light chain variable region comprises a sequence that has at least 90% sequence identity to the sequence set forth in SEQ ID NO:13.

In certain embodiments of the above aspects or any other aspect or embodiment disclosed herein, the heavy chain variable region comprises a sequence that has at least 90% sequence identity to the sequence set forth in SEQ ID NO:6 and the light chain variable region comprises a sequence that has at least 90% sequence identity to the sequence set forth in SEQ ID NO:9.

In certain embodiments of the above aspects or any other aspect or embodiment disclosed herein, the heavy chain variable region comprises a sequence that has at least 90% sequence identity to the sequence set forth in SEQ ID NO:6 and the light chain variable region comprises a sequence that has at least 90% sequence identity to the sequence set forth in SEQ ID NO:10.

In certain embodiments of the above aspects or any other aspect or embodiment disclosed herein, the heavy chain variable region comprises a sequence that has at least 90% sequence identity to the sequence set forth in SEQ ID NO:6 and the light chain variable region comprises a sequence that has at least 90% sequence identity to the sequence set forth in SEQ ID NO:11.

In certain embodiments of the above aspects or any other aspect or embodiment disclosed herein, the heavy chain variable region comprises a sequence that has at least 90% sequence identity to the sequence set forth in SEQ ID NO:6 and the light chain variable region comprises a sequence that has at least 90% sequence identity to the sequence set forth in SEQ ID NO:12.

In certain embodiments of the above aspects or any other aspect or embodiment disclosed herein, the heavy chain variable region comprises a sequence that has at least 90% sequence identity to the sequence set forth in SEQ ID NO:6 and the light chain variable region comprises a sequence that has at least 90% sequence identity to the sequence set forth in SEQ ID NO:13.

In certain embodiments of the above aspects or any other aspect or embodiment disclosed herein, the heavy chain variable region comprises a sequence that has at least 90% sequence identity to the sequence set forth in SEQ ID NO:7 and the light chain variable region comprises a sequence that has at least 90% sequence identity to the sequence set forth in SEQ ID NO:9.

In certain embodiments of the above aspects or any other aspect or embodiment disclosed herein, the heavy chain variable region comprises a sequence that has at least 90% sequence identity to the sequence set forth in SEQ ID NO:7 and the light chain variable region comprises a sequence that has at least 90% sequence identity to the sequence set forth in SEQ ID NO:10.

In certain embodiments of the above aspects or any other aspect or embodiment disclosed herein, the heavy chain variable region comprises a sequence that has at least 90% sequence identity to the sequence set forth in SEQ ID NO:7 and the light chain variable region comprises a sequence that has at least 90% sequence identity to the sequence set forth in SEQ ID NO:11.

In certain embodiments of the above aspects or any other aspect or embodiment disclosed herein, the heavy chain variable region comprises a sequence that has at least 90% sequence identity to the sequence set forth in SEQ ID NO:7 and the light chain variable region comprises a sequence that has at least 90% sequence identity to the sequence set forth in SEQ ID NO:12.

In certain embodiments of the above aspects or any other aspect or embodiment disclosed herein, the heavy chain variable region comprises a sequence that has at least 90% sequence identity to the sequence set forth in SEQ ID NO:7 and the light chain variable region comprises a sequence that has at least 90% sequence identity to the sequence set forth in SEQ ID NO:13.

In certain aspects, the invention provides an antibody or antigen-binding fragment thereof that specifically binds to an epitope of human EPH Receptor A5.

In certain embodiments of the above aspects or any other aspect or embodiment disclosed herein, the antibody or antigen-binding fragment comprises a heavy chain comprising a heavy chain variable region comprising a heavy chain complementarity-determining region 1 (HCDR1) comprising the sequence set forth in SEQ ID NO:16, a HCDR2 comprising the sequence set forth in SEQ ID NO:18, a HCDR3 set forth in SEQ ID NO:20.

In certain embodiments of the above aspects or any other aspect or embodiment disclosed herein, the antibody or antigen-binding fragment comprises a light chain comprising a light chain variable region comprising a light chain complementarity determining region 1 (LCDR1) comprising the sequence set forth in SEQ ID NO:21, a LCDR2 comprising the sequence set forth in SEQ ID NO:23, and an LCDR3 comprising the sequence set forth in SEQ ID NO:24.

In certain aspects, the invention provides an antibody or antigen-binding fragment thereof that specifically binds to an epitope of human EPH Receptor A5.

In certain embodiments of the above aspects or any other aspect or embodiment disclosed herein, the antibody or antigen-binding fragment comprises a heavy chain comprising a heavy chain variable region comprising a heavy chain complementarity-determining region 1 (HCDR1) comprising the sequence set forth in SEQ ID NO:16, a HCDR2 comprising the sequence set forth in SEQ ID NO:19, a HCDR3 set forth in SEQ ID NO:20.

In certain embodiments of the above aspects or any other aspect or embodiment disclosed herein, the antibody or antigen-binding fragment comprises a light chain comprising a light chain variable region comprising a light chain complementarity determining region 1 (LCDR1) comprising the sequence set forth in SEQ ID NO:21, an LCDR2 comprising the sequence set forth in SEQ ID NO:23, and an LCDR3 comprising the sequence set forth in SEQ ID NO:24.

In certain aspects, the invention provides an antibody or antigen-binding fragment thereof that specifically binds to an epitope of human EPH Receptor A5.

In certain embodiments of the above aspects or any other aspect or embodiment disclosed herein, the antibody or antigen-binding fragment comprises a heavy chain comprising a heavy chain variable region comprising a heavy chain complementarity-determining region 1 (HCDR1) comprising the sequence set forth in SEQ ID NO:16, a HCDR2 comprising the sequence set forth in SEQ ID NO:17, a HCDR3 set forth in SEQ ID NO:20.

In certain embodiments of the above aspects or any other aspect or embodiment disclosed herein, the antibody or antigen-binding fragment comprises a light chain comprising a light chain variable region comprising a complementarity determining region 1 (LCDR1) comprising the sequence set forth in SEQ ID NO:22, an LCDR2 comprising the sequence set forth in SEQ ID NO:23, and an LCDR3 comprising the sequence set forth in SEQ ID NO:24.

In certain aspects, the invention provides an antibody or antigen-binding fragment thereof that specifically binds to an epitope of human EPH Receptor A5.

In certain embodiments of the above aspects or any other aspect or embodiment disclosed herein, the antibody or antigen-binding fragment comprises a heavy chain comprising a heavy chain variable region comprising a heavy chain complementarity-determining region 1 (HCDR1) comprising the sequence set forth in SEQ ID NO:16, a HCDR2 comprising the sequence set forth in SEQ ID NO:18, a HCDR3 set forth in SEQ ID NO:20.

In certain embodiments of the above aspects or any other aspect or embodiment disclosed herein, the antibody or antigen-binding fragment comprises a light chain comprising a light chain variable region comprising a light chain complementarity determining region 1 (LCDR1) comprising the sequence set forth in SEQ ID NO:22, LCDR2 comprising the sequence set forth in SEQ ID NO:23, and an LCDR3 comprising the sequence set forth in SEQ ID NO:24.

In certain aspects, the invention provides an antibody or antigen-binding fragment thereof.

In certain embodiments of the above aspects or any other aspect or embodiment disclosed herein, the antibody or antigen-binding fragment comprises a heavy chain comprising a heavy chain variable region comprising the amino acid sequence set forth in SEQ ID NO:5.

In certain embodiments of the above aspects or any other aspect or embodiment disclosed herein, the antibody or antigen-binding fragment comprises a light chain comprising a light chain variable region comprising the amino acid sequence set forth in SEQ ID NO:11.

In certain aspects, the invention provides an antibody or antigen-binding fragment thereof.

In certain embodiments of the above aspects or any other aspect or embodiment disclosed herein, the antibody or antigen-binding fragment comprises a heavy chain comprising a heavy chain variable region comprising the amino acid sequence set forth in SEQ ID NO:6.

In certain embodiments of the above aspects or any other aspect or embodiment disclosed herein, the antibody or antigen-binding fragment comprises a light chain comprising a light chain variable region comprising the amino acid sequence set forth in SEQ ID NO:11.

In certain embodiments of the above aspects or any other aspect or embodiment disclosed herein, the antibody or antigen-binding fragment thereof is selected from the group consisting of a full-length antibody, a Fab, and a single-chain variable fragment (scFv).

In certain embodiments of the above aspects or any other aspect or embodiment disclosed herein, the antibody or antigen-binding fragment thereof is a full-length antibody.

In certain embodiments of the above aspects or any other aspect or embodiment disclosed herein, the antibody is humanized.

In certain embodiments of the above aspects or any other aspect or embodiment disclosed herein, the heavy chain further comprises a constant domain of a human immunoglobulin heavy chain and the light chain further comprises a constant domain of a human light chain.

In certain embodiments of the above aspects or any other aspect or embodiment disclosed herein, the constant domain of a human immunoglobulin heavy chain is from a IgG1 heavy chain.

In certain embodiments of the above aspects or any other aspect or embodiment disclosed herein, the constant domain of a human immunoglobulin heavy chain comprises the amino acid sequence set forth in SEQ ID NO:14.

In certain embodiments of the above aspects or any other aspect or embodiment disclosed herein, the constant domain of a human light chain is a from a human kappa light chain.

In certain embodiments of the above aspects or any other aspect or embodiment disclosed herein, the constant domain of a human light chain comprises the amino acid sequence set forth in SEQ ID NO:15.

In certain aspects, the invention provides an antibody or antigen-binding fragment thereof that specifically binds to an epitope of human EPH Receptor A5.

In certain embodiments of the above aspects or any other aspect or embodiment disclosed herein, the antibody or antigen-binding fragment comprises a heavy chain comprising at least about 85%, 90%, 91%, 92%, 93%, 94%, 95%, 96%, 97%, 98%, or 99% sequence identity, and/or with 100% sequence identity, to the amino acid sequence set forth in SEQ ID NO:38.

In certain embodiments of the above aspects or any other aspect or embodiment disclosed herein, the antibody or antigen-binding fragment comprises a light chain comprising at least about 85%, 90%, 91%, 92%, 93%, 94%, 95%, 96%, 97%, 98%, or 99% sequence identity, and/or with 100% sequence identity, to the amino acid sequence set forth in SEQ ID NO:40.

In certain embodiments of the antibody or antigen-binding fragment of the above aspect or any other aspect or embodiment disclosed herein, the variable region of the heavy chain comprises a HCDR1 comprising the amino acid sequence set forth in SEQ ID NO:16, a HCDR2 comprising the amino acid sequence set forth in SEQ ID NO:17, and a HCDR3 comprising the amino acid sequence set forth in SEQ ID NO:20.

In certain embodiments of the above aspects or any other aspect or embodiment disclosed herein, the variable region of the light chain comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24.

In certain embodiments of the above aspects or any other aspect or embodiment disclosed herein, the heavy chain is set forth in SEQ ID NO:38 and the light chain is set forth in SEQ ID NO:40.

In certain aspects, the invention includes an antibody or antigen-binding fragment thereof that specifically binds to an epitope of human EPH Receptor A5.

In certain embodiments of the above aspects or any other aspect or embodiment disclosed herein, the antibody or antigen-binding fragment comprises a heavy chain comprising at least 85%, 90%, 91%, 92%, 93%, 94%, 95%, 96%, 97%, 98%, or 99% sequence identity, and/or with 100% sequence identity, to the amino acid sequence set forth in SEQ ID NO:39.

In certain embodiments of the above aspects or any other aspect or embodiment disclosed herein, the antibody or antigen-binding fragment comprises a light chain comprising at least about 85%, 90%, 91%, 92%, 93%, 94%, 95%, 96%, 97%, 98%, or 99% sequence identity, and/or with 100% sequence identity, to the amino acid sequence set forth in SEQ ID NO:40.

In certain embodiments of the antibody or antigen-binding fragment of the above aspects or any other aspect or embodiment disclosed herein, the variable region of the heavy chain comprises a HCDR1 comprising the amino acid sequence set forth in SEQ ID NO:16, a HCDR2 comprising the amino acid sequence set forth in SEQ ID NO:18, and a HCDR3 comprising the amino acid sequence set forth in SEQ ID NO:20.

In certain embodiments of the above aspects or any other aspect or embodiment disclosed herein, the variable region of the light chain comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24.

In certain embodiments of the above aspects or any other aspect or embodiment disclosed herein, the heavy chain is set forth in SEQ ID NO:39 and the light chain is set forth in SEQ ID NO:40.

In certain embodiments of the above aspects or any other aspect or embodiment disclosed herein, the dissociation constant $(K_D)$ for binding to human EpHA5 is less than $1.25 \times 10^{-9}$ M.

In certain embodiments of the above aspects or any other aspect or embodiment disclosed herein, the dissociation constant $(K_D)$ for binding to human EpHA5 is between $8 \times 10^{-10}$ M and $1.1 \times 10^{-9}$ M.

In certain embodiments of the above aspects or any other aspect or embodiment disclosed herein, the antibody or antigen-binding fragment has a dissociation constant $(K_D)$ for binding to human EpHA5 that is within 2-fold better than a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

In certain embodiments of the above aspects or any other aspect or embodiment disclosed herein, the dissociation constant $(K_D)$ for binding to human EpHA5 is more than 1.2 fold better than a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

In certain embodiments of the above aspects or any other aspect or embodiment disclosed herein, the dissociation constant $(K_D)$ is determined by Biacore.

In certain embodiments of the above aspects or any other aspect or embodiment disclosed herein, the antibody or antigen-binding fragment thereof of any of the above aspects or any other aspect or embodiment disclosed herein exhibits increased thermal stability compared to a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

In certain embodiments of the above aspects or any other aspect or embodiment disclosed herein, the antibody or antigen-binding fragment thereof of any of the above aspects or any other aspect or embodiment disclosed herein has a melting temperature profile with a Tm1 that is increased greater than at or about 5° C. compared to a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

In certain embodiments of the above aspects or any other aspect or embodiment disclosed herein, the antibody or antigen-binding fragment thereof of any of the above aspects or any other aspect or embodiment disclosed herein has a melting temperature profile with a Tm1 that is increased greater than about 10° C. compared to a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

In certain embodiments of the above aspects or any other aspect or embodiment disclosed herein, the Tm1 of the thermal unfolding curve of the antibody or antigen-binding fragment is greater than 60° C.

In certain embodiments of the above aspects or any other aspect or embodiment disclosed herein, the Tm1 of the antibody or antigen-binding fragment is between about 60° C. and about 70° C.

In certain embodiments of the above aspects or any other aspect or embodiment disclosed herein, the Tm1 of the antibody or antigen-binding fragment is about 64° C., about 65° C., about 66° C., about 67° C., about 68° C., or about 69° C.

In certain embodiments of the above aspects or any other aspect or embodiment disclosed herein, the melting temperature profile is monophasic.

In certain embodiments of the above aspects or any other aspect or embodiment disclosed herein, the onset temperature of aggregation (Tagg) is increased greater than about 1° C., greater than about 2° C., greater than about 3° C., greater than about 4° C. or greater than about 5° C. compared to a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

In certain embodiments of the above aspects or any other aspect or embodiment disclosed herein, the onset temperature of aggregation (Tagg) is greater than about 67° C.

In certain embodiments of the above aspects or any other aspect or embodiment disclosed herein, the onset temperature of aggregation (Tagg) is between about 67° C. and about 71° C.

In certain embodiments the Tagg of the antibody or antigen-binding fragment is about 67° C., about 68° C., about 69° C., about 70° C., or about 71° C.

In certain embodiments of the above aspects or any other aspect or embodiment disclosed herein, the antibody or antigen-binding fragment binds to cell surface human EphA5.

In certain embodiments of the above aspects or any other aspect or embodiment disclosed herein, the antibody or fragment binds human EphA5 expressed on the surface of cells, optionally an H460 cell line, with an EC50 that is increased compared to a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

In certain embodiments of the above aspects or any other aspect or embodiment disclosed herein, the antibody or fragment binds human EphA5 expressed on the surface of cells, optionally an H460 cell line, with an EC50 of less than or equal to 0.020 μg/mL optionally wherein the EC50 is determined by flow cytometry.

In certain embodiments of the above aspects or any other aspect or embodiment disclosed herein, the antibody or fragment binds human EphA5 expressed on the surface of cells, optionally an H460 cell line, with an EC50 of between about 0.010 μg/mL and 0.020 μg/mL, optionally wherein the EC50 is determined by flow cytometry.

In certain embodiments of the above aspects or any other aspect or embodiment disclosed herein, the antibody or fragment binds human EphA5 expressed on the surface of cells, optionally an H460 cell line, with an EC50 of about 0.015 μg/mL, about 0.016 μg/mL, about 0.017 μg/mL, about 0.018 μg/mL, about 0.019 μg/mL, or about 0.020 μg/mL, optionally wherein the EC50 is determined by flow cytometry.

In certain embodiments of the above aspects or any other aspect or embodiment disclosed herein, the antibody or antigen-binding fragment is internalized by human EphA5-expressing cells.

In certain aspects, the invention includes a nucleic acid encoding the heavy chain of the antibody or antigen-binding fragment thereof of any one of the above aspects or any other aspect or embodiment disclosed herein.

In certain aspects, the invention includes a nucleic acid encoding the light chain of the antibody or antigen-binding fragment thereof of any one of the above aspects or any other aspect or embodiments disclosed herein.

In certain aspects, the invention includes a nucleic acid encoding the heavy chain and the light chain of the antibody or antigen-binding fragment thereof of any one of the above aspects or any other aspect or embodiments disclosed herein.

In certain aspects, the invention includes a vector comprising the nucleic acid of any one of the above aspects or any other aspect or embodiments disclosed herein.

In certain embodiments of the above aspects or any other aspect or embodiment disclosed herein, the vector is an expression vector.

In certain aspects, the invention includes a vector comprising a nucleic acid encoding the heavy chain and a nucleic acid encoding the light chain, wherein the heavy chain and light chain is of the antibody or antigen-binding fragment thereof of any one of the above aspects or any other aspect or embodiments disclosed herein.

In certain embodiments of the above aspects or any other aspect or embodiment disclosed herein, the vector is a bicistronic vector.

In certain aspects, the invention includes a vector system, comprising a first vector comprising a first nucleic acid encoding a heavy chain and a second vector comprising a second nucleic acid encoding a light chain, wherein the heavy chain and the light chain is of the antibody or antigen-binding fragment thereof of any one of the above aspects or any other aspect or embodiments disclosed herein.

In certain embodiments of the above aspects or any other aspect or embodiment disclosed herein, the first vector and the second vector are each an expression vector.

In certain aspects, the invention includes a host cell comprising the vector of any one of the above aspects or any other aspect or embodiments disclosed herein.

In certain embodiments of the above aspects or any other aspect or embodiment disclosed herein, the host cell is a mammalian cell.

In certain aspects, the invention includes a method of producing an antibody, comprising introducing a vector of any one of the above aspects or any other aspect or embodiments disclosed herein into a host cell, culturing the host cell under conditions for expression of an antibody or antigen binding fragment from the host cell, and isolating or purifying the antibody or antigen-binding fragment.

In certain embodiments of the above aspects or any other aspect or embodiment disclosed herein, the host cell is a mammalian cell.

In certain aspects, the invention includes an immunoconjugate having the formula Ab-(L-D).

In certain embodiments of the above aspects or any other aspect or embodiment disclosed herein, Ab is the antibody or antigen-binding fragment thereof of any one of Embodiments 1-53.

In certain embodiments of the above aspects or any other aspect or embodiment disclosed herein, L is a linker.

In certain embodiments of the above aspects or any other aspect or embodiment disclosed herein, D is a cytotoxic drug.

In certain embodiments of the above aspects or any other aspect or embodiment disclosed herein, the linker is a cleavable linker.

In certain embodiments of the above aspects or any other aspect or embodiment disclosed herein, the linker is a cathepsin-cleavable linker.

In certain embodiments of the above aspects or any other aspect or embodiment disclosed herein, the cathepsin-cleavable linker comprises a valine-citruline (Val-Cit).

In certain embodiments of the above aspects or any other aspect or embodiment disclosed herein, the linker is MC-VCP, having the structure:

In certain embodiments of the above aspects or any other aspect or embodiment disclosed herein, the linker comprises the structure:

-continued

In certain embodiments of the above aspects or any other aspect or embodiment disclosed herein, the linker is a pH cleavable linker.

In certain embodiments of the above aspects or any other aspect or embodiment disclosed herein, the linker is CL2A, having the structure:

In certain embodiments of the above aspects or any other aspect or embodiment disclosed herein, the cytotoxic drug is an auristatin.

In certain embodiments of the above aspects or any other aspect or embodiment disclosed herein, the auristatin is monomethyl auristatin E (MMAE) having the structure:

In certain embodiments of the above aspects or any other aspect or embodiment disclosed herein, the L-D comprises the structure:

In certain embodiments of the above aspects or any other aspect or embodiment disclosed herein, the L-D comprises the structure:

In certain aspects, the invention includes an immunoconjugate having the formula Ab-(L-D).

In certain embodiments of the above aspects or any other aspect or embodiment disclosed herein, Ab is an antibody that specifically binds to an epitope of human EPH Receptor A5 (EphA5) comprising the heavy chain set forth in SEQ ID NO:38 and the light chain set forth in SEQ ID NO:40.

In certain embodiments of the above aspects or any other aspect or embodiment disclosed herein, the L-D comprises the structure:

In certain aspects, the invention includes an immunoconjugate having the formula Ab-(L-D).

In certain embodiments of the above aspects or any other aspect or embodiment disclosed herein, Ab is an antibody that specifically binds to an epitope of human EPH Receptor A5 (EphA5) comprising the heavy chain set forth in SEQ ID NO:39 and the light chain set forth in SEQ ID NO:40.

In certain embodiments of the above aspects or any other aspect or embodiment disclosed herein, the L-D comprises the structure:

-continued

In certain embodiments of the above aspects or any other aspect or embodiment disclosed herein, the cytotoxic drug is SN38, having the structure:

In certain embodiments of the above aspects or any other aspect or embodiment disclosed herein, the L-D comprises the structure:

In certain embodiments of the above aspects or any other aspect or embodiment disclosed herein, the L-D comprises the structure:

In certain embodiments of the above aspects or any other aspect or embodiment disclosed herein, the drug to antibody ratio is or is about 4.

In certain embodiments of the above aspects or any other aspect or embodiment disclosed herein, the drug to antibody ratio is or is about 8.

In certain aspects, the invention includes a pharmaceutical composition comprising the antibody or antigen-binding fragment thereof of any one of the above aspects or any aspect or embodiment disclosed herein and a pharmaceutically acceptable carrier.

In certain aspects, the invention includes a pharmaceutical composition comprising the immunoconjugate of any one of the above aspects or any aspect or embodiment disclosed herein and a pharmaceutically acceptable carrier.

In certain aspects, the invention includes a method for treating, ameliorating, and/or preventing cancer in a subject in need thereof, the method comprising administering to the subject an effective amount of the antibody or antigen-binding fragment thereof of the above aspects or any aspect or embodiment disclosed herein.

In certain aspects, the invention includes a method for treating, ameliorating, and/or preventing cancer in a subject in need thereof, the method comprising administering to the subject an effective amount of the immunoconjugate of any one of the above aspects or any aspect or embodiment disclosed herein.

In certain aspects, the invention includes a method for treating, ameliorating, and/or preventing cancer in a subject in need thereof, the method comprising administering to the subject an effect amount of the pharmaceutical composition of the above aspects or any aspect or embodiment disclosed herein.

In certain aspects, the invention includes a method for inducing tumor regression in a subject, the method comprising administering to the subject an effective amount of the antibody or antigen-binding fragment thereof of any one of the above aspects or any aspect or embodiment disclosed herein.

In certain aspects, the invention includes a method for inducing tumor regression in a subject in need thereof, the method comprising administering to the subject an effective amount of the immunoconjugate of any one of the above aspects or any aspect or embodiment disclosed herein.

In certain aspects, the invention includes a method for inducing tumor regression in a subject in need thereof, the method comprising administering to the subject an effective amount of the pharmaceutical composition of the above aspects or any aspect or embodiment disclosed herein.

In certain embodiments of the above aspects or any other aspect or embodiment disclosed herein, the cancer is associated with expression of EPH Receptor A5.

In certain embodiments of the above aspects or any other aspect or embodiment disclosed herein, the tumor is associated with expression of EPH Receptor A5.

In certain embodiments of the above aspects or any other aspect or embodiment disclosed herein, the tumor is a cancer.

In certain embodiments of the above aspects or any other aspect or embodiment disclosed herein, the EPH Receptor A5 is expressed on the cancer cells.

In certain embodiments of the above aspects or any other aspect or embodiment disclosed herein, the cancer is selected from the group consisting of lung cancer, breast cancer, esophageal cancer, gastric cancer, and ovarian cancer.

In certain embodiments of the above aspects or any other aspect or embodiment disclosed herein, the cancer is lung cancer.

In certain embodiments of the above aspects or any other aspect or embodiment disclosed herein, the cancer is breast cancer.

In certain embodiments, the invention includes the antibody or antigen-binding fragment thereof of any one of the above aspects or any aspect or embodiment disclosed herein for use in the treatment, amelioration, and/or prevention of cancer in a subject in need thereof, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

In certain embodiments, the invention includes the immunoconjugate of any one of the above aspects or any aspect or embodiment disclosed herein for use in the treatment, amelioration, and/or prevention of cancer in a subject in need thereof, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

In certain embodiments, the invention includes the pharmaceutical composition of any one of the above aspects or any aspect or embodiment disclosed herein for the use in treating, ameliorating, and/or preventing cancer in a subject in need thereof, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

In certain embodiments, the invention includes the pharmaceutical composition of any one of the above aspects or any aspect or embodiment disclosed herein for use in treating, ameliorating, and/or preventing cancer in a subject in need thereof, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

In certain embodiments, the invention includes the antibody or antigen-binding fragment thereof of any one of the above aspects or any aspect or embodiment disclosed herein for use in inducing tumor regression in a subject, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

In certain embodiments, the invention includes the immunoconjugate of any one of the above aspects or any aspect or embodiment disclosed herein for use in inducing tumor regression in a subject in need thereof, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

In certain embodiments, the invention includes the pharmaceutical composition of any one of the above aspects or any aspect or embodiment disclosed herein for use in inducing tumor regression in a subject in need thereof, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

In certain embodiments, the invention includes the pharmaceutical composition of any one of the above aspects or any aspect or embodiment disclosed herein for use in inducing tumor regression in a subject in need thereof, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A, internalization of VH5/VK3 antibody in H460 cells is dose dependent. FIG. 2B, dose response curve of VH5/VK3 and VH0/VK0 antibodies in H460 human lung cancer cells.

FIG. 4A, H460 cells (EphA5-positive); FIG. 4B, H226 (EphA5-negative).

FIG. 8 illustrates summary iTope™ scores for humanized heavy chain and light chain variable region sequences: chimeric (VH0 and VK0) and humanized variants (VH1-VH6 and VK1-VK5).

FIG. 10 is a table illustrating supernatant IgG expression levels (m/mL) of the chimeric (VH0/VK0), two controls (VH1/VK0 and VH0/VK1) and thirty Composite Human™ Ab variants.

FIG. 12 illustrates equations describing (upper) the 1:1 Interaction binding kinetics, and; (lower) closeness of fit assessment.

FIG. 13 is a table illustrating the single cycle kinetic parameters of chimeric (VH0/VK0) and humanized 11C12 variants (tested as cell culture supernatants) binding to rhEphA5 antigen as determined using the Biacore T200. The relative KD was calculated by dividing the KD of the humanized variant by that of the VH0/VK0 (top row) assayed in the same experiment. The variants marked with '*' have KD values that are within two-fold of, or are better than, the chimeric antibody. The chimeric and selected variants marked in '#' were identified as the main leads for purification.

FIG. 15 is a table illustrating supernatant IgG expression levels (µg/mL) of the chimeric (VH0/VK0) and six lead Composite Human™ Ab variants following expression in CHO cells.

(FIG. 16A) reduced, and; (FIG. 16B) non-reduced conditions on a NuPage 4-12% Bis-Tris gel (ThermoFisher, Loughborough, UK). All samples were heated at 95° C. for 5 min and reduction was performed with addition of NuPAGE Sample Reducing Agent (ThermoFisher, Loughborough, UK). Gels were stained with InstantBlue (Expedeon, Swavesey, UK). Mk: PAGERuler™ Plus pre-stained protein ladder (ThermoFisher, Loughborough, UK). For reduced samples two bands were present corresponding to heavy and light chain at 50 and 25 kDa, respectively.

FIG. 18 is a table illustrating the percentage of monomeric antibody observed within the chimeric (VH0/VK0) and humanized variants as determined by SE-HPLC following Hitrap Mab Select PrismA purification.

FIG. 19 is a table illustrating the Multi-cycle kinetic parameters of chimeric (VH0/VK0) and humanized variants (tested as purified proteins) binding to EphA5 antigen as determined using the Biacore T200. The relative KD was calculated by dividing the KD of the humanized variant by that of the VH0VK0 (first row) assayed in the same experiment.

FIG. 21 is a table illustrating a summary of thermal stability values for the six purified lead humanized variants and chimeric antibody, as determined using the UNcle biostability platform. * indicates where a sample was removed from analysis due to poor data.

FIGS. 22A-22B illustrate thermal ramp experiments of the chimeric and six purified lead humanized variant antibodies, as: (FIG. 22A) individual plots, or (FIG. 22B); single replicate of each variant overlaid, as performed on the UNcle biostability platform. Samples were tested in duplicate with averages and standard deviations shown in FIG. 21.

FIG. 24 illustrates dose-response curves showing the MFI values for the six variants tested with the H460 cell line.

FIG. 26 is a table illustrating EC50 values and maximum MFI for each of the samples tested with both the H460 positive cell line and the H226 negative cell line.

FIGS. 27A-27B are diagrams illustrating post-translational sequence liabilities summaries for the 11C12 heavy chain (FIG. 27A) (SEQ ID NO: 1) and light chain (FIG. 27B) (SEQ ID NO: 8).

Figure 29A:
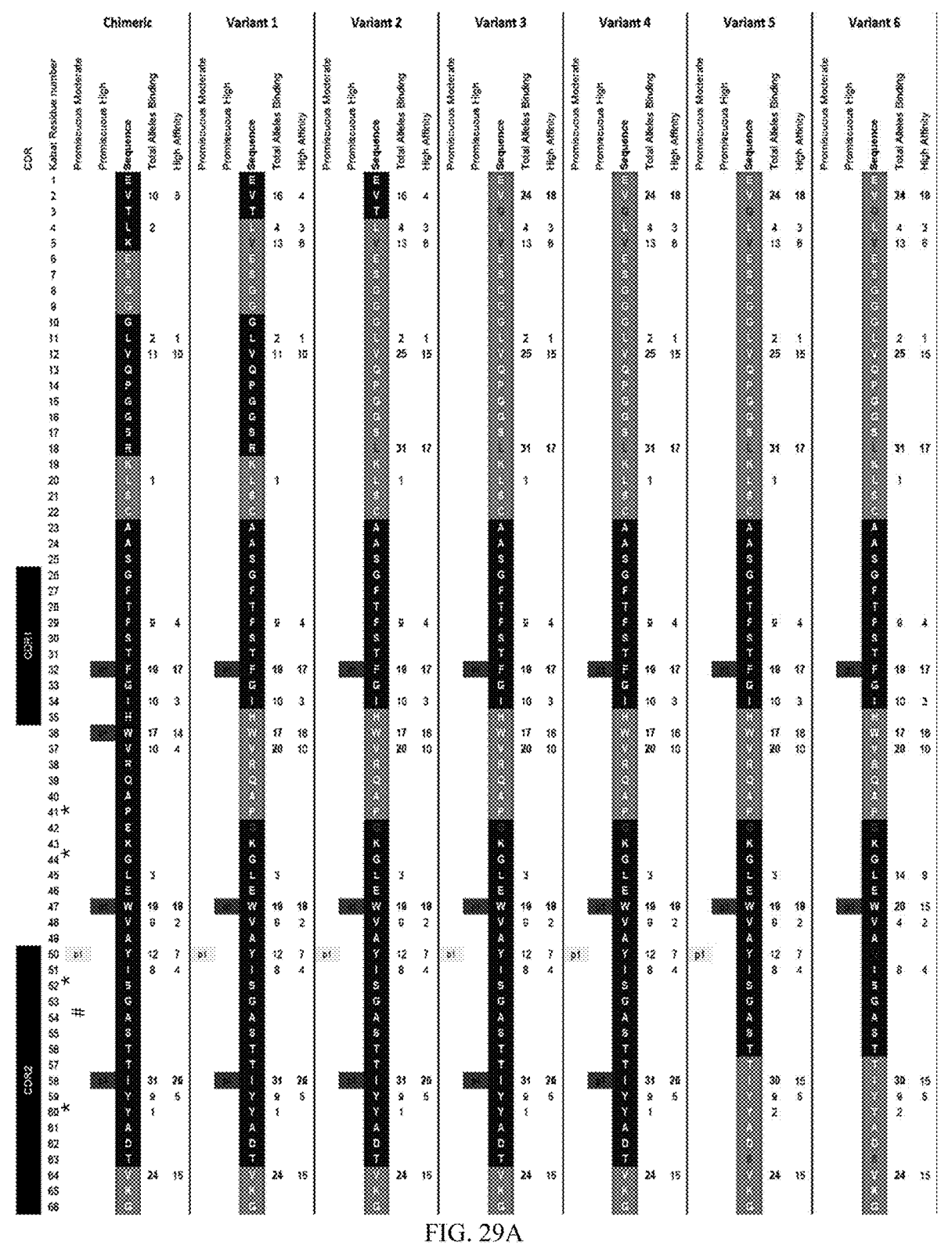
Figure 29B:
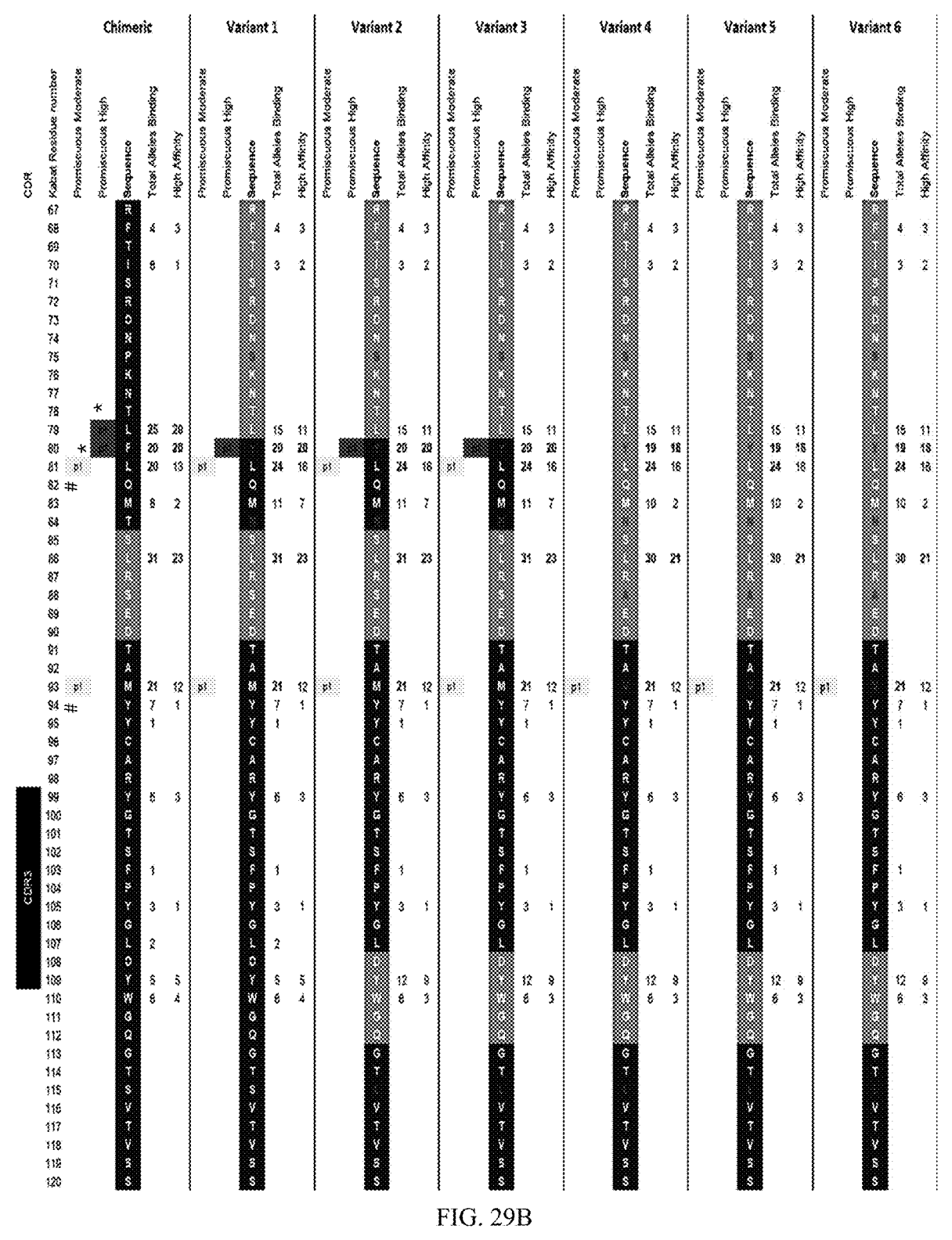

FIGS. 29A and 29B illustrate a summary of iTope™ analysis of humanized heavy chain variable region sequences: Chimeric VH0 (SEQ ID NO: 1) and variants VH1-VH6 (SEQ ID Nos 2-7, respectively). Differences from Chimeric VH are highlighted in the "Sequence" column. Peptides were tested as 9mer peptides in one amino acid increments. Regions containing potentially immunogenic peptides are indicated in the "iTope" columns; '*' (p1) indicates promiscuous high affinity MHC class II binding peptides, '#' (p1) indicates promiscuous moderate affinity MHC class II binding peptides. Matches to germline sequence are shown in grey in the "Sequence" column.

Figure 30A:
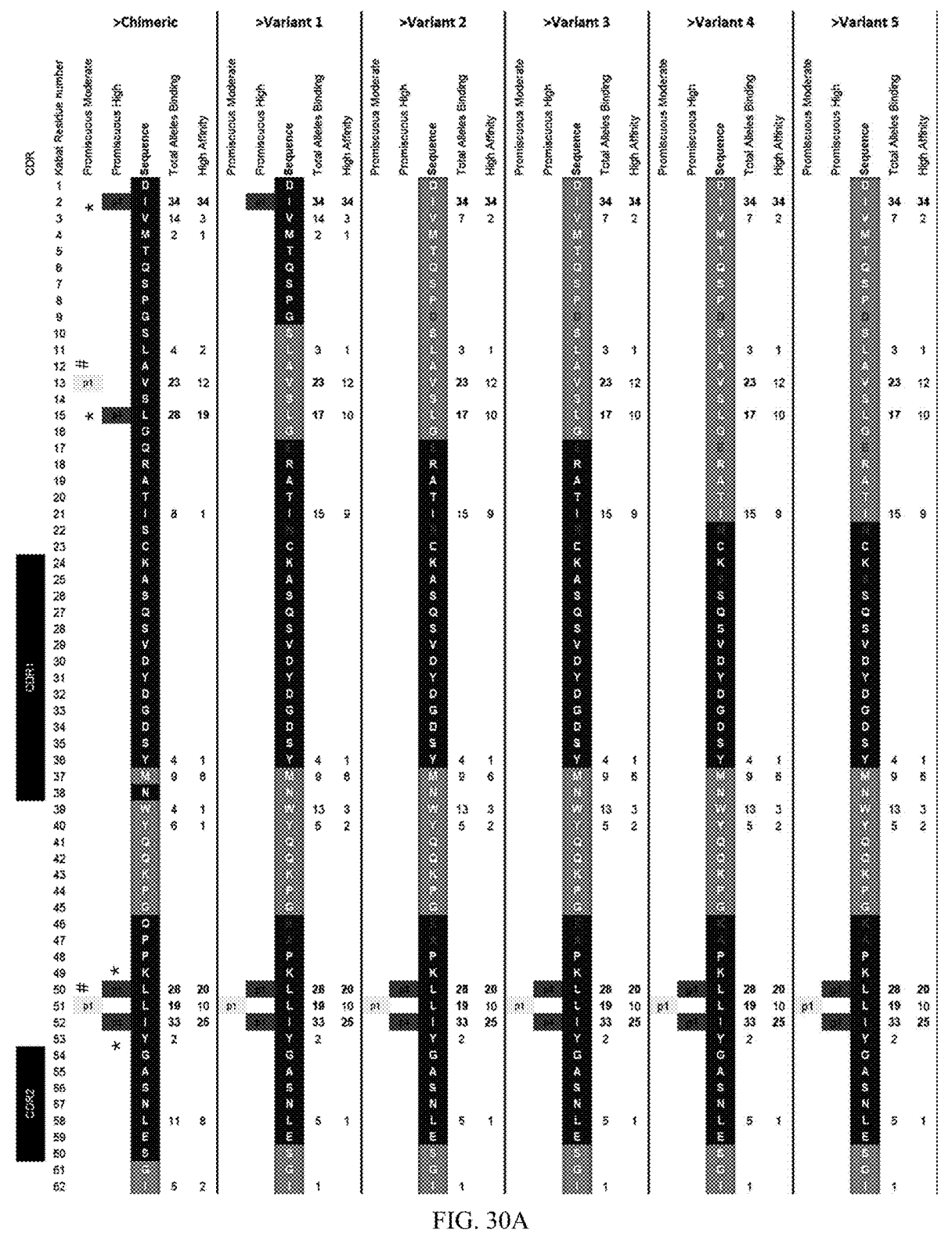
Figure 30B:
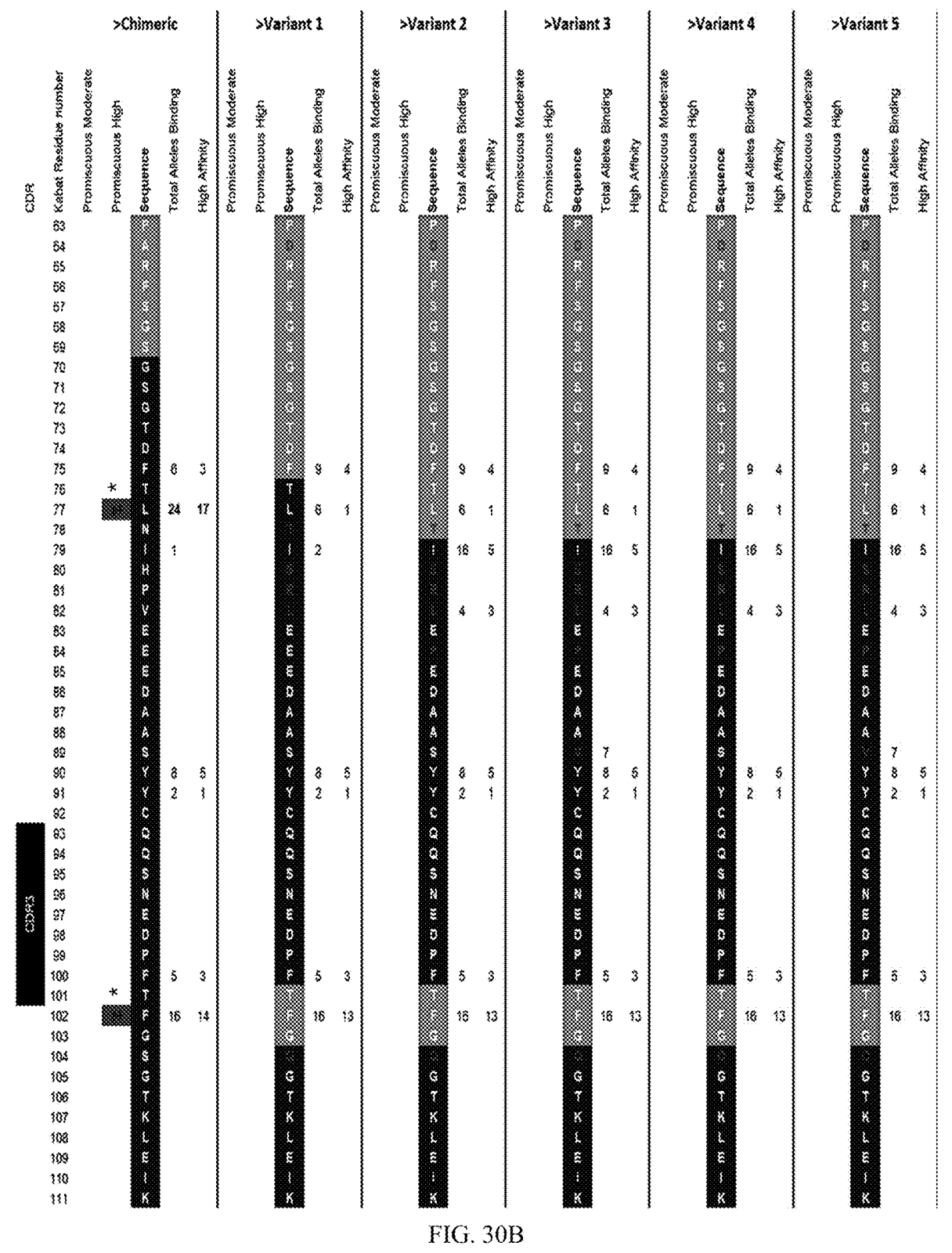

FIGS. 30A and 30B illustrate a Summary iTope™ analysis of humanized light chain variable region sequences: Chimeric VK0 (SEQ ID NO: 8) and variants VK1-VK5 (SEQ ID Nos. 9-13, respectively. Differences from Chimeric VK are highlighted in the "Sequence" column. Peptides were tested as 9mer peptides in one amino acid increments. Regions containing potentially immunogenic peptides are indicated in the "iTope" columns; red (p1) indicates promiscuous high affinity MHC class II binding peptides, yellow (p1) indicates promiscuous moderate affinity MHC class II binding peptides. Matches to germline sequence are shown in grey in the "Sequence" column.

FIGS. 31A-31D illustrate SE-HPLC chromatograms of Hitrap Mab Select PrismA purified antibodies.

FIG. 32 illustrates structures of the maleimide linker-payloads used for conjugation to VH4Vk3.

FIGS. 59A-59B are illustrations of equations used in LC-MS analysis (FIG. 59A) and HIC analysis (FIG. 59B)

FIG. 60 is a series of graphs and a table illustrating binding validation of the H4K3 antibody.

FIG. 61 is a series of graphs and a table illustrating binding validation of the H5K3 antibody.

FIG. 62 illustrates optimization of MAbs against the target protein.

FIG. 63 illustrates optimization of Fabs against target protein.

FIG. 65 is a table listing primary residues for binding of Ab(s) to the target protein.

FIG. 72 illustrates the in vivo efficacy of VH4Vk3-ThioBridge®-VCP-MMAE in H522-derived Xenograft Model of Human Lung Cancer.

FIG. 73 illustrates body weight of tumor-bearing mice pre- and post-treatment (ref. FIG. 72)

FIG. 74 illustrates a second experiment demonstrating the efficacy of VH4Vk3-ThioBridge®-VCP-MMAE in H522-derived xenograft model of human lung cancer.

FIG. 75 illustrates body weight of tumor-bearing mice pre- and post-treatment (ref. FIG. 74)

FIG. 76 illustrates the efficacy of VH4Vk3-ThioBridge®-(VCP-SN-38)2 in a H522-derived xenograft model of human lung cancer.

FIG. 77 illustrates body weight of tumor-bearing mice pre- and post-treatment (ref. FIG. 76)

FIG. 78 illustrates the efficacy of VH4Vk3-ThioBridge®-VCP-MMAE in a A549-derived xenograft model of human lung cancer.

FIG. 78).

FIG. 80 illustrates the efficacy of VH4Vk3-ThioBridge®-(VCP-SN-38)2 in a A549-derived xenograft model of human lung cancer.

FIG. 80)

FIG. 82 illustrates the efficacy of VH4Vk3-ThioBridge®-VCP-MMAE in a H460-derived xenograft model of human lung cancer.

FIG. 82).

FIG. 84 illustrates efficacy of VH4Vk3-ThioBridge®-(VCP-SN-38)2 in a H460-derived xenograft model of human lung cancer.

FIG. 84).

FIG. 86 illustrates the efficacy of VH5Vk3-ThioBridge®-VCP-MMAE in a H522-derived xenograft model of human lung cancer.

FIG. 86).

FIG. 88 illustrates a second study demonstrating the efficacy of VH5Vk3-ThioBridge®-VCP-MMAE in a H522-derived xenograft model of human lung cancer.

FIG. 89 illustrates body weights of tumor-bearing mice pre- and post-treatment (ref. FIG. 88).

FIG. 90 illustrates the efficacy of VH5Vk3-ThioBridge®-VCP-MMAE in a A549-derived xenograft model of human lung cancer.

FIG. 90).

FIG. 92 illustrates efficacy of VH5Vk3-ThioBridge®-(VCP-SN-38)2 in a A549-derived xenograft model of human lung cancer.

FIG. 92).

FIG. 94).

FIG. 96).

FIG. 98 illustrates the efficacy of VH4Vk3-ThioBridge®-VCP-MMAE and VH5Vk3-ThioBridge®-VCP-MMAE in an ER, PR, and HER2 negative (triple-negative) invasive ductal carcinoma of the breast that was derived from xeno-grafted patient tissue (PDX). The histograms on the left illustrate EphA5 expression in xenograft tissue. The growth curve on the right illustrates growth of xenograft tumor in indicated MMAE-conjugate treatment and control mice. Arrows indicate administration of five weekly doses of 10 mg/kg MMAE-conjugate. PBS was used as a vehicle control.

(FIG. 101B)

FIGS. 108A-108C illustrate tumor volume in mice treated weekly for 5 weeks with ADC1 or PBS (placebo) over 50-day test period (FIG. 108A), weight of tumors removed from TM00098-bearing mice following treatment with ADC1 or PBS (placebo) (FIG. 108B), and body weight of TM00098-bearing mice before and after treatment with ADC1 (FIG. 108C).

FIGS. 109A-109C illustrate tumor volume in mice treated weekly for 5 weeks with ADC2 or PBS (placebo) over 50-day test period (FIG. 109A), weight of tumors removed from TM00098-bearing mice following treatment with ADC2 or PBS (placebo) (FIG. 109B), and body weight of TM00098-bearing mice before and after treatment with ADC2 (FIG. 109C).

FIGS. 112A-112C illustrate tumor volume in TM0188-bearing mice treated weekly for 5 weeks with ADC2 or PBS (placebo) over 50-day test period (FIG. 112A), weight of tumors removed from TM0188-bearing mice following treatment with ADC2 (FIG. 112B), and body weight of TM0188-bearing mice before and after treatment with ADC2 (FIG. 112C).

FIGS. 117A-117C illustrate tumor volume in mice treated weekly for 5 weeks with ADC1 or PBS (placebo) over 50-day test period (FIG. 117A), weight of tumors removed from TM00226-bearing mice following treatment with ADC1 or PBS (placebo) (FIG. 117B), and body weight of TM00226-bearing mice before and after treatment with ADC1 (FIG. 117C).

FIGS. 118A-118C illustrate tumor volume in TM00226-bearing mice treated weekly for 5 weeks with ADC2 or PBS (placebo) over 50-day test period (FIG. 118A), weight of tumors removed from TM00226-bearing mice following treatment with ADC2 (FIG. 118B), and body weight of TM00226-bearing mice before and after treatment with ADC2 (FIG. 118C).

DETAILED DESCRIPTION

Definitions

Figure 1:
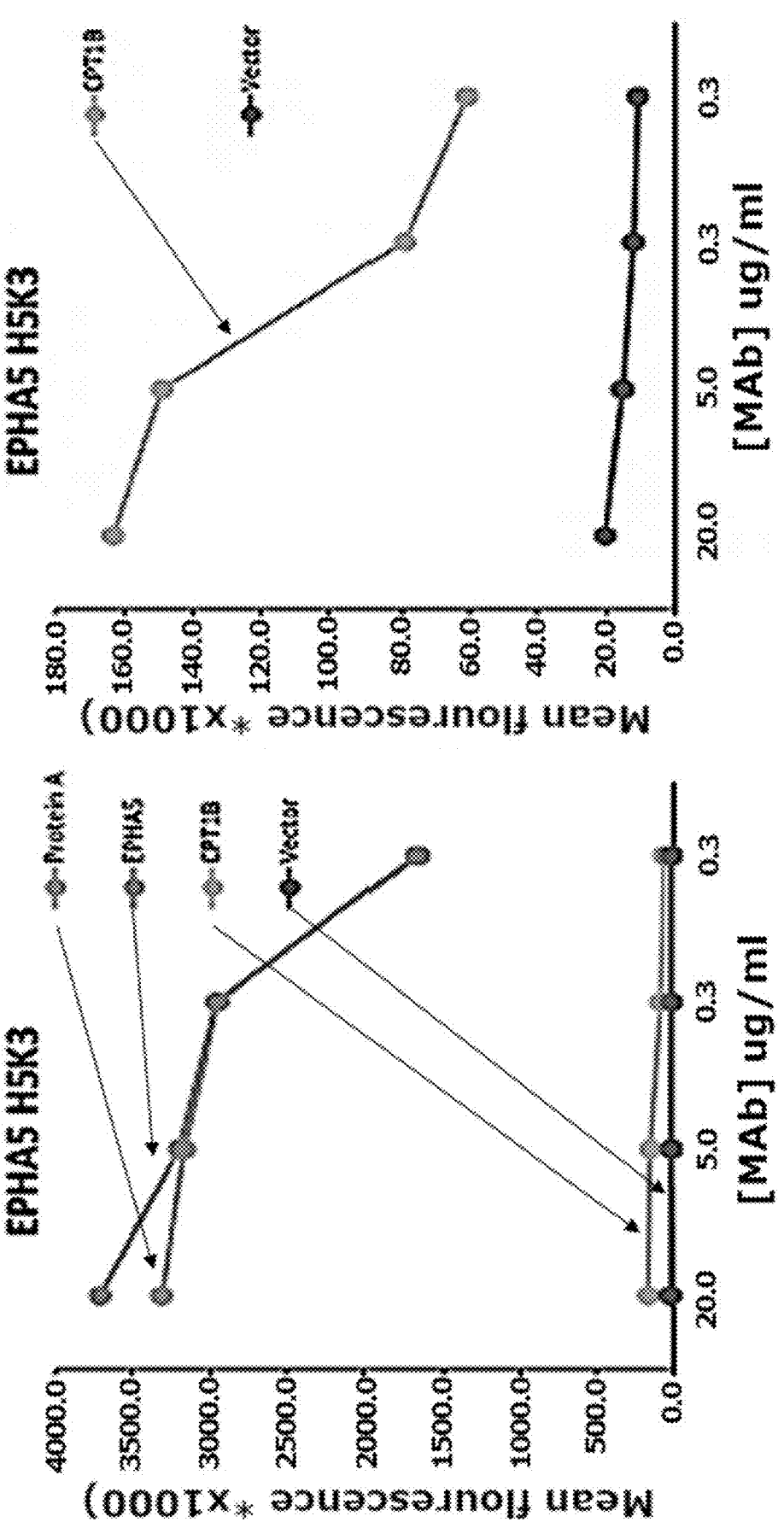
FIG. 1 illustrates detection of VH5/VK3 (H5K3) antibody binding using a high-throughput immunofluorescence flow cytometry assay.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "recombinant," as used herein, refers to nucleic acid or protein molecules formed by artificial (e.g., laboratory-derived) methods of genetic engineering (e.g., molecular cloning) that bring together genetic sequences from multiple sources, thus creating sequences that would not otherwise be found in natural genomes.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules comprising two heavy chain and two light chain polypeptides. Each polypeptide chain contains three complementarity-determining regions (CDRs), which bind to the antigen and defines the antibody's antigen specificity.

As used herein, the term "antibody" and "antibodies" can also include polypeptides or polypeptide complexes derived from full-length antibodies. These polypeptide complexes may be naturally occurring or constructed from single chain antibodies or antibody fragments and retain an antigen-specific binding ability. The antibodies of the present invention may exist in a variety of forms including, for example, polyclonal antibodies, monoclonal antibodies, Fv, Fab and $F(ab')_2$, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). "Antibody" also includes single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

The term "antibody fragment" refers to a polypeptide comprising or derived from a portion of an intact antibody and may comprise the antigen-binding fragment of an intact antibody.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

The term "specifically binds" to an antigen or epitope is a term that is well understood in the art, and methods to determine such specific binding are also well known in the art. A binding molecule, such as an antibody or antigen-binding fragment, is said to exhibit "specific binding," such as "preferential binding" if it reacts or associates more frequently, more rapidly, with greater duration and/or with greater affinity with a particular target than it does with alternative targets. An antibody specifically binds or preferentially binds to a target if it binds with greater affinity, avidity, more readily, and/or with greater duration than it binds to other substances. For example, an antibody that specifically or preferentially binds to an EphA8 is an antibody that binds EphA8 with greater affinity, avidity, more readily, and/or with greater duration than it binds to a non-target protein epitope. It is also understood by reading this definition that; for example, a binding molecule that specifically or preferentially binds to a first target may or may not specifically or preferentially bind to a second target. It is also understood by reading this definition that specific binding or preferential binding does not necessarily require (although it can include) exclusive binding. Methods to determine such specific or preferential binding are also well known in the art, e.g., an immunoassay.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macro-molecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "antibody-drug conjugate" or "ADC" as used herein refers to an antibody-based molecular complex comprising an antibody or antigen-binding polypeptide fragment derived from an antibody conjugated to a biologically active drug molecule, often referred to as the "payload". ADC-associated drug molecules are often cytotoxic in function, which allows the ADC complex to kill cells expressing specific molecular targets, especially tumor cells.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "Kd", "$K_D$" or "equilibrium dissociation constant," as used herein, refers to a calculated, quantitative measurement of an antibody's affinity for its epitope. The $K_D$ represents a ratio of the rate of binding (Kon) and dissociation (Koff) between the antibody and its epitope. $K_D$ and affinity are inversely related in that a high affinity interaction is characterized by a low $K_D$.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is medullary thyroid carcinoma.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind epitopes such as EPH receptor A5 using the functional assays described herein.

The term "dysregulated" when used in the context of the level of expression or activity of EphA5 refers to the level of expression or activity that is different from the expression level or activity of EphA5 in an otherwise identical healthy animal, organism, tissue, cell or component thereof. The term "dysregulated" also refers to the altered regulation of the level of expression and activity of EphA5 compared to the regulation in an otherwise identical healthy animal, organism, tissue, cell or component thereof. In certain embodiments, the dysregulation of expression or activity is associated with a disease state including cancer in which expression level or activity of EphA5 is dysregulated within cancer cells.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" and "chimeric" forms of non-human (e.g., murine) antibodies are immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized and chimeric antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized and chimeric antibodies can comprise residues which are found neither in the recipient antibody nor in the imported CDR or framework sequences. These modifications are made to further refine and optimize antibody performance. In general, the humanized and chimeric antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized and chimeric antibody optimally also will comprise at least a portion of an immunoglobulin constant region (Fc), typically that of a human immunoglobulin. The World Health Organization (WHO) International Nonproprietary Name (INN) Expert Group has defined requirements for non-human derived antibodies to be considered "humanized". According to guidelines, comparison of a candidate antibody to human sequences should be done through the International Immunogenetics Information System® (IMGT®) DomainGapAlign tool (www.imgt.org). This tool interrogates the IMGT® database of antibody germline variable region genes where the alignment score is made only against germline sequence variable region exons, thus omitting part of CDR3 and the J region from the analysis. For an antibody to be "humanized", in addition to being "closer to human than to other species", the top "hit" should be human and the identity to human sequences must be at least 85%, otherwise the antibody would be designated as "chimeric". For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

"Single chain antibodies" refer to antibodies formed by recombinant DNA techniques in which immunoglobulin heavy and light chain fragments are linked to each other using an engineered span of amino acids to recapitulate the Fv region of an antibody as a single polypeptide. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "treating" as used herein can refer to medical interventions performed with the purpose of ameliorating or preventing a disease state. The term refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), or a combination thereof. The Kabat and Clothia numbering systems may also be used to determine the position of other features of antibodies or antibody-derived fragments such as framework regions (FRs) and the like.

The term "thermal melting point" or "thermal melting temperature", often abbreviated "Tm" or "Tmelt", when used herein refers to the temperature at which a protein undergoes denaturation, an unfolding process in which quaternary, tertiary, and secondary structure are lost. The Tm of a protein can be measured directly via observing changes in intrinsic fluorescence due to tryptophan and tyrosine residues. Such Tm assays based on fluorescence can be used to rank the stability of protein constructs or compare different formulations to optimize various conditions. Other methods of measuring Tm are known in the art, and include but are not limited to static light scattering (SLS), dynamic light scattering (DLS), differential scanning calorimetry, circular dichromism, and the like and may be used to determine the Tm of the antibodies and antibody-derived fragments of the current invention.

The term "thermal aggregation" or "thermal aggregation temperature", often abbreviated "Tagg" as used herein refers to the temperature at which protein molecules in suspension begin to oligomerize or aggregate. The temperature at which Tagg occurs depends on the physical properties of the protein itself and by the composition of the buffer solution.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Provided herein are binding molecules, such as antibodies (including antigen-binding antibody fragments and immunoconjugates (e.g., antibody drug conjugates) that bind EphA5 and can be used to target EphA5 for treating, ameliorating, and/or preventing a disease or condition, such as a cancer. Also provided are nucleic acid molecules encoding the antibodies. Also provided are methods of making and using the antibodies and antigen-binding fragments as well as immunoconjugates (e.g., antibody drug conjugates) containing the antibodies and antigen-binding fragments. Also provided are compositions, including pharmaceutical compositions, containing such antibodies or antigen-binding fragments or immunoconjugates (e.g., antibody drug conjugates) containing the antibodies or antigen-binding fragments. In some aspects, the provided compositions, antibodies or antigen-binding fragments or immunoconjugates (e.g., antibody drug conjugates) containing the antibodies or antigen-binding fragments can be used in connection with a therapy or a method of treatment, amelioration, and/or prevention.

The present invention is based on the observation that humanized antibodies or antibody derived antigen-binding fragments specific for human EPH receptor A5 can be used to treat, ameliorate, and/or prevent cancers and diseases associated with the expression of EPH receptor A5. The antibodies of the invention can also be used in antibody drug conjugates useful for the same. Also provided are methods and compositions comprising the human EPH receptor A5 specific antibodies or antigen-binding fragments of the invention for the treatment, amelioration, and/or prevention of cancers.

EPH receptor A5, also referred to as ephrin type-A receptor 5 and EphA5, is protein encoded by the EPHA5 gene in humans and is a member of the ephrin receptor family of protein-tyrosine kinases. Receptors of this family are known to be involved in mediating signaling events primarily during development, especially in the nervous system. Ephrin family members including EPH receptor A5 typically possess a single kinase domain and an extracellular domain comprising a cystine-rich domain and two fibronec-tin type III repeats. Ephrin receptors are organized into two main groups based on the affinity their extracellular domain has for ephrin-A or ephrin-B ligands. Ephrin ligands, including the ligands for EPH receptor A5, share the distinctive property of being membrane anchored. Ligands of the ephrin-A family are linked to the membrane via a GPI linkage, while ligands of the ephrin-B family are transmembrane proteins.

In human cancer, EPHA5 overexpression has been linked to, for example, breast, liver, brain, and lung cancers, where it's inhibition generally leads to reduced growth of tumor cells. Recent studies in lung cancer identified that EPH receptor A5 is a key regulator of radiation resistance and treatment by activating and enhancing the DNA damage response (DDR). As such, the provided embodiments related to EPH receptor A5 inhibition, particularly by specific antibodies (e.g., the antibodies and antigen-binding fragments thereof of the invention), can slow tumor growth both alone and as a sensitization treatment in combination with other cytotoxic therapies and treatments. Thus, in certain aspects, the current invention provides human EPH receptor A5 antibodies and antigen-fragments thereof useful for the inhibition of EPH receptor A5 for the treatment of cancers. In certain embodiments, the EPH receptor A5 antibodies of the invention can be used in antibody drug conjugates in which the EPH receptor A5 specific antibodies are conjugated to cytotoxic agents that act to kill EPH receptor A5-expressing cells, especially cancer cells.

The provided antibodies (e.g., the antibodies and antigen-binding fragments thereof of the invention), as well as antibody drug conjugates containing the same, exhibit advantageous features compared to existing antibodies directed to EphA5 and immunoconjugates related to the same. In particular, the provided embodiments, produce a new antibody-based molecule that retains high affinity target binding for EphA5 with increased conformational stability, reduced immunogenicity risks and hence desirable manufacturable properties and features suitable for use as a therapeutic. In particular, the provided antibodies (e.g., the antibodies and antigen-binding fragments thereof) have been humanized rendering them suitable for administration to humans with reduced immunogenicity compared to other existing EphA5 antibodies, such as murine antibodies. Moreover, while humanization is known to impact certain properties of an antibody that could lead to reduced target binding affinity, aggregation, chemical stability, and/or physical stability during drug production and delivery, antibodies provided herein have been found to exhibit one or more features that are improved compared to the parental or reference antibody (e.g., 11C12). For instance, provided antibodies exhibit improved binding affinity for human EphA5 compared to the reference antibody (e.g., antibody with variable heavy and light chains from murine 11C12 antibody). In addition, provided antibodies also exhibit improvements in their stability as evidenced by improved thermal stability (e.g., higher Tm and Tagg compared to the reference 11C12 antibody). Conformational stability is commonly used as surrogate measurement for successful antibody stabilization as thermal stability is correlated with high expression, easier purification, longer shelf life and optimal pharmacokinetic/pharmacodynamic properties (Goswami et al. (2013) Antibodies 2:452:500; Thiagarajan et al. (2016) MAbs 8:1088-1097). Finally, among provided antibodies are antibodies that are able to bind to specifically bind cell surface EphA5 on target cells and can be internalized into the bound cell. As EphA5 is highly expressed on cancer cells, a provided antibody drug conjugate is able to recognize cancer cells that overexpress EphA5 and readily internalize the bound ADC to initiate cytotoxic effect on the cancer cell.

Thus, among provided antibodies are antibodies that exhibit one or more, or in some cases, all of the improved features of reduced immunogenicity, higher binding affinity to the EphA5 target, better thermostability and ability to be internalized by an EphA5-expressing cells. For instance, among provided antibodies that exhibit such features are the antibodies designated VH5/VK3 and VH4/VK3. In some embodiments, there also are provided antibody drug conjugates (ADCs) containing a provided antibody (e.g., VH5/VK3 or VH4/VK3) linked to a cytotoxic drug and uses thereof for treating, ameliorating, and/or preventing EphA5-expressing cancers, such as lung cancer.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section heading used herein are for organizational purposes only and are not to be construed as limiting the subject matter described.

Antibodies and Antigen-Binding Fragments

Provided herein are binding polypeptides that bind to ephrin type-A receptor 5 (EphA5). For example, the binding polypeptides and antibodies specifically bind to human EPH receptor A5. Such binding polypeptides include antibodies (including antigen-binding fragments thereof) that specifically bind to EphA5, such as human EphA5. In provided embodiments, an anti-EphA5 antibody or antigen-binding fragment provided herein is a humanized antibody or an antigen-binding fragment thereof. In some embodiments, an anti-EphA5 antibody or antigen-binding fragment thereof provided herein binds human EPH receptor A5 protein. In some embodiments the human EPH receptor A5 protein comprises the amino acid set forth in SEQ ID NO:41. In some embodiments, the binding polypeptides and antibodies of the invention bind to human EPH receptor A5 with high affinity. Preferably, the binding polypeptides and antibodies of the invention specifically recognize naturally expressed human EPH receptor A5 protein on a cell and do not cross-react to other surface molecules on that cell.

In certain aspects, the invention provides an antibody comprising an antigen-binding domain that specifically binds to an epitope of human EPH receptor A5 (EPHA5). In certain embodiments, the antigen-binding domain comprises a heavy chain variable region that comprises three heavy chain complementarity-determining regions (HCDRs) and a light chain variable region that comprises three light chain complementarity-determining regions (LCDRs).

In some embodiments, amino acid residues in variable domain sequences and full-length antibody sequences are numbered according to the Kabat numbering convention. Kabat et al. (1991), "Sequences of Proteins of Immunological Interest," 5th Ed. Public Health Service, National Institutes of Health, Bethesda, MD Under the Kabat numbering scheme, in some embodiments, the CDR amino acid residues in the heavy chain variable domain (VH) are numbered 31-35/35A/35B (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

However, although CDR sequences are exemplified according to the Kabat numbering convention, it will be apparent to those skilled in the art that there are alternative numbering conventions for amino acid residues in variable domain sequences and full-length antibody sequences. For instance, an alternative numbering convention is the Chothia numbering scheme, for example as set out in Chothia et al. (1989) Nature 342:877-883. Under the Chothia numbering scheme, in some embodiments, the CDR amino acids in the VH are numbered 26-32/33/34 (HCDR1), 52-56 (HCDR2), and 95-102 (HCDR3); and the CDR amino acid residues in the light chain variable domain (VL) are numbered 24-34 (LCDR1), 50-56 (LCDR2), and 89-97 (LCDR3). In some examples, amino acid residues in variable domain sequences and full-length antibody sequences are numbered according to a combination of both Chothia and Kabat CDR definitions. In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35/35A/35B (HCDR1), 50-65 (HCDR2), and 95-102 (HCDR3) in a VH, e.g., a mammalian VH, e.g., a humanized VH; and amino acid residues 24-34 (LCDR1), 50-56 (LCDR2), and 89-97 (LCDR3) in a VL, e.g., a mammalian VL, e.g., a humanized VL.

Other numbering conventions for CDR sequences available to a skilled person include, for example, "AbM" (university of Bath) and "contact" (University College London) methods. Databases can be used for CDR identification such as to identify CDRs based on Kabat numbering, Chechia or other numbering scheme. It also is understood that, in some cases, other residues are part of the CDR sequence depending on the particular convention used and factors such as the structure and protein folding of the antibody and would be understood to be so by a skilled person.

In certain aspects, the invention provides an antibody or antigen-binding fragment thereof comprising an HCDR1 comprising the amino acid sequence TFGIH (SEQ ID NO:16) or GFTFSTFGIH (SEQ ID NO:42). Also provided is an isolated binding polypeptide comprising an HCDR2 comprising the amino acid sequences YISGASTTIYY-ADTVKG (SEQ ID NO:17), YISGASTTIYYADSVKG (SEQ ID NO:18), or SISGASTTIYYADSVKG (SEQ ID NO:19). Also provided is an isolated binding polypeptide comprising an HCDR3 comprising the amino acid sequence YGTSFPYGLDY (SEQ ID NO:20). Also provided is an isolated binding polypeptide comprising a light chain variable region that comprises an LCDR1 comprising the amino acid sequences KASQSVDYDGDSYMN (SEQ ID NO:21) or KASQSVDYDGDSYMN (SEQ ID NO:22). Also provided is an isolated binding polypeptide comprising an LCDR2 comprising the amino acid sequence GASNLES (SEQ ID NO:23). Also provided is an isolated binding polypeptide comprising an LCDR3 comprising the amino acid sequence QQSNEDPFT (SEQ ID NO:24).

In certain aspects, the invention provides an antibody comprising an HCDR1 comprising the amino acid sequence TFGIH (SEQ ID NO:16), an HCDR2 comprising the amino acid sequence YISGASTTIYYADTVKG (SEQ ID NO:17), an HCDR3 comprising the amino acid sequence YGTSFPYGLDY (SEQ ID NO:20), an LCDR1 comprising the amino acid sequence KASQSVDYDGDSYMN (SEQ ID NO:21), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence GFTFSTFGIH (SEQ ID NO:42), an HCDR2 comprising the amino acid sequence YISGASTTIYYADTVKG (SEQ ID NO:17), an HCDR3 comprising the amino acid sequence YGTSFPYGLDY (SEQ ID NO:20), an LCDR1 comprising the amino acid sequence KASQSVDYDGDSYMN (SEQ ID NO:21), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence TFGIH (SEQ ID NO:16), an HCDR2 comprising the amino acid sequence YISGASTTIYYADSVKG (SEQ ID NO:18), an HCDR3 comprising the amino acid sequence YGTSFPYGLDY (SEQ ID NO:20), an LCDR1 comprising the amino acid sequence KASQSVDYDGDSYMN (SEQ ID NO:21), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence GFTFSTFGIH (SEQ ID NO:42), an HCDR2 comprising the amino acid sequence YISGASTTIYYADSVKG (SEQ ID NO:18), an HCDR3 comprising the amino acid sequence YGTSFPYGLDY (SEQ ID NO:20), an LCDR1 comprising the amino acid sequence KASQSVDYDGDSYMN (SEQ ID NO:21), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence TFGIH (SEQ ID NO:16), an HCDR2 comprising the amino acid sequence SISGASTTIYYADSVKG (SEQ ID NO:19), an HCDR3 comprising the amino acid sequence YGTSFPYGLDY (SEQ ID NO:20), an LCDR1 comprising the amino acid sequence KASQSVDYDGDSYMN (SEQ ID NO:21), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence GFTFSTFGIH (SEQ ID NO:42), an HCDR2 comprising the amino acid sequence SISGASTTIYYADSVKG (SEQ ID NO:19), an HCDR3 comprising the amino acid sequence YGTSFPYGLDY (SEQ ID NO:20), an LCDR1 comprising the amino acid sequence KASQSVDYDGDSYMN (SEQ ID NO:21), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence TFGIH (SEQ ID NO:16), an HCDR2 comprising the amino acid sequence YISGASTTIYYADTVKG (SEQ ID NO:17), an HCDR3 comprising the amino acid sequence YGTSFPYGLDY (SEQ ID NO:20), an LCDR1 comprising the amino acid sequence KSSQSVDYDGDSYMN (SEQ ID NO:22), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence GFTFSTFGIH (SEQ ID NO:42), an HCDR2 comprising the amino acid sequence YISGASTTIYYADTVKG (SEQ ID NO:17), an HCDR3 comprising the amino acid sequence YGTSFPYGLDY (SEQ ID NO:20), an LCDR1 comprising the amino acid sequence KSSQSVDYDGDSYMN (SEQ ID NO:22), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence TFGIH (SEQ ID NO:16), an HCDR2 comprising the amino acid sequence YISGASTTIYYADSVKG (SEQ ID NO: 18), an HCDR3 comprising the amino acid sequence YGTSFPYGLDY (SEQ ID NO:20), an LCDR1 comprising the amino acid sequence KSSQSVDYDGDSYMN (SEQ ID NO:22), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence GFTFSTFGIH (SEQ ID NO:42), an HCDR2 comprising the amino acid sequence YISGASTTIYYADSVKG (SEQ ID NO:18), an HCDR3 comprising the amino acid sequence YGTSFPYGLDY (SEQ ID NO:20), an LCDR1 comprising the amino acid sequence KSSQSVDYDGDSYMN (SEQ ID NO:22), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence TFGIH (SEQ ID NO:16), an HCDR2 comprising the amino acid sequence SISGASTTIYYADSVKG (SEQ ID NO:19), an HCDR3 comprising the amino acid sequence YGTSFPYGLDY (SEQ ID NO:20), an LCDR1 comprising the amino acid sequence KSSQSVDYDGDSYMN (SEQ ID NO:22), an LCDR2 comprising the amino acid sequence GASNLES (SEQ ID NO:23), and an LCDR3 comprising the amino acid sequence QQSNEDPFT (SEQ ID NO:24).

In certain aspects, the invention provides an antibody comprising an HCDR1 comprising the amino acid sequence GFTFSTFGIH (SEQ ID NO:42), an HCDR2 comprising the amino acid sequence SISGASTTIYYADSVKG (SEQ ID NO:19), an HCDR3 comprising the amino acid sequence YGTSFPYGLDY (SEQ ID NO:20), an LCDR1 comprising the amino acid sequence KSSQSVDYDGDSYMN (SEQ ID NO:22), an LCDR2 comprising the amino acid sequence GASNLES (SEQ ID NO:23), and an LCDR3 comprising the amino acid sequence QQSNEDPFT (SEQ ID NO:24).

Tolerable variations of the complementarity determining regions (CDR) sequences will be known to those of skill in the art. For example, in some embodiments the polypeptide comprises a complementarity determining region (HCDR or LCDR) that comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NOs:16 or 42, 17, 18, 19, 20, 21, 22, 23, or 24.

In certain embodiments, the binding polypeptide, such as a provided antibody or antigen-binding fragment, comprises a heavy chain variable region comprising an amino acid sequence having at least 80%, 85%, 90%, 95%, 96%, 96%, 97%, 98%, or 99% identity, and/or having 100% identity, to the amino acid sequence of the heavy chain variable region set forth in SEQ ID NOs:1, 2, 3, 4, 5, 6, or 7. In certain embodiments, the binding polypeptide, such as a provided antibody or antigen-binding fragment, comprises a heavy chain variable region comprising the amino acid sequence set forth in any one of SEQ ID NOs:1, 2, 3, 4, 5, 6, or 7. In certain embodiments, the binding polypeptide, such as a provided antibody or antigen-binding fragment, has a heavy chain variable region consisting of the amino acid sequence set forth in any one of SEQ ID NOs:1, 2, 3, 4, 5, 6, or 7.

In certain embodiments, the binding polypeptide, such as a provided antibody or antigen-binding fragment, comprises a light chain variable region comprising an amino acid sequence having at least 80%, 85%, 90%, 95%, 96%, 97%, 98%, or 99% identity, and/or having 100% identity, to the amino acid sequence set forth in SEQ ID NOs:8, 9, 10, 11, 12, or 13. In certain embodiments, the binding polypeptide, such as a provided antibody or antigen-binding fragment, comprises a light chain variable region comprising the amino acid sequence set forth in any one of SEQ ID NOs:8, 9, 10, 11, 12, or 13. In certain embodiments, the binding polypeptide, such as an antibody or antigen-binding fragment, has a light chain variable region consisting of the amino acid sequence set forth in any one of SEQ ID NOs:8, 9, 10, 11, 12, or 13.

Among the provided binding polypeptides are humanized antibodies. In some embodiments, the binding polypeptide, such as an antibody or antigen-binding fragment thereof, comprises a heavy chain variable region comprising any of the above HCDRs and in which the amino acid has equal to or less than 100% sequence identity to SEQ ID NO:1, and a light chain variable region comprising any of the above LCDRs and in which the amino acid sequence has equal to or less than 100% sequence identity to SEQ ID NO:8. In some embodiments, the heavy chain variable region comprises an amino acid sequence that has at least 80% sequence identity to SEQ ID NO:1. In some embodiments, the heavy chain variable region comprises an amino acid sequence that has at least 85% sequence identity to SEQ ID NO:1. For instance, the heavy chain variable region comprises an amino acid sequence that has at least 86%, 87%, 87%, 88%, 89%, 90%, 91%, 92%, 93% 94%, or 95% sequence identity to SEQ ID NO:1. In some embodiments, the light chain variable region comprises an amino acid sequence that has at least 80% sequence identity to SEQ ID NO:8. In some embodiments, the light chain variable region comprises an amino acid sequence that has at least 85% sequence identity to SEQ ID NO:8. For instance, the light chain variable region comprises an amino acid sequence that has at least 86%, 87%, 87%, 88%, 89%, 90%, 91%, 92%, 93% 94%, 95% sequence identity to SEQ ID NO:8.

In certain embodiments, the binding polypeptide, such as a provided antibody or antigen-binding fragment, comprises a heavy chain variable region comprising an amino acid sequence having at least 80%, 85%, 90%, 95%, 96%, 96%, 97%, 98%, or 99% identity, and/or having 100% identity, to the amino acid sequence of the heavy chain variable region set forth in SEQ ID NOs:2, 3, 4, 5, 6, or 7. In certain embodiments, the binding polypeptide, such as a provided antibody or antigen-binding fragment, comprises a heavy chain variable region comprising the amino acid sequence set forth in any one of SEQ ID NOs:2, 3, 4, 5, 6, or 7. In certain embodiments, the binding polypeptide, such as a provided antibody or antigen-binding fragment, has a heavy chain variable region consisting of the amino acid sequence set forth in any one of SEQ ID NOs:2, 3, 4, 5, 6, or 7.

In certain embodiments, the binding polypeptide, such as a provided antibody or antigen-binding fragment, comprises a light chain variable region comprising an amino acid sequence having at least 80%, 85%, 90%, 95%, 96%, 97%, 98%, or 99% identity, and/or having 100% identity, to the amino acid sequence set forth in SEQ ID NOs:9, 10, 11, 12, or 13. In certain embodiments, the binding polypeptide, such as a provided antibody or antigen-binding fragment, comprises a light chain variable region comprising the amino acid sequence set forth in any one of SEQ ID NOs:9, 10, 11, 12, or 13. In certain embodiments, the binding polypeptide, such as an antibody or antigen-binding fragment, has a light chain variable region consisting of the amino acid sequence set forth in any one of SEQ ID NOs:9, 10, 11, 12, or 13.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:2 and a light chain variable region that has at least 80%, 85%, 90%, 95%, 96%, 96%, 97%, 98%, or 99% sequence identity to the sequence set forth in SEQ ID NO:9. In some embodiments, the heavy chain variable region is set forth in SEQ ID NO:2 and the light chain variable region is set forth in SEQ ID NO:9. In some embodiments, the antibody is antibody H1K1, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:2 and a light chain variable region that has at least 80%, 85%, 90%, 95%, 96%, 96%, 97%, 98%, or 99% sequence identity, and/or has 100% identity, to the sequence set forth in SEQ ID NO:10. In some embodiments, the heavy chain variable region is set forth in SEQ ID NO:2 and the light chain variable region is set forth in SEQ ID NO:10. In some embodiments, the antibody is antibody H1K2, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:2 and a light chain variable region that has at least 80%, 85%, 90%, 95%, 96%, 96%, 97%, 98%, or 99% sequence identity, and/or has 100% identity, to the sequence set forth in SEQ ID NO:11. In some embodiments, the heavy chain variable region is set forth in SEQ ID NO:2 and the light chain variable region is set forth in SEQ ID NO:11. In some embodiments, the antibody is antibody H1K3, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:2 and a light chain variable region that has at least 80%, 85%, 90%, 95%, 96%, 96%, 97%, 98%, or 99% sequence identity, and/or has 100% identity, to the sequence set forth in SEQ ID NO:12. In some embodiments, the heavy chain variable region is set forth in SEQ ID NO:2 and the light chain variable region is set forth in SEQ ID NO:12. In some embodiments, the antibody is antibody H1K4, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:2 and a light chain variable region that has at least 80%, 85%, 90%, 95%, 96%, 96%, 97%, 98%, or 99% sequence identity, and/or has 100% identity, to the sequence set forth in SEQ ID NO:13. In some embodiments, the heavy chain variable region is set forth in SEQ ID NO:2 and the light chain variable region is set forth in SEQ ID NO:13. In some embodiments, the antibody is antibody H1K5, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:3 and a light chain variable region that has at least 80%, 85%, 90%, 95%, 96%, 96%, 97%, 98%, or 99% sequence identity, and/or has 100% identity, to the sequence set forth in SEQ ID NO:9. In some embodiments, the heavy chain variable region is set forth in SEQ ID NO:3 and the light chain variable region is set forth in SEQ ID NO:9. In some embodiments, the antibody is antibody H2K1, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:3 and a light chain variable region that has at least 80%, 85%, 90%, 95%, 96%, 96%, 97%, 98%, or 99% sequence identity, and/or has 100% identity, to the sequence set forth in SEQ ID NO:10. In some embodiments, the heavy chain variable region is set forth in SEQ ID NO:3 and the light chain variable region is set forth in SEQ ID NO:10. In some embodiments, the antibody is antibody H2K2, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:3 and a light chain variable region that has at least 80%, 85%, 90%, 95%, 96%, 96%, 97%, 98%, or 99% sequence identity, and/or has 100% identity, to the sequence set forth in SEQ ID NO:11. In some embodiments, the heavy chain variable region is set forth in SEQ ID NO:3 and the light chain variable region is set forth in SEQ ID NO:11. In some embodiments, the antibody is antibody H2K3, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:3 and a light chain variable region that has at least 80%, 85%, 90%, 95%, 96%, 96%, 97%, 98%, or 99% sequence identity, and/or has 100% identity, to the sequence set forth in SEQ ID NO:12. In some embodiments, the heavy chain variable region is set forth in SEQ ID NO:3 and the light chain variable region is set forth in SEQ ID NO:12. In some embodiments, the antibody is antibody H2K4, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:3 and a light chain variable region that has at least 80%, 85%, 90%, 95%, 96%, 96%, 97%, 98%, or 99% sequence identity, and/or has 100% identity, to the sequence set forth in SEQ ID NO:13. In some embodiments, the heavy chain variable region is set forth in SEQ ID NO:3 and the light chain variable region is set forth in SEQ ID NO:13. In some embodiments, the antibody is antibody H2K5, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:4 and a light chain variable region that has at least 80%, 85%, 90%, 95%, 96%, 96%, 97%, 98%, or 99% sequence identity, and/or has 100% identity, to the sequence set forth in SEQ ID NO:9. In some embodiments, the heavy chain variable region is set forth in SEQ ID NO:4 and the light chain variable region is set forth in SEQ ID NO:9. In some embodiments, the antibody is antibody H3K1, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:4 and a light chain variable region that has at least 80%, 85%, 90%, 95%, 96%, 96%, 97%, 98%, or 99% sequence identity, and/or has 100% identity, to the sequence set forth in SEQ ID NO:10. In some embodiments, the heavy chain variable region is set forth in SEQ ID NO:4 and the light chain variable region is set forth in SEQ ID NO:10. In some embodiments, the antibody is antibody H3K2, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:4 and a light chain variable region that has at least 80%, 85%, 90%, 95%, 96%, 96%, 97%, 98%, or 99% sequence identity, and/or has 100% identity, to the sequence set forth in SEQ ID NO:11. In some embodiments, the heavy chain variable region is set forth in SEQ ID NO:4 and the light chain variable region is set forth in SEQ ID NO:11. In some embodiments, the antibody is antibody H3K3, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:4 and a light chain variable region that has at least 80%, 85%, 90%, 95%, 96%, 96%, 97%, 98%, or 99% sequence identity, and/or has 100% identity, to the sequence set forth in SEQ ID NO:12. In some embodiments, the heavy chain variable region is set forth in SEQ ID NO:4 and the light chain variable region is set forth in SEQ ID NO:12. In some embodiments, the antibody is antibody H3K4, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:4 and a light chain variable region that has at least 80%, 85%, 90%, 95%, 96%, 96%, 97%, 98%, or 99% sequence identity to the sequence set forth in SEQ ID NO:13. In some embodiments, the heavy chain variable region is set forth in SEQ ID NO:4 and the light chain variable region is set forth in SEQ ID NO:13. In some embodiments, the antibody is antibody H3K5, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:5 and a light chain variable region that has at least 80%, 85%, 90%, 95%, 96%, 96%, 97%, 98%, or 99% sequence identity, and/or has 100% identity, to the sequence set forth in SEQ ID NO:9. In some embodiments, the heavy chain variable region is set forth in SEQ ID NO:5 and the light chain variable region is set forth in SEQ ID NO:9. In some embodiments, the antibody is antibody H4K1, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:5 and a light chain variable region that has at least 80%, 85%, 90%, 95%, 96%, 96%, 97%, 98%, or 99% sequence identity, and/or has 100% identity, to the sequence set forth in SEQ ID NO:10. In some embodiments, the heavy chain variable region is set forth in SEQ ID NO:5 and the light chain variable region is set forth in SEQ ID NO:10. In some embodiments, the antibody is antibody H4K2, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:5 and a light chain variable region that has at least 80%, 85%, 90%, 95%, 96%, 96%, 97%, 98%, or 99% sequence identity, and/or has 100% identity, to the sequence set forth in SEQ ID NO:11. In some embodiments, the heavy chain variable region is set forth in SEQ ID NO:5 and the light chain variable region is set forth in SEQ ID NO:11. In some embodiments, the antibody is antibody H4K3, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:5 and a light chain variable region that has at least 80%, 85%, 90%, 95%, 96%, 96%, 97%, 98%, or 99% sequence identity, and/or has 100% identity, to the sequence set forth in SEQ ID NO:12. In some embodiments, the heavy chain variable region is set forth in SEQ ID NO:5 and the light chain variable region is set forth in SEQ ID NO:12. In some embodiments, the antibody is antibody H4K4, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:5 and a light chain variable region that has at least 80%, 85%, 90%, 95%, 96%, 96%, 97%, 98%, or 99% sequence identity, and/or has 100% identity, to the sequence set forth in SEQ ID NO:13. In some embodiments, the heavy chain variable region is set forth in SEQ ID NO:5 and the light chain variable region is set forth in SEQ ID NO:13. In some embodiments, the antibody is antibody H4K5, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:6 and a light chain variable region that has at least 80%, 85%, 90%, 95%, 96%, 96%, 97%, 98%, or 99% sequence identity, and/or has 100% identity, to the sequence set forth in SEQ ID NO:9. In some embodiments, the heavy chain variable region is set forth in SEQ ID NO:6 and the light chain variable region is set forth in SEQ ID NO:9. In some embodiments, the antibody is antibody H5K1, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:6 and a light chain variable region that has at least 80%, 85%, 90%, 95%, 96%, 96%, 97%, 98%, or 99% sequence identity, and/or has 100% identity, to the sequence set forth in SEQ ID NO:10. In some embodiments, the heavy chain variable region is set forth in SEQ ID NO:6 and the light chain variable region is set forth in SEQ ID NO:10. In some embodiments, the antibody is antibody H5K2, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:6 and a light chain variable region that has at least 80%, 85%, 90%, 95%, 96%, 96%, 97%, 98%, or 99% sequence identity, and/or has 100% identity, to the sequence set forth in SEQ ID NO:11. In some embodiments, the heavy chain variable region is set forth in SEQ ID NO:6 and the light chain variable region is set forth in SEQ ID NO:11. In some embodiments, the antibody is antibody H5K3, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:6 and a light chain variable region that has at least 80%, 85%, 90%, 95%, 96%, 96%, 97%, 98%, or 99% sequence identity, and/or has 100% identity, to the sequence set forth in SEQ ID NO:12. In some embodiments, the heavy chain variable region is set forth in SEQ ID NO:6 and the light chain variable region is set forth in SEQ ID NO:12. In some embodiments, the antibody is antibody H5K4, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:6 and a light chain variable region that has at least 80%, 85%, 90%, 95%, 96%, 96%, 97%, 98%, or 99% sequence identity, and/or has 100% identity, to the sequence set forth in SEQ ID NO:13. In some embodiments, the heavy chain variable region is set forth in SEQ ID NO:6 and the light chain variable region is set forth in SEQ ID NO:13. In some embodiments, the antibody is antibody H5K5, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:7 and a light chain variable region that has at least 80%, 85%, 90%, 95%, 96%, 96%, 97%, 98%, or 99% sequence identity, and/or has 100% identity, to the sequence set forth in SEQ ID NO:9. In some embodiments, the heavy chain variable region is set forth in SEQ ID NO:7 and the light chain variable region is set forth in SEQ ID NO:9. In some embodiments, the antibody is antibody H6K1, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:7 and a light chain variable region that has at least 80%, 85%, 90%, 95%, 96%, 96%, 97%, 98%, or 99% sequence identity, and/or has 100% identity, to the sequence set forth in SEQ ID NO:10. In some embodiments, the heavy chain variable region is set forth in SEQ ID NO:7 and the light chain variable region is set forth in SEQ ID NO:10. In some embodiments, the antibody is antibody H6K2, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:7 and a light chain variable region that has at least 80%, 85%, 90%, 95%, 96%, 96%, 97%, 98%, or 99% sequence identity, and/or has 100% identity, to the sequence set forth in SEQ ID NO:11. In some embodiments, the heavy chain variable region is set forth in SEQ ID NO:7 and the light chain variable region is set forth in SEQ ID NO:11. In some embodiments, the antibody is antibody H6K3, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:7 and a light chain variable region that has at least 80%, 85%, 90%, 95%, 96%, 96%, 97%, 98%, or 99% sequence identity, and/or has 100% identity, to the sequence set forth in SEQ ID NO:12. In some embodiments, the heavy chain variable region is set forth in SEQ ID NO:7 and the light chain variable region is set forth in SEQ ID NO:12. In some embodiments, the antibody is antibody H6K4, such as a full-length humanized antibody or an antigen-binding fragment thereof.

In some embodiments, the binding polypeptide, such as an anti-EphA5 antibody or antigen-binding fragment, comprises a heavy chain variable region with an amino acid sequence that has at least 80%, 85%, 90%, 95%, 96%, 96%, 97%, 98%, or 99% sequence identity, and/or has 100% identity, to the sequence set forth in SEQ ID NO:7 and a light chain variable region that has at least 80%, 85%, 90%, 95%, 96%, 96%, 97%, 98%, or 99% sequence identity, and/or has 100% identity, to the sequence set forth in SEQ ID NO:13. In some embodiments, the heavy chain variable region is set forth in SEQ ID NO:7 and the light chain variable region is set forth in SEQ ID NO:13. In some embodiments, the antibody is antibody H6K5, such as a full-length humanized antibody or an antigen-binding fragment thereof.

Provided is an antibody comprising a heavy chain variable region comprising the amino acid sequence set forth in SEQ ID NO:5 and a light chain variable region comprising the amino acid sequence set forth in SEQ ID NO:11 (i.e., H4K3).

Provided is an antibody comprising a heavy chain variable region comprising the amino acid sequence set forth in SEQ ID NO:6 and a light chain variable region comprising the amino acid sequence set forth in SEQ ID NO:11 (i.e., H5K3).

An antibody of the invention can be prepared using an antibody having one or more of the VH and/or VL sequences disclosed herein as a starting material to engineer a modified antibody, which modified antibody may have altered properties as compared with the starting antibody. An antibody can be engineered by modifying one or more amino acids within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

In some embodiments, the binding polypeptide is an antibody or an antigen-binding fragment thereof.

Among the provided antibodies are antibody fragments. Examples of antibody fragments include but are not limited to Fv, Fab, Fab', Fab'-SH, F(ab')$_2$; diabodies; linear antibodies; heavy chain variable (VH) regions, single-chain antibody molecules such as scFvs and single-domain antibodies comprising only the VH region. In some embodiments, the antigen-binding fragment is selected from the group consisting of a Fab, a single-chain variable fragment (scFv), a single-domain antibody, and a nanobody. In further embodiments, the antibody is a full-length antibody. In provided embodiments, the antibody or antigen-binding fragment is a humanized antibody or an antigen-binding fragment thereof.

In some embodiments, the antibody or antigen-binding fragment thereof may contain at least a portion of an immunoglobulin constant region, such as one or more constant region domain. In some embodiments, the constant region of the heavy chain includes at least the heavy chain constant region 1 (CH1) and the constant region of the light chain includes the light chain constant region. In some embodiments, the constant region of the heavy chain further includes a hinge domain, a CH2 and/or CH3 domain. In some embodiments, the heavy chain constant domain is from a constant chain, or a portion thereof containing the CH1, hinge, CH2 and/or CH3, of a human IgG, such as a human IgG1 or IgG4. In some embodiments, the light chain constant domain is from a constant chain of a human kappa light or lambda light chain.

Among the provided antibodies are full-length antibodies containing a heavy chain with any one of the heavy chain variable regions provided herein combined with a human heavy chain constant region; and a light chain with any one of the light chain variable regions provided herein combined with a human light chain constant region. In some embodiments, the constant region of the heavy chain is a human IgG1 heavy chain constant region. In some embodiments, the heavy chain constant region is set forth in SEQ ID NO:14 or a sequence that has at least 85%, 86%, 87%, 88%, 89%, 90%, 91%, 92%, 93%, 94%, 95%, 96%, 97%, 98%, or 99% sequence identity to SEQ ID NO:14. In some embodiments, the heavy chain constant region is set forth in SEQ ID NO:14. In some embodiments, the constant region of the light chain is a human kappa light chain constant region. In some embodiments, the light chain constant region is set forth in SEQ ID NO:15 or a sequence that has at least 85%, 86%, 87%, 88%, 89%, 90%, 91%, 92%, 93%, 94%, 95%, 96%, 97%, 98%, or 99% sequence identity to SEQ ID NO:15. In some embodiments, the heavy chain constant region is set forth in SEQ ID NO:15. Any of the heavy chain variable regions provided herein may be combined with a suitable human constant region. Any of the light chain variable regions may be combined with a suitable human light chain constant region.

In some embodiments, provided herein is a full-length antibody (e.g., chimeric antibody) comprising a heavy chain comprising a heavy chain variable domain comprising the amino acid sequence set forth in SEQ ID NO:1 and a heavy chain constant domain comprising the amino acid sequence set forth in SEQ ID NO:14, and a light chain comprising a light chain variable domain comprising an amino acid sequence set forth in SEQ ID NOs:8 and a light chain constant domain comprising the amino acid sequence set forth in SEQ ID NO:15. In some embodiments, the full-length antibody is composed of a heavy chain comprising a heavy chain variable domain consisting of the amino acid sequence set forth in SEQ ID NO:1 and a heavy chain constant domain consisting of the amino acid sequence set forth in SEQ ID NO:14, and a light chain comprising a light chain variable domain consisting of the amino acid sequence set forth in any one of SEQ ID NO:8 and a light chain constant domain consisting of the amino acid sequence set forth in SEQ ID NO:15.

In some embodiments, provided herein is a full-length antibody (e.g., humanized antibody) comprising a heavy chain comprising a heavy chain variable domain comprising an amino acid sequence set forth in SEQ ID NOs:2, 3, 4, 5, 6, or 7 and a heavy chain constant domain comprising the amino acid sequence set forth in SEQ ID NO:14, and a light chain comprising a light chain variable domain comprising an amino acid sequence set forth in SEQ ID NOs:9, 10, 11, 12, or 13 and a light chain constant domain comprising the amino acid sequence set forth in SEQ ID NO:15.

In some embodiments, the full-length antibody is composed of a heavy chain comprising a heavy chain variable domain consisting of the amino acid sequence set forth in any one of SEQ ID NOs:2, 3, 4, 5, 6, or 7 and a heavy chain constant domain consisting of the amino acid sequence set forth in SEQ ID NO:14, and a light chain comprising a light chain variable domain consisting of the amino acid sequence set forth in any one of SEQ ID NOs:9, 10, 11, 12, or 13 and a light chain constant domain consisting of the amino acid sequence set forth in SEQ ID NO:15.

In some embodiments, provided herein is a full-length antibody comprising a heavy chain comprising the amino acid sequence set forth in SEQ ID NOs:38 or 39 and a light chain comprising the amino acid sequence set forth in SEQ ID NO:40.

In some embodiments, provided herein is a full-length antibody comprising a full-length heavy chain consisting of the amino acid sequence set forth in SEQ ID NOs:38 or 39 and a full-length light chain consisting of the amino acid sequence set forth in SEQ ID NO:40.

Tolerable variations of the full-length antibody sequences will be known to those of skill in the art. For example, in some embodiments the antibody comprises an amino acid sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NOs:38, 39, and 40.

In some embodiments, the provided anti-EpHA5 antibody is a full-length antibody composed of (i) a heavy chain comprising at least 85%, 90%, 91%, 92%, 93%, 94%, 95%, 96%, 97%, 98%, or 99% sequence identity, and/or 100% identity, to the amino acid sequence set forth in SEQ ID NOs:38; and (ii) a light chain comprising at least at or about 85%, 90%, 91%, 92%, 93%, 94%, 95%, 96%, 97%, 98%, or 99% sequence identity, and/or 100% identity, to the amino acid sequence set forth in SEQ ID NOs:40. In some embodiments, the variable region of the heavy chain comprises a HCDR1 comprising the amino acid sequence set forth in SEQ ID NO:16, a HCDR2 comprising the amino acid sequence set forth in SEQ ID NO:17, and a HCDR3 comprising the amino acid sequence set forth in SEQ ID NO:20; and the variable region of the light chain comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24.

Provided is an anti-EphA5 antibody comprising a full-length heavy chain comprising the amino acid sequence set forth in SEQ ID NO:38 and a full-length light chain comprising the amino acid sequence set forth in SEQ ID NO:40 (i.e., H4K3).

In some embodiments, the provided anti-EphA5 antibody is a full-length antibody composed of (i) a heavy chain comprising at least 85%, 90%, 91%, 92%, 93%, 94%, 95%, 96%, 97%, 98%, or 99% sequence identity, and/or 100% identity, to the amino acid sequence set forth in SEQ ID NOs:39; and (ii) a light chain comprising at least 85%, 90%, 91%, 92%, 93%, 94%, 95%, 96%, 97%, 98%, or 99% sequence identity, and/or 100% identity, to the amino acid sequence set forth in SEQ ID NOs:40. In some embodiments, the variable region of the heavy chain comprises a HCDR1 comprising the amino acid sequence set forth in SEQ ID NO:16, a HCDR2 comprising the amino acid sequence set forth in SEQ ID NO:18, and a HCDR3 comprising the amino acid sequence set forth in SEQ ID NO:20; and the variable region of the light chain comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24.

Also provided is an anti-EpHA5 antibody comprising a full-length heavy chain comprising the amino acid sequence set forth in SEQ ID NO:39 and a full-length light chain comprising the amino acid sequence set forth in SEQ ID NO:40 (i.e., H5K3).

In certain embodiments, the invention includes an antibody that binds to the same epitope on human EPH receptor A5 as an antibody of the invention (i.e., antibodies that have the ability to cross-compete for binding to human EPH receptor A5 with any of the antibodies of the invention). In a preferred embodiment, the reference antibody or antibody fragment for cross-competition studies can be one of the antibodies or antibody fragments described herein, as comparisons are made using equivalent molecules (e.g., a Fab to a Fab, full-length antibody to a full-length antibody, etc.). For example, Biacore analysis, ELISA assays or flow cytometry may be used to demonstrate cross-competition with the antibodies of the current invention. The ability of a test antibody to inhibit the binding of, for example H4K3 or H5K3, to human EPH receptor A5 demonstrates that the test antibody can compete with H4K3 or H5K3 for binding to human EPH receptor A5 and thus is considered to bind to the same epitope of human EPH receptor A5 as H4K3 or H5K3.

In some embodiments, any one of the provided anti-EphA5 antibodies are isolated, purified or semi-purified such that they retain specificity in the desired application. Proteins may be recombinant, or synthesized in vitro, although in most embodiments, the proteins are recombinant. Alternatively, a non-recombinant or recombinant protein may be isolated from bacteria.

TABLE 1

Sequences used in the invention

| SEQ ID NO: | Name | Type | Sequence |
|---|---|---|---|
| 1 | Chimeric VH0 Variable Heavy Chain | PRT | EVTLKESGGGLVQPGGSRKLSCAASGFTFSTFGIHWVRQAPE KGLEWVAYISGASTTIYYADTVKGRFTISRDNPKNTLFLQMT SLRSEDTAMYYCARYGTSFPYGLDYWGQGTSVTVSS |
| 2 | VH1 Variable Heavy Chain | PRT | EVTLVESGGGLVQPGGSRKLSCAASGFTFSTFGIHWVRQAP GKGLEWVAYISGASTTIYYADTVKGRFTISRDNSKNTLYLQ MNSLRSEDTAMYYCARYGTSFPYGLDYWGQGTSVTVSS |
| 3 | VH2 Variable Heavy Chain | PRT | EVTLVESGGGLVQPGGSLKLSCAASGFTFSTFGIHWVRQAPG KGLEWVAYISGASTTIYYADTVKGRFTISRDNSKNTLYLQM NSLRSEDTAMYYCARYGTSFPYGLDYWGQGTLVTVSS |
| 4 | VH3 Variable Heavy Chain | PRT | EVQLVESGGGLVQPGGSLKLSCAASGFTFSTFGIHWVRQAP GKGLEWVAYISGASTTIYYADTVKGRFTISRDNSKNTLYLQ MNSLRSEDTAMYYCARYGTSFPYGLDYWGQGTLVTVSS |
| 5 | VH4 Variable Heavy Chain | PRT | EVQLVESGGGLVQPGGSLKLSCAASGFTFSTFGIHWVRQAP GKGLEWVAYISGASTTIYYADTVKGRFTISRDNSKNTLYLQ MNSLRAEDTAVYYCARYGTSFPYGLDYWGQGTLVTVSS |
| 6 | VH5 Variable Heavy Chain | PRT | EVQLVESGGGLVQPGGSLKLSCAASGFTFSTFGIHWVRQAP GKGLEWVAYISGASTTIYYADSVKGRFTISRDNSKNTLYLQ MNSLRAEDTAVYYCARYGTSFPYGLDYWGQGTLVTVSS |
| 7 | VH6 Variable Heavy Chain | PRT | EVQLVESGGGLVQPGGSLKLSCAASGFTFSTFGIHWVRQAP GKGLEWVASISGASTTIYYADSVKGRFTISRDNSKNTLYLQM NSLRAEDTAVYYCARYGTSFPYGLDYWGQGTLVTVSS |
| 8 | Chimeric VK0 Variable Light Chain | PRT | DIVMTQSPGSLAVSLGQRATISCKASQSVDYDGDSYMNWY QQKPGQPPKLLIYGASNLESGIPARFSGSGSGTDFTLNIHPVE EEDAASYYCQQSNEDPFTFGSGTKLEIK |
| 9 | VK1 Variable Light Chain | PRT | DIVMTQSPGSLAVSLGERATINCKASQSVDYDGDSYMNWY QQKPGKAPKLLIYGASNLESGIPDRFSGSGSGTDFTLTISRLE EEDAASYYCQQSNEDPFTFGQGTKLEIK |
| 10 | VK2 Variable Light Chain | PRT | DIVMTQSPDSLAVSLGERATINCKASQSVDYDGDSYMNWY QQKPGKAPKLLIYGASNLESGIPDRFSGSGSGTDFTLTISRLEP EDAASYYCQQSNEDPFTFGQGTKLEIK |
| 11 | VK3 Variable Light Chain | PRT | DIVMTQSPDSLAVSLGERATINCKASQSVDYDGDSYMNWY QQKPGKAPKLLIYGASNLESGIPDRFSGSGSGTDFTLTISRLEP EDAAVYYCQQSNEDPFTFGQGTKLEIK |
| 12 | VK4 Variable Light Chain | PRT | DIVMTQSPDSLAVSLGERATINCKSSQSVDYDGDSYMNWYQ QKPGKAPKLLIYGASNLESGIPDRFSGSGSGTDFTLTISRLEPE DAASYYCQQSNEDPFTFGQGTKLEIK |
| 13 | VK5 Variable Light Chain | PRT | DIVMTQSPDSLAVSLGERATINCKSSQSVDYDGDSYMNWYQ QKPGKAPKLLIYGASNLESGIPDRFSGSGSGTDFTLTISRLEPE DAAVYYCQQSNEDPFTFGQGTKLEIK |
| 14 | Heavy Chain Constant Domain | PRT | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKRVEPKSCDKTHTCPPCPAPELLGGPSVFLFP PKPKDTLMISRTPEVTCVVVDVSHEDPEVKFNWYVDGVEV HNAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLYS KLTVDKSRWQQGNVFSCSVMHEALHNHYTQKSLSLSPGK |
| 15 | Light Chain Constant Domain | PRT | RTVAAPSVFIFPPSDEQLKSGTASVVCLLNNFYPREAKVQWK VDNALQSGNSQESVTEQDSKDSTYSLSSTLTLSKADYEKHK VYACEVTHQGLSSPVTKSFNRGEC |
| 16 | VH0-6 CDR1 | PRT | TFGIH |
| 17 | VH0-4 CDR2 | PRT | YISGASTTIYYADTVKG |

TABLE 1-continued

Sequences used in the invention

| SEQ ID NO: | Name | Type | Sequence |
|---|---|---|---|
| 18 | VH5 CDR2 | PRT | YISGASTTIYYADSVKG |
| 19 | VH6 CDR2 | PRT | SISGASTTIYYADSVKG |
| 20 | VH0-6 CDR3 | PRT | YGTSFPYGLDY |
| 21 | VK0-3 CDR1 | PRT | KASQSVDYDGDSYMN |
| 22 | VK4-5 CDR1 | PRT | KSSQSVDYDGDSYMN |
| 23 | VK0-5 CDR2 | PRT | GASNLES |
| 24 | VK0-5 CDR3 | PRT | QQSNEDPFT |
| 25 | VH0 Variable heavy chain | DNA | GAAGTGACCCTGAAAGAGTCTGGCGGAGGACTGGTTCAG CCTGGCGGATCTAGAAAGCTGTCTTGTGCCGCCTCCGGCT TCACCTTCTCTACCTTTGGCATCCACTGGGTCCGACAGGC CCCTGAGAAAGGATTGGAGTGGGTCGCCTACATCTCCGGC GCTTCCACCACCATCTACTACGCCGATACCGTGAAGGGCA GATTCACCATCAGCCGGGACAACCCCAAGAACACCCTGTT TCTGCAGATGACCAGCCTGCGGAGCGAGGACACCGCCAT GTACTACTGTGCCAGATACGGCACCAGCTTTCCCTACGGC CTGGATTATTGGGGCCAGGGAACCTCCGTTACAGTCTCCT CA |
| 26 | VH1 Variable heavy chain | DNA | GAAGTGACCCTGGTTGAATCTGGCGGAGGACTGGTTCAG CCTGGCGGCTCTAGAAAGCTGTCTTGTGCCGCCTCTGGCT TCACCTTCTCCACCTTTGGCATCCACTGGGTCCGACAGGC CCCTGGCAAAGGATTGGAGTGGGTCGCCTATATCTCCGGC GCCTCCACCACCATCTACTACGCCGATACCGTGAAGGGCA GATTCACCATCAGCCGGGACAACTCCAAGAACACCCTGT ACCTGCAGATGAACTCCCTGCGGAGCGAGGACACCGCCA TGTACTACTGTGCCAGATACGGCACCAGCTTTCCCTACGG CCTGGATTATTGGGGCCAGGGAACCTCCGTTACAGTCTCC TCA |
| 27 | VH2 Variable heavy chain | DNA | GAAGTGACCCTGGTTGAATCTGGCGGAGGACTGGTTCAG CCTGGCGGATCTCTGAAGCTGTCTTGTGCCGCCTCTGGCT TCACCTTCTCCACCTTTGGCATCCACTGGGTCCGACAGGC CCCTGGCAAAGGATTGGAGTGGGTCGCCTATATCTCCGGC GCCTCCACCACCATCTACTACGCCGATACCGTGAAGGGCA GATTCACCATCAGCCGGGACAACTCCAAGAACACCCTGT ACCTGCAGATGAACTCCCTGCGGAGCGAGGACACCGCCA TGTACTACTGTGCCAGATACGGCACCAGCTTTCCCTACGG CCTGGATTATTGGGGCCAGGGAACCCTGGTTACAGTCTCC TCA |
| 28 | VH3 Variable heavy chain | DNA | GAAGTGCAGCTGGTTGAATCTGGCGGAGGACTGGTTCAG CCTGGCGGATCTCTGAAGCTGTCTTGTGCCGCCTCTGGCT TCACCTTCTCCACCTTTGGCATCCACTGGGTCCGACAGGC CCCTGGCAAAGGATTGGAGTGGGTCGCCTATATCTCCGGC GCCTCCACCACCATCTACTACGCCGATACCGTGAAGGGCA GATTCACCATCAGCCGGGACAACTCCAAGAACACCCTGT ACCTGCAGATGAACTCCCTGCGGAGCGAGGACACCGCCA TGTACTACTGTGCCAGATACGGCACCAGCTTTCCCTACGG CCTGGATTATTGGGGCCAGGGAACCCTGGTTACAGTCTCC TCA |
| 29 | VH4 Variable heavy chain | DNA | GAAGTGCAGCTGGTTGAATCTGGCGGAGGACTGGTTCAG CCTGGCGGATCTCTGAAGCTGTCTTGTGCCGCCTCTGGCT TCACCTTCTCCACCTTTGGCATCCACTGGGTCCGACAGGC CCCTGGCAAAGGATTGGAGTGGGTCGCCTATATCTCCGGC GCCTCCACCACCATCTACTACGCCGATACCGTGAAGGGCA GATTCACCATCAGCCGGGACAACTCCAAGAACACCCTGT ACCTGCAGATGAACTCCCTGAGAGCCGAGGACACCGCCG TGTACTACTGTGCCAGATACGGCACCAGCTTTCCCTACGG CCTGGATTATTGGGGCCAGGGAACCCTGGTTACAGTCTCC TCA |
| 30 | VH5 Variable heavy chain | DNA | GAAGTGCAGCTGGTTGAATCTGGCGGAGGACTGGTTCAG CCTGGCGGATCTCTGAAGCTGTCTTGTGCCGCCTCTGGCT TCACCTTCTCCACCTTTGGCATCCACTGGGTCCGACAGGC CCCTGGCAAAGGATTGGAGTGGGTCGCCTATATCTCCGGC GCCTCCACCACCATCTACTACGCCGATTCTGTGAAGGGCA GATTCACCATCAGCCGGGACAACTCCAAGAACACCCTGT ACCTGCAGATGAACTCCCTGAGAGCCGAGGACACCGCCG |

TABLE 1-continued

Sequences used in the invention

| SEQ ID NO: | Name | Type | Sequence |
|---|---|---|---|
| | | | TGTACTACTGTGCCAGATACGGCACCAGCTTTCCCTACGG CCTGGATTATTGGGGCCAGGGAACCCTGGTTACAGTCTCC TCA |
| 31 | VH6 Variable heavy chain | DNA | GAAGTGCAGCTGGTTGAATCTGGCGGAGGACTGGTTCAG CCTGGCGGATCTCTGAAGCTGTCTTGTGCCGCCTCTGGCT TCACCTTCTCCACCTTTGGCATCCACTGGGTCCGACAGGC CCCTGGCAAAGGATTGGAATGGGTCGCCTCTATCTCCGGC GCCTCCACCACCATCTACTACGCCGATTCTGTGAAGGGCA GATTCACCATCAGCCGGGACAACTCCAAGAACACCCTGT ACCTGCAGATGAACTCCCTGAGAGCCGAGGACACCGCCG TGTACTACTGTGCCAGATACGGCACCAGCTTTCCCTACGG CCTGGATTATTGGGGCCAGGGAACCCTGGTTACAGTCTCC TCA |
| 32 | VK0 Variable light chain | DNA | GACATCGTGATGACACAGTCTCCAGGCAGCCTGGCTGTGT CCTTGGGACAGAGAGCTACCATCTCCTGCAAGGCCTCTCA GTCCGTGGACTACGACGGCGACTCCTACATGAACTGGTAT CAGCAGAAGCCCGGCCAGCCTCCTAAGCTGTTGATCTACG GCGCCTCCAACCTGGAAAGCGGCATCCCTGCTAGATTCTC CGGCTCTGGCTCTGGCACCGACTTCACCCTGAACATCCAT CCTGTGGAAGAAGAGGACGCCGCCTCCTACTACTGCCAG CAGTCTAACGAGGACCCCTTCACCTTCGGCTCCGGCACAA AATTGGAGATCAAA |
| 33 | VK1 Variable light chain | DNA | GACATCGTGATGACACAGTCTCCAGGCAGCCTGGCTGTGT CTCTGGGAGAGAGAGCCACCATCAACTGCAAGGCCTCTC AGTCCGTGGACTACGACGGCGACTCCTACATGAACTGGTA TCAGCAGAAGCCCGGCAAGGCCCCTAAGCTGTTGATCTAC GGCGCCTCCAACCTGGAAAGCGGCATCCCTGATAGATTCT CCGGCTCTGGCTCTGGCACCGACTTCACCCTGACCATCTC TCGGCTGGAAGAGGAAGATGCCGCCTCCTACTACTGCCA GCAGTCCAACGAGGACCCCTTCACCTTTGGCCAGGGCACA AAGTTGGAGATCAAA |
| 34 | VK2 Variable light chain | DNA | GACATCGTGATGACCCAGTCTCCAGACAGCCTGGCTGTGT CTCTGGGCGAGAGAGCCACCATCAACTGCAAGGCCTCTC AGTCCGTGGACTACGACGGCGACTCCTACATGAACTGGTA TCAGCAGAAGCCCGGCAAGGCCCCTAAGCTGTTGATCTAC GGCGCCTCCAACCTGGAAAGCGGCATCCCTGATAGATTCT CCGGCTCTGGCTCTGGCACCGACTTCACCCTGACCATCTC CAGACTGGAACCTGAGGACGCCGCCTCCTACTACTGCCAG CAGTCTAACGAGGACCCCTTCACCTTTGGCCAGGGCACAA AGTTGGAGATCAAA |
| 35 | VK3 Variable light chain | DNA | GACATCGTGATGACCCAGTCTCCAGACAGCCTGGCTGTGT CTCTGGGCGAGAGAGCCACCATCAACTGCAAGGCCTCTC AGTCCGTGGACTACGACGGCGACTCCTACATGAACTGGTA TCAGCAGAAGCCCGGCAAGGCCCCTAAGCTGTTGATCTAC GGCGCCTCCAACCTGGAAAGCGGCATCCCTGATAGATTCT CCGGCTCTGGCTCTGGCACCGACTTCACCCTGACCATCTC CAGACTGGAACCTGAGGATGCCGCCGTGTACTACTGCCA GCAGTCTAACGAGGACCCCTTCACCTTTGGCCAGGGCACA AAGTTGGAGATCAAA |
| 36 | VK4 Variable light chain | DNA | GACATCGTGATGACCCAGTCTCCAGACAGCCTGGCTGTGT CTCTGGGCGAGAGAGCCACCATCAACTGCAAGTCCTCTCA GTCCGTGGACTACGACGGCGACTCCTACATGAACTGGTAT CAGCAGAAGCCCGGCAAGGCCCCTAAGCTGTTGATCTAC GGCGCCTCCAACCTGGAAAGCGGCATCCCTGATAGATTCT CCGGCTCTGGCTCTGGCACCGACTTCACCCTGACCATCTC CAGACTGGAACCTGAGGACGCCGCCTCCTACTACTGCCAG CAGTCTAACGAGGACCCCTTCACCTTTGGCCAGGGCACAA AGTTGGAGATCAAA |
| 37 | VK5 Variable light chain | DNA | GACATCGTGATGACCCAGTCTCCAGACAGCCTGGCTGTGT CTCTGGGCGAGAGAGCCACCATCAACTGCAAGTCCTCTCA GTCCGTGGACTACGACGGCGACTCCTACATGAACTGGTAT CAGCAGAAGCCCGGCAAGGCCCCTAAGCTGTTGATCTAC GGCGCCTCCAACCTGGAAAGCGGCATCCCTGATAGATTCT CCGGCTCTGGCTCTGGCACCGACTTCACCCTGACCATCTC CAGACTGGAACCTGAGGATGCCGCCGTGTACTACTGCCA GCAGTCTAACGAGGACCCCTTCACCTTTGGCCAGGGCACA AAGTTGGAGATCAAA |

TABLE 1-continued

| | | | Sequences used in the invention |
|---|---|---|---|
| SEQ ID NO: | Name | Type | Sequence |
| 38 | VH4 Full-length heavy chain | PRT | EVQLVESGGGLVQPGGSLKLSCAASGFTFSTFGIHWVRQAP GKGLEWVAYISGASTTIYYADTVKGRFTISRDNSKNTLYLQ MNSLRAEDTAVYYCARYGTSFPYGLDYWGQGTLVTVSSAS TKGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSREEMTKNQVSLTC LVKGFYPSDIAVEWESNGQPENNYKTTPPVLDSDGSFFLYSK LTVDKSRWQQGNVFSCSVMHEALHNHYTQKSLSLSPGK |
| 39 | VH5 Full-length heavy chain | PRT | EVQLVESGGGLVQPGGSLKLSCAASGFTFSTFGIHWVRQAP GKGLEWVAYISGASTTIYYADSVKGRFTISRDNSKNTLYLQ MNSLRAEDTAVYYCARYGTSFPYGLDYWGQGTLVTVSS ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKRVEPKSCDKTHTCPPCPAPELLGGPSVFLFP PKPKDTLMISRTPEVTCVVVDVSHEDPEVKFNWYVDGVEV HNAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLYS KLTVDKSRWQQGNVFSCSVMHEALHNHYTQKSLSLSPGK |
| 40 | VK3 Full-length light chain | PRT | DIVMTQSPDSLAVSLGERATINCKASQSVDYDGDSYMNWY QQKPGKAPKLLIYGASNLESGIPDRFSGSGSGTDFTLTISRLEP EDAAVYYCQQSNEDPFTFGQGTKLEIKRTVAAPSVFIFPPSD EQLKSGTASVVCLLNNFYPREAKVQWKVDNALQSGNSQES VTEQDSKDSTYSLSSTLTLSKADYEKHKVYACEVTHQGLSS PVTKSFNRGEC |
| 41 | Human EPH receptor A5 protein | PRT | MRGSGPRGAGRRRPPSGGGDTPITPASLAGCYSAPRRAPLW TCLLLCAALRTLLASPSNEVNLLDSRTVMGDLGWIAFPKNG WEEIGEVDENYAPIHTYQVCKVMEQNQNNWLLTSWISN EGASRIFIELKFTLRDCNSLPGGLGTCKETFNMYYFESDDQN GRNIKENQYIKIDTIAADESFTELDLGDRVMKLNTEVRDVGP LSKKGFYLAFQDVGACIALVSVRVYYKKCPSVVRHLAVFPD TITGADSSQLLEVSGSCVNHSVTDEPPKMHCSAEGEWLVPIG KCMCKAGYEEKNGTCQVCRPGFFKASPHIQSCGKCPPHSYT HEEASTSCVCEKDYFRRESDPPTMACTRPPSAPRNAISNVNE TSVFLEWIPPADTGGRKDVSYYIACKKCNSHAGVCEECGGH VRYLPRQSGLKNTSVMMVDLLAHTNYTFEIEAVNGVSDLSP GARQYVSVNVTTNQAAPSPVTNVKKGKIAKNSISLSWQEPD RPNGIILEYEIKYFEKDQETSYTIIKSKETTITAEGLKPASVYV FQIRARTAAGYGVFSRRFEFETTPVFAASSDQSQIPVIAVSVT VGVILLAVVIGVLLSGSCCECGCGRASSLCAVAHPSLIWRCG YSKAKQDPEEEKMHFHNGHIKLPGVRTYIDPHTYEDPNQAV HEFAKEIEASCITIERVIGAGEFGEVCSGRLKLPGKRELPVAIK TLKVGYTEKQRRDFLGEASIMGQFDHPNIIHLEGVVTKSKPV MIVTEYMENGSLDTFLKKNDGQFTVIQLVGMLRGISAGMKY LSDMGYVHRDLAARNILINSNLVCKVSDFGLSRVLEDDPEA AYTTRGGKIPIRWTAPEAIAFRKFTSASDVWSYGIVMWEVV SYGERPYWEMTNQDVIKAVEEGYRLPSPMDCPAALYQLML DCWQKERNSRPKFDEIVNMLDKLIRNPSSLKTLVNASCRVS NLLAEHSPLGSGAYRSVGEWLEAIKMGRYTEIFMENGYSSM DAVAQVTLEDLRRLGVTLVGHQKKIMNSLQEMKVQLVNG MVPL |
| 42 | VH0-6 CDR1 | PRT | GFTFSTFGIH |

Exemplary Features

The binding polypeptides, including antibodies and antigen-binding fragments thereof, of the invention are characterized by particular functional features or properties of the antibodies.

In some embodiments, the antibodies or antigen-binding fragments thereof specifically bind to EphA5 protein. In some embodiments, the antibodies or antigen-binding fragments thereof specifically bind to human EphA5. The observation that an antibody or other binding molecule binds to EphA5 protein or specifically binds to EphA5 protein does not necessarily mean that it binds to an EphA5 protein of every species. For example, in some embodiments, features of binding to EphA5 protein, such as the ability to specifically bind thereto and/or to bind with a particular affinity to a particular degree, in some embodiments, refers to the ability with respect to a human EphA5 protein and the antibody may not have this feature with respect to a EphA5 protein of another species, such as mouse.

In some embodiments, the antibodies specifically bind to human EphA5 protein, such as to an epitope or region of human EphA5 protein, such as the human BCMA protein comprising the amino acid sequence of SEQ ID NO:41 (NCBI No. NP_004430.4) or an allelic variant or splice variant thereof.

In some embodiments, the antibodies or antigen-binding fragment thereof, binds, e.g., specifically binds, and/or recognizes, one or more epitopes in EphA5, e.g., human EphA5. In some embodiments, the epitopes are epitopes present on the extracellular domain of EphA5, e.g., human EphA5. In some embodiments, the epitopes include peptide epitopes. In some embodiments, the epitope includes linear epitopes or conformational epitopes or combination thereof.

In some embodiments, the epitope recognized by a provided antibody includes an epitope containing amino acid residues R306, F309, K321, T328, and H329, with reference to numbering of SEQ ID NO:41. In some embodiments, the epitope recognized by a provided antibody includes an epitope containing amino acid residues R306, G308, F309, K321, T328, and H329, with reference to numbering of SEQ ID NO:41. In some embodiments, the epitope recognized by a provided antibody includes an epitope containing amino acid residues R306, G308, F309, K321, T328, H329 and E330, with reference to numbering of SEQ ID NO:41. In some embodiments, the epitope recognized by a provided antibody includes an epitope containing amino acid residues R306, G308, F309, K321, Y327, T328, H329 and E330, with reference to numbering of SEQ ID NO:41. In some embodiments, the epitope is a contiguous sequence of amino acids including the above amino acid residues. In some embodiments, a provided antibody or antigen-binding fragment does not bind to an epitope that includes amino acid residues R413, R417 and/or D430.

In provided embodiment, the extent of binding of an anti-EphA5 antibody to an unrelated, non-EphA5 protein, such as a non-human EphA5 protein or other non-EphA5 protein, is less than at or about 10% of the binding of the antibody to human EphA5 protein as measured, e.g., by a radioimmunoassay (RIA).

In some embodiments, the provided antibodies are capable of binding EphA5 protein, such as human EphA5 protein or other EphA5 protein containing an epitope recognized by a provided antibody, with at least a certain affinity, as measured by any of a number of known methods. In some embodiments, the affinity is represented by an equilibrium dissociation constant ($K_D$); in some embodiments, the affinity is represented by $EC_{50}$.

A variety of assays are known for assessing binding affinity and/or determining whether a binding molecule (e.g., an antibody or fragment thereof) specifically binds to a particular ligand (e.g., an antigen, such as a EphA5 protein). It is within the level of a skilled artisan to determine the binding affinity of a binding molecule, e.g., an antibody, for an antigen, e.g., EphA5, such as human EphA5, such as by using any of a number of binding assays that are well known in the art. For example, in some embodiments, a BIAcore® instrument can be used to determine the binding kinetics and constants of a complex between two proteins (e.g., an antibody or fragment thereof, and an antigen, such as a EphA5 protein), using surface plasmon resonance (SPR) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283, 173, 5,468,614, or the equivalent).

SPR measures changes in the concentration of molecules at a sensor surface as molecules bind to or dissociate from the surface. The change in the SPR signal is directly proportional to the change in mass concentration close to the surface, thereby allowing measurement of binding kinetics between two molecules. The dissociation constant for the complex can be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy, flow cytometry, sequencing and other methods for detection of expressed nucleic acids or binding of proteins.

In some embodiments, the binding molecule, e.g., antibody or fragment thereof, binds, such as specifically binds, to an antigen, e.g., a EphA5 protein or an epitope therein, with a binding affinity with a $K_A$ (i.e., an equilibrium association constant of a particular binding interaction with units of 1/M; equal to the ratio of the on-rate [$k_{on}$ or $k_a$] to the off-rate [$k_{off}$ or $k_d$] for this association reaction, assuming bimolecular interaction) equal to or greater than $10^5$ $M^{-1}$. In some embodiments, the antibody or fragment thereof binds, such as specifically binds, to an antigen, e.g., a EphA5 protein or an epitope therein, with a binding affinity with a $K_D$ (i.e., an equilibrium dissociation constant of a particular binding interaction with units of M; equal to the ratio of the off-rate [$k_{off}$ or $k_d$] to the on-rate [$k_{on}$ or $k_d$] for this association reaction, assuming bimolecular interaction) of equal to or less than $10^{-5}$ M. For example, the equilibrium dissociation constant $K_D$ ranges from $10^{-5}$ M to $10^{-13}$ M, such as $10^{-7}$ M to $10^{-11}$ M, $10^{-8}$ M to $10^{-10}$ M, or $10^{-9}$ M to $10^{-10}$ M. The on-rate (association rate constant; $k_{on}$ or $k_a$; units of 1/s) and the off-rate (dissociation rate constant; $k_{off}$ or $k_d$; units of 1/s) can be determined using any of the assay methods known in the art, for example, surface plasmon resonance (SPR).

In some embodiments, the binding molecule, e.g., antibody or fragment thereof, binds, such as specifically binds, to an antigen, e.g., an EphA5 protein or an epitope therein, with a $K_D$ of $1.3 \times 10^{-9}$ M or less. In some embodiments, the dissociation constant ($K_D$) for binding to human EpHA5 is less than $1.25 \times 10^{-9}$ M. In some embodiments, the $K_D$ is at or about $1.2 \times 10^{-9}$ M, $1.1 \times 10^{-9}$ M, $1.0 \times 10^{-9}$ M, $9.5 \times 10^{-10}$ M, $9.0 \times 10^{-10}$ M or $8.5 \times 10^{-10}$ M, including any values between any of the foregoing. In some embodiments, the dissociation constant ($K_D$) for binding to human EpHA5 is between $8 \times 10^{-10}$ M and $1.1 \times 10^{-9}$ M. In some embodiments, the $K_D$ is at or about 1.0 nM±0.1 nM. In particular embodiments, binding affinity is determined using a BIAcore® instrument.

In some embodiments, properties or features of the provided antibodies (e.g., antigen-binding fragments) are described in relation to properties observed for another antibody, e.g., a reference antibody. In some embodiments, the reference antibody is a non-human anti-EphA5 antibody, such as a murine anti-EphA5 antibody. In some aspects, the reference antibody is the murine antibody designated 11C12, and/or a fragment derived therefrom such as an scFv fragment thereof, and/or an antibody containing the $V_H$ and $V_L$ regions of such an antibody and/or the heavy and light chain CDRs of such an antibody. For example, in some embodiments, the reference antibody has a $V_H$ region containing the amino acid sequence set forth in SEQ ID NO:1 and a $V_L$ region containing the amino acid sequence set forth in SEQ ID NO:8. In some embodiments, the reference antibody may be a fully murine anti-EphA5 antibody further containing a murine constant domain. In some embodiments, the reference antibody may be a chimeric antibody that contains a heavy chain comprising a murine $V_H$ region containing the amino acid sequence set forth in SEQ ID NO:1 and a heavy chain constant domain set forth in SEQ ID NO:14, and a light chain comprising a light chain variable domain containing the amino acid sequence set forth in SEQ ID NO:8 and a light chain constant domain consisting of the amino acid sequence set forth in SEQ ID NO:15. Typically, it is understood that comparison of binding or other feature or property of a provided antibody to the reference antibody is to the corresponding form or same form of the reference antibody. A "corresponding form" of an antibody means that when comparing a property or activity of two antibodies, the property is compared using the same form (e.g., full-length or Fab or other antigen-binding fragment form) of the antibody. Hence, reference to "corresponding form" and "same form" herein are used interchangeably. For example, if it is stated that an antibody has greater activity compared to the activity of the corresponding form of a first antibody (e.g., reference antibody), that means that a particular form, such as a Fab of that antibody, has greater activity compared to the Fab form of the first antibody.

In some embodiments, among the provided antibodies, such as full length antibodies or antigen-binding fragments thereof, are antibodies in which the dissociation constant ($K_D$) for binding to human EphA5 is more than 1.2 fold better (e.g., lower $K_D$) than the reference antibody (e.g., 11C12, such as an antibody containing the $V_H$ and $V_L$ set forth in SEQ ID NOS:1 and 8, respectively). In some embodiments, the $K_D$ for binding to human EphA5 is at or about 1.2-fold, 1.3-fold, 1.4-fold, 1.5-fold, 1.6-fold, 1.7-fold, 1.8-fold, 1.9-fold, 2.0-fold or better (e.g., lower $K_D$) than the reference antibody.

Among the provided antibodies (e.g., antigen-binding fragments) are those that compete for binding with and/or bind to the same or overlapping epitopes of EphA5 protein as those bound by the reference antibody described herein but contain a distinct $V_H$ and $V_L$ region. In some embodiments, among provided antibodies are antibodies that contain distinct set of CDRs, e.g., distinct heavy and light chain CDR1, CDR2, and CDR3.

In some embodiments, the provided binding molecules, such as antibodies or antigen-binding fragments thereof, bind to cell surface EphA5, such as an EphA5 that is a transmembrane protein expressed on the outer membrane of the cell. In some embodiments, the provided binding molecules, such as antibodies or antigen-binding fragments thereof, display a binding preference for EphA5-expressing cells as compared to EphA5-negative cells, such as particular cells known and/or described herein to express EphA5 and known not to express EphA5. The EphA5 expressing cell may be a primary cell or a cell line. An exemplary EphA5 (e.g., human EphA5) expressing cell is the H460 cell line. In some embodiments, the binding preference is observed where a significantly greater degree of binding is measured to the EphA5-expressing, as compared to the non-expressing cells. In some embodiments, the fold change in degree of binding (e.g., EC50) detected, for example, as measured by mean fluorescence intensity in a flow cytometry-based assay and/or dissociation constant or $EC_{50}$, to the EphA5-expressing cells as compared to the non-EphA5-expressing cells, is at least 1.5, 2, 3, 4, 5, 6, or more, and/or is about as great, about the same, at least as great or about as great, or greater, than the fold change observed for the corresponding form of the reference antibody. In some cases, the total degree of observed binding to EphA5 or to the EphA5-expressing cells is approximately the same, at least as great as, or greater than that observed for the corresponding form of the reference antibody In some embodiments, the provided binding molecules, such as antibodies or antigen-binding fragments, are capable of being internalized by the cell into which it binds, such as an EphA5-expressing cell. Hence, a provided binding molecule, such as a provided antibody or antigen-binding fragment thereof, is capable of being taken through the cell's lipid bilayer membrane to an internal compartment (i.e., "internalized") upon binding to the cell. For example, an internalizing anti-EphA5 antibody is one that is capable of being taken into the cell after binding to EphA5 on the cell membrane.

In some embodiments, the binding molecule, such as a provided antibody or antigen-binding fragment thereof, when administered to a subject (e.g., alone or as a conjugate) results in a treatment that does not induce an immune response by the subject to the therapy, and/or does not induce such a response to a degree that prevents effective treatment of the disease or condition. In some aspects, the degree of immunogenicity and/or graft versus host response is less than that observed with a different but comparable treatment, such as binding molecule containing the reference antibody (e.g., 11C12, such as an antibody containing the $V_H$ and $V_L$ set forth in SEQ ID NOS:1 and 8, respectively). For example, in the case of an antibody drug conjugate (ADC) including the provided anti-EphA5 antibodies, the degree of immunogenicity is reduced compared to a similar ADC including a different antibody that binds to a similar, e.g., overlapping epitope and/or that competes for binding to EphA5 with the provided antibody, such as a mouse antibody. For instance, in provided embodiments, the degree of immunogenicity of an ADC containing a provided anti-EphA5 antibody is reduced compared to similar ADC but that contains a reference antibody (e.g., 11C12, such as an antibody containing the $V_H$ and $V_L$ set forth in SEQ ID NOS:1 and 8, respectively).

In some embodiments, a provided binding molecule, such as an antibody or antigen-binding fragment, exhibits features that favor stability of the antibody or binding fragment thereof. In some embodiments, the stability of a provided binding molecule, e.g., antibody or antigen-binding fragment, is evidenced by its thermal stability. Detection of thermal stability of a protein can be used to determine the denaturation effectively and thus is used as a stability test for protein during the development of therapeutic proteins. A skilled artisan is familiar with assays to assess thermal stability of a protein. In some embodiments, a provided binding molecule, such as an antibody or antigen-binding fragment thereof, has high thermal stability and therefore is less prone to protein aggregation so that activity and/or purity of the protein is improved.

In some embodiments, the binding molecules, such as antibodies or antigen-binding fragments thereof, have an onset temperature of aggregation (Tagg) that is greater than at or about 67° C., greater than at or about 68° C., greater than at or about 69° C., greater than at or about 70° C., greater than at or about 71° C., or greater than at or about 72° C., or is any value between any of the foregoing. In some embodiments, the Tagg is between at or about 67° C. and at or about 71° C. In some embodiments, the Tagg of the antibody or antigen-binding fragment is at or about 67° C., at or about 68° C., at or about 69° C., at or about 70° C., or at or about 71° C.

In some embodiments, the binding molecules, such as antibodies or antigen-binding fragments thereof, have a Tagg that is increased or improved compared to a reference antibody, such as antibody 11C12, such as an antibody containing the $V_H$ and $V_L$ set forth in SEQ ID NOS:1 and 8, respectively. In some embodiments, the Tagg is increased greater than at or about 1° C., greater than at or about 2° C., greater than at or about 3° C., greater than at or about 4° C. or greater than at or about 5° C. compared to a reference antibody (e.g., antibody 11C12, such as an antibody containing the $V_H$ and $V_L$ set forth in SEQ ID NOS:1 and 8, respectively).

In some embodiments, the binding molecules, such as antibodies or antigen-binding fragments thereof, has a melting temperature (Tm) for unfolding that is greater than 60° C. In some embodiments, the Tm is greater than at or about 61° C., greater than at or about 62° C., greater than at or about 63° C., greater than at or about 64° C., greater than at or about 65° C., greater than at or about 66° C., greater than at or about 67° C., greater than at or about 68° C., greater than at or about 69° C. or greater than at or about 70° C., or any value between any of the foregoing. In some embodiments, the Tm is between at or about 60° C. and at or about 70° C. In some embodiments, the Tm is at or about 64° C., at or about 65° C., at or about 66° C., at or about 67° C., at or about 68° C., or at or about 69° C.

Among provided binding molecules, such as antibodies or antigen-binding fragments, are those that exhibit improved features related to denaturation. Denaturation is the transition of a protein from the native conformation to an unfolded state and is generally accompanied by a major loss of protein function. As is understood by a skilled artisan, as IgG can be described as a multi-domain protein, the melting curve sometimes shows two transitions, or three transitions, with a first denaturation temperature, Tm1, and a second denaturation temperature Tm2, and optionally a third denaturation temperature Tm3. See e.g., Akazawa-Ogawa et al. Biophys. Rev. 2018, 10:255-258.

In some embodiments, the Tm (e.g., Tm1) is increased or improved compared to a reference antibody, such as antibody 11C12, such as an antibody containing the $V_H$ and $V_L$ set forth in SEQ ID NOS:1 and 8, respectively. In some embodiments, the Tm (e.g., Tm1) is increased greater than at or about 2° C., greater than at or about 3° C., greater than at or about 4° C., greater than at or about 5° C., greater than at or about 6° C., greater than at or about 7° C., greater than at or about 8° C., greater than at or about 9° C., or greater than at or about 10° C. compared to a reference antibody (e.g., antibody 11C12, such as an antibody containing the $V_H$ and $V_L$ set forth in SEQ ID NOS:1 and 8, respectively). In some embodiments, the Tm (e.g., Tm1) is increased greater than at or about 5° C. compared to a reference antibody (e.g., antibody 11C12, such as an antibody containing the $V_H$ and $V_L$ set forth in SEQ ID NOS:1 and 8, respectively). In some embodiments, the Tm (e.g., Tm1) is increased greater than at or about 10° C. compared to a reference antibody (e.g., antibody 11C12, such as an antibody containing the $V_H$ and $V_L$ set forth in SEQ ID NOS:1 and 8, respectively).

In some embodiments, the binding molecules, such as antibodies or antigen-binding fragments thereof, has a Tm1 for unfolding that is greater than 60° C. In some embodiments, the Tm1 is greater than at or about 61° C., greater than at or about 62° C., greater than at or about 63° C., greater than at or about 64° C., greater than at or about 65° C., greater than at or about 66° C., greater than at or about 67° C., greater than at or about 68° C., greater than at or about 69° C. or greater than at or about 70° C., or any value between any of the foregoing. In some embodiments, the Tm1 is between at or about 60° C. and at or about 70° C. In some embodiments, the Tm1 is at or about 64° C., at or about 65° C., at or about 66° C., at or about 67° C., at or about 68° C., or at or about 69° C.

In some embodiments, among provided binding molecules, such as antibodies or antigen-binding fragments, are those in which the denaturation curve for unfolding is monophasic such that only a single Tm, i.e., TM1, is observed. In some embodiments, without wishing to be bound by theory, it is believed that this property of such antibodies may reduce the likelihood of aggregation and hence improve purity and/or activity of such an antibody preparation. For instance, typically due to the different domains of an antibody folded and unfolded domains may be present at different denaturation temperatures, which can lead to reduced heat resistance and thereby increase tendency to aggregate or have reduced activity. An antibody preparation with a single transition (e.g., monophasic thermal denaturation) would be expected to exhibit improved thermostability and developability.

Nucleic Acids and Expression Vectors

The present disclosure also provides a nucleic acid, e.g., polynucleotide, encoding any one of the provided binding molecule, including any one of the provided anti-EpHA5 antibody or antigen-binding fragment thereof, or a chain thereof. The provided nucleic acid of the present disclosure may comprise a polynucleotide sequence encoding a heavy and/or light chain of any one of the antibodies or antigen-binding fragments thereof disclosed herein. In some embodiments, the nucleic acid is an isolated nucleic acid. In some embodiments, the nucleic acid is a recombinant or synthetic nucleic acid. In some embodiments, the nucleic acid is a complementary DNA (cDNA).

In some embodiments, the nucleic acid encodes a heavy chain of an antibody or antigen-binding fragment provided herein, such as any described above. In some embodiments, the nucleic acid encodes a light chain of an antibody or antigen-binding fragment provided herein, such as any described above. In some embodiments, the nucleic acid encodes a heavy chain and a light chain of an antibody or antigen-binding fragment provided herein, such as any described above.

In some embodiments, the heavy chain variable region is encoded by a nucleic acid comprising a polynucleotide sequence having has at least 80% sequence identity to SEQ ID NO:25 but less than 100% sequence identity to SEQ ID NO:25. In some embodiments, the heavy chain variable region is encoded by a nucleic acid comprising a polynucleotide sequence having has at least 85% sequence identity to SEQ ID NO:25 but less than 100% sequence identity to SEQ ID NO:25. For instance, the heavy chain variable region is encoded by a nucleic acid comprising a polynucleotide sequence having has at least 86%, 87%, 87%, 88%, 89%, 90%, 91%, 92%, 93% 94%, 95% sequence identity to SEQ ID NO:25 but less than 100% sequence identity to SEQ ID NO:25. In some embodiments, the light chain variable region is encoded by a nucleic acid comprising a polynucleotide sequence having has at least 80% sequence identity to SEQ ID NO:32 but less than 100% sequence identity to SEQ ID NO:32. In some embodiments, the light chain variable region is encoded by a nucleic acid comprising a polynucleotide sequence having has at least 85% sequence identity to SEQ ID NO:32 but less than 100% sequence identity to SEQ ID NO:32. For instance, the light chain variable region is encoded by a nucleic acid comprising a polynucleotide sequence having at least 86%, 87%, 87%, 88%, 89%, 90%, 91%, 92%, 93% 94%, 95% sequence identity to SEQ ID NO:32 but less than 100% sequence identity to SEQ ID NO:32.

In certain embodiments, the heavy chain variable region is encoded by a nucleic acid comprising a polynucleotide sequence having at least 80%, 85%, 90%, 95%, 96%, 96%, 97%, 98%, or 99% identity to SEQ ID NOs:26, 27, 28, 29, 30, or 31. In certain embodiments, the heavy chain variable region is encoded by a nucleic acid comprising the polynucleotide sequence set forth in SEQ ID NOs:26, 27, 28, 29, 30, or 31. In certain embodiments, the heavy chain variable region is encoded by a nucleic acid consisting of the polynucleotide sequence set forth in SEQ ID NO:26, 27, 28, 29, 30, or 31.

In certain embodiments, the light chain variable region is encoded by a nucleic acid comprising a polynucleotide sequence having at least 80%, 85%, 90%, 95%, 96%, 96%, 97%, 98%, or 99% identity to the amino acid sequence of the light chain variable region set forth in SEQ ID NOs:33, 34, 35, 36, or 37. In certain embodiments, the light chain variable region is encoded by a nucleic acid comprising the polynucleotide sequence set forth in SEQ ID NOs:33, 34, 35, 36, or 37. In certain embodiments, the light chain variable region is encoded by a nucleic acid consisting of a polynucleotide sequence set forth in SEQ ID NOs:33, 34, 35, 36, or 37.

Tolerable variations of the nucleic acid sequences will be known to those of skill in the art. For example, in some embodiments the nucleic acid comprises a nucleotide sequence that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the nucleotide sequences set forth in SEQ ID NO:26, 27, 28, 29, 30, 31, 33, 34, 35, 36, and 37.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:26 and a polynucleotide sequence encoding a light chain variable region that has at least 80%, 85%, 90%, 95%, 96%, 96%, 97%, 98%, or 99% sequence identity to the sequence set forth in SEQ ID NO:33. In some embodiments, the polynucleotide sequence encoding the heavy chain variable region is set forth in SEQ ID NO:26 and the polynucleotide sequence encoding the light chain variable region is set forth in SEQ ID NO:33. In some embodiments, the nucleic acid(s) encode the antibody H1K1, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:27 and a polynucleotide sequence encoding a light chain variable region that has at least 80%, 85%, 90%, 95%, 96%, 96%, 97%, 98%, or 99% sequence identity to the sequence set forth in SEQ ID NO:33. In some embodiments, the polynucleotide sequence encoding the heavy chain variable region is set forth in SEQ ID NO:27 and the polynucleotide sequence encoding the light chain variable region is set forth in SEQ ID NO:33. In some embodiments, the nucleic acid(s) encode the antibody H2K1, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:28 and a polynucleotide sequence encoding a light chain variable region that has at least 80%, 85%, 90%, 95%, 96%, 96%, 97%, 98%, or 99% sequence identity to the sequence set forth in SEQ ID NO:33. In some embodiments, the polynucleotide sequence encoding the heavy chain variable region is set forth in SEQ ID NO:28 and the polynucleotide sequence encoding the light chain variable region is set forth in SEQ ID NO:33. In some embodiments, the nucleic acid(s) encode the antibody H3K1, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:29 and a polynucleotide sequence encoding a light chain variable region that has at least 80%, 85%, 90%, 95%, 96%, 96%, 97%, 98%, or 99% sequence identity to the sequence set forth in SEQ ID NO:33. In some embodiments, the polynucleotide sequence encoding the heavy chain variable region is set forth in SEQ ID NO:29 and the polynucleotide sequence encoding the light chain variable region is set forth in SEQ ID NO:33. In some embodiments, the nucleic acid(s) encode the antibody H4K1, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:30 and a polynucleotide sequence encoding a light chain variable region that has at least 80%, 85%, 90%, 95%, 96%, 96%, 97%, 98%, or 99% sequence identity to the sequence set forth in SEQ ID NO:33. In some embodiments, the polynucleotide sequence encoding the heavy chain variable region is set forth in SEQ ID NO:30 and the polynucleotide sequence encoding the light chain variable region is set forth in SEQ ID NO:33. In some embodiments, the nucleic acid(s) encode the antibody H5K1, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:31 and a polynucleotide sequence encoding a light chain variable region that has at least 80%, 85%, 90%, 95%, 96%, 96%, 97%, 98%, or 99% sequence identity to the sequence set forth in SEQ ID NO:33. In some embodiments, the polynucleotide sequence encoding the heavy chain variable region is set forth in SEQ ID NO:31 and the polynucleotide sequence encoding the light chain variable region is set forth in SEQ ID NO:33. In some embodiments, the nucleic acid(s) encode the antibody H6K1, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:26 and a polynucleotide sequence encoding a light chain variable region that has at least 80%, 85%, 90%, 95%, 96%, 96%, 97%, 98%, or 99% sequence identity to the sequence set forth in SEQ ID NO:34. In some embodiments, the polynucleotide sequence encoding the heavy chain variable region is set forth in SEQ ID NO:26 and the polynucleotide sequence encoding the light chain variable region is set forth in SEQ ID NO:34. In some embodiments, the nucleic acid(s) encode the antibody H1K2, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:27 and a polynucleotide sequence encoding a light chain variable region that has at least 80%, 85%, 90%, 95%, 96%, 96%, 97%, 98%, or 99% sequence identity to the sequence set forth in SEQ ID NO:34. In some embodiments, the polynucleotide sequence encoding the heavy chain variable region is set forth in SEQ ID NO:27 and the polynucleotide sequence encoding the light chain variable region is set forth in SEQ ID NO:34. In some embodiments, the nucleic acid(s) encode the antibody H2K2, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:28 and a polynucleotide sequence encoding a light chain variable region that has at least 80%, 85%, 90%, 95%, 96%, 96%, 97%, 98%, or 99% sequence identity to the sequence set forth in SEQ ID NO:34. In some embodiments, the polynucleotide sequence encoding the heavy chain variable region is set forth in SEQ ID NO:28 and the polynucleotide sequence encoding the light chain variable region is set forth in SEQ ID NO:34. In some embodiments, the nucleic acid(s) encode the antibody H3K2, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:29 and a polynucleotide sequence encoding a light chain variable region that has at least 80%, 85%, 90%, 95%, 96%, 96%, 97%, 98%, or 99% sequence identity to the sequence set forth in SEQ ID NO:34. In some embodiments, the polynucleotide sequence encoding the heavy chain variable region is set forth in SEQ ID NO:29 and the polynucleotide sequence encoding the light chain variable region is set forth in SEQ ID NO:34. In some embodiments, the nucleic acid(s) encode the antibody H4K2, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:30 and a polynucleotide sequence encoding a light chain variable region that has at least 80%, 85%, 90%, 95%, 96%, 96%, 97%, 98%, or 99% sequence identity to the sequence set forth in SEQ ID NO:34. In some embodiments, the polynucleotide sequence encoding the heavy chain variable region is set forth in SEQ ID NO:30 and the polynucleotide sequence encoding the light chain variable region is set forth in SEQ ID NO:34. In some embodiments, the nucleic acid(s) encode the antibody H5K2, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:31 and a polynucleotide sequence encoding a light chain variable region that has at least 80%, 85%, 90%, 95%, 96%, 96%, 97%, 98%, or 99% sequence identity to the sequence set forth in SEQ ID NO:34. In some embodiments, the polynucleotide sequence encoding the heavy chain variable region is set forth in SEQ ID NO:31 and the polynucleotide sequence encoding the light chain variable region is set forth in SEQ ID NO:34. In some embodiments, the nucleic acid(s) encode the antibody H6K2, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:26 and a polynucleotide sequence encoding a light chain variable region that has at least 80%, 85%, 90%, 95%, 96%, 96%, 97%, 98%, or 99% sequence identity to the sequence set forth in SEQ ID NO:35. In some embodiments, the polynucleotide sequence encoding the heavy chain variable region is set forth in SEQ ID NO:26 and the polynucleotide sequence encoding the light chain variable region is set forth in SEQ ID NO:35. In some embodiments, the nucleic acid(s) encode the antibody H1K3, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:27 and a polynucleotide sequence encoding a light chain variable region that has at least 80%, 85%, 90%, 95%, 96%, 96%, 97%, 98%, or 99% sequence identity to the sequence set forth in SEQ ID NO:35. In some embodiments, the polynucleotide sequence encoding the heavy chain variable region is set forth in SEQ ID NO:27 and the polynucleotide sequence encoding the light chain variable region is set forth in SEQ ID NO:35. In some embodiments, the nucleic acid(s) encode the antibody H2K3, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:28 and a polynucleotide sequence encoding a light chain variable region that has at least 80%, 85%, 90%, 95%, 96%, 96%, 97%, 98%, or 99% sequence identity to the sequence set forth in SEQ ID NO:35. In some embodiments, the polynucleotide sequence encoding the heavy chain variable region is set forth in SEQ ID NO:28 and the polynucleotide sequence encoding the light chain variable region is set forth in SEQ ID NO:35. In some embodiments, the nucleic acid(s) encode the antibody H3K3, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:29 and a polynucleotide sequence encoding a light chain variable region that has at least 80%, 85%, 90%, 95%, 96%, 96%, 97%, 98%, or 99% sequence identity to the sequence set forth in SEQ ID NO:35. In some embodiments, the polynucleotide sequence encoding the heavy chain variable region is set forth in SEQ ID NO:29 and the polynucleotide sequence encoding the light chain variable region is set forth in SEQ ID NO:35. In some embodiments, the nucleic acid(s) encode the antibody H4K3, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:30 and a polynucleotide sequence encoding a light chain variable region that has at least 80%, 85%, 90%, 95%, 96%, 96%, 97%, 98%, or 99% sequence identity to the sequence set forth in SEQ ID NO:35. In some embodiments, the polynucleotide sequence encoding the heavy chain variable region is set forth in SEQ ID NO:30 and the polynucleotide sequence encoding the light chain variable region is set forth in SEQ ID NO:35. In some embodiments, the nucleic acid(s) encode the antibody H5K3, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:31 and a polynucleotide sequence encoding a light chain variable region that has at least 80%, 85%, 90%, 95%, 96%, 96%, 97%, 98%, or 99% sequence identity to the sequence set forth in SEQ ID NO:35. In some embodiments, the polynucleotide sequence encoding the heavy chain variable region is set forth in SEQ ID NO:31 and the polynucleotide sequence encoding the light chain variable region is set forth in SEQ ID NO:35. In some embodiments, the nucleic acid(s) encode the antibody H6K3, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:26 and a polynucleotide sequence encoding a light chain variable region that has at least 80%, 85%, 90%, 95%, 96%, 96%, 97%, 98%, or 99% sequence identity to the sequence set forth in SEQ ID NO:36. In some embodiments, the polynucleotide sequence encoding the heavy chain variable region is set forth in SEQ ID NO:26 and the polynucleotide sequence encoding the light chain variable region is set forth in SEQ ID NO:36. In some embodiments, the nucleic acid(s) encode the antibody H1K4, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:27 and a polynucleotide sequence encoding a light chain variable region that has at least 80%, 85%, 90%, 95%, 96%, 96%, 97%, 98%, or 99% sequence identity to the sequence set forth in SEQ ID NO:36. In some embodiments, the polynucleotide sequence encoding the heavy chain variable region is set forth in SEQ ID NO:27 and the polynucleotide sequence encoding the light chain variable region is set forth in SEQ ID NO:36. In some embodiments, the nucleic acid(s) encode the antibody H2K4, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:28 and a polynucleotide sequence encoding a light chain variable region that has at least 80%, 85%, 90%, 95%, 96%, 96%, 97%, 98%, or 99% sequence identity to the sequence set forth in SEQ ID NO:36. In some embodiments, the polynucleotide sequence encoding the heavy chain variable region is set forth in SEQ ID NO:28 and the polynucleotide sequence encoding the light chain variable region is set forth in SEQ ID NO:36. In some embodiments, the nucleic acid(s) encode the antibody H3K4, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:29 and a polynucleotide sequence encoding a light chain variable region that has at least 80%, 85%, 90%, 95%, 96%, 96%, 97%, 98%, or 99% sequence identity to the sequence set forth in SEQ ID NO:36. In some embodiments, the polynucleotide sequence encoding the heavy chain variable region is set forth in SEQ ID NO:29 and the polynucleotide sequence encoding the light chain variable region is set forth in SEQ ID NO:36. In some embodiments, the nucleic acid(s) encode the antibody H4K4, such as a full-length humanized antibody or an antigen-binding fragment thereof.

In some embodiments, the provided nucleic acid(s) encoding a binding polypeptide, such as an anti-EphA5 antibody or antigen-binding fragment, comprises a polynucleotide sequence encoding a heavy chain variable region that has at least 80%, 85%, 90%, 95%, 96%, 96%, 97%, 98%, or 99% sequence identity to the sequence set forth in SEQ ID NO:30 and a polynucleotide sequence encoding a light chain variable region that has at least 80%, 85%, 90%, 95%, 96%, 96%, 97%, 98%, or 99% sequence identity to the sequence set forth in SEQ ID NO:36. In some embodiments, the polynucleotide sequence encoding the heavy chain variable region is set forth in SEQ ID NO:30 and the polynucleotide sequence encoding the light chain variable region is set forth in SEQ ID NO:36. In some embodiments, the nucleic acid(s) encode the antibody H5K4, such as a full-length humanized antibody or an antigen-binding fragment thereof.

In some embodiments, the provided nucleic acid(s) encoding a binding polypeptide, such as an anti-EphA5 antibody or antigen-binding fragment, comprises a poly-nucleotide sequence encoding a heavy chain variable region that has at least 80%, 85%, 90%, 95%, 96%, 96%, 97%, 98%, or 99% sequence identity to the sequence set forth in SEQ ID NO:31 and a polynucleotide sequence encoding a light chain variable region that has at least 80%, 85%, 90%, 95%, 96%, 96%, 97%, 98%, or 99% sequence identity to the sequence set forth in SEQ ID NO:36. In some embodiments, the polynucleotide sequence encoding the heavy chain vari-able region is set forth in SEQ ID NO:31 and the polynucle-otide sequence encoding the light chain variable region is set forth in SEQ ID NO:36. In some embodiments, the nucleic acid(s) encode the antibody H6K4, such as a full-length humanized antibody or an antigen-binding fragment thereof.

In some embodiments, the provided nucleic acid(s) encoding a binding polypeptide, such as an anti-EphA5 antibody or antigen-binding fragment, comprises a poly-nucleotide sequence encoding a heavy chain variable region that has at least 80%, 85%, 90%, 95%, 96%, 96%, 97%, 98%, or 99% sequence identity to the sequence set forth in SEQ ID NO:26 and a polynucleotide sequence encoding a light chain variable region that has at least 80%, 85%, 90%, 95%, 96%, 96%, 97%, 98%, or 99% sequence identity to the sequence set forth in SEQ ID NO:37. In some embodiments, the polynucleotide sequence encoding the heavy chain vari-able region is set forth in SEQ ID NO:26 and the polynucle-otide sequence encoding the light chain variable region is set forth in SEQ ID NO:37. In some embodiments, the nucleic acid(s) encode the antibody H1K5, such as a full-length humanized antibody or an antigen-binding fragment thereof.

In some embodiments, the provided nucleic acid(s) encoding a binding polypeptide, such as an anti-EphA5 antibody or antigen-binding fragment, comprises a poly-nucleotide sequence encoding a heavy chain variable region that has at least 80%, 85%, 90%, 95%, 96%, 96%, 97%, 98%, or 99% sequence identity to the sequence set forth in SEQ ID NO:27 and a polynucleotide sequence encoding a light chain variable region that has at least 80%, 85%, 90%, 95%, 96%, 96%, 97%, 98%, or 99% sequence identity to the sequence set forth in SEQ ID NO:37. In some embodiments, the polynucleotide sequence encoding the heavy chain vari-able region is set forth in SEQ ID NO:27 and the polynucle-otide sequence encoding the light chain variable region is set forth in SEQ ID NO:37. In some embodiments, the nucleic acid(s) encode the antibody H2K5, such as a full-length humanized antibody or an antigen-binding fragment thereof.

In some embodiments, the provided nucleic acid(s) encoding a binding polypeptide, such as an anti-EphA5 antibody or antigen-binding fragment, comprises a poly-nucleotide sequence encoding a heavy chain variable region that has at least 80%, 85%, 90%, 95%, 96%, 96%, 97%, 98%, or 99% sequence identity to the sequence set forth in SEQ ID NO:28 and a polynucleotide sequence encoding a light chain variable region that has at least 80%, 85%, 90%, 95%, 96%, 96%, 97%, 98%, or 99% sequence identity to the sequence set forth in SEQ ID NO:37. In some embodiments, the polynucleotide sequence encoding the heavy chain vari-able region is set forth in SEQ ID NO:28 and the polynucle-otide sequence encoding the light chain variable region is set forth in SEQ ID NO:37. In some embodiments, the nucleic acid(s) encode the antibody H3K5, such as a full-length humanized antibody or an antigen-binding fragment thereof.

In some embodiments, the provided nucleic acid(s) encoding a binding polypeptide, such as an anti-EphA5 antibody or antigen-binding fragment, comprises a poly-nucleotide sequence encoding a heavy chain variable region that has at least 80%, 85%, 90%, 95%, 96%, 96%, 97%, 98%, or 99% sequence identity to the sequence set forth in SEQ ID NO:29 and a polynucleotide sequence encoding a light chain variable region that has at least 80%, 85%, 90%, 95%, 96%, 96%, 97%, 98%, or 99% sequence identity to the sequence set forth in SEQ ID NO:37. In some embodiments, the polynucleotide sequence encoding the heavy chain vari-able region is set forth in SEQ ID NO:29 and the polynucle-otide sequence encoding the light chain variable region is set forth in SEQ ID NO:37. In some embodiments, the nucleic acid(s) encode the antibody H4K5, such as a full-length humanized antibody or an antigen-binding fragment thereof.

In some embodiments, the provided nucleic acid(s) encoding a binding polypeptide, such as an anti-EphA5 antibody or antigen-binding fragment, comprises a poly-nucleotide sequence encoding a heavy chain variable region that has at least 80%, 85%, 90%, 95%, 96%, 96%, 97%, 98%, or 99% sequence identity to the sequence set forth in SEQ ID NO:30 and a polynucleotide sequence encoding a light chain variable region that has at least 80%, 85%, 90%, 95%, 96%, 96%, 97%, 98%, or 99% sequence identity to the sequence set forth in SEQ ID NO:37. In some embodiments, the polynucleotide sequence encoding the heavy chain vari-able region is set forth in SEQ ID NO:30 and the polynucle-otide sequence encoding the light chain variable region is set forth in SEQ ID NO:37. In some embodiments, the nucleic acid(s) encode the antibody H5K5, such as a full-length humanized antibody or an antigen-binding fragment thereof.

In some embodiments, the provided nucleic acid(s) encoding a binding polypeptide, such as an anti-EphA5 antibody or antigen-binding fragment, comprises a poly-nucleotide sequence encoding a heavy chain variable region that has at least 80%, 85%, 90%, 95%, 96%, 96%, 97%, 98%, or 99% sequence identity to the sequence set forth in SEQ ID NO:31 and a polynucleotide sequence encoding a light chain variable region that has at least 80%, 85%, 90%, 95%, 96%, 96%, 97%, 98%, or 99% sequence identity to the sequence set forth in SEQ ID NO:37. In some embodiments, the polynucleotide sequence encoding the heavy chain vari-able region is set forth in SEQ ID NO:31 and the polynucle-otide sequence encoding the light chain variable region is set forth in SEQ ID NO:37. In some embodiments, the nucleic acid(s) encode the antibody H6K5, such as a full-length humanized antibody or an antigen-binding fragment thereof.

Also provided is a nucleic acid(s) encoding a binding polypeptide, such as an antibody or antigen-binding frag-ment, comprising a heavy chain variable region encoded by a nucleic acid sequence comprising the polynucleotide sequence set forth in SEQ ID NO:29, and a light chain variable region encoded by a nucleic acid sequence com-prising the polynucleotide sequence set forth in SEQ ID NO:35.

Also provided is a nucleic acid(s) encoding a binding polypeptide, such as an antibody or antigen-binding frag-ment, comprising a heavy chain variable region encoded by a nucleic acid sequence comprising the polynucleotide sequence set forth in SEQ ID NO:30, and a light chain variable region encoded by a nucleic acid sequence com-prising the polynucleotide sequence set forth in SEQ ID NO:35.

Another aspect of the invention provides a vector comprising any one of the nucleic acids disclosed herein. In certain embodiments, the vector is selected from the group consisting of a DNA vector, an RNA vector, a plasmid, a lentiviral vector, an adenoviral vector, an adeno-associated viral vector, and a retroviral vector. In certain embodiments, the vector is an expression vector.

Also provided is a host cell comprising any of the vectors or nucleic acids disclosed herein. The host cell may be of eukaryotic, prokaryotic, mammalian, or bacterial origin. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells; and NSO cells. In some embodiments, the antibody heavy chains and/or light chains (e.g., $V_H$ region and/or $V_L$ region) may be expressed in yeast. See, e.g., U.S. Publication No. US 2006/0270045 A1. In some embodiments, a particular eukaryotic host cell is selected based on its ability to make desired post-translational modifications to the heavy chains and/or light chains (e.g., $V_H$ region and/or $V_L$ region). For example, in some embodiments, CHO cells produce polypeptides that have a higher level of sialylation than the same polypeptide produced in 293 cells.

A method of producing an antibody or antigen-binding fragment thereof that binds to human EPH receptor A5 is also provided herein, wherein the method comprises culturing the host cell. For recombinant production of the anti-EphA5 antibody, a nucleic acid sequence(s) encoding an antibody, e.g., as described above, may be isolated and inserted into one or more vectors for further cloning and/or expression in a host cell. Such nucleic acid sequences may be readily isolated and sequenced using conventional procedures (e.g., by using oligonucleotide probes that are capable of binding specifically to genes encoding the heavy and light chains of the antibody). In some embodiments, a method of making the anti-EphA5 antibody is provided, wherein the method comprises culturing a host cell comprising a nucleic acid sequence encoding the antibody, as provided above, under conditions suitable for expression of the antibody, and optionally recovering or purifying the antibody from the host cell (or host cell culture medium).

In some embodiments, a nucleic acid of the present disclosure may be operably linked to a transcriptional control element, e.g., a promoter, and enhancer, etc. Suitable promoter and enhancer elements are known to those of skill in the art.

In certain embodiments, the nucleic acid is in operable linkage with a promoter. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; phosphoglycerate kinase-1 (PGK) promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art.

Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHOS promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (Lad repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g., viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the nucleic acid into a host cell. Accordingly, an expression vector (e.g., a lentiviral vector) of the present invention may comprise a nucleic acid encoding a polypeptide. In some embodiments, the expression vector (e.g., lentiviral vector) will comprise additional elements that will aid in the functional expression of the polypeptide encoded therein. In some embodiments, an expression vector comprising a nucleic acid encoding for a polypeptide further comprises a mammalian promoter. In some embodiments, the vector further comprises an elongation-factor-1-alpha promoter (EF-1α promoter). Use of an EF-1α promoter may increase the efficiency in expression of downstream transgenes. Physiologic promoters (e.g., an EF-1α promoter) may be less likely to induce integration mediated genotoxicity and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In some embodiments, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a polypeptide of the present disclosure. Methods for introducing RNA into a host cell are known in the art. See, e.g., Zhao et al. Cancer Res. (2010) 15: 9053. Introducing RNA comprising a nucleotide sequence encoding a polypeptide of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a polypeptide of the present disclosure.

In order to assess the expression of a polypeptide (e.g., an antibody) or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

In some embodiments, a nucleic acid of the present disclosure is provided for the production of an antibody or antigen-binding fragment as described herein, e.g., in a host cell. In some embodiments, a nucleic acid of the present disclosure provides for amplification of the polypeptide-encoding nucleic acid.

Antibody Drug Conjugates (ADCs)

Also provided in the invention are immunoconjugates, such as antibody drug conjugates (ADCs), comprising any of the antibodies or antigen-binding fragments thereof disclosed herein linked or conjugated to a drug (e.g., a cytotoxic drug), or a toxin, or a radioisotope molecule. In particular embodiments, the ADC is composed of an antibody or antigen-binding fragment disclosed herein and a cytotoxic drug, such as MMAE or SN38. In certain embodiments, the ADCs of the invention can be specifically targeted to human EPH receptor A5 expressing cells in order to effectively eradicate said cells. In provided embodiments, the ADC is able to be internalized by the cell upon binding of the antibody or antigen-binding fragment to EphA5, such as human EphA5.

Exemplary antibodies or antigen-binding fragments in a provided ADC include any as described herein, such as in section "Antibodies and Antigen-Binding Fragments."

In some embodiments, the immunoconjugate, such as an ADC, has the formula Ab-(L-D), wherein Ab is the antibody or antigen-binding fragment thereof, such as any described herein; L is a linker; and D is a cytotoxic drug.

In certain embodiments, the ADC comprises an antibody or antigen-binding fragment thereof comprising a heavy chain variable region comprising the amino acid sequence set forth in SEQ ID NO:5 and a light chain variable region comprising the amino acid sequence set forth in SEQ ID NO:11. In some embodiments, the ADC is a full-length antibody in which the heavy chain additionally includes a heavy chain human constant domain (e.g., SEQ ID NO:14) and the light chain additionally includes a light chain human constant domain (e.g., SEQ ID NO:15). In some embodiments, the ADC comprises an antibody comprising a heavy chain set forth in SEQ ID NO:38 and a light chain set forth in SEQ ID NO:40.

In certain embodiments, the ADC comprises an antibody or antigen-binding fragment thereof comprising a heavy chain variable region comprising the amino acid sequence set forth in SEQ ID NO:6 and a light chain variable region comprising the amino acid sequence set forth in SEQ ID NO:11. In some embodiments, the ADC is a full-length antibody in which the heavy chain additionally includes a heavy chain human constant domain (e.g., SEQ ID NO:14) and the light chain additionally includes a light chain human constant domain (e.g., SEQ ID NO:15). In some embodiments, the ADC comprises an antibody comprising a heavy chain set forth in SEQ ID NO:39 and a light chain set forth in SEQ ID NO:40.

Any of a variety of cytotoxic drugs may be employed as known to a skilled artisan. The antibodies or antigen-binding fragments thereof of the current invention can be linked or conjugated to any drug or cytotoxic agent known to one of skill in the art, including but not limited to maytansinoid (DM1), or SSTR2-binding octreotide, or toxin, including but not limited to paclitaxel, daunorubicin, duocarmycin A, 5-fluoruracil, methotrexate, tubulin polymerization inhibitors, ravtansine (DM4), and Ricin A. In certain embodiments, the ADCs of the invention may be linked or conjugated to an auristatin including but not limited to monomethyl auristatin E (MMAE) or monomethyl auristatin F (MMAF). In certain embodiments, the ADCs of the invention may be linked or conjugated to an active metabolite of a drug. A nonlimiting example of such drug is SN-38, an active metabolite of irinotecan. One of skill in the art would be able to select a drug or cytotoxic agent to conjugate to the antibodies of the invention based on the desired properties of the drug or cytotoxic agent and the properties of the cell to be targeted by the ADC. Exemplary cytotoxic drugs are further described below. In some embodiments, the cytotoxic drug is monomethyl auristatin E (MMAE). In some embodiments, the cytotoxic drug is SN-38.

Any of a variety of linkers may be employed as known to a skilled artisan. Exemplary linkers are described below. In some embodiments, the linker is a cleavable linker. In some embodiments, the linker is a cathepsin-cleavable linker. In some embodiments, the linker is a pH cleavable linker.

In some embodiments, the drug antibody ratio (DAR) in a provided conjugate is from at or about 4 to at or about 8. In some embodiments, the DAR is at or about 4. In some embodiments, the DAR is at or about 8.

In certain embodiments, among the provided ADCs are those in which the antibody or antigen-binding fragment is internalized into a target cell upon binding, e.g., into a degradative compartment in the cell. In some embodiments, provided ADCs are thus those that internalize upon binding to a target cell, undergo degradation, and release the drug moiety to kill cancer cells. The drug moiety may be released from the antibody and/or the linker moiety of the ADC by enzymatic action, hydrolysis, oxidation, or any other mechanism. For instance, in some embodiments, the antibody of the ADC binds to EphA5 expressed on the surface of a cell (e.g., cancer cell) and enters the cell upon binding. In some embodiments, the drug moiety of the ADC is released from the antibody moiety of the ADC after the ADC enters and is present in a cell expressing the EphA5 antigen (i.e., after the ADC has been internalized).

Cytotoxic Drugs

In certain embodiments, the cytotoxic drug is (S)—N-((3R,4S,5S)-1-((S)-2-(((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino) butanamido)butanamide, (monomethyl auristatin E (MMAE)). In certain embodiments, the cytotoxic drug is (S)-4,11-diethyl-4,9-dihydroxy-1,12-dihydro-14H-pyrano [3',4':6,7]indolizino[1,2-b]quinoline-3,14(4H)-dione, (SN38).

Linkers

In certain embodiments, the antibody or antigen-binding fragment of the present disclosure (Ab) is conjugated to a cytotoxic drug (D) via a linker (L). In certain embodiments, the linker comprises an antibody conjugating terminus and a carboxy terminus.

In certain embodiments, the antibody conjugating terminus comprises a thiol-conjugating terminus. In certain embodiments, the antibody conjugating terminus comprises a disulfide-conjugating terminus. In certain embodiments, thiol-conjugating terminus comprises a Michael acceptor. In certain embodiments, the thiol-conjugating terminus is conjugated to the antibody via a Michael addition between a Michael acceptor of the linker and a cysteine of the antibody. In certain embodiments, the Michael acceptor is a maleimide. In certain embodiments, the disulfide-conjugating terminus comprises a moiety selected from the group consisting of a bissulfone, 3,4-disubstituted maleimide, bromomaleimide, and/or allyl sulfone. Further examples of disulfide-conjugating moieties are found in Kuan et al. (Chem. Eur. J. 2016, 22(48):17112-17129). In certain embodiments, the bissulfone comprises a 3-(arylsulfonyl)-2-((arylsulfonyl)methyl)propanoyl moiety. In certain embodiments, the disulfide-conjugating terminus is conjugated to the antibody via a reaction with the 3-(arylsulfonyl)-2-((arylsulfonyl)methyl)propanoyl moiety of the linker and a disulfide of the antibody.

In certain embodiments, the linker is conjugated to the cytotoxic drug via a carbamate. In certain embodiments, the carbamate is derived from an amine of the cytotoxic drug and a carboxy moiety of the linker. In certain embodiments, the linker is conjugated to the cytotoxic drug via a carbonic ester. In certain embodiments, the carbonic ester is derived from an alcohol moiety of the cytotoxic drug and a carboxy moiety of the linker. In certain embodiments, the linker is conjugated to more than one cytotoxic drug.

The linkers may comprise ethylene glycol/propylene glycol moieties. For example, in some embodiments both the first linking component and the second linking component (and thus the overall linker) contain ethylene glycol/propylene glycol repeats. Ethylene glycol/propylene glycol-based linkers may provide distinct advantages over linkers not containing ethylene glycol/propylene glycol. For example, ethylene glycol/propylene glycol-based linkers may provide greater flexibility, so that, for example, in an instance where the linker is conjugated to an amino acid residue that is in close proximity to the antigen-binding domain (e.g., the hypervariable region), there would be a reduced chance that the linker/therapeutic agent would bind to or interact with the surface elements of the antigen/receptor, thus making the overall immunoconjugate more therapeutically effective. Additionally, in such embodiments where the linker is generated through click chemistry (e.g., using DBCO and $N_3$), while not wishing to be bound by theory, the use of ethylene glycol and/or propylene glycol in the linking components may act as a spacer to prevent non-specific interactions (pi-pi interactions) between the tetracyclic ring structure found in the triazole moiety and any exposed aromatic side chains, especially tryptophan side chains. The ethylene glycol/propylene glycol-based linkers of the present disclosure may comprise repeats of anywhere between 1-30 ethylene glycol and/or propylene glycol units total, e.g., 1-10 ethylene glycol and/or propylene glycol units per each of the first linking component and the second linking component in such embodiments that utilize a first linking component and a second linking component.

The covalent linkages in such immunoconjugates may comprise a cleavable linking moiety, for example a cathepsin cleavable linker such as Val-Cit linker or Val-Cit-PAB, which is cleavable by Cathepsin B inside the lysosome. A commercially available Val-Cit linker has been used as described herein. Other cleavable linking moieties may comprise a Phe-Lys linker, which is also cleavable by Cathespin B. Some of the simplest cleavable linking moieties include disulfide (S-S) bridges, which are cleavable in a reductive (i.e., intracellular) environment. However, cleavable linking moieties such as Val-Cit linkers provide more specificity than, for example, disulfide bridges, which may be subject to indiscriminate cleavage, and thus present a superior option, although any such cleavable linking moiety is to be considered within the scope of the present disclosure. An overview of cleavable linking moieties which may be suitable in the context of the present disclosure is provided in Leriche et al. (Bioorg. Med. Chem. 2012, 20(2):571-582), which is hereby incorporated by reference in its entirety.

Alternatively, the linker may be non-cleavable. Non-cleavable linkers may comprise any linking moiety that is resistant to cleavage in an intracellular environment.

In certain embodiments, the linker comprises (MC-VCP)

In certain embodiments, the linker comprises (CL2A)

In Certain Embodiments, the Linker Comprises

In Certain Embodiments, the Linker Comprises

In Certain Embodiments, L-D Comprises (MC-VCP-MMAE)

97

In Certain Embodiments, L-D Comprises (CL2A-SN38)

98

In Certain Embodiments, L-D Comprises

In Certain Embodiments, L-D Comprises (ThioBridge®-(VCP-SN38)$_2$)

In some embodiments, there is provided an immunoconjugate, such as an ADC, having the formula Ab-(L-D), wherein Ab is an antibody that specifically binds to an epitope of human EPH Receptor A5 (EphA5) comprising the heavy chain set forth in SEQ ID NO:38 and the light chain set forth in SEQ ID NO:40; and the L-D comprises the structure:

In some embodiments, there is provided an immunoconjugate, such as an ADC, having the formula Ab-(L-D), wherein: Ab is an antibody that specifically binds to an epitope of human EPH Receptor A5 (EphA5) comprising the heavy chain set forth in SEQ ID NO:39 and the light chain set forth in SEQ ID NO:40; and the L-D comprises the structure:

Pharmaceutical Compositions and Formulations

Also provided are pharmaceutical composition comprising any one of the antibodies, antigen-binding fragments, and immunoconjugates (e.g., antibody drug conjugates) disclosed herein. Among the compositions are pharmaceutical compositions and formulations for administration, such as for treatment, amelioration, and/or prevention of a disease or disorder. Also provided are therapeutic methods for administering the pharmaceutical compositions to subjects, e.g., patients.

The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects the choice of carrier is determined in part by the particular composition and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

In some embodiments, the formulations can include aqueous solutions. In some embodiments, the formulations can include lyophilized formulations.

The formulation or composition may also contain more than one active ingredient useful for the particular indication, disease, or condition being treated, ameliorated, and/or prevented with the composition, preferably those with activities complementary to the composition, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as an anti-cancer drug. In some embodiments, the anti-cancer drug is a chemotherapeutic agent, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

The pharmaceutical composition in some embodiments contains the composition in an amount effective to treat, ameliorate, and/or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

Formulations include those for oral, intravenous, intraperitoneal, subcutaneous, pulmonary, transdermal, intramuscular, intranasal, buccal, sublingual, or suppository administration. In some embodiments, the composition is administered parenterally. The term "parenteral," as used herein, includes intravenous, intramuscular, subcutaneous, rectal, vaginal, and intraperitoneal administration. In some embodiments, the composition is administered to the subject using peripheral systemic delivery by intravenous, intraperitoneal, or subcutaneous injection. The provided compositions may be administered using standard administration techniques, formulations, and/or devices. Provided are formulations and devices, such as syringes and vials, for storage and administration of the compositions.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the composition in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

Methods of Treatment, Amelioration, and/or Prevention

Also provided are methods, such as methods of treatment and uses for treating, ameliorating, and/or preventing a disease or condition, such as a cancer, with any one of the provided antibodies (including a full-length antibody or antigen-binding fragments thereof) and immunoconjugates (e.g., antibody drug conjugates) described herein. In some embodiments, any one of the provided antibodies, and immunoconjugates (e.g., antibody drug conjugates) may be included in a composition for treating, ameliorating, and/or preventing the disease or condition in a subject in need thereof. The composition may include a pharmaceutical composition and further include a pharmaceutically acceptable carrier. A therapeutically effective amount of the pharmaceutical composition may be administered to the subject.

In some embodiments, the methods include methods of administering and uses, such as therapeutic and prophylactic uses, of any one of the antibodies and immunoconjugates (e.g., antibody drug conjugates) described herein or compositions containing the same. Such methods and uses include therapeutic methods and uses, for example, involving administration any one of the provided antibodies and immunoconjugates (e.g., antibody drug conjugates), or compositions containing the same, to a subject having a disease, condition, or disorder associated with EphA5. Also provided herein are uses of any one of the provided antibodies and immunoconjugates (e.g., antibody drug conjugates), or compositions containing the same, in such methods and treatments, and in the preparation of a medicament in order to carry out such therapeutic methods. In some embodiments, the disease, condition, or disorder is associated with EphA5 expression, and/or in which cells or tissues express, e.g., specifically express EphA5.

In some embodiments, a composition containing a provided antibody or immunoconjugates (e.g., antibody drug conjugates) is administered in an effective amount to effect treatment, amelioration, and/or prevention of the disease or disorder. In some embodiments, the methods are carried out by administering any one of the provided antibodies and immunoconjugates (e.g., antibody drug conjugates), or compositions containing the same, to the subject having, having had, or suspected of having the disease or condition. In some embodiments, the methods thereby treat, ameliorate, and/or prevent the disease or condition or disorder in the subject. Also provided herein are of use of any of the compositions, such as pharmaceutical compositions provided herein, for the treatment, amelioration, and/or prevention of a disease or disorder associated with EphA5, for example, a cancer.

Among the diseases to be treated, ameliorated, and/or prevented is any disease or disorder associated with EphA5, such as any disease or disorder in which BCMA is specifically expressed and/or in which EphA5 has been targeted for treatment (also referred to herein interchangeably as an "EphA5-associated disease or disorder"). In some embodiments, the disease or disorder is a cancer. In certain embodiments, the cancer is associated with human EPH receptor A5 (human EphA5)-expressing cells. In certain embodiments, the EPH receptor A5-expressing cell is a cancer cell.

In certain aspects, the cancer may be a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer. In specific aspects, the cancer is an epithelial cancer. In other aspects, cancer may be a colorectal adenocarcinoma, lung adenocarcinoma, lung squamous cell carcinoma, breast cancer, hepatocellular carcinoma, ovarian cancer, kidney renal clear cell carcinoma, lung cancer or kidney cancer.

In some embodiments, the provided antibodies and immunoconjugates (e.g., antibody drug conjugates), and compositions containing the same, can be used to treat, ameliorate, and/or prevent a cancer in which tumor cells express EphA5 on their surface. Exemplary tumor types that express EphA5 include, but are not limited to lung cancer (Staquicini, F. I., et al. (2015). Receptor tyrosine kinase EphA5 is a functional molecular target in human lung cancer. The Journal of Biological Chemistry, 290(12), 7345-7359), breast cancer, cervical cancer, head and neck cancer, esophageal cancer (Zhang R, et al. EphA5 knockdown enhances the invasion and migration ability of esophageal squamous cell carcinoma via epithelial-mesenchymal transition through activating Wnt/beta-catenin pathway. Cancer Cell Int. 2020; Jan. 13, 20:20), gastric cancer (Zhang, W., et al. (2019). Differential expression of EphA5 protein in gastric carcinoma and its clinical significance. Oncology letters, 17(6), 5147-5153), pancreatic ductal adenocarcinoma (Giaginis C, et al. Clinical significance of ephrin (eph)-A1, -A2, -a4, -a5 and -a7 receptors in pancreatic ductal adenocarcinoma. Pathol Oncol Res. 2010; 16(2):267-276), and ovarian cancer (Chen X, et al. EphA5 protein, a potential marker for distinguishing histological grade and prognosis in ovarian serous carcinoma. J Ovarian Res. 2016; 9:83).

In some embodiments, the provided antibodies and immunoconjugates (e.g., antibody drug conjugates), and compositions containing the same, may be used to treat, ameliorate, and/or prevent a lung cancer, a breast cancer, a cervical cancer, pancreatic ductal adenocarcinoma, or ovarian cancer. In particular embodiments, the cancer is a lung cancer. In some embodiments, the cancer is a non-small cell lung cancer (NSCLC).

In some embodiments, the methods may identify a subject who has, is suspected to have, or is at risk for developing a EphA5-associated disease or disorder. Hence, provided are methods for identifying subjects with diseases or disorders associated with elevated EphA5 expression and selecting them for treatment with any one of the provided antibodies and immunoconjugates (e.g., antibody drug conjugates) or compositions containing the same. For example, a subject may be screened for the presence of a disease or disorder associated with elevated EphA5 expression, such as an EphA5-expressing cancer. In some aspects, a sample may be obtained from a patient suspected of having a disease or disorder associated with elevated EphA5 expression and assayed for the expression level of EphA5. In some aspects, a subject who tests positive for a EphA5-associated disease or disorder may be selected for treatment by the present methods, and may be administered a therapeutically effective amount of any one of the provided antibodies and immunoconjugates (e.g., antibody drug conjugates) or compositions containing the same as described herein. In some embodiments, the methods can be used to monitor the size or density of a EphA5-expressing tissue, e.g., tumor, over time, e.g., before, during, or after treatment by the methods.

Compositions of the invention can be administered in dosages and routes and at times to be determined in appropriate pre-clinical and clinical experimentation and trials. Compositions may be administered multiple times at dosages within these ranges. Administration of the compositions may be combined with other methods useful to treat, ameliorate, and/or prevent the desired disease or condition as determined by those of skill in the art.

In some embodiments, a composition herein may contain an effective amount of a provided antibody or immunoconjugate (e.g., antibody drug conjugate) that may be from 0.001 mg to 1000 mg, such as from 0.001 mg to 100 mg, 0.001 mg to 10 mg, 0.001 mg to 1 mg, 0.001 mg to 0.1 mg or 0.001 mg to 0.01 mg. Depending on the type and severity of the disease, dosages of antibody or immunoconjugate (e.g., antibody drug conjugate) may include about 1 µg/kg to about 15 mg/kg (e.g., 0.1 mg/kg-10 mg/kg), about 1 µg/kg to about 100 mg/kg, about 0.05 mg/kg to about 10 mg/kg, about 0.5 mg/kg, about 2.0 mg/kg, about 4.0 mg/kg or about 10 mg/kg. Multiple doses may be administered intermittently, e.g., every week or every three weeks. An initial higher loading dose, followed by one or more lower doses may be administered.

In some embodiments, the antibody may be administered systemically. In additional aspects, the antibody may be administered intravenously, intradermally, intratumorally, intramuscularly, intraperitoneally, subcutaneously, or locally. The method may further comprise administering at least a second anticancer therapy to the subject. Examples of the second anticancer therapy include, but are not limited to, surgical therapy, chemotherapy, radiation therapy, cryotherapy, hormonal therapy, immunotherapy, or cytokine therapy.

In some embodiments, the treatment does not induce an immune response by the subject to the therapy, and/or does not induce such a response to a degree that prevents effective treatment of the disease or condition. In some aspects, the degree of immunogenicity and/or graft versus host response is less than that observed with a different but comparable treatment. For example, the degree of immunogenicity in some embodiments is reduced compared to a similar antibody drug conjugate including a different antibody that binds to a similar, e.g., overlapping epitope and/or that competes for binding to EphA5 with the provided antibody, such as a reference antibody as described.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made, and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples, therefore, specifically point out the preferred embodiments of the present invention and are not to be construed as limiting in any way the remainder of the disclosure.

Example 1: Generation and Characterization of Humanized 11C12 Antibodies Using Composite Human Antibody Technology The present disclosure details work in which the V region sequences encoding the anti-human EphA5 monoclonal murine 11C12 antibody were used to construct a chimeric antibody containing murine variable regions and human constant regions (VH0/VK0) and a series of humanized antibodies containing humanized variable regions and a human constant region using Composite Human Antibody™ technology. The chimeric and designed humanized variants were cloned into vectors encoding human IgG1 heavy chain constant region (SEQ ID NO:14) and human kappa light chain constant region (SEQ ID NO:15).

The chimeric and 30 Humanized antibody variants (Table E1) were transiently expressed small scale in HEK293 EBNA adherent cells and supernatants were tested for binding to rhEphA5 antigen using Biacore (single-cycle kinetic analysis). Six lead humanized antibody variants (VH3/VK4, VH4/VK3, VH4/VK4, VH5/VK2, VH5/VK3 and VH5/VK4) were transiently expressed large scale in CHO suspension cells. Antibodies were purified from CHO supernatants using 1 mL Hitrap™ MabSelect™ PrismA columns and buffer exchanged into DPBS pH 7.4. Chimeric and humanized antibody variants were analyzed by SDS-PAGE and analytical SE-HPLC assessed by multi-cycle kinetic analysis and using UNcle biostability platform.

Table E1 lists sequence identifiers (SEQ ID NO) corresponding to amino acid (aa) and nucleotide (nt) sequences of the amino acid sequences of the corresponding heavy chain ($V_H$) or light chain ($V_L$) variable regions and CDRs. CDRs are exemplified based on Kabat numbering convention. A skilled artisan is familiar with alternative numbering conventions for amino acid residues of CDRs in variable domain sequences and full-length antibody sequences. For instance, an alternative to a CDRH1 designated by SEQ ID NO:16 is a CDRH1 designated by SEQ ID NO:42. Table E1 also sets forth the sequence of exemplary chimeric mouse variable/human constant anti-EphA5 reference antibody used as a control and for comparison studies as described in subsequent Examples.

Figure 27A:
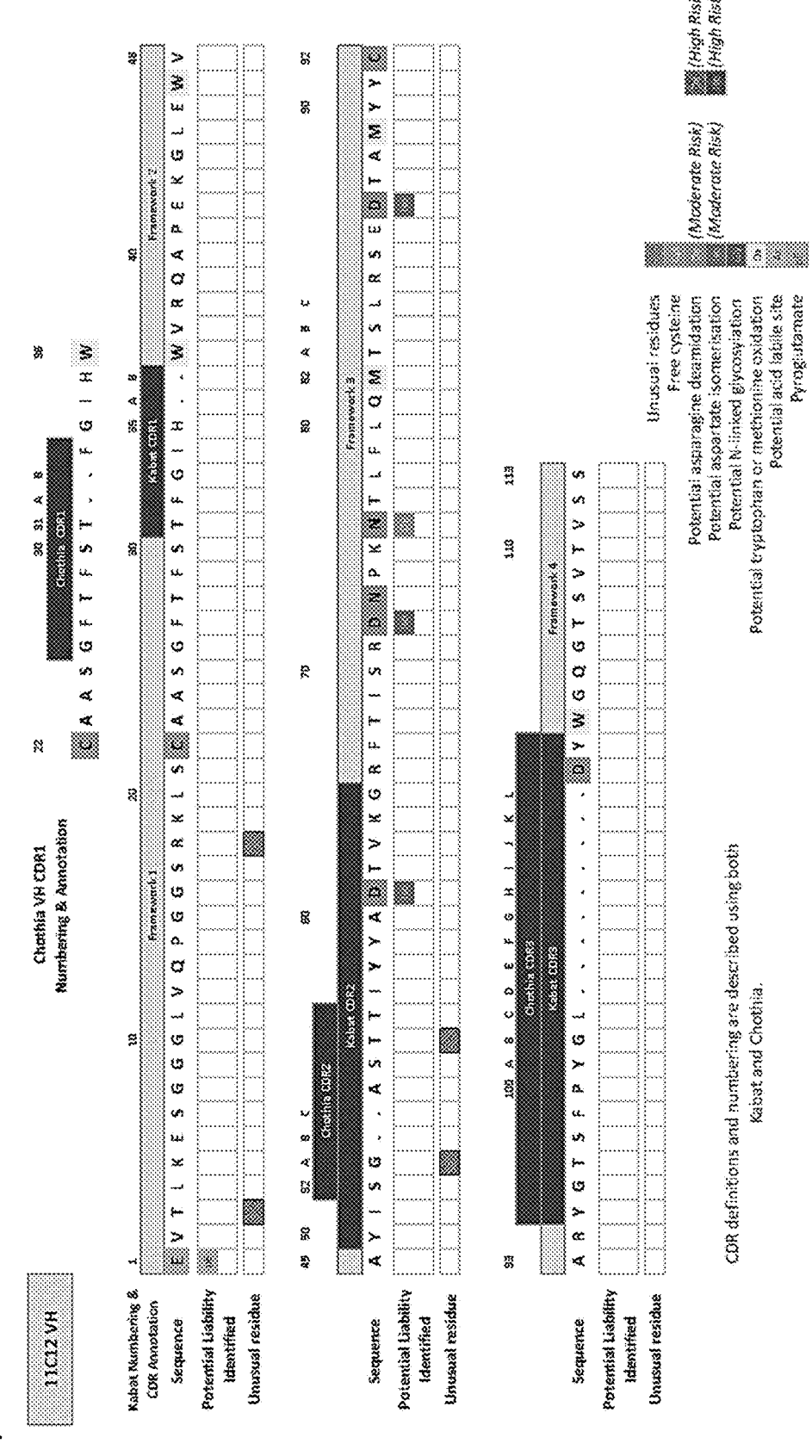
Figure 27B:
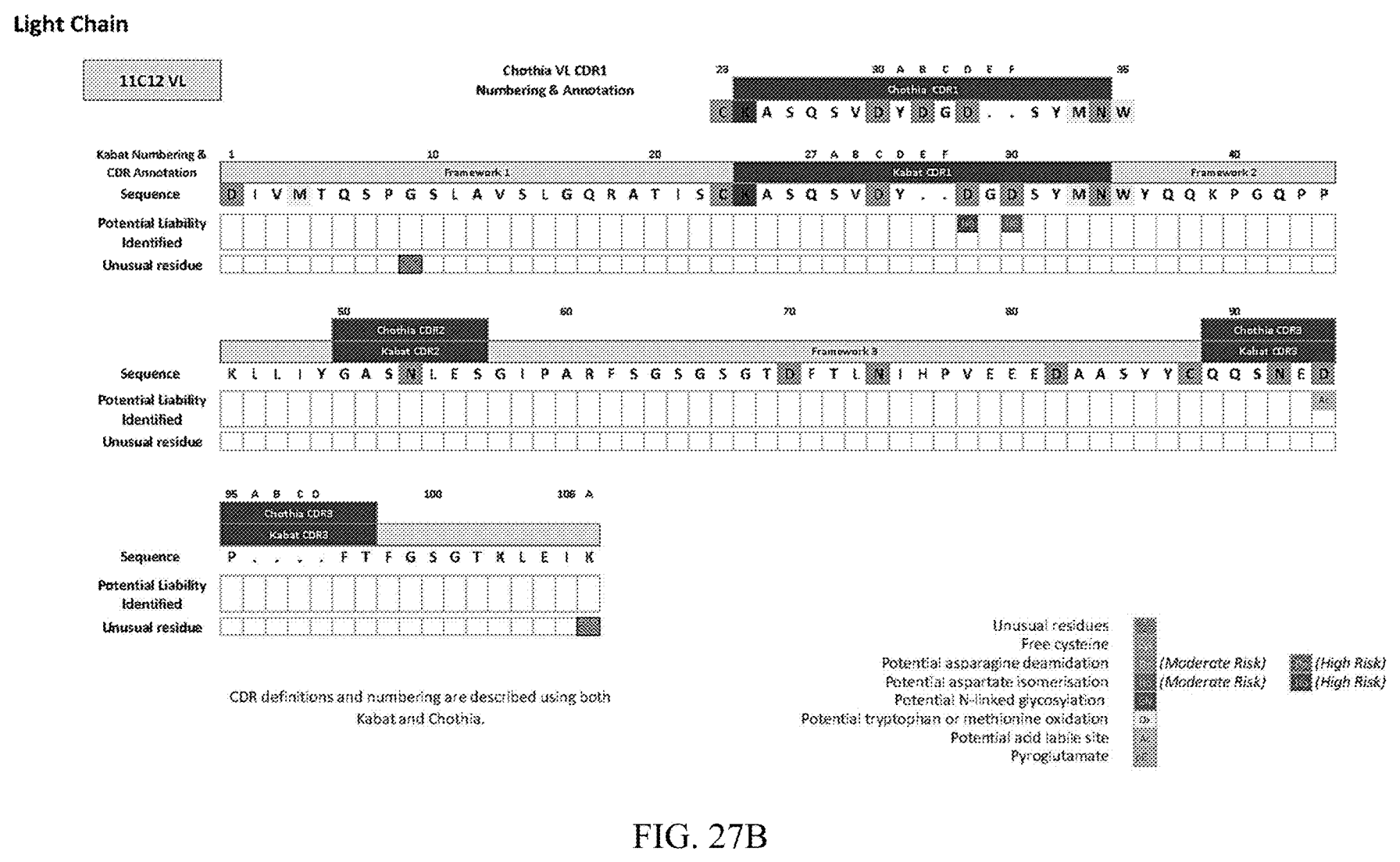
Figure 28:
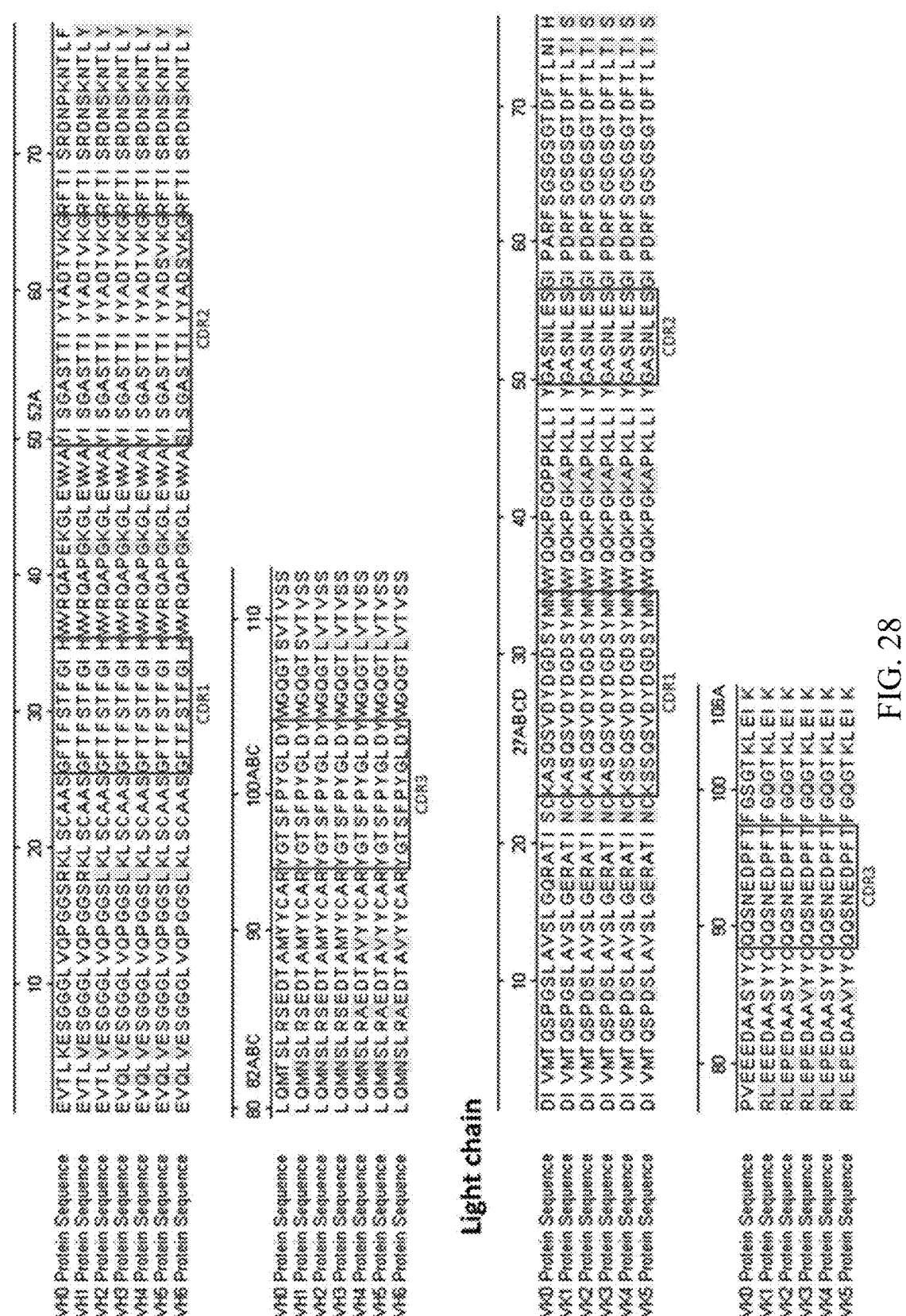
FIG. 28 is an alignment of chimeric and composite human antibody sequences. Residues that differ from the chimeric are highlighted and CDRs are enclosed in the indicated boxes. VH0 heavy chain protein sequence is provided in SEQ ID NO: 1. The VH1 heavy chain protein sequence is provided in SEQ ID NO: 2. The VH2 heavy chain protein sequence is provided in SEQ ID NO: 3. The VH3 heavy chain protein sequence is provided in SEQ ID NO: 4. VH4 heavy chain protein sequence is provided in SEQ ID NO: 5. The VH5 heavy chain protein sequence is provided in SEQ ID NO: 6. The VH6 heavy chain protein sequence is provided in SEQ ID NO: 7. VH0 light chain protein sequence is provided in SEQ ID NO: 8. The heavy chain CDR1 sequences are provided in SEQ ID NO: 16 (VH0-6). The heavy chain CDR2 sequences are provided in SEQ ID NO: 17 (VH0-4), 18 (VH5) and 19 (VH6), respectively. The heavy chain CDR3 sequences are provided in SEQ ID NO: 20 (VH0-6). The VH1 light chain protein sequence is provided in SEQ ID NO: 9. The VH2 light chain protein sequence is provided in SEQ ID NO: 10. The VH3 light chain protein sequence is provided in SEQ ID NO: 11. VH4 light chain protein sequence is provided in SEQ ID NO: 12. The VH5 heavy chain protein sequence is provided in SEQ ID NO: 13. The variable light chain CDR1 sequences are provided in SEQ ID NO: 21 (VH0-3), and 22 (VK4-5). The variable light chain CDR3 sequences are provided in SEQ ID NO: 24 (VK0-5).

CDRs but with only a narrow menu of possible residues within the CDR sequences. Preliminary analysis indicated that corresponding sequence segments from several human antibodies could be combined to create CDRs similar, or identical, to those in the murine sequences. For regions outside of, and flanking, the CDRs a wide selection of human sequence segments was identified as possible components of the novel humanized V regions. Some moderate-risk potential aspartate isomerization and deamidation risks were identified (see FIGS. 27A-27B) in the VH and VK with one higher risk isomerization site (VK CDR1) and one acid labile site (VK CDR3) also identified. Some of these may be

TABLE E1

| | | | | Full length $V_H +$ IgG1 constant SEQ ID | | | | Full-length $V_L +$ kappa constant SEQ ID |
|---|---|---|---|---|---|---|---|---|
| | CDR-H1, CDR-H2, | $V_H$ | | NO: 14 | CDR-L1, CDR-L2, | $V_L$ | | NO: 15 |
| Clone # | CDR-H3 | aa | nt | | CDR-L3 | aa | nt | |
| VH1/VK1 | 16, 17, 20 | 2 | 26 | | 21, 23, 24 | 9 | 33 | |
| VH1/VK2 | 16, 17, 20 | 2 | 26 | | 21, 23, 24 | 10 | 34 | |
| VH1/VK3 | 16, 17, 20 | 2 | 26 | | 21, 23, 24 | 11 | 35 | 40 |
| VH1/VK4 | 16, 17, 20 | 2 | 26 | | 22, 23, 24 | 12 | 36 | |
| VH1/VK5 | 16, 17, 20 | 2 | 26 | | 22, 23, 24 | 13 | 37 | |
| VH2/VK1 | 16, 17, 20 | 3 | 27 | | 21, 23, 24 | 9 | 33 | |
| VH2/VK2 | 16, 17, 20 | 3 | 27 | | 21, 23, 24 | 10 | 34 | |
| VH2/VK3 | 16, 17, 20 | 3 | 27 | | 21, 23, 24 | 11 | 35 | 40 |
| VH2/VK4 | 16, 17, 20 | 3 | 27 | | 22, 23, 24 | 12 | 36 | |
| VH2/VK5 | 16, 17, 20 | 3 | 27 | | 22, 23, 24 | 13 | 37 | |
| VH3/VK1 | 16, 17, 20 | 4 | 28 | | 21, 23, 24 | 9 | 33 | |
| VH3/VK2 | 16, 17, 20 | 4 | 28 | | 21, 23, 24 | 10 | 34 | |
| VH3/VK3 | 16, 17, 20 | 4 | 28 | | 21, 23, 24 | 11 | 35 | 40 |
| VH3/VK4 | 16, 17, 20 | 4 | 28 | | 22, 23, 24 | 12 | 36 | |
| VH3/VK5 | 16, 17, 20 | 4 | 28 | | 22, 23, 24 | 13 | 37 | |
| VH4/VK1 | 16, 17, 20 | 5 | 29 | 38 | 21, 23, 24 | 9 | 33 | |
| VH4/VK2 | 16, 17, 20 | 5 | 29 | 38 | 21, 23, 24 | 10 | 34 | |
| VH4/VK3 | 16, 17, 20 | 5 | 29 | 38 | 21, 23, 24 | 11 | 35 | 40 |
| VH4/VK4 | 16, 17, 20 | 5 | 29 | 38 | 22, 23, 24 | 12 | 36 | |
| VH4/VK5 | 16, 17, 20 | 5 | 29 | 38 | 22, 23, 24 | 13 | 37 | |
| VH5/VK1 | 16, 18, 20 | 6 | 30 | 39 | 21, 23, 24 | 9 | 33 | |
| VH5/VK2 | 16, 18, 20 | 6 | 30 | 39 | 21, 23, 24 | 10 | 34 | |
| VH5/VK3 | 16, 18, 20 | 6 | 30 | 39 | 21, 23, 24 | 1 | 35 | 40 |
| VH5/VK4 | 16, 18, 20 | 6 | 30 | 39 | 22, 23, 24 | 12 | 36 | |
| VH5/VK5 | 16, 18, 20 | 6 | 30 | 39 | 22, 23, 24 | 13 | 37 | |
| VH6/VK1 | 16, 19, 20 | 7 | 31 | | 21, 23, 24 | 9 | 33 | |
| VH6/VK2 | 16, 19, 20 | 7 | 31 | | 21, 23, 24 | 10 | 34 | |
| VH6/VK3 | 16, 19, 20 | 7 | 31 | | 21, 23, 24 | 11 | 35 | 40 |
| VH6/VK4 | 16, 19, 20 | 7 | 31 | | 22, 23, 24 | 12 | 36 | |
| VH6/VK5 | 16, 19, 20 | 7 | 31 | | 22, 23, 24 | 13 | 37 | |
| Reference chimeric VH0/VK0 | 16, 17, 20 | 1 | 25 | | 21, 23, 24 | 8 | 32 | |

Design of Composite Human Antibody™ Variable Regions

Structural models of the murine antibody V regions were produced using Swiss PDB Viewer and analyzed in order to identify important "constraining" amino acids in the V regions that were likely to be essential for the binding properties of the antibody. Most residues contained within the CDRs (using both Kabat and Chothia definitions) together with a number of framework residues were considered to be important.

From this analysis, it was considered that Composite Human sequences of the murine antibody could be created with a wide latitude for alternative residues outside of the addressed through humanization, however several of the liabilities are found within CDR regions and will likely be retained.

CD4+ T Cell Epitope Avoidance

Figure 7:
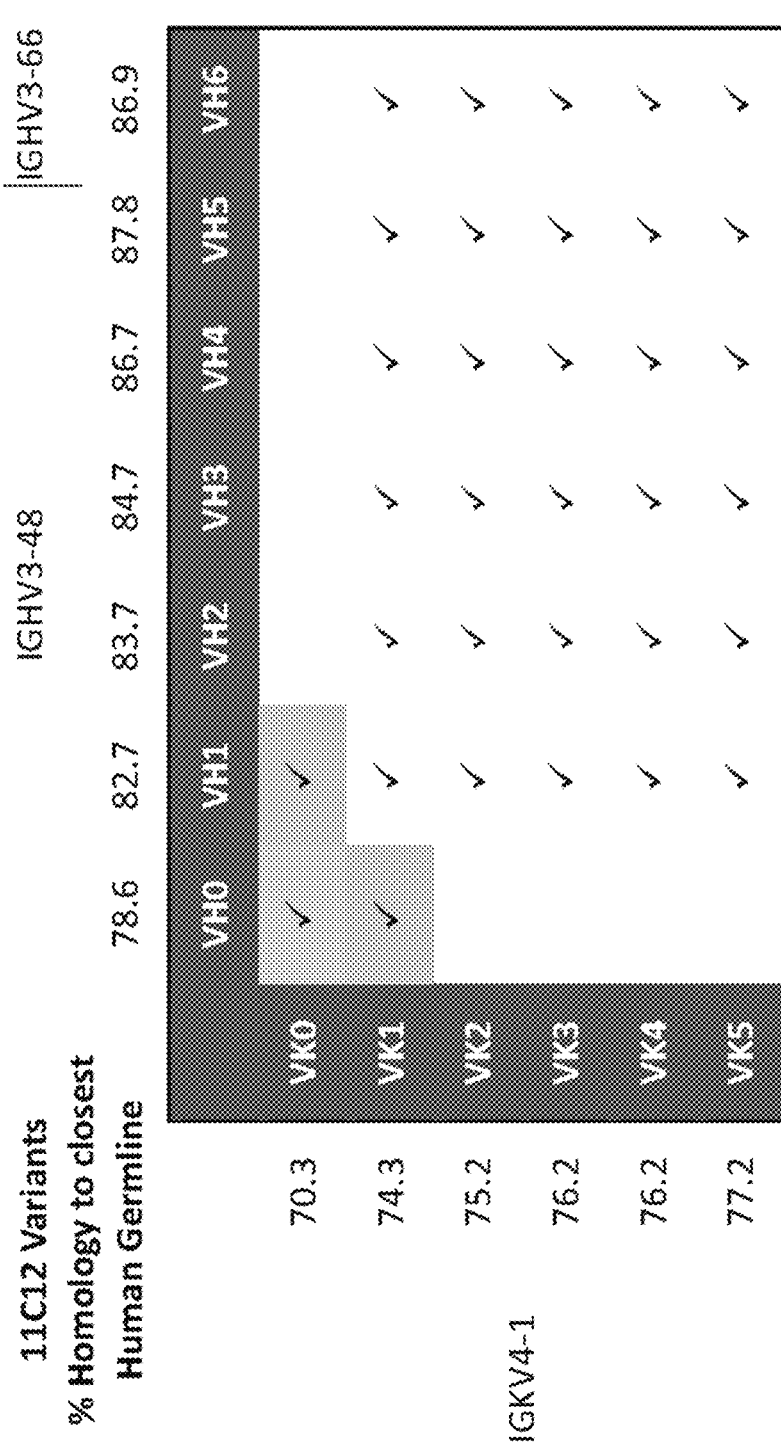
FIG. 7 is a summary table of the Abs produced by transient transfection (I boxes) including a chimeric (VH0/VK0), two controls (VH1/VK0 and VH0/VK1) and thirty mouse 11C12 Composite Human™ Ab variants. The percentage humanness (as determined by the percent homology against the closest matching human germline) are indicated.

Based upon the structural analysis, a large preliminary set of sequence segments that could be used to create humanized variants were selected and analyzed using iTope™ technology for in silico analysis of peptide binding to human MHC class II alleles (Perry et al 2008). Where possible, sequence segments that were identified as significant non-human germline binders to human MHC class II were discarded. This resulted in a reduced set of segments, and combinations of these were again analyzed, as above, to ensure that the junctions between segments did not contain potential T cell epitopes. Selected sequence segments were assembled with the aim of generating complete V region sequences that were devoid of, or reduced in, significant T cell epitopes. A total of six heavy chain (VH1 to VH6) and five light chain (VK1 to VK5) sequences were designed. See FIG. 7 and Table E1.

Analysis by iTope™

Variant sequences were analyzed for the occurrence of potential T cell epitopes as determined by application of proprietary in silico technology, iTope™ (Perry et al. 2008).

The iTope™ software predicts favorable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by eight amino acids spanning the test protein sequence. However, results should be assessed in the light of the fact that all predictive methods for MHC class II binding inherently over-predict the number of T cell epitopes since they do not allow for other important processes during antigen presentation such as protein/peptide processing, recognition by the T cell receptor or T cell tolerance to the peptide.

iTope™ analysis was performed with overlapping 9mer peptides (with each overlapping the last peptide by 8 residues). Each 9mer was scored based on the potential 'fit' and interactions against each of the 34 MHC class II allotypes with the resultant peptide scores ranging between 0 and 1. MHC Class II epitopes are then defined by iTope™ as follows:

Promiscuous high affinity MHC Class II binding peptides bind >50% of alleles with a majority (17 out of 34 alleles) having a binding score >0.6.

Promiscuous moderate affinity MHC class II binding peptides bind >50% of alleles with a binding score >0.55 (but without a majority >0.6).

These criteria are altered in the case of a large aromatic amino acid (i.e., F, W, Y) occurring in the p1 anchor position where the open p1 pocket of 20 of the 34 alleles allows the binding of a large aromatic residue. Where this occurs, a promiscuous peptide is defined as binding to 10 or more of the subset of 20 alleles.

A number of germline promiscuous high and moderate affinity MHC Class II binding ligands were identified in the parental antibody and designed variants however it is unlikely that these epitopes have immunogenic potential due to T cell tolerance, and so were excluded from any further analysis. Several non-germline promiscuous high and moderate affinity MHC class II binding ligands were identified in both the heavy and light chain sequences however, it was observed that during the humanization design process the majority of such epitopes were either removed or showed a reduction in affinity to MHC Class II. However, a subset of epitopes identified in both the VH sequence and VK sequence were found to be associated with CDR regions and it is likely that these could not be easily removed without the probability of affecting the ability of the antibody to bind to its antigen.

iTope™ in silico analysis of the humanized variants is shown in FIGS. 29 and 30 with the number of promiscuous moderate and high epitopes associated with the variable domains of each humanized heavy and light chain summarized in FIG. 8.

Construction of Chimeric IgG1 and Humanized Variants

Figure 9:
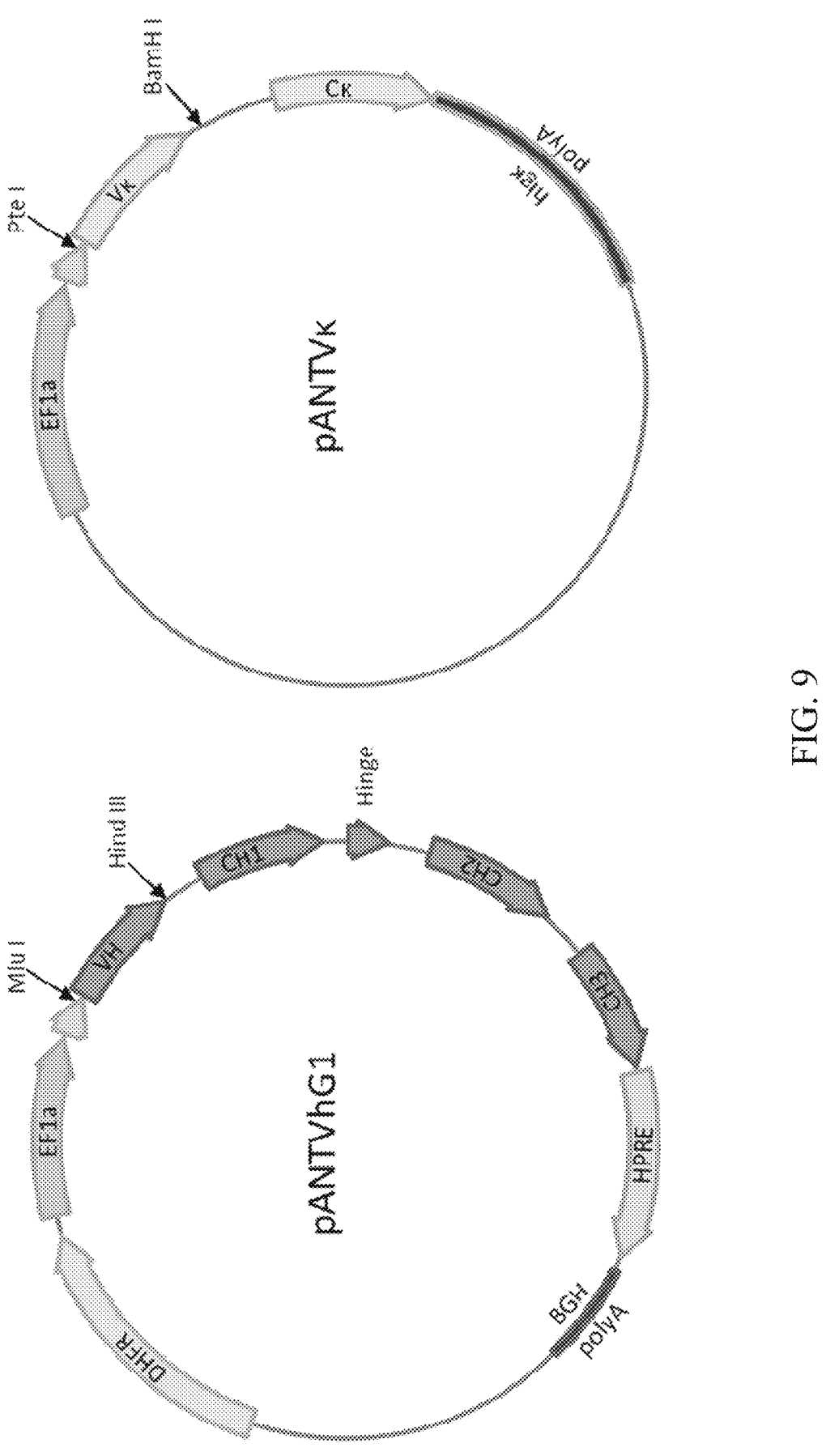
FIG. 9 illustrates plasmid maps for human heavy chain expression vector pANTVhG1 and light chain expression vector pANTVK. The VH and VK vectors contain genomic DNA fragments encoding the variable and constant domains, incorporating introns and polyA sequences. Expression of both chains is driven by an EF1a promoter.

The VH and VK sequences of mouse 11C12 (VH0 and VK0) together with the humanized variants were synthesized with flanking restriction enzyme sites for cloning into the pANT expression vector system for human IgG1 VH and kappa light chain (FIG. 9). The VH regions were cloned between the Mlu I and Hind III restriction sites, and the VK regions were cloned between the Pte I and BamH I restriction sites. All constructs were confirmed by sequencing.

Small Scale Transient Expression of 11C12 Chimeric and Humanized Antibodies

Chimeric VH0/VK0 and combinations of humanized heavy and light chain DNA constructs (a total of 30 humanized pairings, FIG. 7 and Table E1) were transiently transfected into HEK293 EBNA adherent cells (LGC Standards, Teddington, UK) using a PEI transfection method in 6-well plates, topped up with fresh media the following day and incubated for 5 days post-transfection.

HEK supernatants were harvested 5 days post transfection and filtered using 0.2 μM filter systems (Corning, New York, US). Antibody concentrations were measured on the Octet QK 384 using Protein A biosensors (Molecular Devices, Wokingham, Berkshire, UK), using an IgG1 antibody as standard (FIG. 10).

Single Cycle Kinetic Analysis of Chimeric and Humanized Variants

Figure 11:
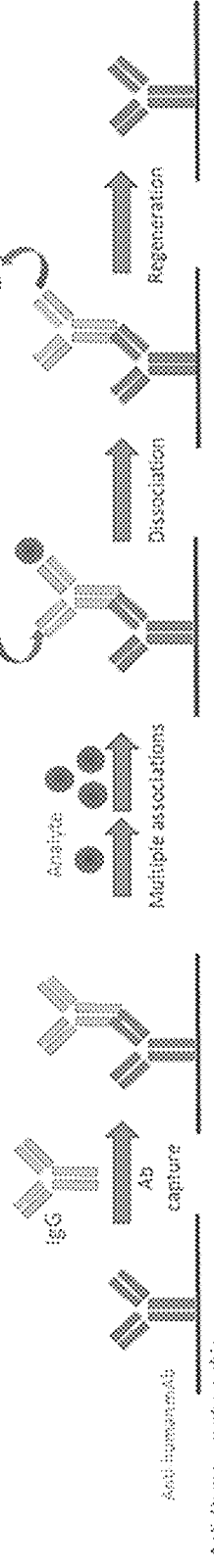
FIG. 11 is an illustration of the Biacore schematic used to assess the binding of the humanized IgG to rhEphA5 by single cycle kinetic analysis.

In order to assess the binding of all of the variants to recombinant human EphA5 (rhEphA5) antigen and select lead humanized IgGs with the closest affinity to the chimeric (VH0/VK0) antibody, single cycle kinetic analysis (FIG. 11) was performed on supernatants from transfected cell cultures. Kinetic experiments were performed at 25° C. on a Biacore T200 running Biacore T200 Control software V2.0.1 and Evaluation software V3.0 (Cytiva, Uppsala, Sweden).

HBS-P+(Cytiva, Uppsala, Sweden), supplemented with 1% BSA (Sigma, Dorset, UK) was used as running buffer as well as for ligand and analyte dilutions. Supernatants containing IgG were diluted in running buffer to 1 μg/mL. At the start of each cycle, antibodies were loaded onto Fc2, Fc3 and Fc4 of an anti-human IgG CMS sensor chip (Cytiva, Little Chalfont, UK). Ig were captured at a flow rate of 10 μl/min to give an immobilization level (RL) of ~60 RU. The surface was then allowed to stabilize.

Single cycle kinetic data was obtained using human EphA5 (R and D systems, Cat. No. 3036-A5) as the analyte injected at a flow rate of 40 μl/min to minimize any potential mass transfer effects. A three point, three-fold dilution range from 1.0 nM to 9.0 nM of antigen in running buffer was used without regeneration between each concentration. The association phases were monitored for 150 seconds for each of the three injections of increasing concentrations of antigen and a single dissociation phase was measured for 400 seconds following the last injection of antigen. Regeneration of the sensor chip surface was conducted using one injection of 3 M MgCl2 solution.

Figure 14:
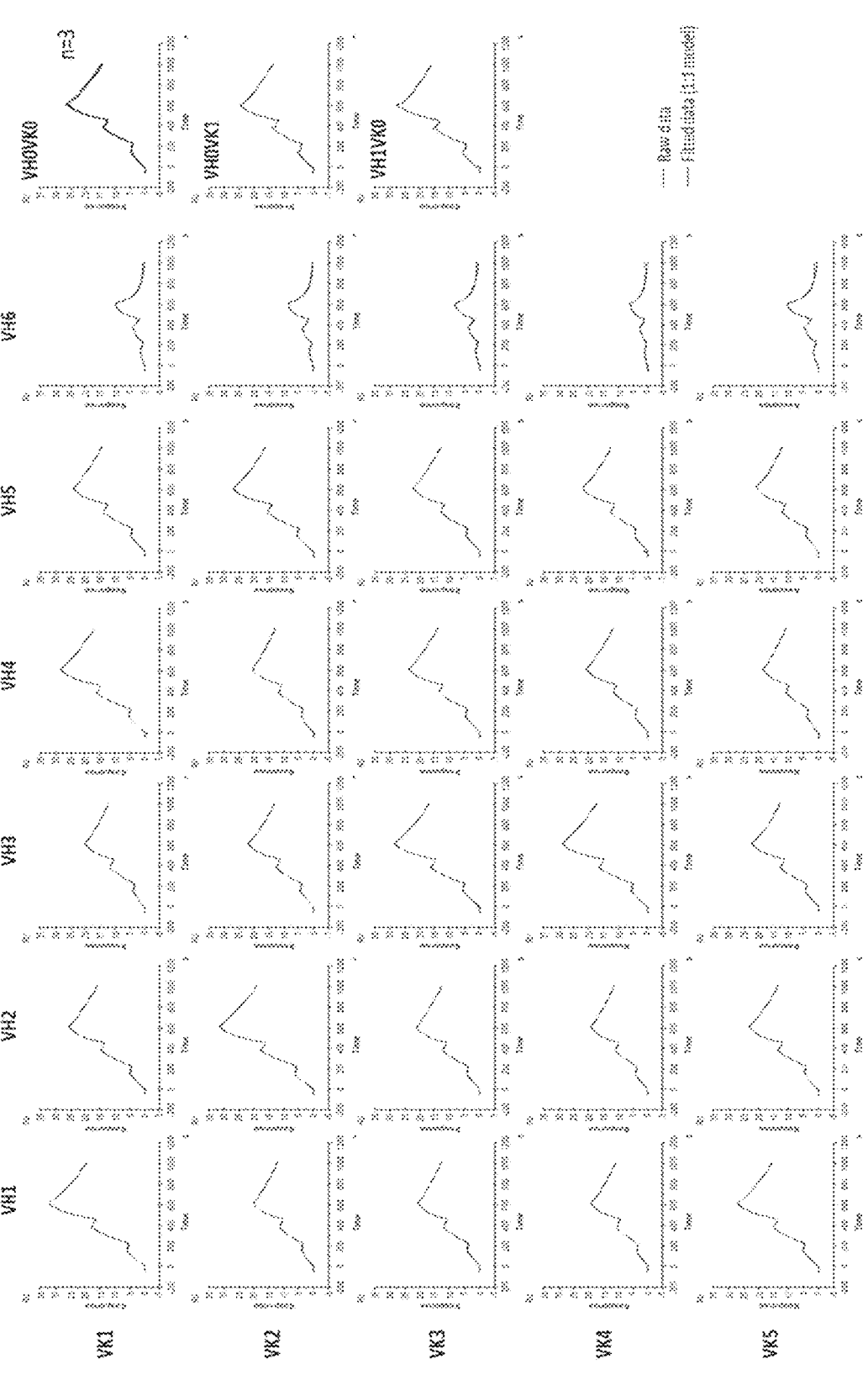
FIG. 14 illustrates single cycle kinetics raw sensorgrams (in grey) and fitted curves with a 1:1 model (in black) for the binding of chimeric (VH0/VK0) and humanized 11C12 variants to rhEphA5 antigen. Kinetic analysis was carried out on a Biacore T200. Each antibody was captured on a CMS chip coupled with an anti-human IgG using standard amine chemistry before increasing concentrations of antigen were injected and a single off-rate was determined.

Multiple repeats with the reference chimeric IgG were performed to check the stability of the surface and analyte over the kinetic cycles. The signal from the reference channel Fc1 (no IgG captured) was subtracted from that of Fc2, Fc3 and Fc4 to correct for bulk effect and differences in non-specific binding to a reference surface. The signal from each IgG blank run (IgG captured but no antigen) was subtracted to correct for differences in surface stability. The double referenced sensorgrams were fitted with the Langmuir (1:1) binding model (FIG. 12, top) where the closeness of fit of the data to the model is evaluated using the Chi square value which describes the deviation between the experimental and fitted (observed and expected) curves (FIG. 12, bottom). The fitting algorithm seeks to minimize the Chi square value. The fitting is not necessarily the most appropriate model, however it allows comparative ranking of variants. As shown in FIG. 13 and FIG. 14, most of the humanized variant antibodies appeared to bind EphA5 within two-fold of the chimeric antibody. The only exceptions were the VH6 combinations that did not bind as well. Chimeric and lead antibodies highlighted in orange and blue respectively were transiently expressed in CHO cells on a large scale.

Large Scale Transient Expression and Purification of 11C12 Chimeric and Lead Humanized Antibodies Chimeric VH0/VK0 and combinations of the selected humanized heavy and light chain DNA constructs (a total of 6 lead antibodies, highlighted in FIG. 13) were transiently transfected into CHO cells using the MaxCyte STX® electroporation system (MaxCyte Inc., Gaithersburg, USA) with OC-400 processing assemblies. Following cell recovery, cells were diluted to $3\times106$ cells/mL into CD Opti-CHO medium (ThermoFisher, Loughborough, UK) containing 8 mM L-Glutamine (ThermoFisher, Loughborough, UK) and 1× Hypoxanthine-Thymidine (ThermoFisher, Loughborough, UK). Two hours after resuspension 0.5× Penicillin Streptomycin solution (ThermoFisher, Loughborough, UK) was added to the culture (5 mL/L). The culture temperature was reduced 24 hours post-transfection, from 37° C. to 32° C. and 1 mM sodium butyrate (Sigma, Dorset, UK) was added. Cultures were fed 24 hours and 7 days after transfection by adding 30% and 15% (of the culture volume) CHO CD Efficient Feed B (ThermoFisher, Loughborough, UK) respectively, and 3.3% and 1.65% Function Max Titre Enhancer (ThermoFisher, Loughborough, UK) respectively. CHO supernatants were harvested 11 days post transfection. Antibody concentrations were measured on the Octet QK 384 using Protein A biosensors (Molecular Devices, Wokingham, Berkshire, UK), using an IgG1 antibody as standard (FIG. 15).

Following culture harvest, antibody supernatants were filtered using 0.2 μM filter systems (Corning, New York, US) to remove remaining cell debris and supplemented with 10×PBS to neutralize pH. The antibodies were then purified from supernatants using 1 mL Hitrap Mab Select PrismA columns (Cytiva, Little Chalfont, UK) previously equilibrated with 10 CV (column volume) of 1×DPBS, pH 7.2-7.4. Following the sample loading, the columns were washed with 10 CV of 1×DPBS and protein eluted with 0.1 M sodium citrate, pH 3.0. Fractions were collected, and pH adjusted with 1 M Tris-HCl, pH 9.0 followed by OD280 nm quantification. Antibody-containing fractions for each variant were pooled and buffer exchanged into 1×DPBS, pH 7.2-7.4 and filter sterilized with 0.2 μM syringe filters (Sartorius, Epsom, UK) before quantification by OD280 nm using an extinction coefficient (Ec (0.1%)) based on the predicted amino acid sequence.

Figure 16B:
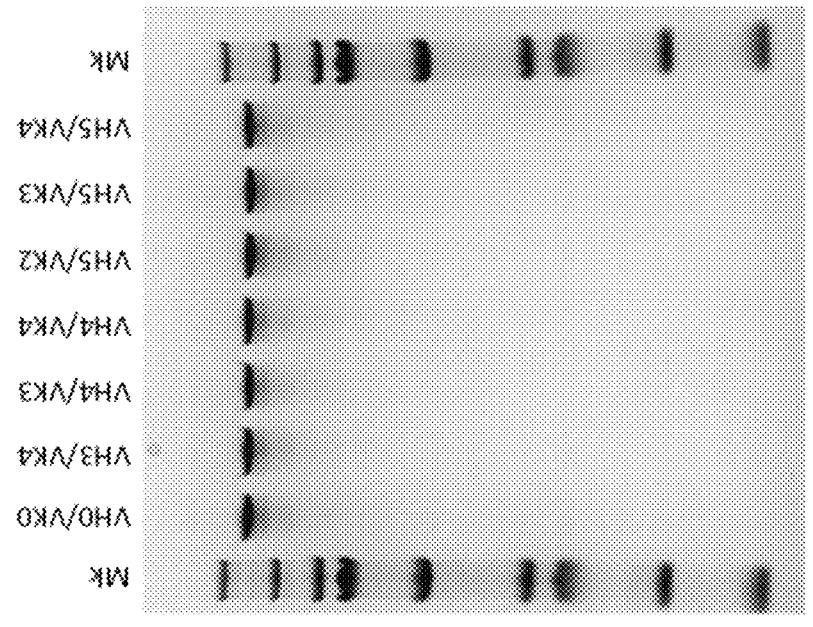
FIGS. 16A-16B are images of SDS-PAGE gels of chimeric (VH0/VK0) and humanized 11C12 variants. 1 µg of each sample was loaded under.
Figure 16A:
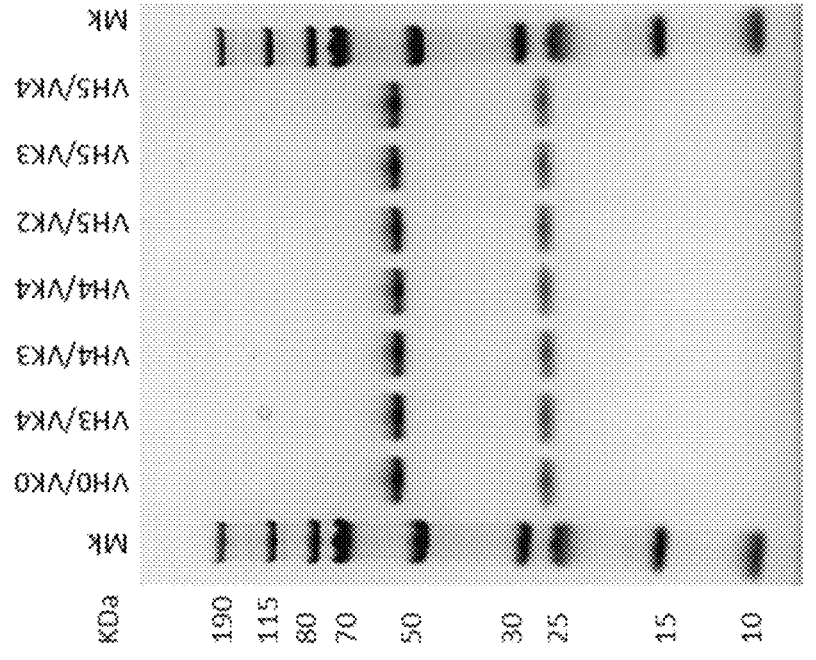
Figure 17:
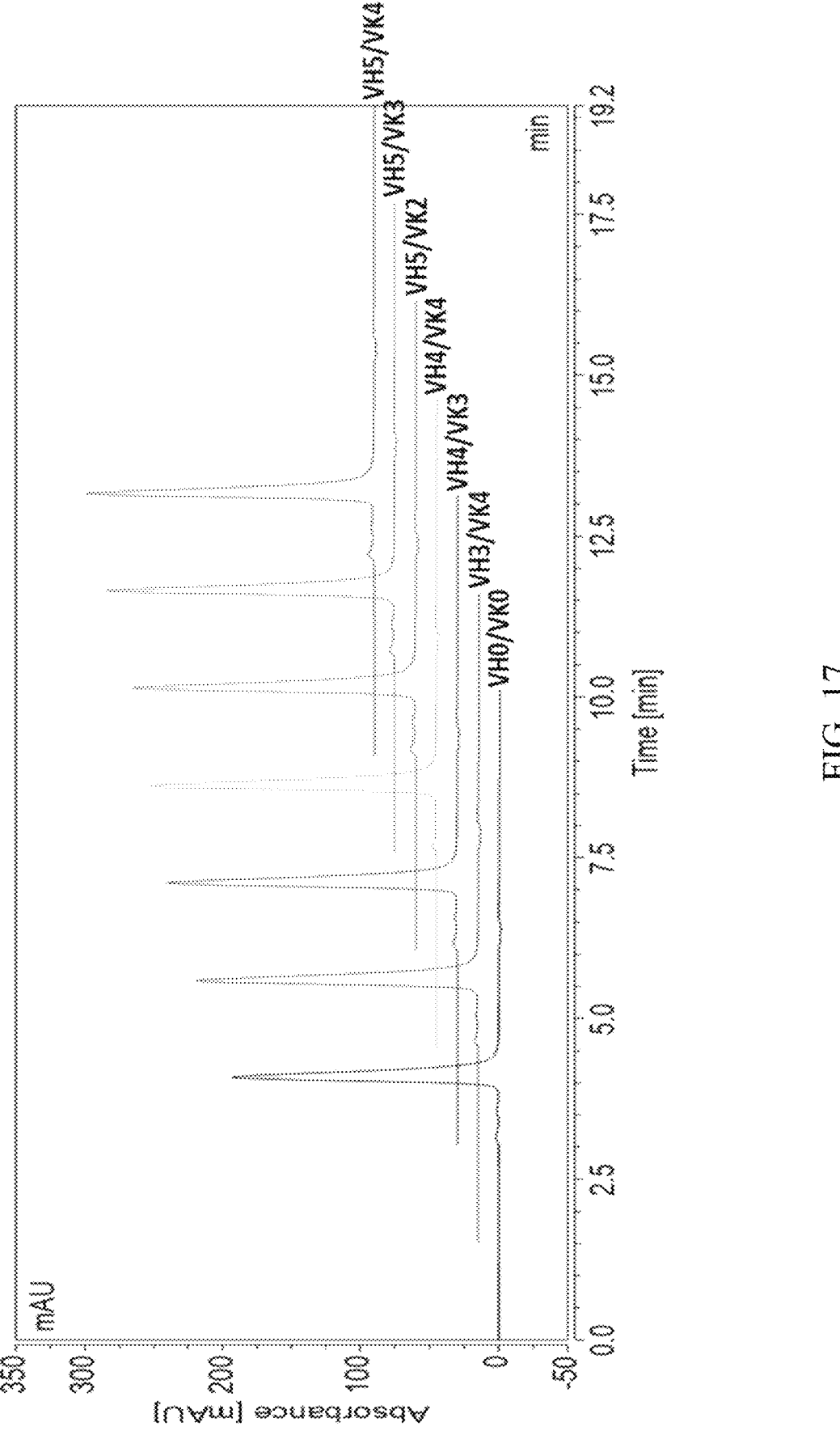
FIG. 17 illustrates SE-HPLC analysis of chimeric (VH0/VK0) and humanized 11C12 variants post protein A capture purification. 10 µg of purified IgG was loaded on an Acquity UPLC Protein BEH SEC 200 Å analytical column (Waters, Hertfordshire, UK) using 0.2 M potassium phosphate, pH 6.8, 0.2 M potassium chloride as mobile phase. Individual SE-HPLC chromatograms are shown in FIGS. 31A-31D.

PrismA purified material was then analyzed by SDS-PAGE as shown in FIGS. 16A-16B and analytical SE-HPLC (See FIG. 17 for Overlay and FIG. 31 for individual traces). FIG. 18 shows the percentage of monomers observed for each variant as determined by analytical SE-HPLC.

Multicycle Kinetics Biacore of Chimeric and Humanized 11C12 Variants

Figure 68:
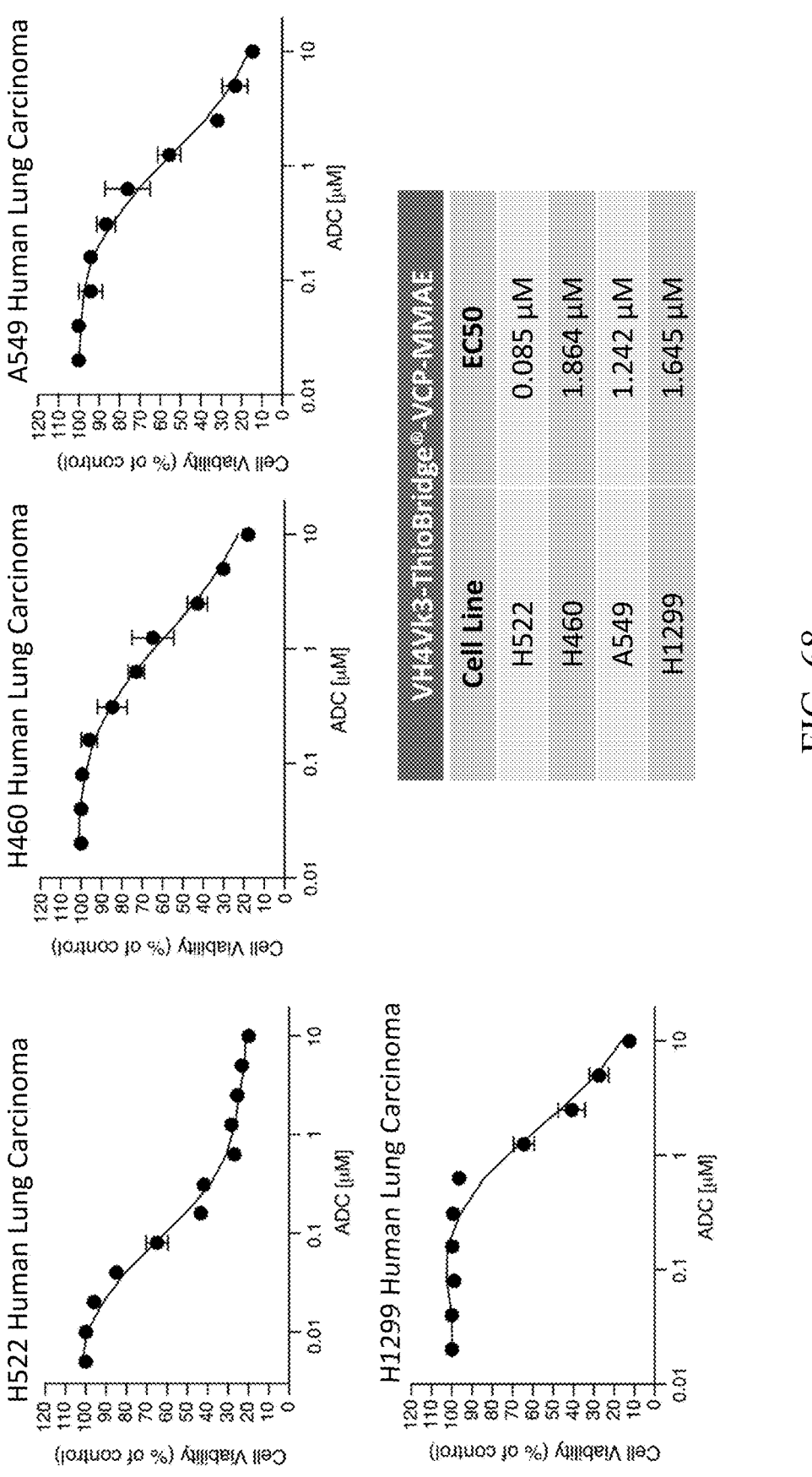
FIG. 68 illustrates the cytotoxicity of VH4Vk3-Thio-Bridge®-VCP-MMAE.

In order to assess the binding of the six lead humanized variants to rhEphA5 antigen, multi-cycle kinetic analysis (FIG. 68) was performed on purified material. Kinetic experiments were performed at 25° C. on a Biacore T200 running Biacore T200 Control software V2.0.1 and Evaluation software V3.0 (GE Healthcare, Uppsala, Sweden).

HBS-P+ (GE Healthcare, Uppsala, Sweden), supplemented with 1% BSA w/v (Sigma, Dorset, UK) was used as running buffer as well as for ligand and analyte dilutions. Purified lead antibodies were diluted to 0.5 μg/mL in running buffer and at the start of each cycle, loaded onto Fc2, Fc3 and Fc4 of an anti-human IgG CMS sensor chip (GE Healthcare, Little Chalfont, UK). Antibodies were captured at a flow rate of 10 μl/min to give an immobilization level (RL) of 50 RU. The surface was then allowed to stabilize.

Multi-cycle kinetic data was obtained using recombinant EphA5 as the analytes injected at a flow rate of 30 μl/min to minimize any potential mass transfer effects. A five point, three-fold dilution range from 1.11 nM to 270 nM of EphA5 was prepared in running buffer. For each concentration, the association phases were monitored for 210 seconds and the dissociation phase was measured for 900 seconds. Regeneration of the sensor chip surface was conducted between cycles using two injections of 3 M MgCl2. Multiple repeats of a blank and of EphA5 were programmed into the kinetic run in order to check the stability of both the surface and analyte over the kinetic cycles.

The signal from the reference channel Fc1 (no IgG captured) was subtracted from that of Fc2, Fc3 and Fc4 to correct for bulk effect and differences in non-specific binding to a reference surface. The signal from each IgG blank run (IgG captured but no antigen) was subtracted to correct for differences in surface stability. The double referenced sensorgrams were fitted with the Langmuir (1:1) binding model where the closeness of fit of the data to the model is evaluated using the Chi square value which describes the deviation between the experimental and fitted (observed and expected) curves. The fitting algorithm seeks to minimize the Chi square value.

Figure 20:
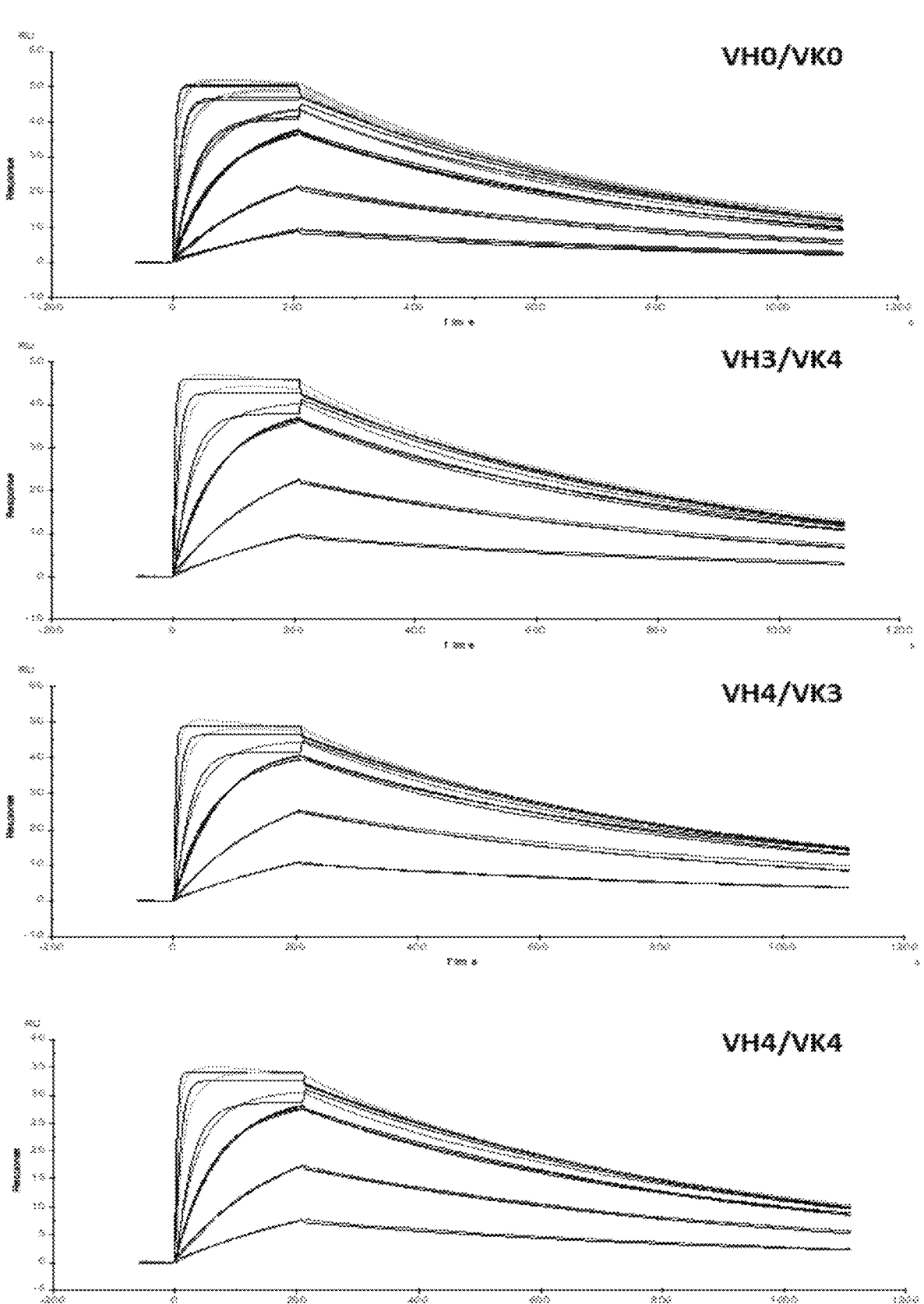
FIG. 20 illustrates multi-cycle kinetics raw sensorgrams and fitted curves with a 1:1 model (in black) for the binding of the chimeric antibody and six purified lead humanized variants to human EphA5. Kinetic analysis was carried out on a Biacore T200. Each IgG was captured on an anti-human IgG sensor chip before increasing concentrations of antigen were injected.

A summary of the kinetic constants determined from the 1:1 model fitted curves is shown in FIG. 19 with fitted curves shown in FIG. 20. Biacore analysis showed that all variants bind within two-fold of the chimeric.

Thermal Stability Analysis of Chimeric and Humanized 11C12 Variants.

Thermal ramp stability experiments (Tm and Tagg) are well established methods for ranking proteins and formulations for stability. A protein's denaturation profile provides information about its thermal stability and represents a structural 'fingerprint' for assessing structural and formulation buffer modifications. A widely used measure of the thermal structural stability of a protein is the temperature at which it unfolds from the native state to a denatured state. For many proteins, this unfolding process occurs over a narrow temperature range and the mid-point of this transition is termed 'melting temperature' or 'Tm'. To determine the melting temperature of a protein, UNcle measures the fluorescence of Sypro Orange (which binds to exposed hydrophobic regions of proteins) as the protein undergoes conformational changes.

Figure 22A:
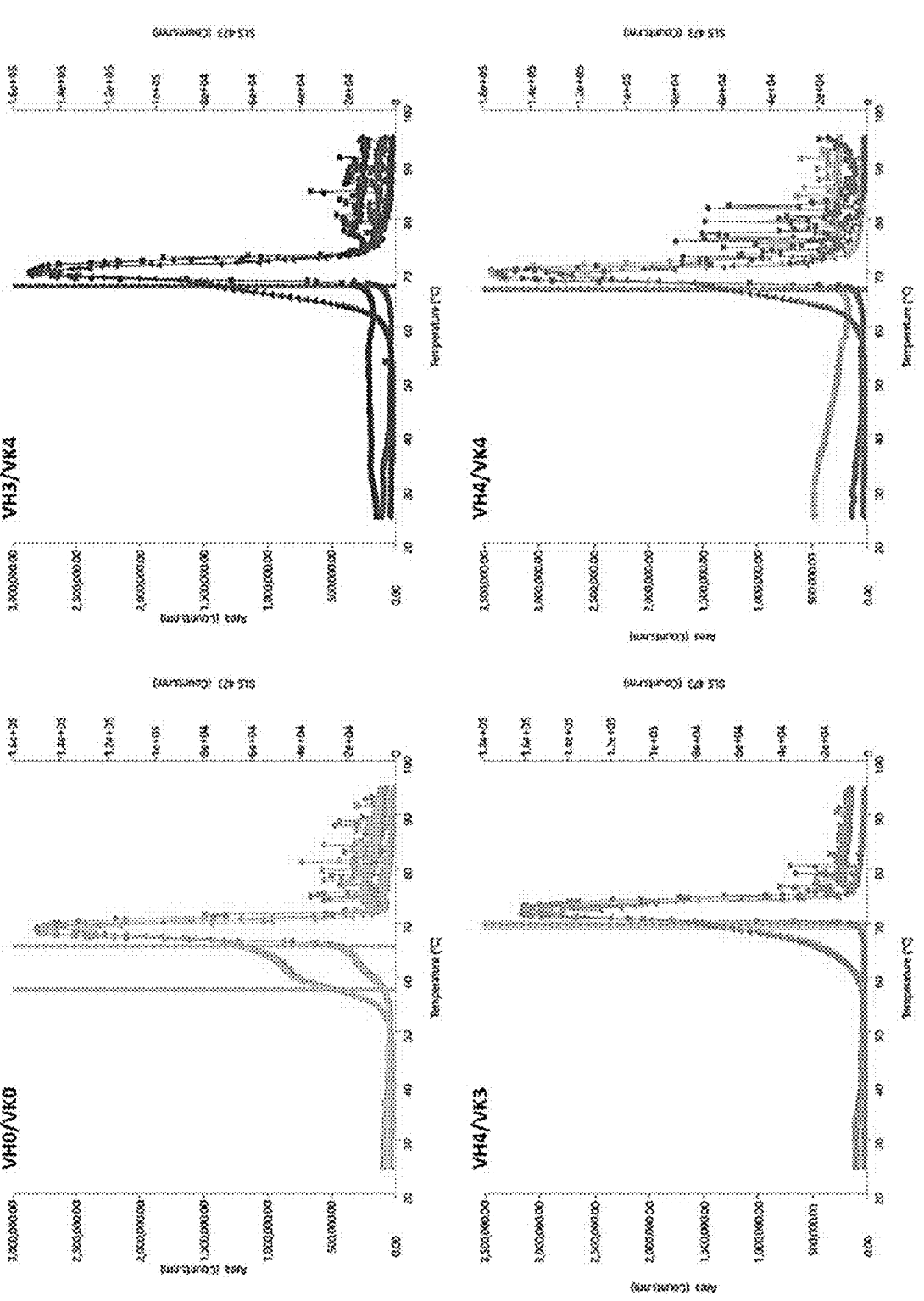
Figure 22B:
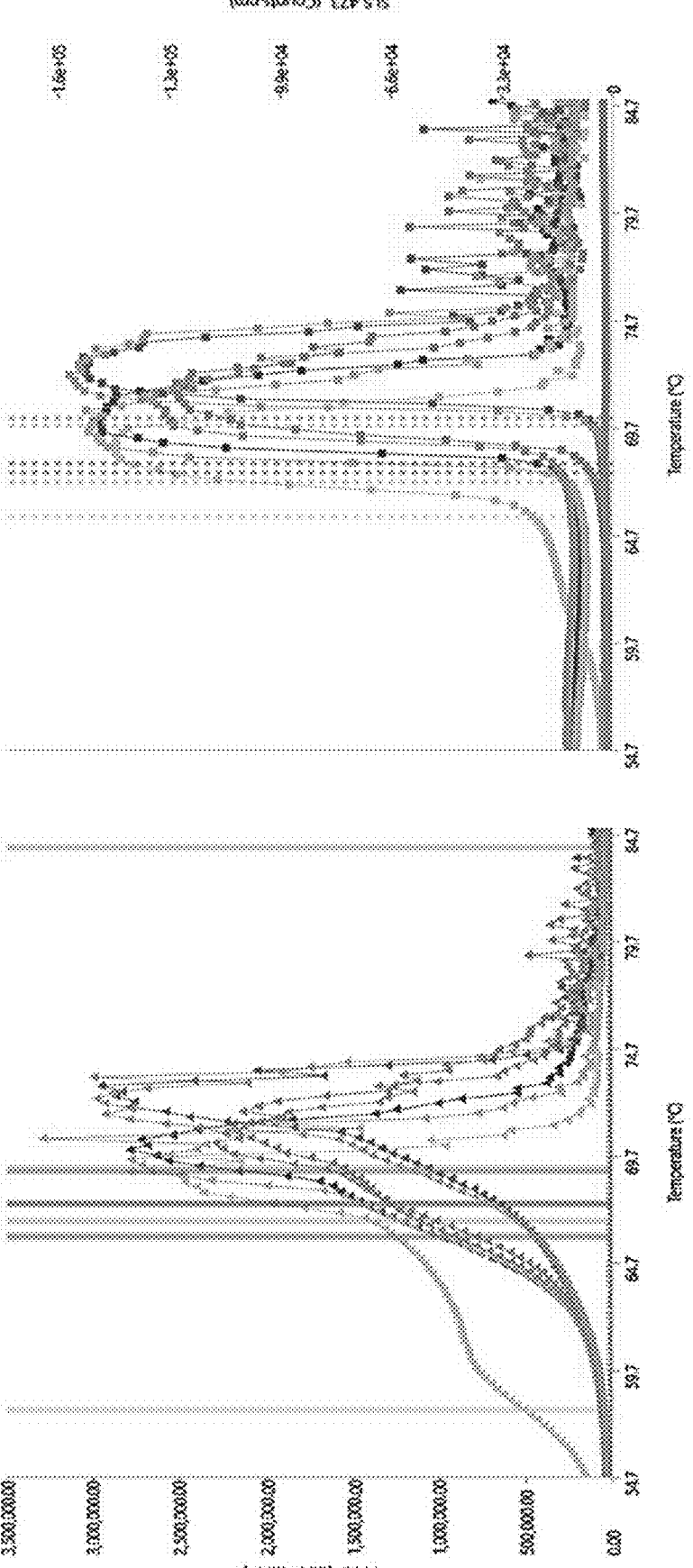

Samples for each variant were formulated in PBS and Sypro Orange at a final concentration of 1 mg/mL. 9 μL of each sample mixture was loaded in duplicate into UNi microcuvettes. Samples were subjected to a thermal ramp from 25-95° C., with a ramp rate of 0.3° C./minute and excitation at 473 nm. Full emission spectra were collected from 250-720 nm, and the area under the curve between 510-680 nm was used to calculate the inflection points of the transition curves (Tonset and Tm). Monitoring of static light scattering (SLS) at 473 nm allowed the detection of protein aggregation, and Tagg (onset of aggregation) was calculated from the resulting SLS profiles. Data analysis was performed using UNcle™ software version 4.0 and is shown in FIG. 21 and FIGS. 22A-22B. Thermal stability values determined lie in a broad range from 57.9 to 69.6° C. (Tm1), 55.1 to 65.2° C. (Tonset) and 65.6 to 70.2° C. (Tagg) with the humanized leads generally showing improved profiles when compared to the chimeric antibody. For all humanized antibodies tested one transition (Tm1) was detected, whereas two transitions (Tm1 and Tm2) were detected for the chimeric VH0/VK0 antibody. All humanized antibodies appear to have a higher Tm1, Tonset and Tagg compared to the chimeric antibody. Based on the SLS profiles, the suggested top three leads would be variants VH5/VK3, VH4/VK3 and VH5/VK4 with the highest Tagg values.

Flow Cytometry Analysis of Cell Binding to EphA5

Figures 23A, 23B:
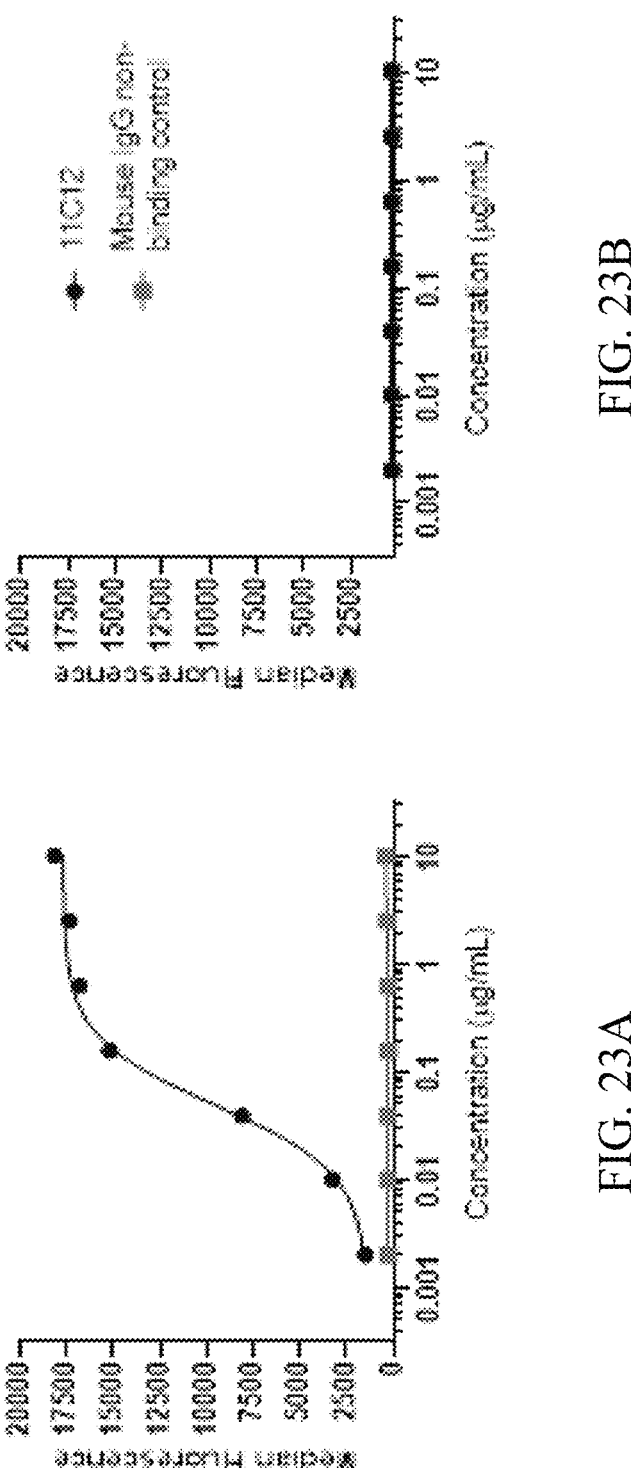
FIGS. 23A-23B illustrate dose-response curves showing the MFI values for the 11C12 positive control and the MolgG1 nonbinding control tested with (FIG. 23A) H460 (EphA5+) cells and (FIG. 23B) H226 (EphA5−) cells.

A H460 cell line stably expressing EphA5 (provided by Rutgers) was used, alongside H226 cells as a negative control, to test for antibody binding in a flow cytometry assay. The cell lines were first assessed for target expression using 10 μg/ml of the murine 11C12 provided by Rutgers) and MolgG1 non-binging control (Biolegend, California, US). Goat anti-mouse Alexa Fluor 647 (Thermo Fisher, Loughborough, UK) was used for antibody detection. The 11C12 positive control bound to the positive cell line in a concentration dependent manner (FIG. 23). As expected, no binding of the positive control was observed with the H226 cell line.

For cell binding assays, both cell lines were resuspended in FACS buffer (PBS+1% BSA+0.1% sodium azide) and seeded in 96 well U bottom plates at 1×105 (100 μl) cells per well. The chimeric and six purified humanized variants were tested in the assay alongside the 11C12 murine positive control, MolgG1 and HuIgG1 non-binding controls. Samples were prepared at a starting concentration of 10 μg/ml in FACS buffer and underwent a four-fold seven point serial dilution for testing with H460 cells and a three-fold three point serial dilution for the H226 cells. Cell pellets were resuspended in 100 μl of the serially diluted samples and incubated at 4° C. for 30 minutes. After the incubation, cells were pelleted, washed twice with 100 μl of FACS buffer and resuspended in either Alexa Fluor 647 anti-mouse or anti-human (Thermo Fisher) diluted to 5 μg/ml in FACS buffer. After incubation at 4° C. for 30 minutes, cells were pelleted, washed twice with 100 μl of FACS buffer and resuspended in 200 μl per well 1×BD CellFix solution (BD Pharmingen, Berkshire, UK). Median fluorescence intensity (MFI) was measured using an Attune N×T Flow Cytometer (Thermo Fisher, Loughborough, UK) and 10,000 gated events were acquired per sample. For data analysis, live cell populations were gated based on the forward and side scatter dot plot allowing the Alexa Fluor 647 MFI values to be measured in the RL1 channel.

Figure 25:
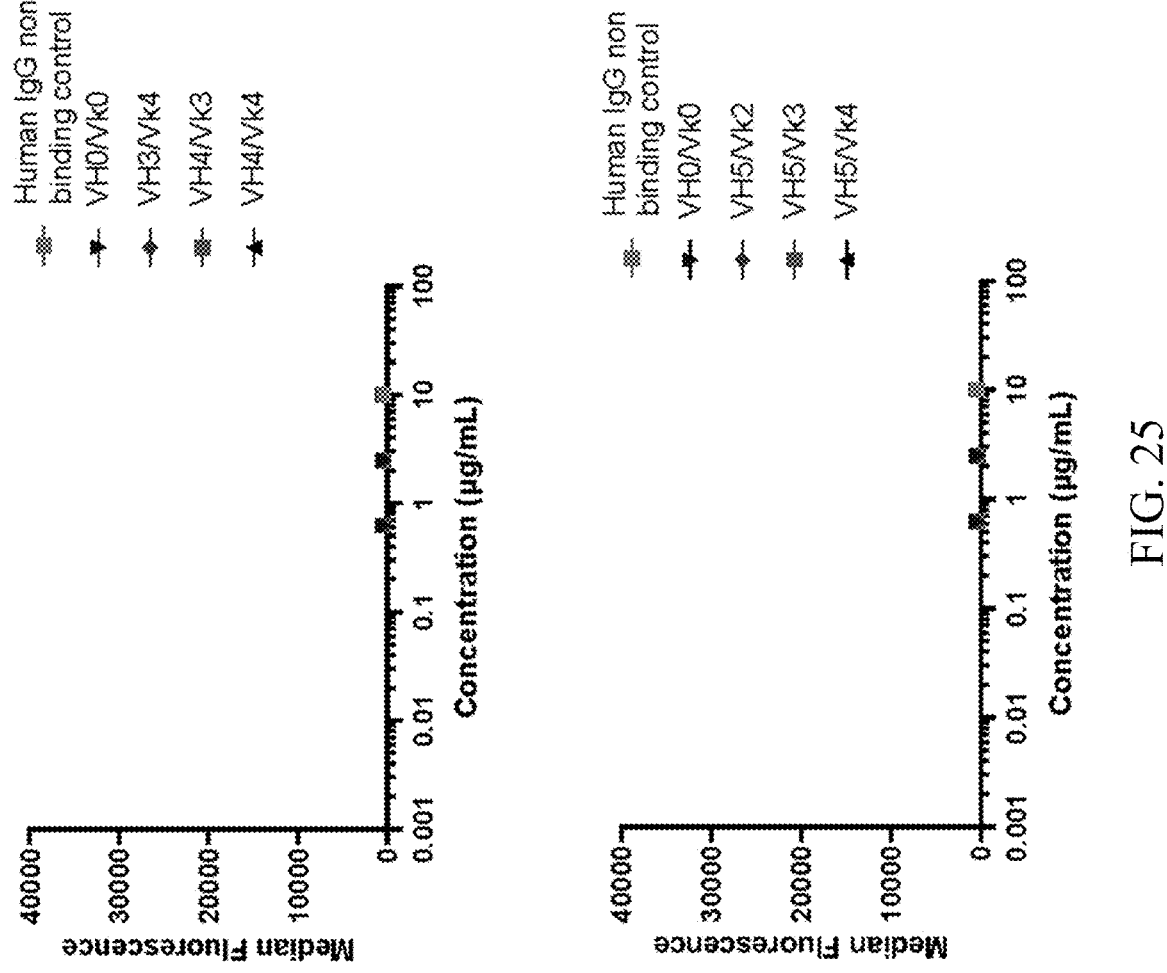
FIG. 25 illustrates dose-response curves showing the MFI values for the six variants tested with the H226 cell line.

Full dose response curves and specific binding were observed for all of the humanized variants tested and the antibodies performed comparably to VH0/VK0. No binding was observed with the H226 cell line which was negative for the target. Binding curves are shown in FIGS. 24, 25, and 26).

Selected Conclusion and Discussion

The V-region sequences encoding the anti-human EphA5 monoclonal murine antibody, 11C12, were used to construct a chimeric antibody (VH0/VK0) and thirty humanized antibody variants. After expression in HEK cells, the antibody supernatants were tested for binding to EphA5 antigen using single cycle kinetics (SCK) Biacore. Six antigen-binding humanized antibody variants and the chimeric antibody, were purified from CHO supernatant, using Mab Select PrismA chromatography. The purified antibodies were characterized on SE-HPLC and reducing and non-reducing SDS-PAGE. SE-HPLC showed that the percentage of monomer for chimeric antibody was >90% for all humanized variants.

Multi-cycle kinetic analysis and UNcle biostability platform assessment was performed on the chimeric antibody and six lead humanized variants, (VH3/VK4, VH4/VK3, VH4/VK4, VH5/VK2, VH5/VK3 and VH5/VK4). Biacore analysis showed that all humanized variants bind within two-fold of the chimeric antibody. Thermal stability analysis using Sypro Orange and the UNcle biostability platform showed humanized variants VH5/VK3, VH4/VK3 and VH5/VK4 had the highest Tagg values.

Full dose response curves and specific binding were observed for all of the humanized variants. No binding was observed with the EphA5 negative H226 cell line.

Tables E2 and E3 summarize results for improvements in binding affinity and temperature stability for the exemplary antibody VH5/VK3 as compared to the reference chimeric antibody VH0/VK0.

TABLE E2

| | | | | | | |
|---|---|---|---|---|---|---|
| VH5/VK3 Antibody has lower KD, suggesting a higher affinity to target. | | | | | | |
| Antibody | $k_a$ (1/Ms) | $k_d$ (1/s) | $K_D$ (M) | Relative $K_D$ | $R_{MAX}$ | $Chi^2$ ($RU^2$) |
| VH0/VK0 | $9.65 \times 10^{-5}$ | $1.50 \times 10^{-3}$ | $1.56 \times 10^{-9}$ | 1.00 | 47.8 | 1.23 |
| VH5/VK3 | $1.21 \times 10^{-6}$ | $1.35 \times 10^{-3}$ | $1.11 \times 10^{-9}$ | 0.71 | 35.3 | 0.429 |

TABLE E3

| | | | | | | | | |
|---|---|---|---|---|---|---|---|---|
| VH5/VK3 has a higher Tm1, Tonset and Tagg compared to VH0/VK0. | | | | | | | | |
| Sample | Tm1 (° C.) | Average Tm1 (° C.) | Tm2 (° C.) | Average Tm2 (° C.) | Tonset (° C.) | Average Tonset (° C.) | Tagg 473 (° C.) | Average Tagg 473 (° C.) |
| VH0/VK0 | 57.83 | 57.9 | 65.83 | 65.83 | 54.92 | 55.1 | 65.72 | 65.6 |
| | 57.87 | | 65.83 | | 55.23 | | 65.60 | |

TABLE E3-continued

| | Tm1 (° C.) | Average Tm1 (° C.) | Tm2 (° C.) | Average Tm2 (° C.) | Tonset (° C.) | Average Tonset (° C.) | Tagg 473 (° C.) | Average Tagg 473 (° C.) |
|---|---|---|---|---|---|---|---|---|
| | | | VH5/VK3 has a higher Tm1, Tonset and Tagg compared to VH0/VK0. | | | | | |
| Sample | | | | | | | | |
| VH5/VK3 | * 68.99 | 69.0 | | | * 63.59 | 63.6 | * 70.17 | 70.2 |

Example 2: Specificity Profiling of H4K3 and H5K3 Antibodies

To optimize conditions for test antibody detection, HEK-293T cells and QT6 cells were transfected with plasmids encoding known test antibody targets, Protein A (binds antibody Fc; positive control), or vector alone (pUC; negative control) in 384-well cell-culture plates. After incubation, four four-fold dilutions starting at 20 µg/ml of each test antibody were added in quadruplicate to transfected cells and detected using a single dilution of secondary antibody in a high-throughput immunofluorescence flow cytometry assay. Data from assay setup experiments were used to determine the optimal screening conditions for high-throughput immunodetection (Table E4). Optimal screening concentrations were determined by the background signal (mean fluorescence intensity (MFI)), and false positive rate in the vector control.

Materials and Methods

Membrane Proteome Array: Membrane Proteome Array (MPA) screening was conducted at Integral Molecular. The MPA is a protein library composed of 6,000 human membrane protein clones, each overexpressed in live cells from expression plasmids. Each clone was individually transfected in separate wells of a 384-well plate followed by a 36 h incubation (Tucker et al., 2018). Cells expressing each individual MPA protein clone were arrayed in duplicate in a matrix format for high-throughput screening. Before screening on the MPA, the test antibody concentration for screening was determined on cells expressing positive (membrane-tethered Protein A) and negative (mock-transfected) binding controls, followed by detection by flow cytometry using a fluorescently-labeled secondary antibody. Each test antibody was added to the MPA at the predetermined concentration, and binding across the protein library was measured on an Intellicyt iQue using a fluorescently-labeled secondary antibody. Each array plate contains both positive (Fc-binding) and negative (empty vector) controls to ensure plate-to-plate reproducibility. Test antibody interactions with any off targets identified by MPA screening were confirmed in a second flow cytometry experiment using serial dilutions of the test antibody, and the target identity was re-verified by sequencing.

TABLE E4

Experimental parameters optimized for high-throughput immunodetection.

| Parameter | EPHA5 H4K3 | EPHA5 H5K3 |
|---|---|---|
| Cells | HEK-293T | HEK-293T |
| Blocking Buffer | 10% Goat Serum | 10% Goat Serum |

TABLE E4-continued

Experimental parameters optimized for high-throughput immunodetection.

| Parameter | EPHA5 H4K3 | EPHA5 H5K3 |
|---|---|---|
| | 1° Ab | |
| Ab name | EPHA5 H4K3 | EPHA5 H5K3 |
| Optimal Conc. | 20 µg/ml | 20 µg/ml |
| Incubation (RT) | 60 min | 60 min |
| | 2° Ab | |
| Target | Human IgG | Human IgG |
| Optimal Conc. | 1:400 (3.75 µg/ml) | 1:400 (3.75 µg/ml) |
| Incubation (RT) | 30 min | 30 min |
| Manufacturer | Jackson ImmunoResearch | Jackson ImmunoResearch |
| Cat # | 109-606-008 | 109-606-008 |
| Antibody ID | AlexaFluor ® 647-AffiniPure Goat F(ab')2 Anti-Human Fc | AlexaFluor ® 647-AffiniPure Goat F(ab')2 Anti-Human Fc |
| Washes | PBS (without Ca2+, Mg2+) | PBS (without Ca2+, Mg2+) |

Membrane Proteome Array Screen

Figure 70:
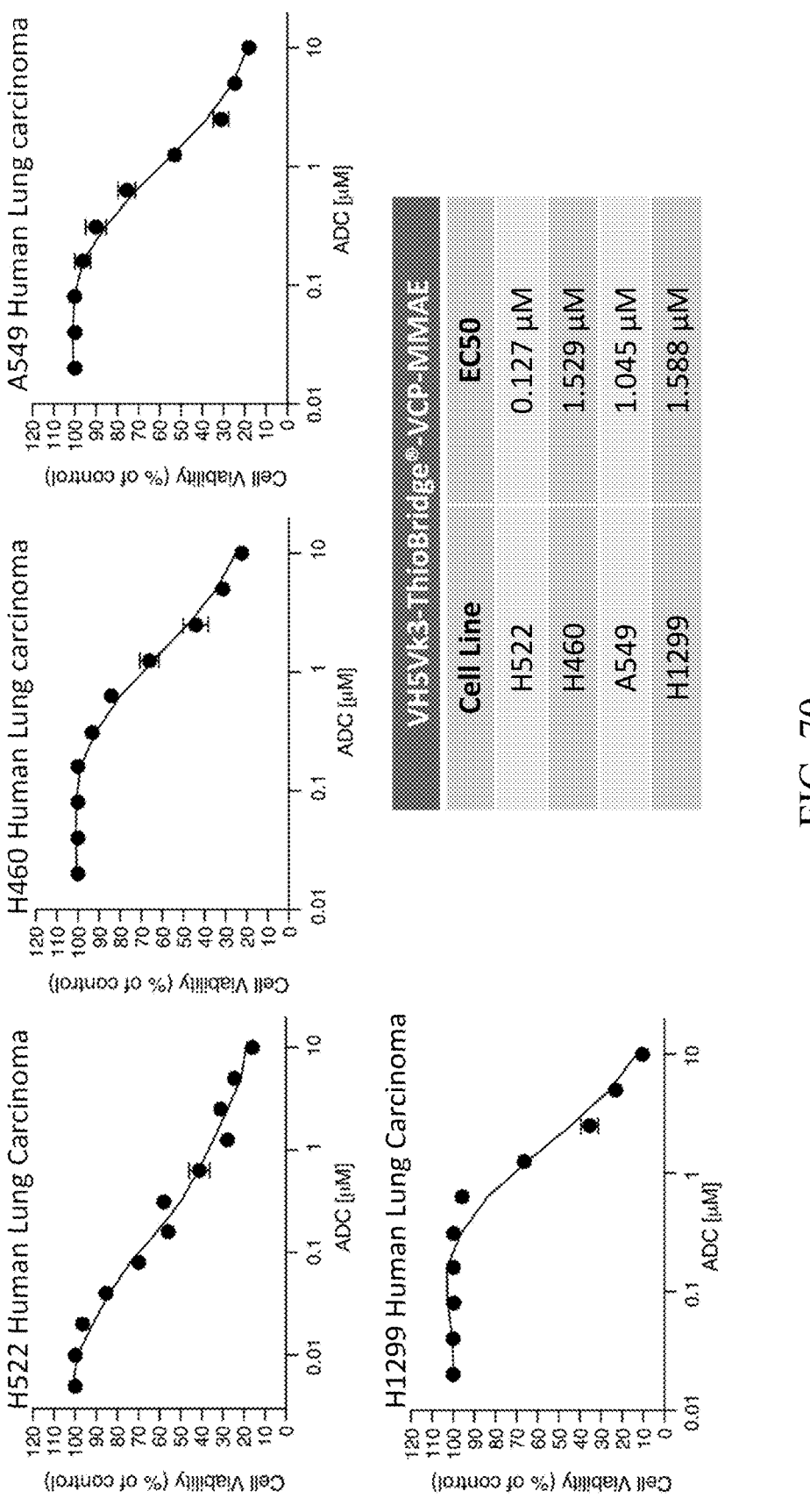
FIG. 70 illustrates the cytotoxicity of VH5Vk3-Thio-Bridge®-VCP-MMAE.
Figure 71:
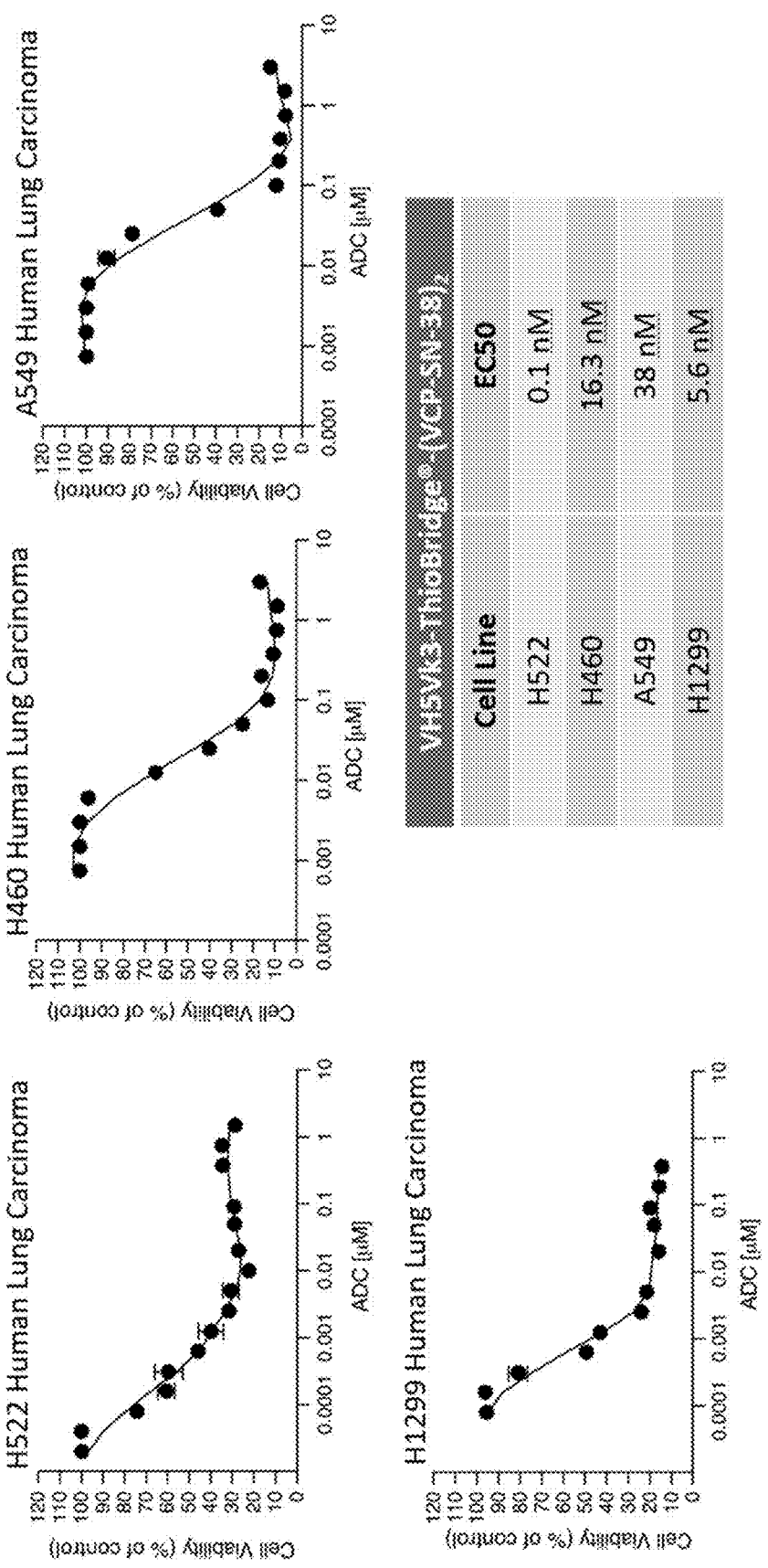
FIG. 71 illustrates the cytotoxicity of VH5Vk3-Thio-Bridge®-(VCP-SN-38)$_2$.

To identify antibody binding targets, ~6,000 different membrane proteins were each expressed in individual wells of HEK-293T or QT6 cells arrayed in 384 well plates. The cells were then matrixed by pooling individual columns and rows of each 384 well plate so each protein was represented in a unique combination of two different wells of the matrix plate. Targets were then identified by detecting MAb binding (using previously optimized conditions; Table E4) to overlapping column and row pools, thereby allowing specific deconvolution (Table E5; FIGS. 70 and 71). Each individual membrane protein target was assigned values corresponding to the binding values of their unique row and column pools, and targets displaying binding of greater than 3 standard deviations above background in both wells were selected for downstream validation experiments. The resulting paired binding values were subsequently normalized and transformed to give a single numerical value for binding of the MAb against each target protein (Target Binding). Non-specific fluorescence was determined to be any value below 3 standard deviations of the mean background value.

TABLE E5

Identified membrane protein targets

| Ligand | Target gene (HGNC) | Uniprot |
|---|---|---|
| EPHA5 H4K3 | EPHA5 | P54756 |
| EPHA5 H5K3 | EPHA5 | P54756 |
| | CPT1B | Q92523 |

Validation of Antibody Targets

To validate any off-target interaction identified, cells were transfected with plasmids encoding the identified targets, protein A, or vector alone in 384-well format. After incubation four four-fold dilutions of each test antibody, starting at 20 µg/ml, were added to transfected cells followed by detection of antibody binding using a high-throughput immunofluorescence flow cytometry assay (same conditions as described in Table E4). No validation was performed if a molecule's known target was the only protein identified in the MPA screen, as the Assay Setup results already demonstrate specific reactivity in a screen equivalent to the validation screen.

Figures 2A, 2B:
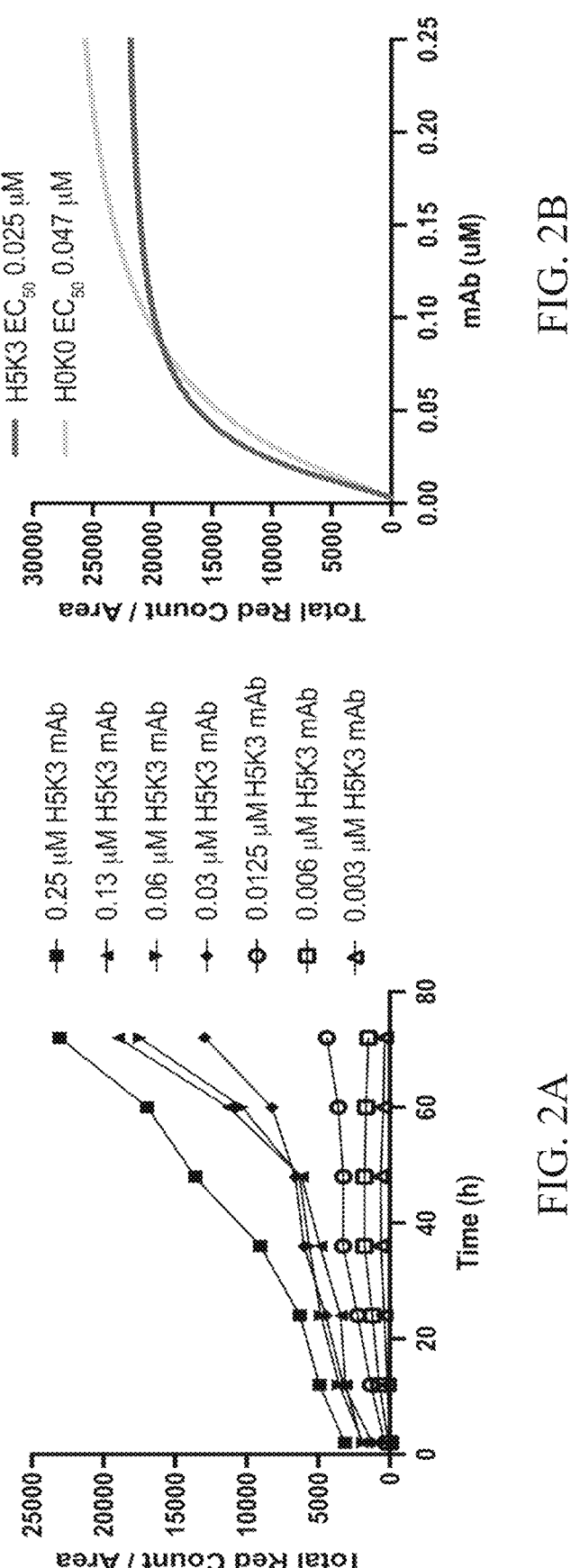
FIGS. 2A-2B illustrate internalization of EphA5 antibodies.

Similar studies observing the behavior of VH5/VK3 antibody after binding to cell-surface EPHA5 expressed on target cells at various concentrations found that bound antibody was internalized into EphA5+ cells but not EphA5− cells and trafficked to lysosome after binding to the cell surface target (FIGS. 2A and 2B).

Optimization of Conditions for Binding and Screening of Antibodies

Conditions for binding and screening of MAbs and Fabs using high-throughput flow cytometry were optimized using wild-type target protein cloned into a proprietary vector and expressed in HE-293T cells. In order to map the epitopes of MAbs and Fabs, an alanine-scan library of the target protein was constructed. The test antibodies were then screened for binding to each individual target protein variant, allowing identification of the target protein residues involved in test MAb binding.

Shotgun Mutagenesis epitope mapping services were provided by Integral Molecular (Philadelphia, PA) as described in Davidson and Doranz, 2014. Briefly, a mutation library of the target protein was created by high-throughput, site-directed mutagenesis. Each residue was individually mutated to alanine, with alanine codons mutated to serine. The mutant library was arrayed in 384-well microplates and transiently transfected into HEK-293T cells. Following transfection, cells were incubated with the indicated antibodies at concentrations pre-determined using an independent immunofluorescence titration curve on wild type protein. MAbs were detected using an Alexa Fluor 488-conjugated secondary antibody and mean cellular fluorescence was determined using Intellicyt iQue flow cytometry platform. Mutated residues were identified as being critical to the MAb epitope if they did not support the reactivity of the test MAb but did support the reactivity of the reference MAb. This counter screen strategy facilitates the exclusion of mutants that are locally misfolded or that have an expression defect.

Initial studies sought to optimize binding and screening of the MAbs against the target protein. Cells were transfected with a wild-type (WT) construct of the target protein or with vector alone in 384-well format, followed by detection of cellular expression via high-throughput flow cytometry (FIG. 72). Serial dilutions of each MAb were tested for immunoreactivity against cells expressing target protein (WT) or vector alone. Each point represents the mean of four replicates. The optimal screening concentration for each MAb was determined based on the raw signal values and signal to background calculations. See Table E6.

TABLE E6

| Experimental Parameter | Test MAb | Test MAb |
| --- | --- | --- |
| | Experimental parameters optimized for high-throughput flow cytometry. | |
| Cell Type Fixative | HEK293T | HEK293T |
| Blocking Buffer | None | None |
| | 10% Goat Serum | 10% Goat Serum |

TABLE E6-continued

| Experimental Parameter | Test MAb | Test MAb |
| --- | --- | --- |
| | Experimental parameters optimized for high-throughput flow cytometry. | |
| Name | H5K3 | H4K3 |
| Target | EPHA5 | EPHA5 |
| Optimal Conc.(ug/mL) Incubation (25° C.) | 0.25 µg/ml 60 min | 0.25 µg/ml 60 min |
| Target Optimal Conc. Incubation (25° C.) | Human IgG 1:400 (3.75 ug/ml) | Human IgG 1:400 (3.75 ug/ml) |
| Manufacturer Cat # Antibody ID | 30 min Jackson ImmunoResearch 109-545-003 AlexaFluor ® 488 AffiniPure Goat Anti-Human IgG (H+L) | 30 min Jackson ImmunoResearch 109-545-003 AlexaFluor ® 488 AffiniPure Goat Anti-Human IgG (H+L) |
| Wash Buffer | PBS (Ca2+, Mg2+ free) | PBS (Ca2+, Mg2+ free) |
| Signal:Background | 24:1 | 30:1 |

A series of studies was then undertaken to optimize screening of Fabs derived from the H4K3 and H5K3 antibodies against target proteins. Cells were transfected with a WT construct of the target protein or with vector alone in 384-well format, followed by detection of cellular expression via high-throughput flow cytometry (see FIG. 73. Serial dilutions of each Fab were tested for immunoreactivity against cells expressing target protein (WT) or vector alone. Each point represents the average of four replicates. The optimal screening concentration for each Fab was determined based on the raw signal values and signal-to-background calculations. See Table E7.

TABLE E7

| Experimental Parameter | Test FAb | Test FAb |
| --- | --- | --- |
| | Experimental parameters optimized for high-throughput flow cytometry. | |
| Cell Type Fixative | HEK293T | HEK293T |
| Blocking Buffer | None 10% Goat Serum | None 10% Goat Serum |
| Name Target | H5K3 EPHA5 | H4K3 EPHA5 |
| Optimal Conc.(ug/mL) Incubation (25° C.) | 0.50 µg/ml 60 min | 0.50 µg/ml 60 min |
| Target Optimal Conc. Incubation (25° C.) | Human F(ab')2 1:200 (7.50 ug/ml) 30 min Jackson | Human F(ab')2 1:200 (7.50 ug/ml) 30 min Jackson |
| Manufacturer Cat # Antibody ID | ImmunoResearch 109-546-006 AlexaFluor ® 488 AffiniPure Goat Anti-Human IgG F(ab')2 Fragment | ImmunoResearch 109-546-006 AlexaFluor ® 488 AffiniPure Goat Anti-Human IgG F(ab')2 Fragment |
| Wash Buffer | PBS (Ca2+, Mg2+ free) | PBS (Ca2+, Mg2+ free) |
| Signal:Background | 70:1 | 66:1 |

A series of studies then focused on identification of mutant antigen clones for antibody (Ab) binding (FIG. 74). Binding of each test Ab to each mutant clone in the alanine scanning library was determined, in duplicate, by high-throughput flow cytometry. For each point, background fluorescence was subtracted from the raw data, which were then normalized to Ab reactivity with WT target protein. For each mutant clone, the mean binding value was plotted as a function of expression (represented by control reactivity). To identify preliminary primary mutant clones (red circles), a threshold (dashed lines) of >70% WT binding to control Ab and <20% WT binding to test Abs was applied. Secondary clones (blue circles) are highlighted for clones that did not meet the set thresholds but whose decreased binding activity and proximity to critical residues suggested that the mutated residue may be part of the antibody epitope.

Further studies identified the residues for Ab binding (FIG. 75). Mean binding reactivities (and ranges) are listed for all identified primary residues. Identified primary residues for Ab binding (highlighted in red) were residues whose mutations were negative for binding to test Abs, but positive for binding to control antibody. Additional secondary residues (highlighted in blue) were identified that did not meet the threshold guidelines, but whose decreased binding activity and proximity to primary residues suggested that they may be part of the antibody epitope. Mutated cysteine residues that were identified as preliminary primary residues are not considered critical. The low binding observed is likely due to disruption of the disulfide bonds causing protein misfolding. The loss of binding for both mutations is likely due to protein misfolding.

Having identified binding-primary residues, visualizations of the primary residues for Ab binding were then determined (FIG. 76). Primary residues (red spheres) were visualized on a crystal structure model of the target protein, based on the structure of EPHA4 (PDB ID #4BK4, Seirdake et al., 2013). Secondary residues (blue spheres) that may contribute to binding are also shown.

FIG. 76 illustrates the primary residues whose mutation gave the lowest reactivities with specific antibodies are highlighted in bold and underlined. Validated primary residues represent amino acids whose side chains make the highest energetic contributions to the antibody-epitope interaction (Bogan and Thorn, 1998; Lo Conte et al., 1999); therefore, the highlighted residues are likely the major energetic contributors to binding.

Example 3: Production of ThioBridge® and Maleimide Anti-EphA5 Antibody-Drug Conjugates Antibody-drug conjugates (ADC) have been proven to be a biologic that can deliver drug to targeted cells with high efficiency and minimized off-target effect. The receptor tyrosine kinase EphA5 is a surface molecule expresses in many types of human lung cancer cell lines and human lung cancer biopsies. As lung cancer becomes one of the most common and deadly human cancer types, effective therapies are urgently needed.

Figure 3:
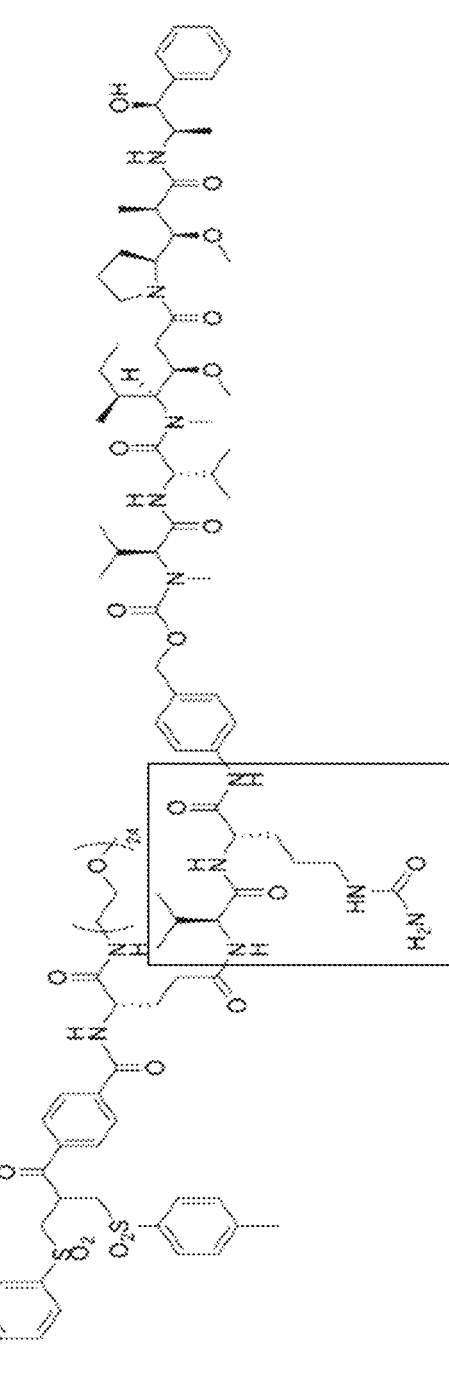
FIG. 3 illustrates the structure of the ThioBridge® linker-payload used for conjugation of MMAE to the antibody VH5/VK3. Boxed is the cleavable linker.

Improved anti-EphA5 monoclonal antibodies described in the above studies, including improved antibodies with reduced immunogenicity, higher binding affinity to the EphA5 target and/or better thermostability, were selected for generation of an ADC. The candidate antibodies, VH5/VK3 and VH4/VK3, which exhibited desirable improved features, were chosen for further investigation of cell surface target binding and antibody internalization. The ADC VH5/VK3-ThioBridge®-VCP-MMAE and the ADC VH5/VK3-ThioBridge®-(VC-PAB-CO-SN-38)₂ (and VH4/VK3 ADCs with the same payloads) were generated by using the ThioBridge® site-directed conjugation technology to deliver payload monomethyl auristatin E (MMAE) or SN-38, a topoisomerase I inhibitor. (see FIG. 3) The efficacy and specificity of the ADCs was assessed in vitro and in vivo using human lung cancer cell lines or human lung cancer xenograft models.

Selected Summary

Figure 32:
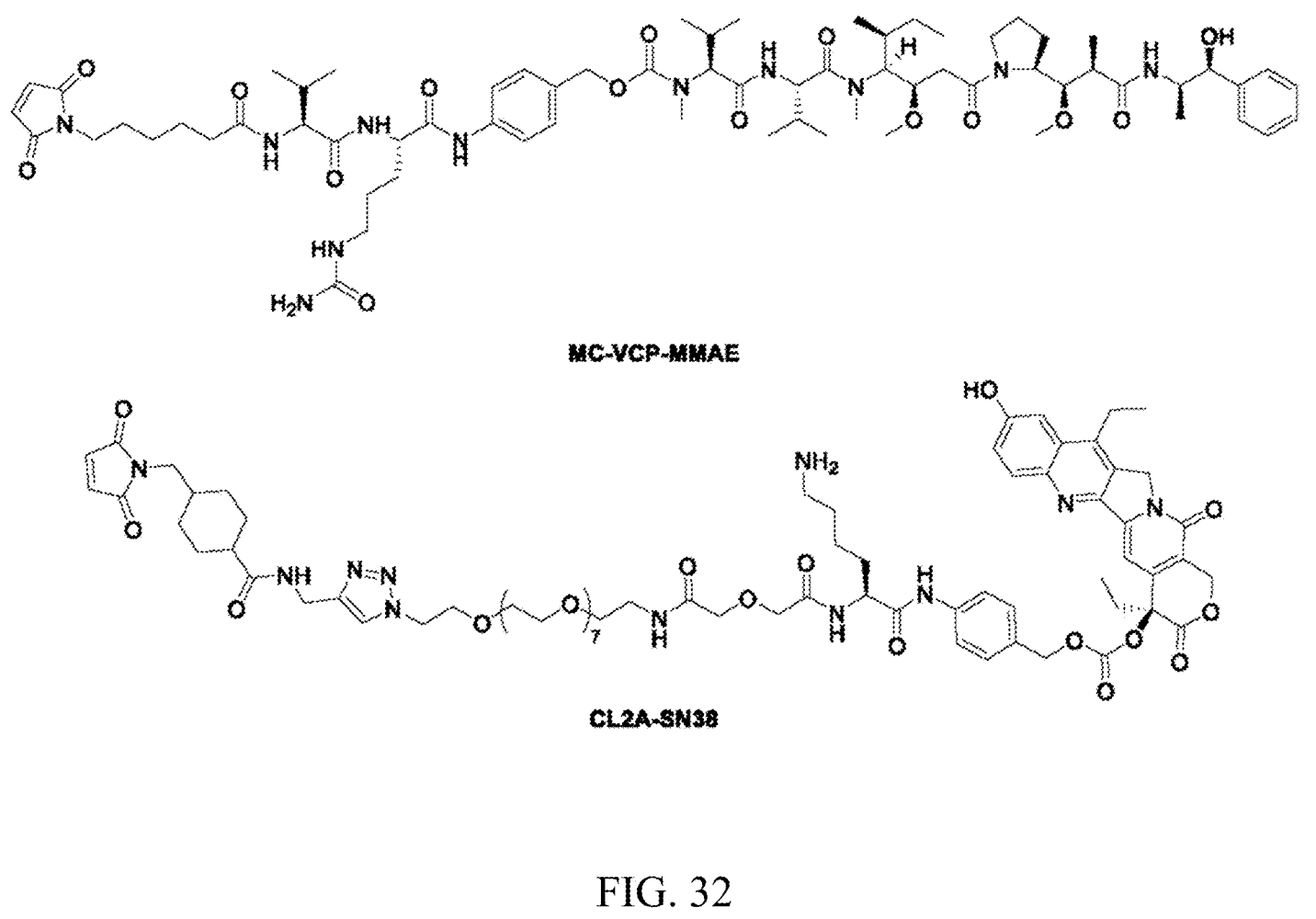

Anti-EphA5 ADCs were prepared from the humanized antibodies VH4Vk3 (SEQ ID NO:38 and SEQ ID NO:40) and VH5Vk3 (SEQ ID NO:39 and SEQ ID NO:40). The cytotoxic payloads MMAE and SN38 were employed for these ADCs. ADCs were prepared with either maleimide conjugation or ThioBridge®, a disulfide rebridging conjugation technology. The VH4Vk3 mAb was also conjugated to MC-VCP-MMAE and CL2A-SN38. ADCs were prepared utilizing ThioBridge® conjugation technology and two cytotoxic payloads: monomethyl auristatin E (MMAE), an auristatin inhibiting microtubules polymerization drug and SN38, an analogue of the DNA topoisomerase I inhibitor, camptothecin. Two ADCs were prepared utilizing maleimide conjugation with either MC-VCP-MMAE or CL2A-SN38 linker-payloads (see FIG. 32 for structures). Two linker-payloads were purchased from commercial vendors—MC-VCP-MMAE (Levena) and CL2A-SN38 (Levena)—and two further linker-payloads, ThioBridge®-VCP-MMAE and ThioBridge®-(VCP-SN38)₂, were synthesized.

Figure 33:
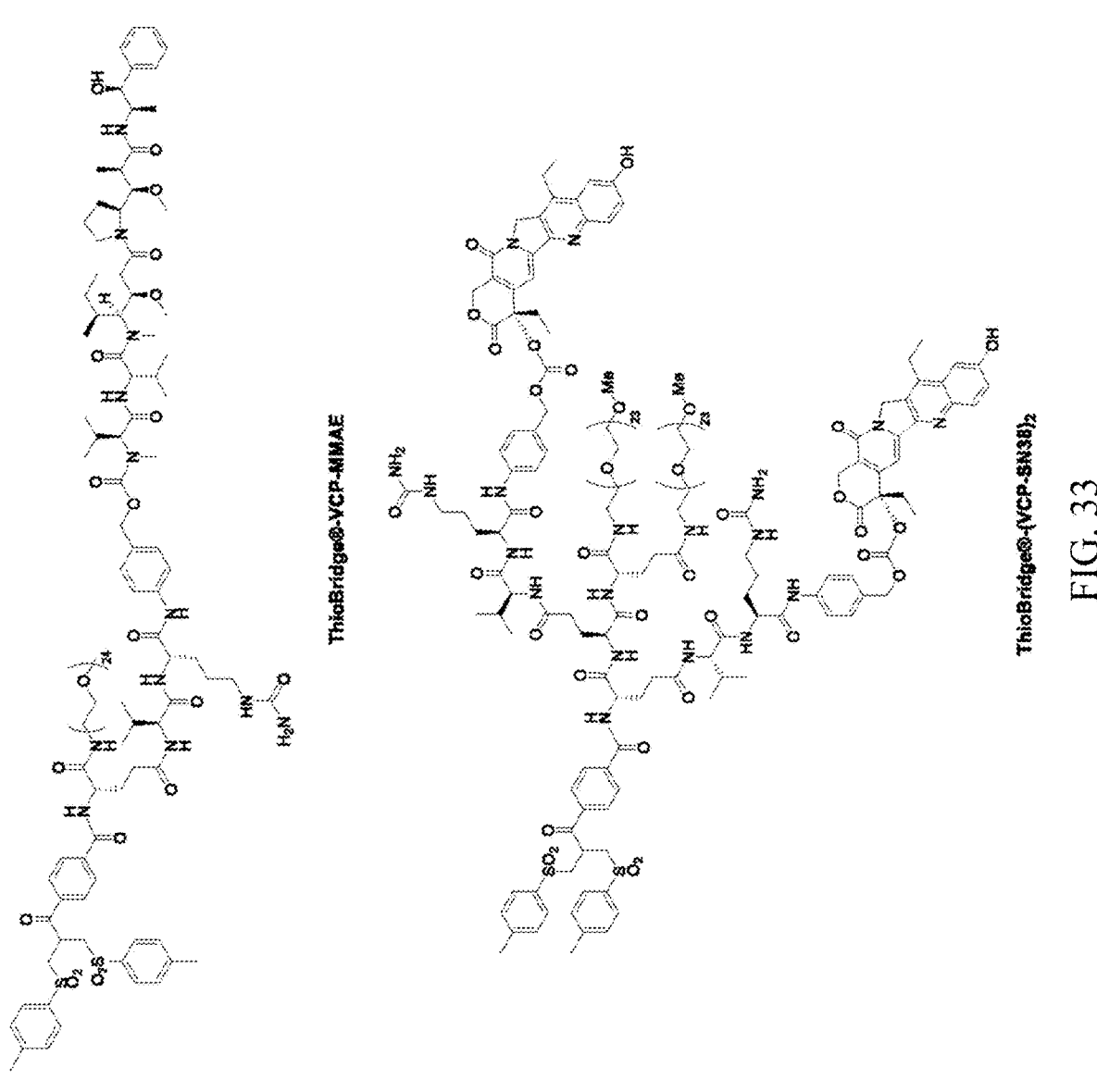
FIG. 33 illustrates structures of the ThioBridge® linker-payloads used for conjugation to the antibodies anti-EphA5-VH4Vk3 and VH5Vk3.

The ThioBridge® reagents used for conjugation in this project were a single loaded ThioBridge®-VCP-MMAE and a double-loaded ThioBridge®-VCP-SN38 reagent (see FIG. 33). For the ThioBridge®-SN38 linker-payload, a double-loaded structure with moieties cleavable by hydrolysis (carbonate) was used for coupling the cytotoxic payload SN38 to the antibody (see FIG. 33 for structures). This linker format was also designed with dual branched 24-unit PEG polymers to reduce aggregation propensity and improve aqueous solubility. For the ThioBridge®-MMAE linker-payload, a moiety cleavable by lysosomal cathepsins ('Val-Cit-PAB') was used for coupling the cytotoxic payload MMAE to the antibody (see FIG. 3 for structures). This linker format was also designed with a branched 24-unit PEG polymer to reduce aggregation propensity and improve aqueous solubility.

Both MC-VCP-MMAE and CL2A-SN38 were conjugated to the VH4VK3 mAb, while both ThioBridge® linker-payloads were conjugated to the mAbs VH4Vk3 and VH5Vk3. The generated ADCs were highly monomeric (>95%) with an average drug-to-antibody ratio (DAR) of 4 for the MMAE payload, or 8 for the SN38 payload. To allow subsequent biological testing, ADCs were prepared in excess of 50-75 mg target amounts.

LC-MS Analysis

Figure 69:
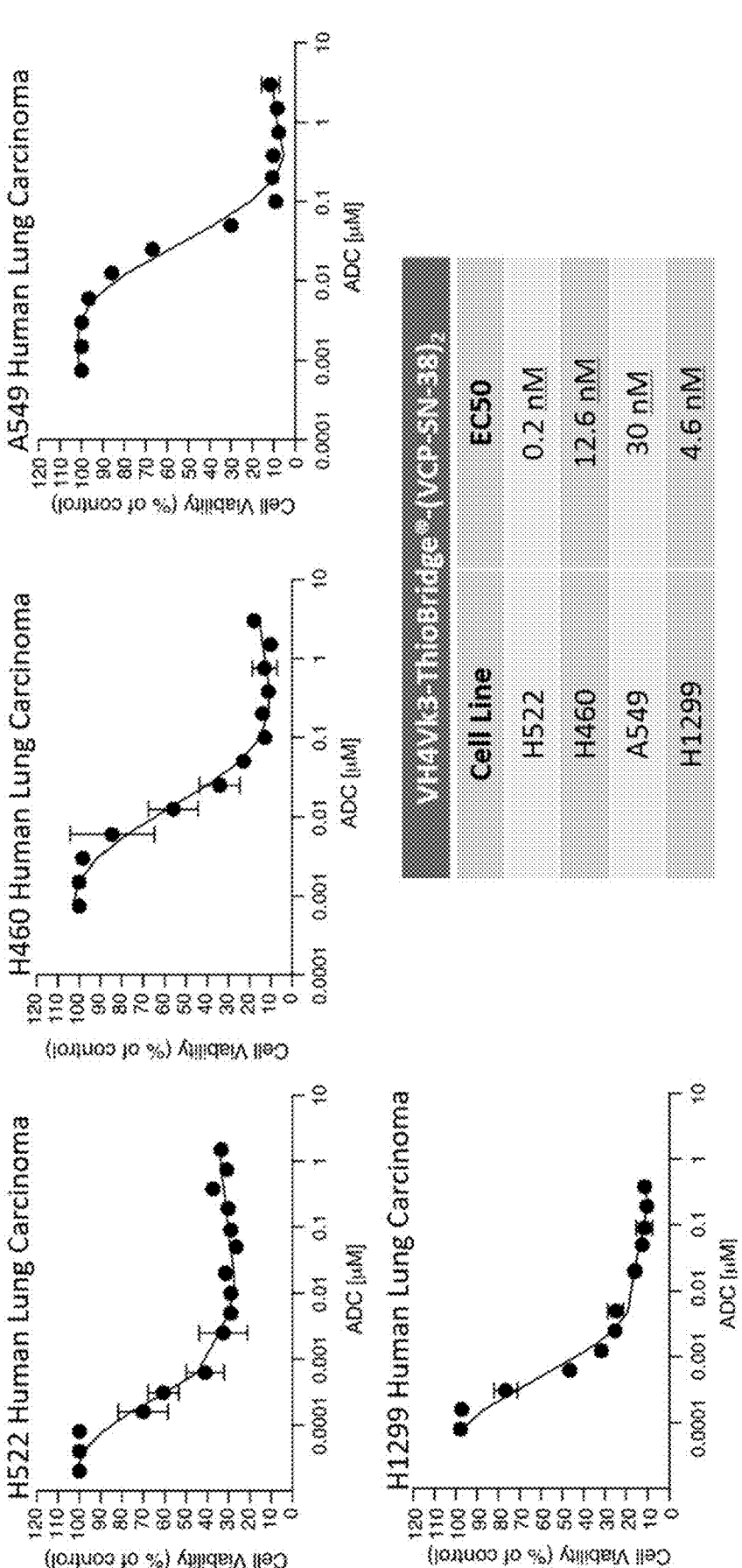
FIG. 69 illustrates the cytotoxicity of VH4Vk3-Thio-Bridge®-(VCP-SN-38)$_2$.

LC-MS analysis was carried out using a Waters XEVO G2S TOF mass spectrometer and a POROSHELL 300SB C3 column (2.1×12.5 mm, 5 µm) connected to a Waters Acquity H Class UPLC system. The mobile phase was buffer A (0.1% formic acid in water). A gradient (2.5 min 10% B, 10-80% B gradient in 3.5 min) was applied using Buffer B (acetonitrile, 0.1% formic acid) at a flow rate of 0.4 mL/min. The column was maintained at 60° C. throughout the analysis. The ADCs were directly analyzed after dilution to 0.05 mg/mL. 10 µL of ADC solution were injected for analysis. Average DAR was calculated as the weighted average of the observed DAR species based on main glycoforms signal intensity (SI) on the deconvoluted m/z spectra for non-reduced samples, and for signal intensities for both light (LSI) and heavy (HSI) chain species for reduced samples according to the formula in FIG. 69A.

SEC Analysis

Analytical SEC (size exclusion chromatography) was carried out using an ACQUITY UPLC BEH 200 SEC column (4.6 mm×15 cm, 200 Å, 1.7 µm) and guard column (4.6 mm×3 cm), connected to a Dionex Ultimate 3000 UPLC system. The mobile phase was 0.2 M potassium phosphate buffer, pH 6.8, 0.2 M potassium chloride, 15% (v/v) isopropanol. The flow rate was kept constant at 0.35 mL/min. The column was maintained at 30° C. throughout the analysis. The analysis was carried out in a 10 min isocratic elution with UV detection at 280 nm and 495 nm.

10 μg of ADC were injected for analysis. The percentage of high molecular weight (HMW) species was calculated by comparing the peak area corresponding to HMW species at 280 nm to total peak area corresponding to HMW and monomeric species at 280 nm.

HIC Analysis

Analytical HIC was carried out using a TOSOH Bioscience TSKgel Butyl-NPR column (4.6 mm×3.5 cm, 2.5 μm), connected to a Dionex Ultimate 3000 UPLC system. The mobile phase was buffer A: 1.5 M ammonium sulfate, 50 mM sodium phosphate, pH 7.0. A linear gradient (0-100% B in 10.5 min) was applied using Buffer B (20% isopropanol, 50 mM sodium phosphate, pH 7.0) at a flow rate of 1.35 mL/min to elute bound species. The column was maintained at 30° C. throughout the analysis. The analysis was carried with UV detection at 280 nm. 10 μg of ADC were injected per analysis. The percentage of each DAR species (i) was calculated by comparing the peak areas of each assigned peak to total peak area. Average DAR was calculated as the weighted average of the observed DAR species based on peak area under the curve (AUCi) and average molecular weight for the ADC was calculated based on DAR and linker-payload mass contribution, according to the formula in FIG. 69B.

SDS-PAGE Analysis

SDS-PAGE analysis was carried out using NuPAGE® 4-12% Bis-Tris gels (Invitrogen) under non-reducing conditions with MES buffer. Prior to analysis, each sample was incubated for 1 h at 40° C. in 10% SDS solution. For analysis, 1 μg of ADC sample (based on protein) was loaded onto the gel per lane. Electrophoresis was carried out at 200 V for 35 min. The gels were stained with InstantBlue™ (Abcam) for protein detection and analyzed using a Chemi-Doc™ imaging system (Bio-Rad).

Concentration and Average DAR Determination by UV Absorbance

The concentration and average DAR of the conjugates were determined by UV absorbance at 280 nm (A280) and at a wavelength λ corresponding to a maximum of absorbance for the linker-payload (Aλ) using a Nanodrop 2000 spectrophotometer. Measurements were taken in triplicate and the average values used for calculations. Molar extinction coefficients used for antibodies and linker-payloads were determined experimentally (Table E8 and Table E9).

TABLE E8

| Molar Extinction coefficients for mAbs at different wavelengths. | | | |
| --- | --- | --- | --- |
| Antibody | λ (nm) | ελ mAb (M$^{-1}$.cm$^{-1}$) | Source |
| VH4Vk3 | 280 | 206624 | Theoretical calculation by ProtParam |
| VH5Vk3 | 280 | 206596 | Theoretical calculation by ProtParam |

TABLE E9

| Linker-Payload | λ (nm) | ελ LP (M$^{-1}$.cm$^{-1}$) | Source |
| --- | --- | --- | --- |
| MC-VCP-MMAE | 280 | 1425 | CellMosaic |PerKit ™ Antibody MMAE Conjugation Kit User Reference Guide, Rev E, 06/03, Doc#: DCM11409 |

TABLE E9-continued

| Linker-Payload | λ (nm) | ελ LP (M$^{-1}$.cm$^{-1}$) | Source |
| --- | --- | --- | --- |
| ThioBridge ®-VCP-MMAE | 280 | 8496 | Experimental |
| ThioBridge ®-(VCP-SN38)2 | 280 | 18989 | Experimental |
| CL2A-SN38 | 280 | 8461 | Experimental |

Endotoxin Level Determination Method

The EndoSafe®-PTS™ platform (Charles River) was used to determine the level of endotoxin. EndoSafe®-PTS™ is a chromogenic kinetic test system aligned with USP <85> and Pharm Eur 2.6.14 that provides quantitative Limulus Amebocyte Lysate (LAL) results. The EndoSafe®-PTS™ utilizes LAL reagents in FDA-licensed disposable test cartridges which are pre-loaded with all the reagents required to perform a LAL test. The EndoSafe®-PTS™ mimics licensed LAL kinetic chromogenic methodology by measuring color intensity directly related to the endotoxin concentration in a sample; the concentrations are calculated against an internal standard curve (0.01-1.00 EU/mL) associated with the lot number of the cartridges.

Analytical Results:

The analytical results of the generated conjugates are summarized in Tables E10.A-E10.F.

TABLE E10.A

Figure 34:
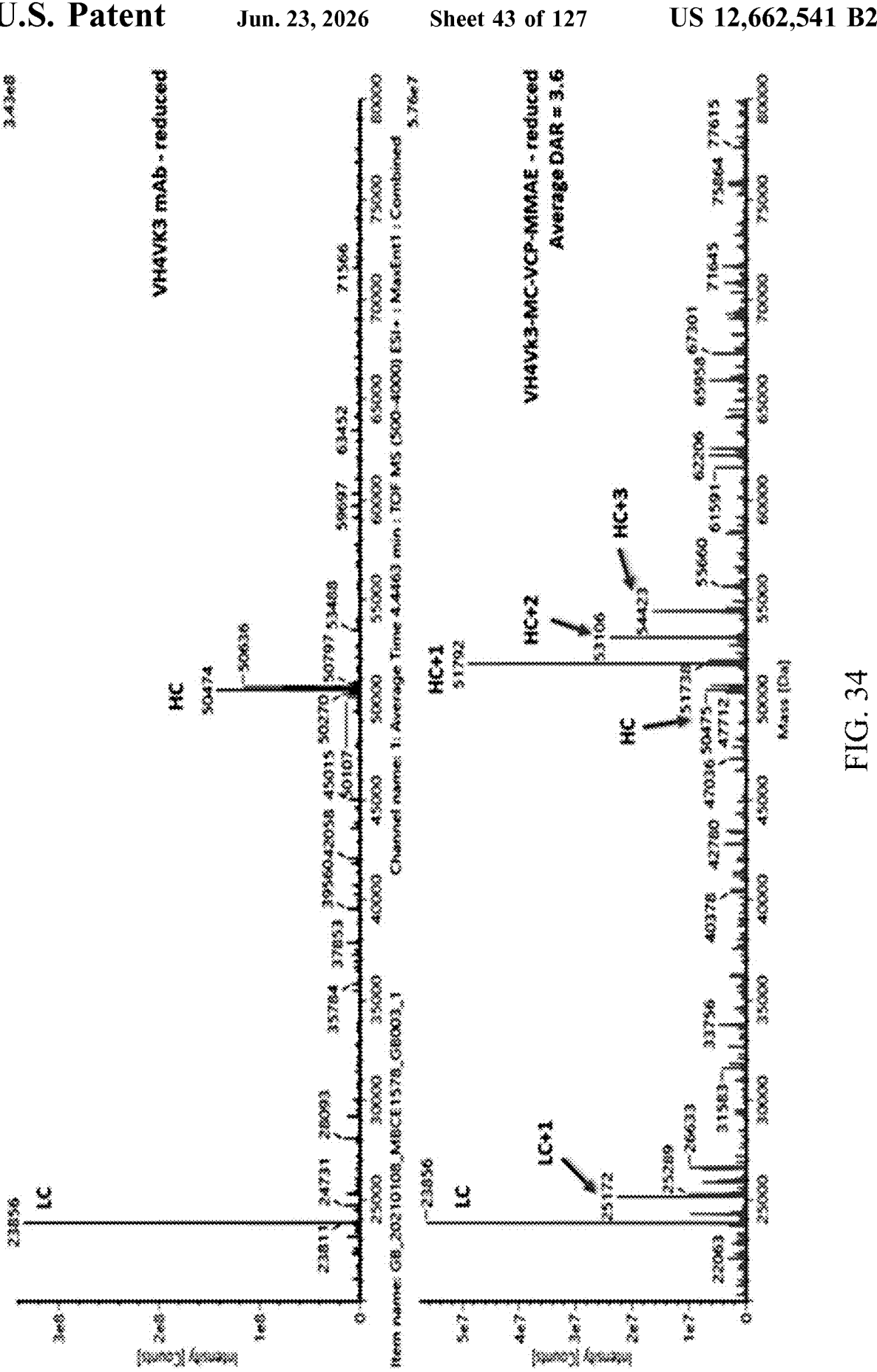
FIG. 34 illustrates the deconvoluted LC-MS spectrum for the VH4Vk3 mAb (top spectrum) and VH4Vk3-MC-VCP-MMAE ADC (bottom spectrum). Samples were reduced with 10 mM DTT for 20 mins at 22° C. prior to analysis.
Figure 35:
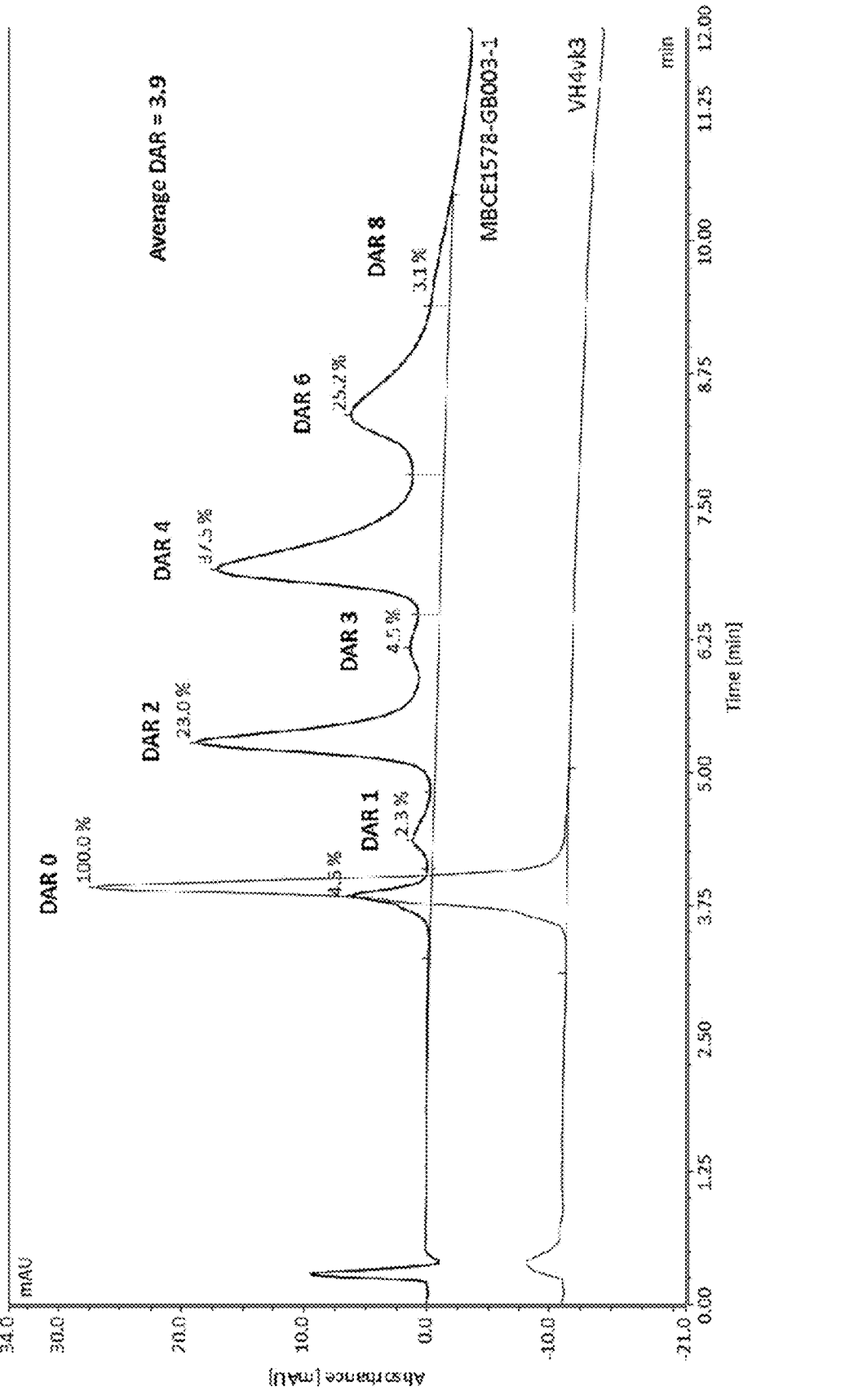
FIG. 35 illustrates a hydrophobic interaction chromatogram ($\lambda$=280 nm) for the VH4Vk3-MC-VCP-MMAE ADC (top trace) and VH4Vk3 mAb (bottom trace).
Figure 36:
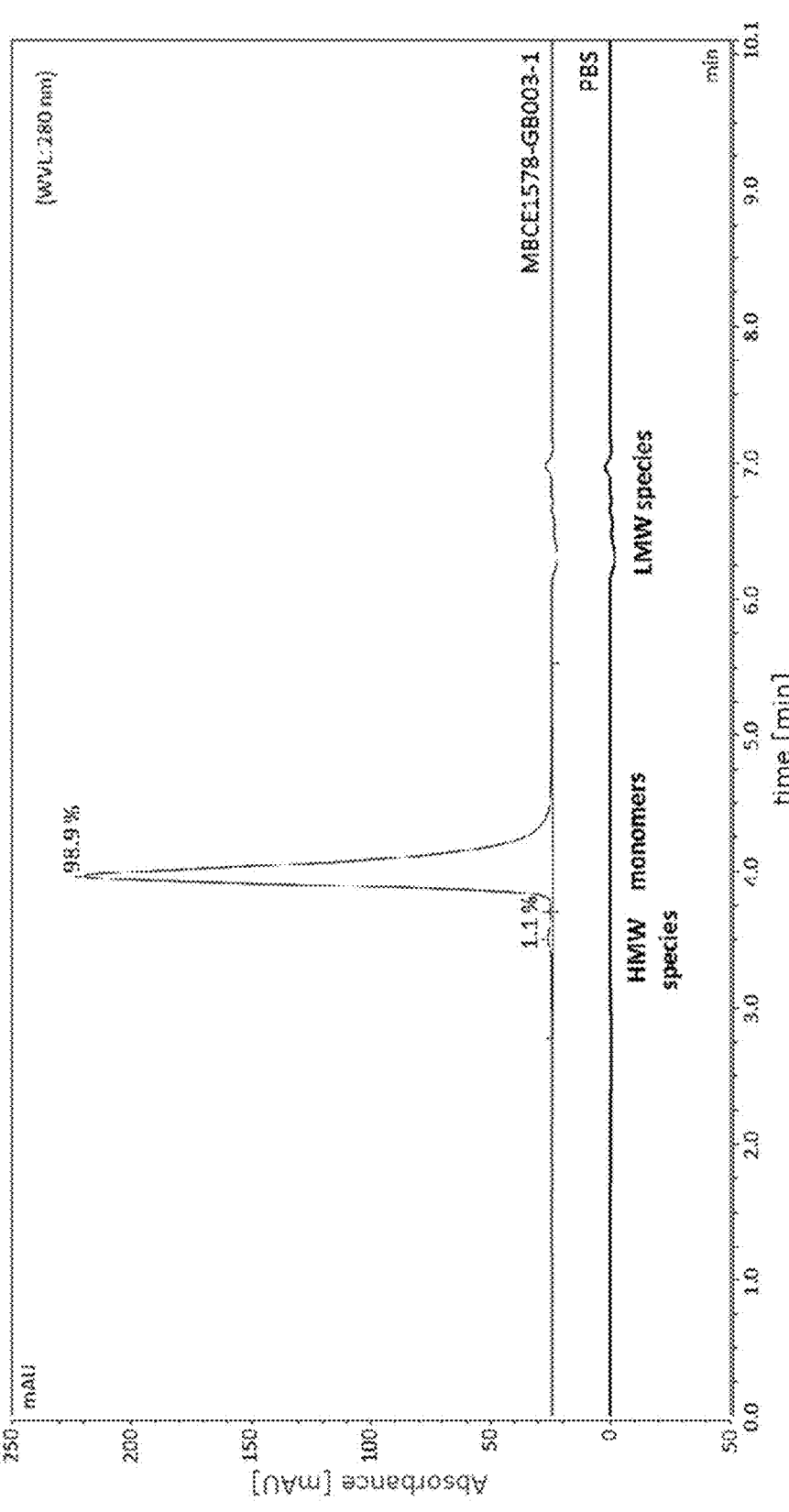
FIG. 36 illustrates a size exclusion chromatogram ($\lambda$=280 nm) for the VH4Vk3-MC-VCP-MMAE ADC (top trace) and PBS buffer (bottom trace).
Figure 37:
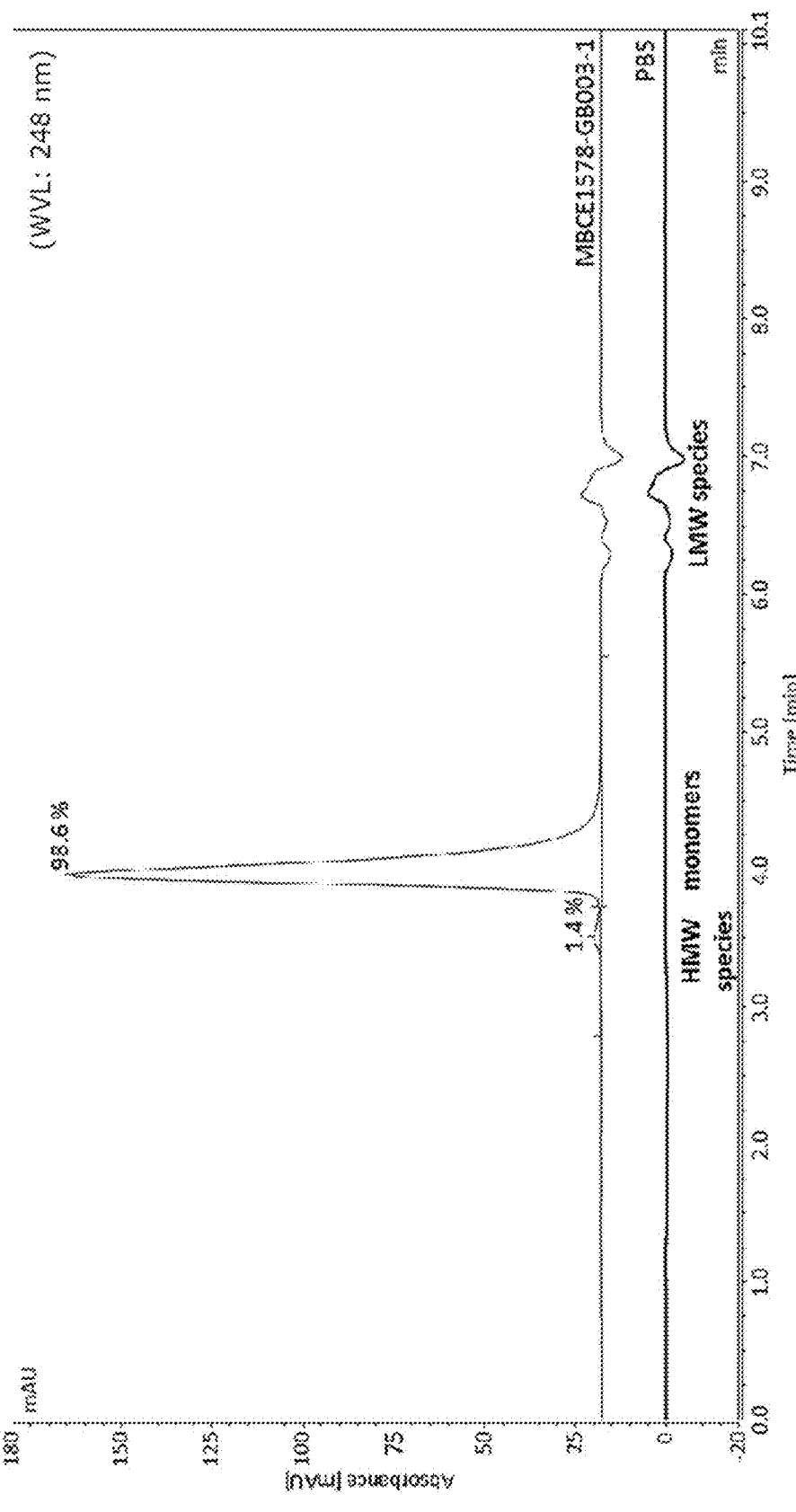
FIG. 37 illustrates a size exclusion chromatogram ($\lambda$=248 nm) for VH4Vk3-MC-VCP-MMAE ADC (top trace) and PBS buffer (bottom trace).

| VH4Vk3-MC-VCP-MMAE | |
| --- | --- |
| Analysis | Results |
| Sample Name | VH4Vk3-MC-VCP-MMAE |
| Batch Code | MBCE1578-GB003-1 |
| Appearance | Clear colorless solution |
| Identity (LC-MS) | MW confirmed |
| | See FIG. 34 for spectra |
| Average DAR (LC-MS) | Average DAR: 3.6 |
| DAR variants (HIC) | DAR 0: 4.5% |
| | DAR 1: 2.3% |
| | DAR 2: 23.0% |
| | DAR 3: 4.5% |
| | DAR 4: 37.5% |
| | DAR 6: 25.2% |
| | DAR 8: 3.1% |
| | Average DAR: 3.9 |
| | See FIG. 35 for chromatogram |
| % Purity (SEC) | 98.9% monomeric |
| | See FIG. 36 for chromatogram |
| % free reagent related species | Not detected |
| | See FIG. 37 for chromatogram |
| Endotoxin (EU/mg) | 0.06 |
| Concentration (UV) | 3.48 mg/mL |
| Amount (UV) | 59 mg |
| Average MW | 148,667 Da |

For spectral, chromatographic, and hydrophobic interaction analysis, see FIGS. 34-37.

TABLE E10.B

Figure 38:
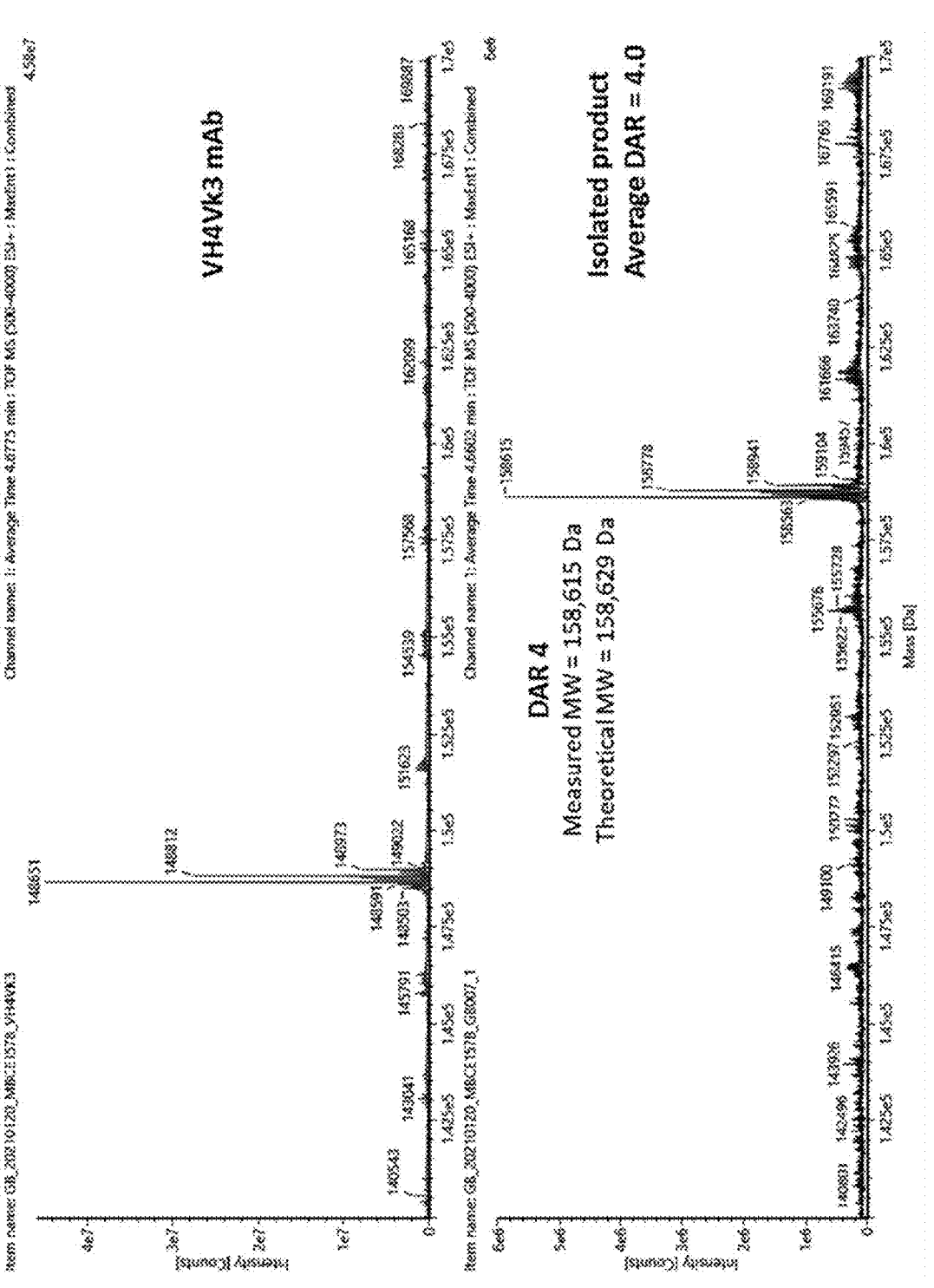
FIG. 38 illustrates a deconvoluted LC-MS spectrum for the VH4Vk3-ThioBridge®-VCP-MMAE ADC (bottom spectrum) and VH4Vk3 mAb (top spectrum).

| H4Vk3-ThioBridge ®-VCP-MMAE | |
| --- | --- |
| Analysis | Results |
| Sample Name | VH4Vk3-ThioBridge ®-VCP-MMAE |
| Batch Code | MBCE1578-GB007-1 |
| Appearance | Clear colorless solution |
| Identity (LC-MS) | MW confirmed |
| | See FIG. 38 for spectra |

TABLE E10.B-continued

Figure 39:
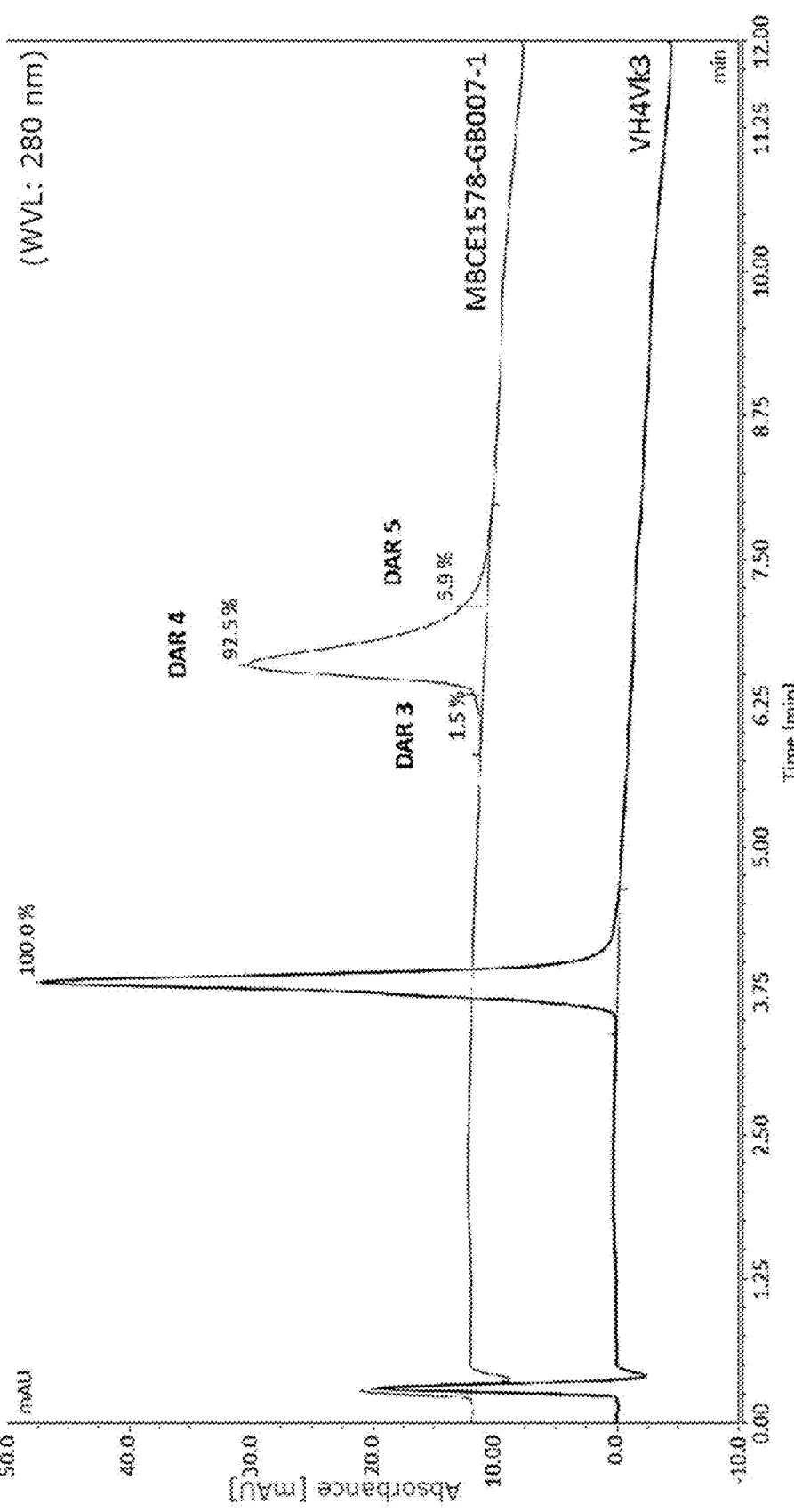
FIG. 39 illustrates a hydrophobic interaction chromatogram ($\lambda$=280 nm) for the VH4Vk3-ThioBridge®-VCP-MMAE ADC (top trace) and VH4Vk3 mAb (bottom trace).
Figure 40:
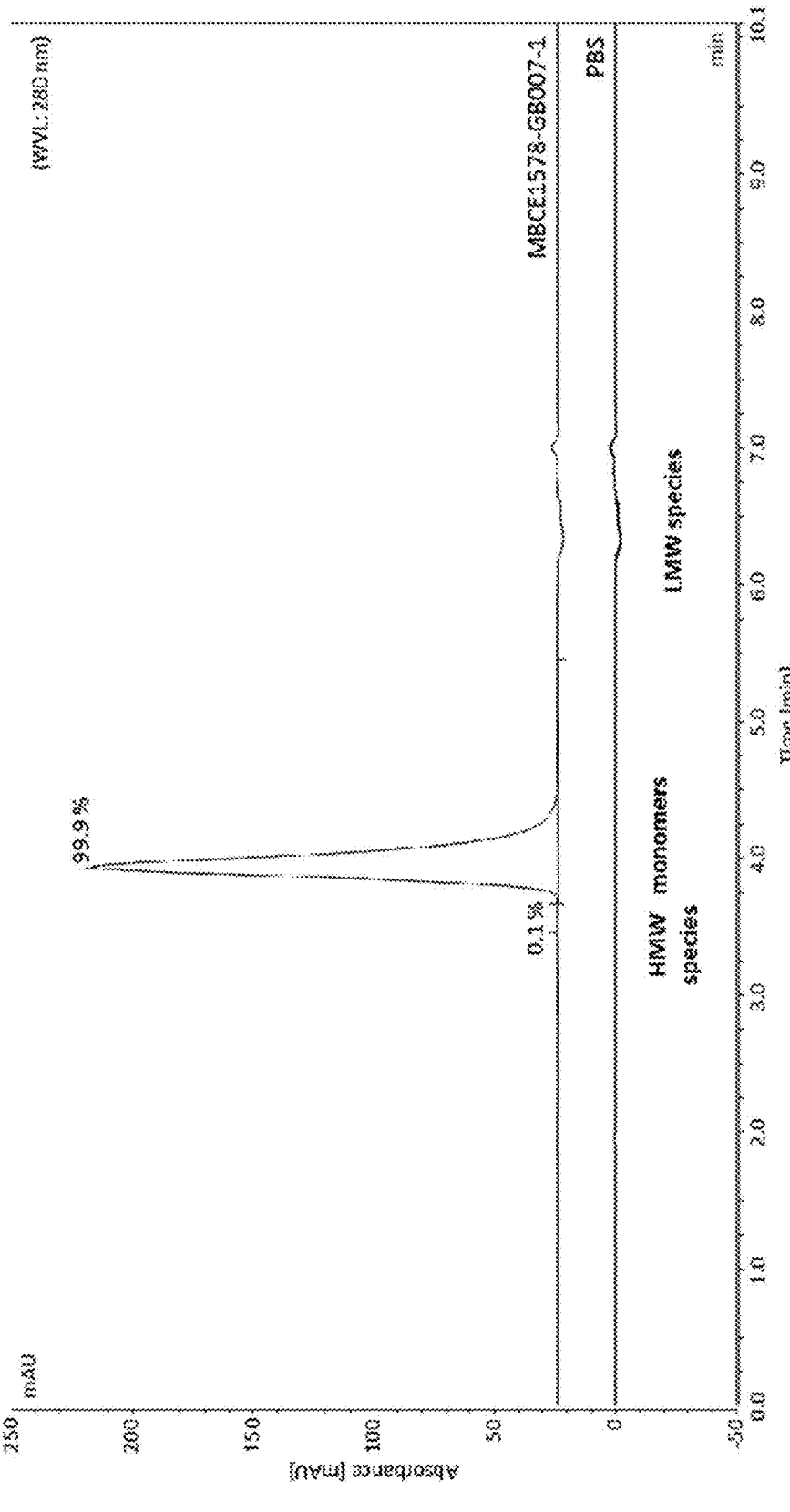
FIG. 40 illustrates a size exclusion chromatogram ($\lambda$=280 nm) for the VH4Vk3-ThioBridge®-VCP-MMAE ADC (top trace) and PBS buffer (bottom trace).
Figure 41:
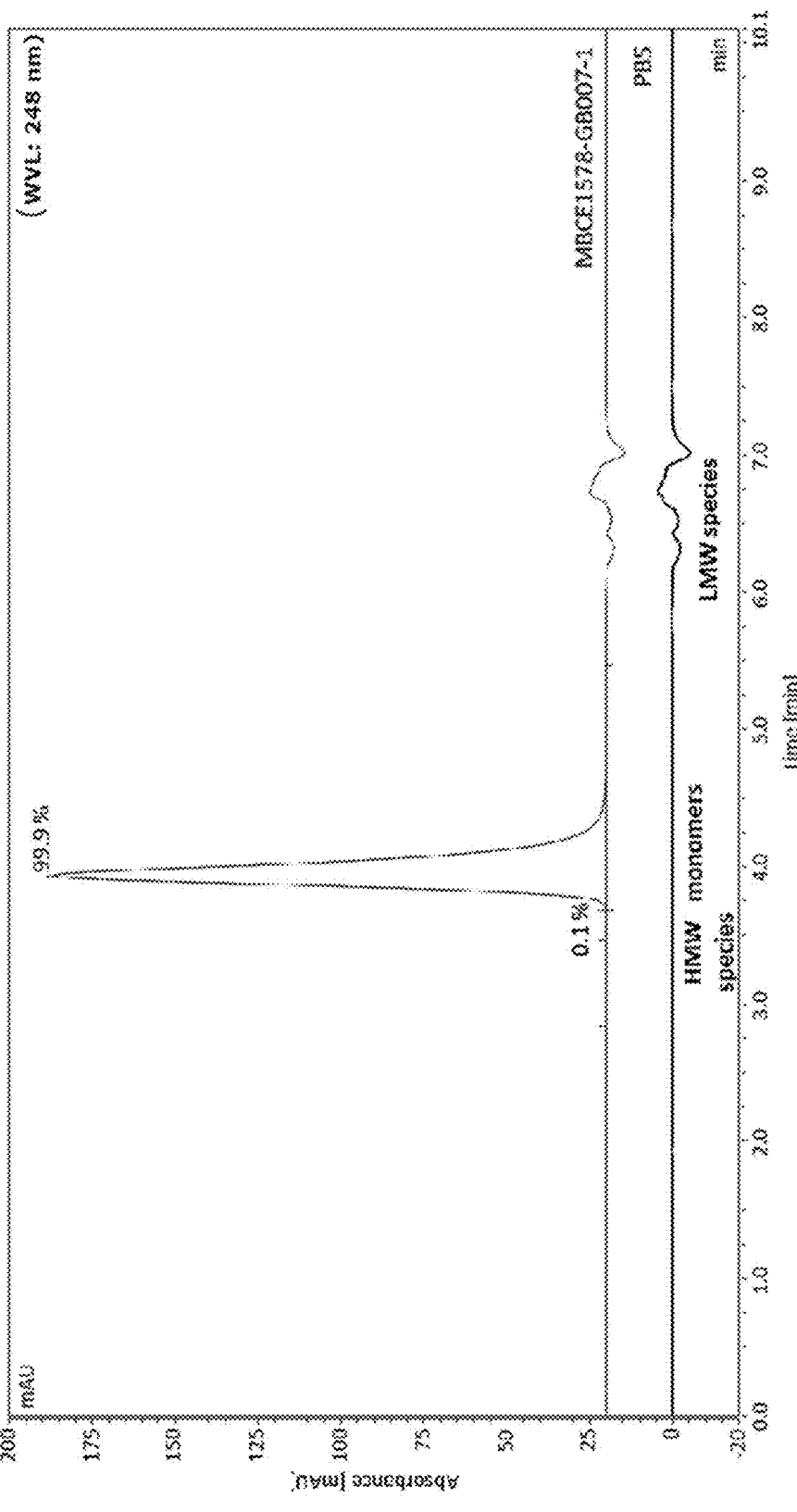
FIG. 41 illustrates a size exclusion chromatogram ($\lambda$=248 nm) for the VH4Vk3-ThioBridge®-VCP-MMAE ADC (top trace) and PBS buffer (bottom trace).
Figure 42:
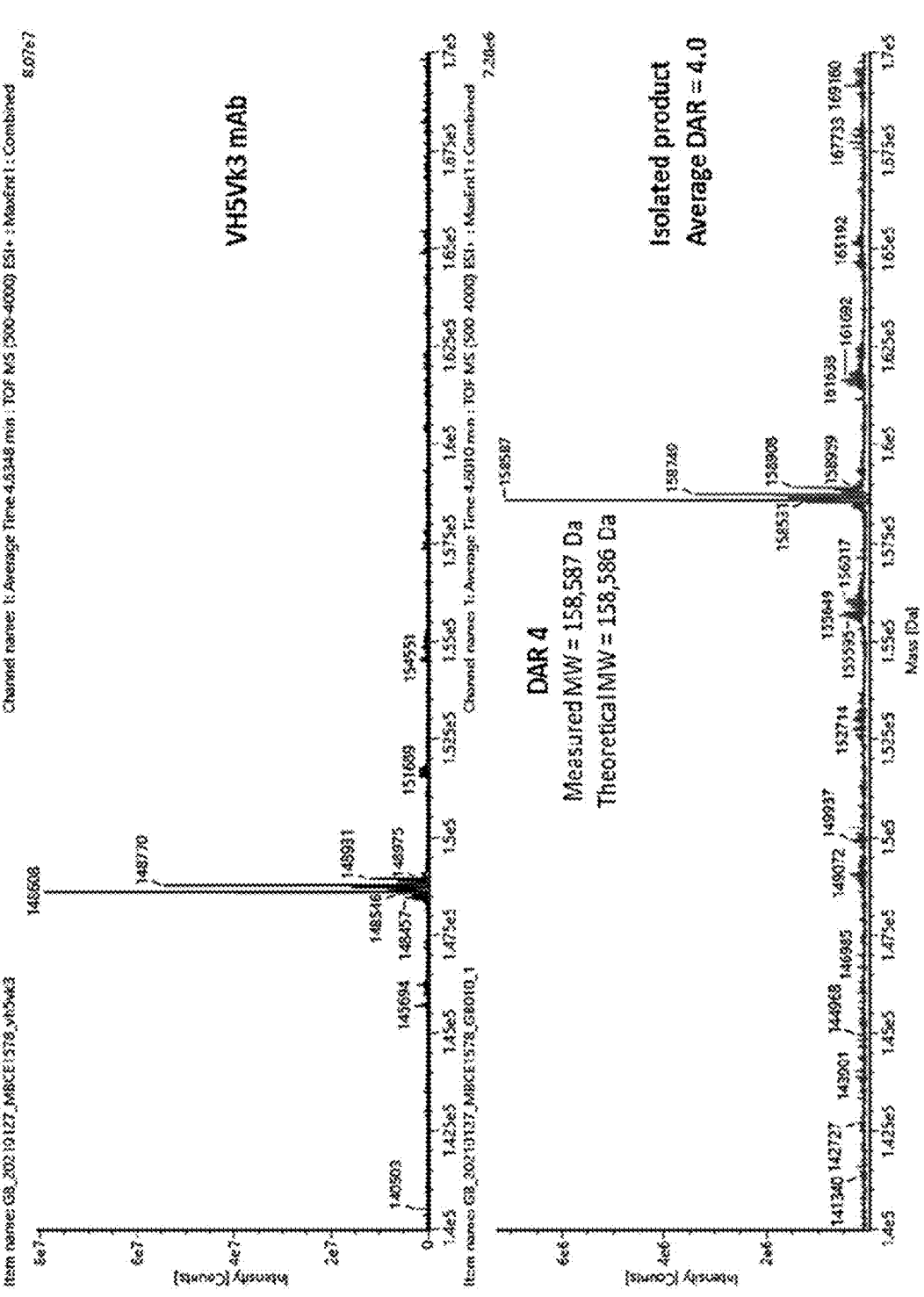
FIG. 42 illustrates a deconvoluted LC-MS spectrum for the VH5Vk3-ThioBridge®-VCP-MMAE ADC (bottom spectrum) and VH5Vk3 mAb (top spectrum).
Figure 43:
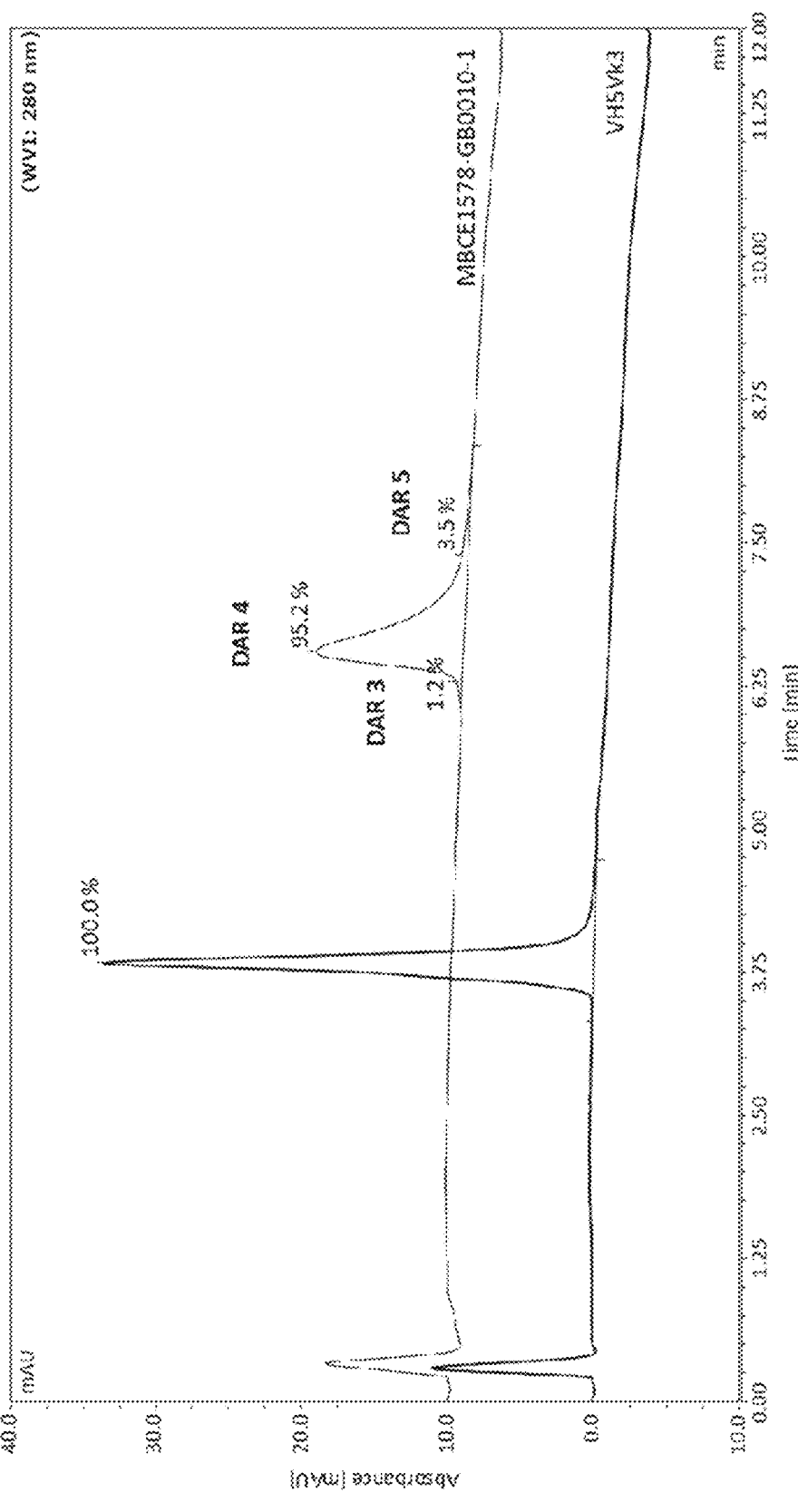
FIG. 43 illustrates a hydrophobic interaction chromatogram ($\lambda$=280 nm) for the VH5Vk3-ThioBridge®-VCP-MMAE ADC (top trace) and VH5Vk3 mAb (bottom trace).
Figure 44:
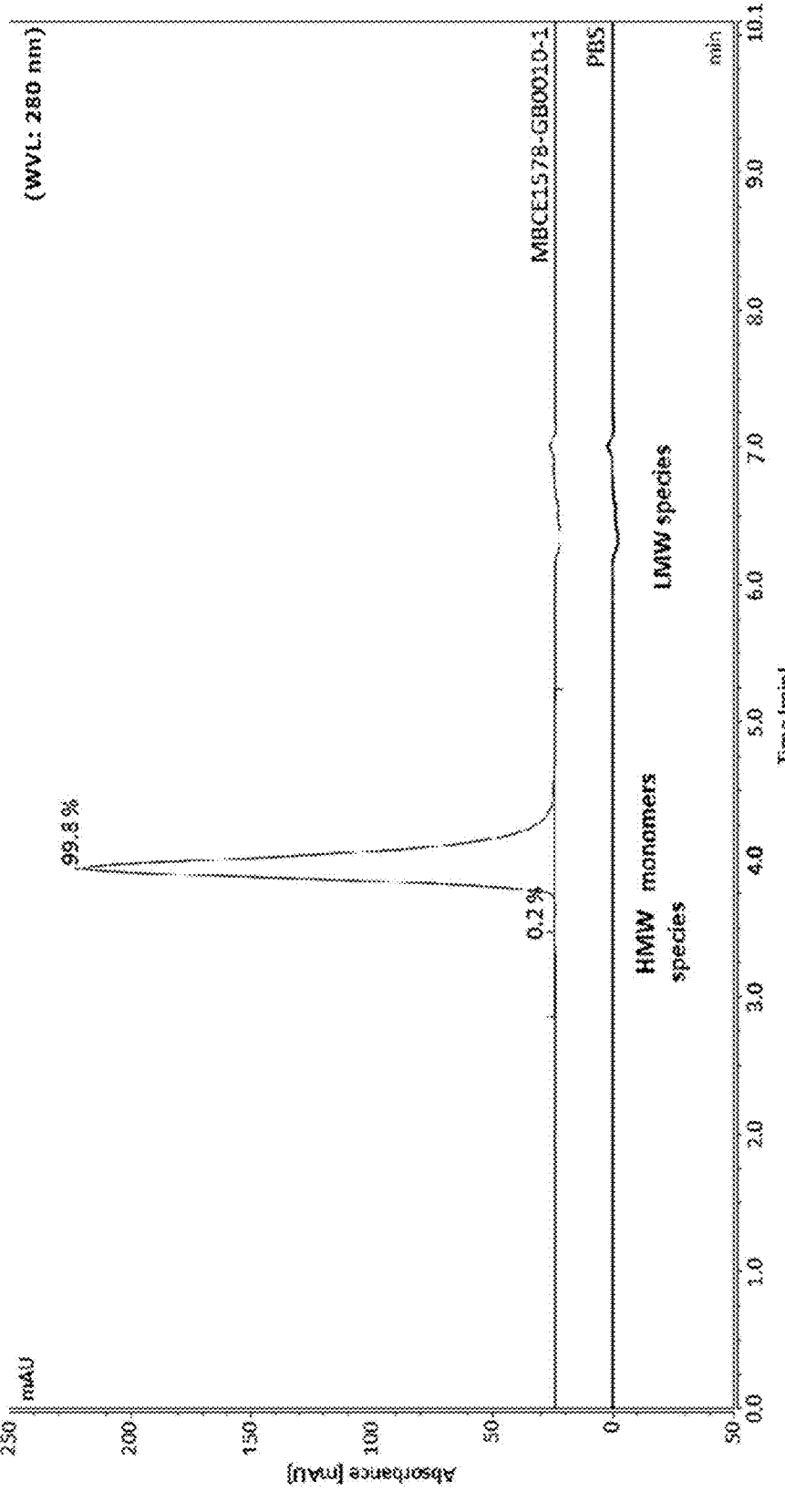
FIG. 44 illustrates a size exclusion chromatogram ($\lambda$=280 nm) for the VH5Vk3-ThioBridge®-VCP-MMAE ADC (top trace) and PBS buffer (bottom trace).
Figure 45:
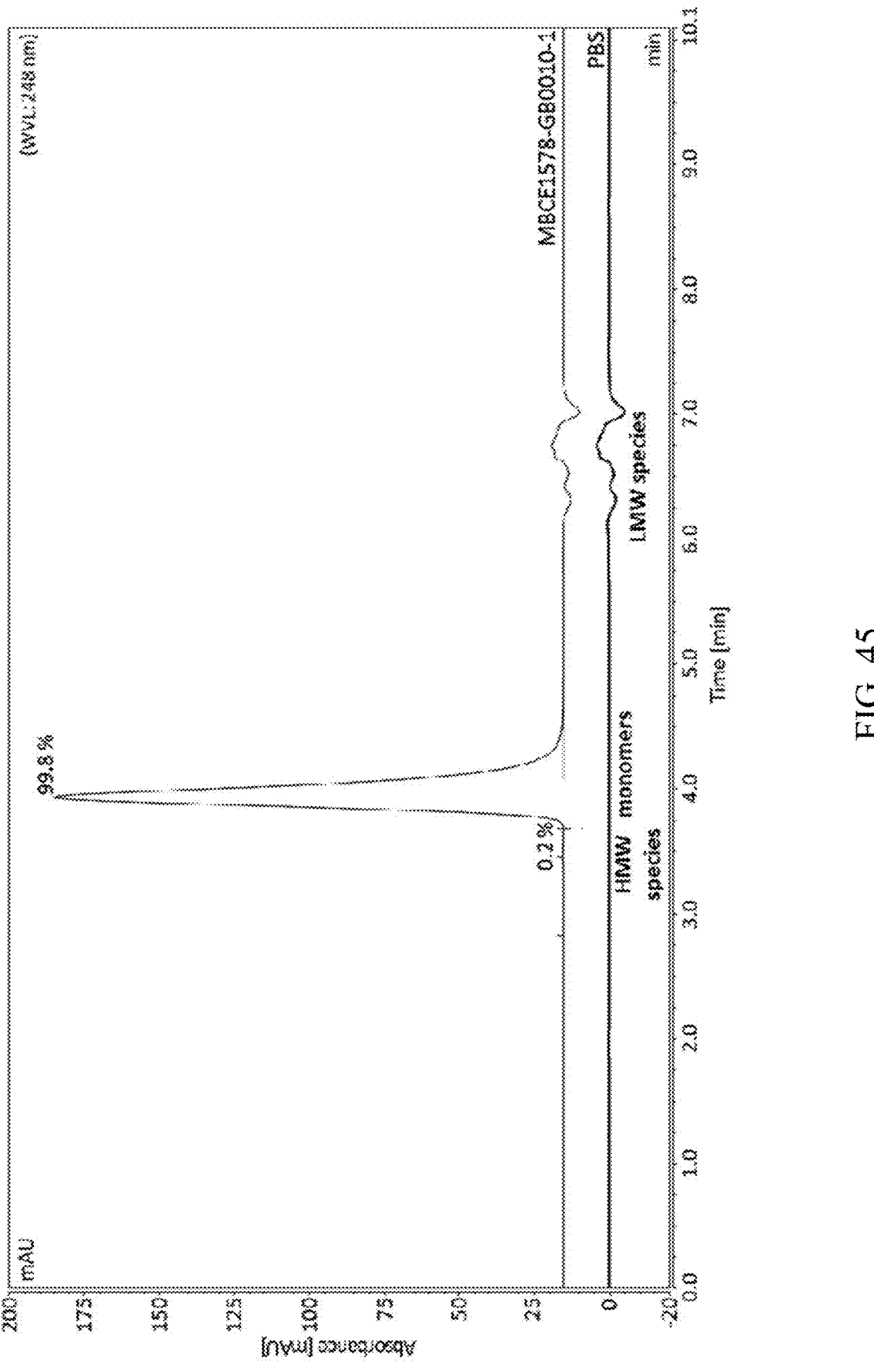
FIG. 45 illustrates a size exclusion chromatogram ($\lambda$=248 nm) for the VH5Vk3-ThioBridge®-VCP-MMAE ADC (top trace) and PBS buffer (bottom trace).

| H4Vk3-ThioBridge ®-VCP-MMAE | |
|---|---|
| Analysis | Results |
| Average DAR (LC-MS) | Average DAR: 4.0 |
| DAR 4 species retention time (HIC) | 6.6 min |
| | See FIG. 39 for chromatogram |
| DAR variants (HIC) | DAR 3: 1.5% |
| | DAR 4: 92.5% |
| | DAR 5: 5.9% |
| | Average DAR: 4.0 |
| | See FIG. 39 for chromatogram |
| SDS-PAGE | See FIG. 35 for gel |
| % Purity (SEC) | 99.9% monomeric |
| | See FIG. 40 for chromatogram |
| % free reagent related species | Not detected |
| | See FIG. 41 for chromatogram |
| Endotoxin (EU/mg) | 0.04 |
| Concentration (UV) | 5.04 mg/mL |
| Amount (UV) | 85 mg |
| Average MW | 158,629 Da |

For spectral, chromatographic, and hydrophobic interaction analysis, see FIGS. 38-41.

TABLE E10.C

Figure 46:
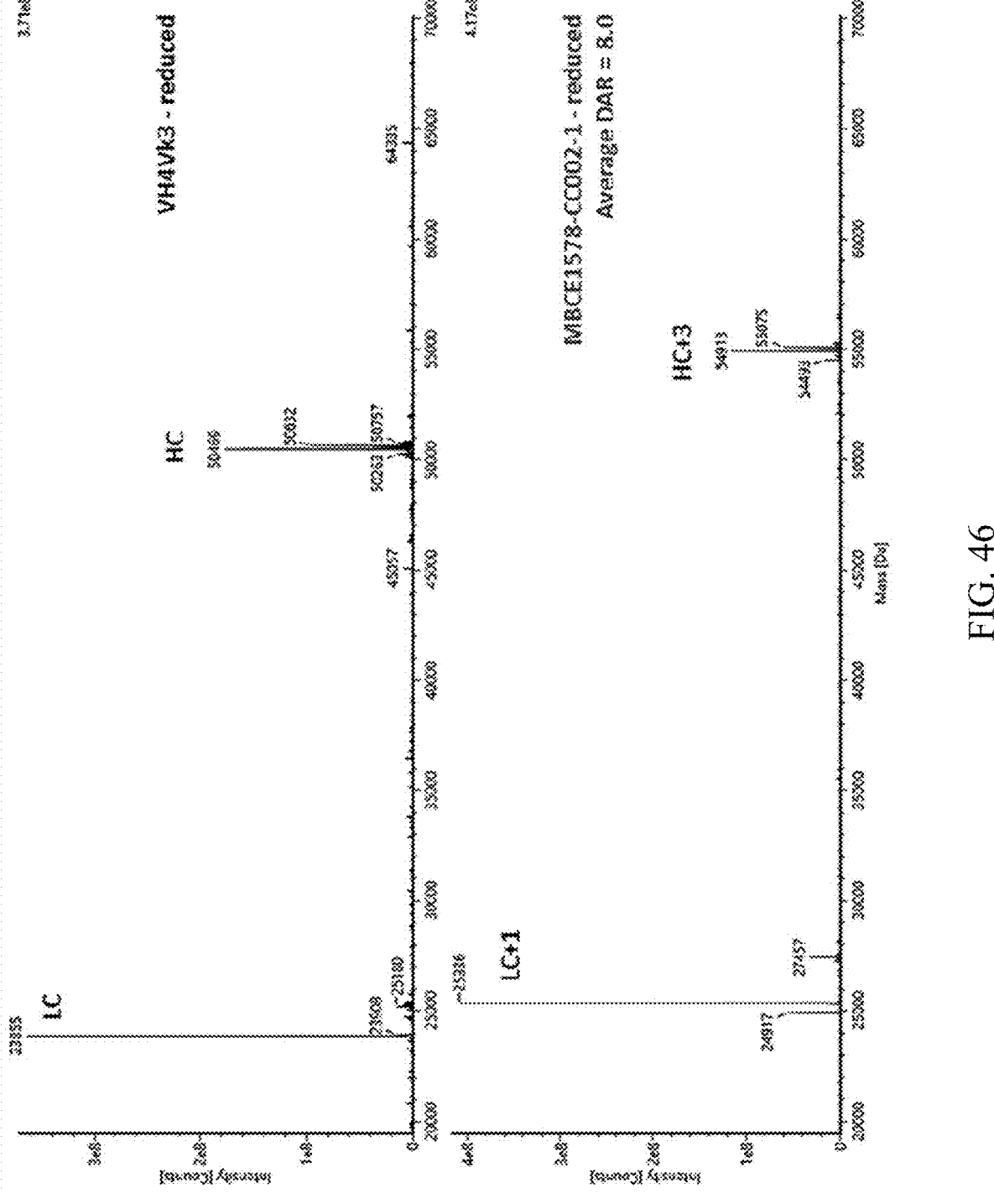
FIG. 46 illustrates a deconvoluted LC-MS spectrum for the VH4Vk3 mAb (top spectrum) and VH4Vk3-CL2A-SN38 ADC (bottom spectrum). Samples were reduced with 10 mM DTT for 20 mins at 22° C. prior to analysis.
Figure 47:
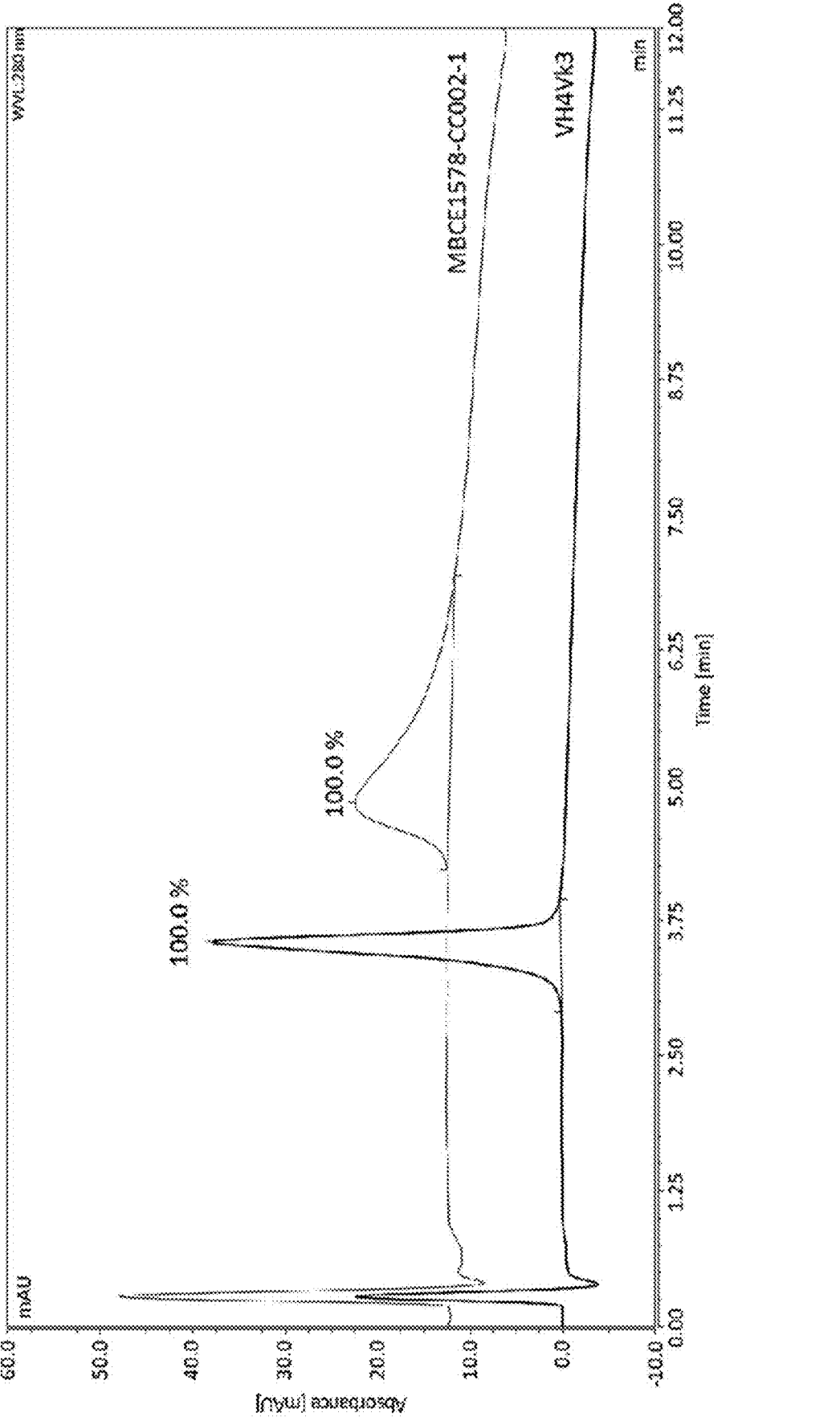
FIG. 47 illustrates a hydrophobic interaction chromatogram ($\lambda$=280 nm) for the VH4Vk3-CL2A-SN38 ADC (top trace) and VH4Vk3 mAb (bottom trace).
Figure 48:
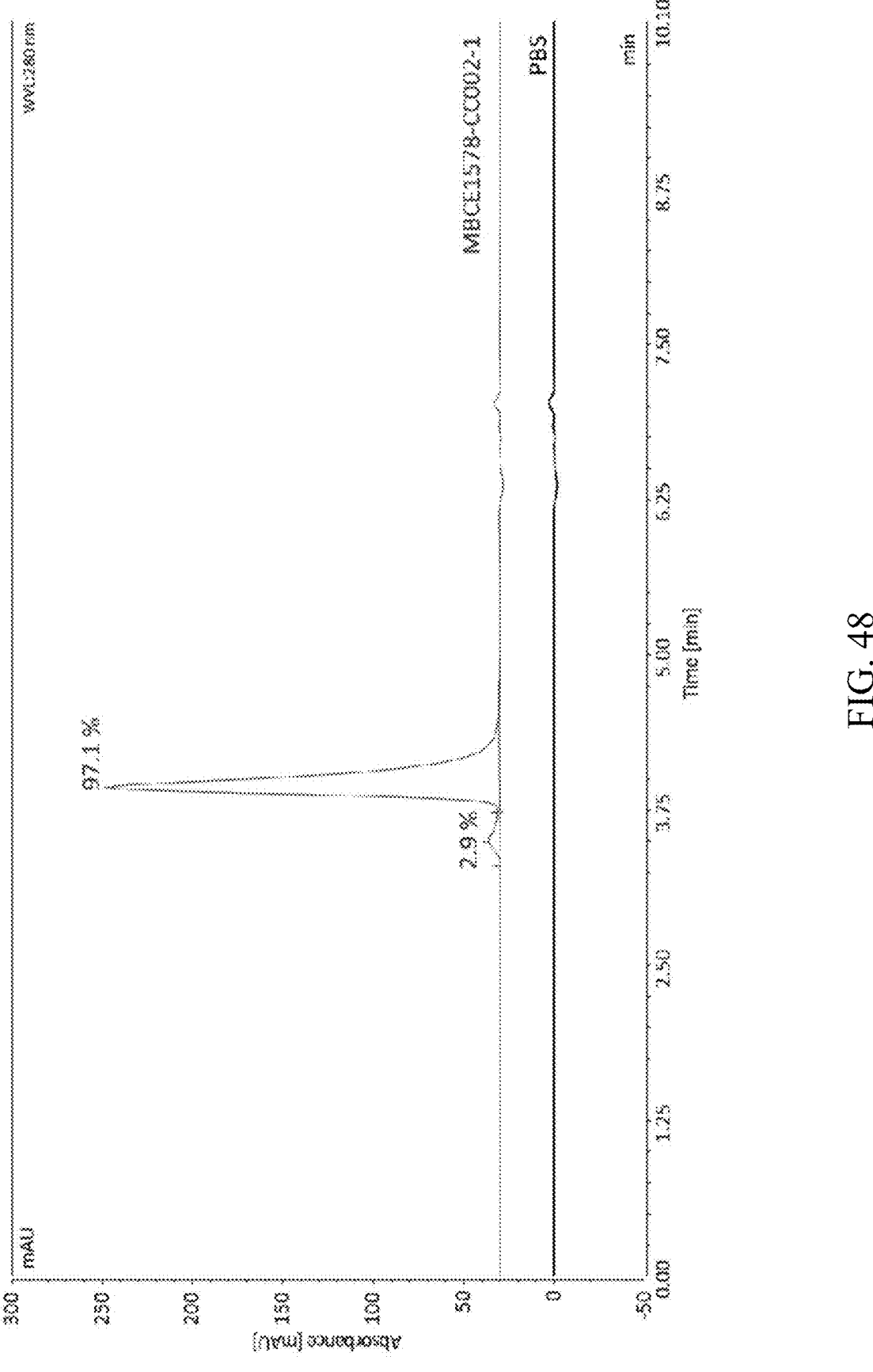
FIG. 48 illustrates a size exclusion chromatogram ($\lambda$=280 nm) for the VH4Vk3-CL2A-SN38 ADC (top trace) and PBS buffer (bottom trace).
Figure 49:
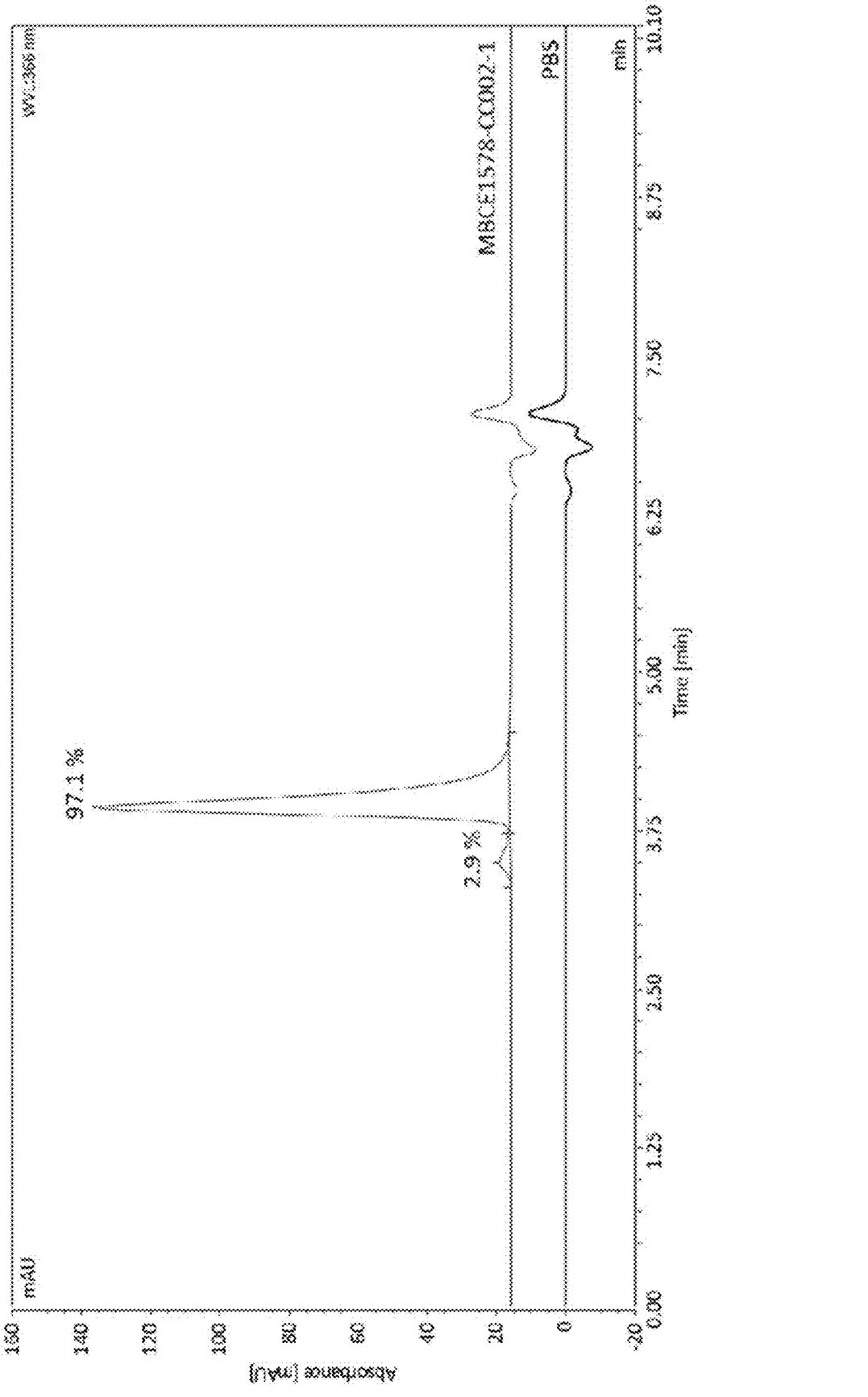
FIG. 49 illustrates a size exclusion chromatogram ($\lambda$=366 nm) for the VH4Vk3-CL2A-SN38 ADC (top trace) and PBS buffer (bottom trace).
Figure 66:
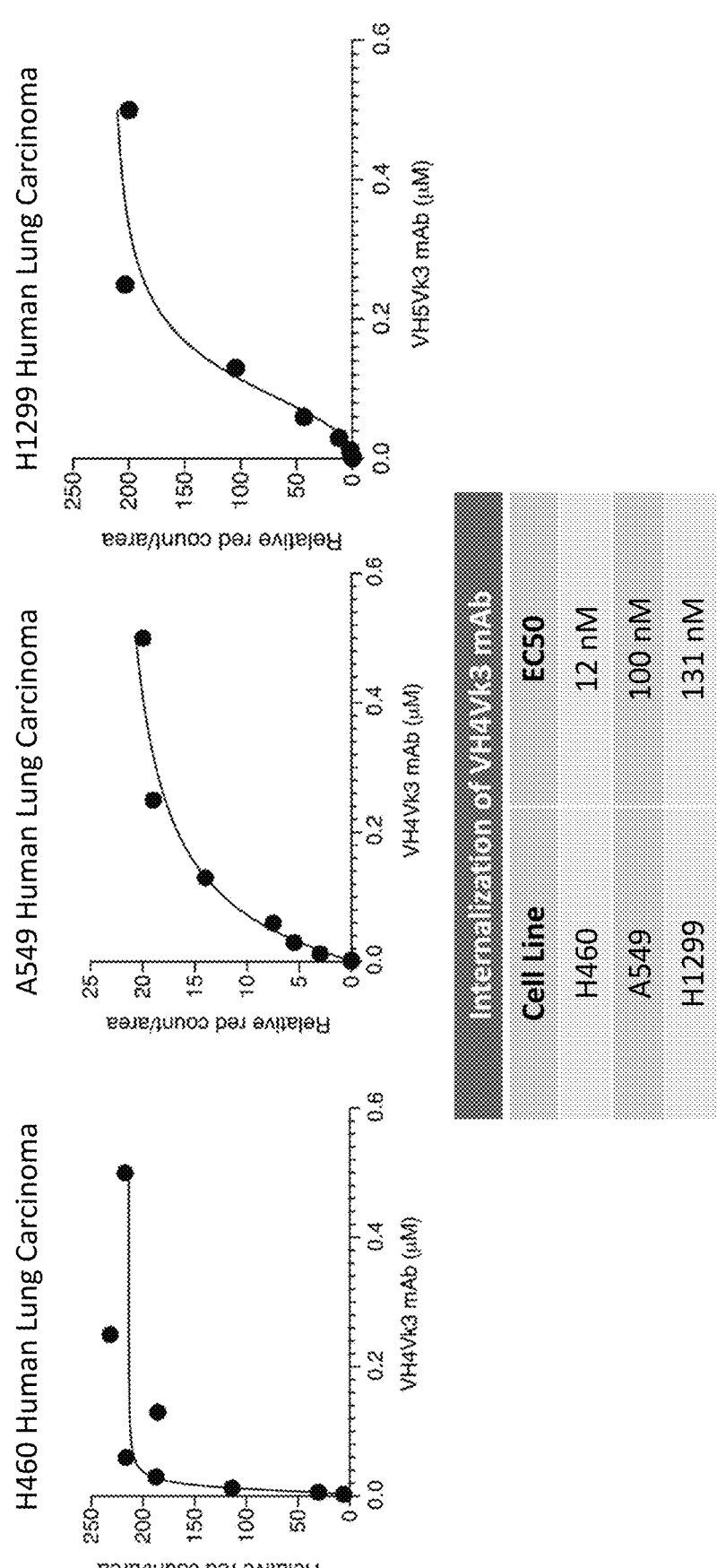
FIG. 66 illustrates the internalization of VH4Vk3 mAb in vitro.

| VH5Vk3-ThioBridge ®-VCP-MMAE | |
|---|---|
| Analysis | Results |
| Sample Name | VH5Vk3-ThioBridge ®-VCP-MMAE |
| Batch Code | MBCE1578-GB010-1 |
| Appearance | Clear colorless solution |
| Identity (LC-MS) | MW confirmed |
| | See FIG. 46 for spectra |
| Average DAR (LC-MS) | Average DAR: 4.0 |
| SDS-PAGE | See FIG. 66 for gel |
| DAR 4 species retention time (HIC) | 6.5 min |
| | See FIG. 47 for chromatogram |
| DAR variants (HIC) | DAR 3: 1.2% |
| | DAR 4: 95.2% |
| | DAR 5: 3.5% |
| | Average DAR: 4.0 |
| | See FIG. 47 for chromatogram |
| % Purity (SEC) | 99.8% monomeric |
| | See FIG. 48 for chromatogram |
| % free reagent related species | Not detected |
| | See FIG. 49 for chromatogram |
| Endotoxin (EU/mg) | 0.04 |
| Concentration (UV) | 4.78 mg/mL |
| Amount (UV) | 92 mg |
| Average MW | 158,586 Da |

For spectral, chromatographic, and hydrophobic interaction analysis, see FIGS. 42-45.

TABLE E10.D

Figure 50:
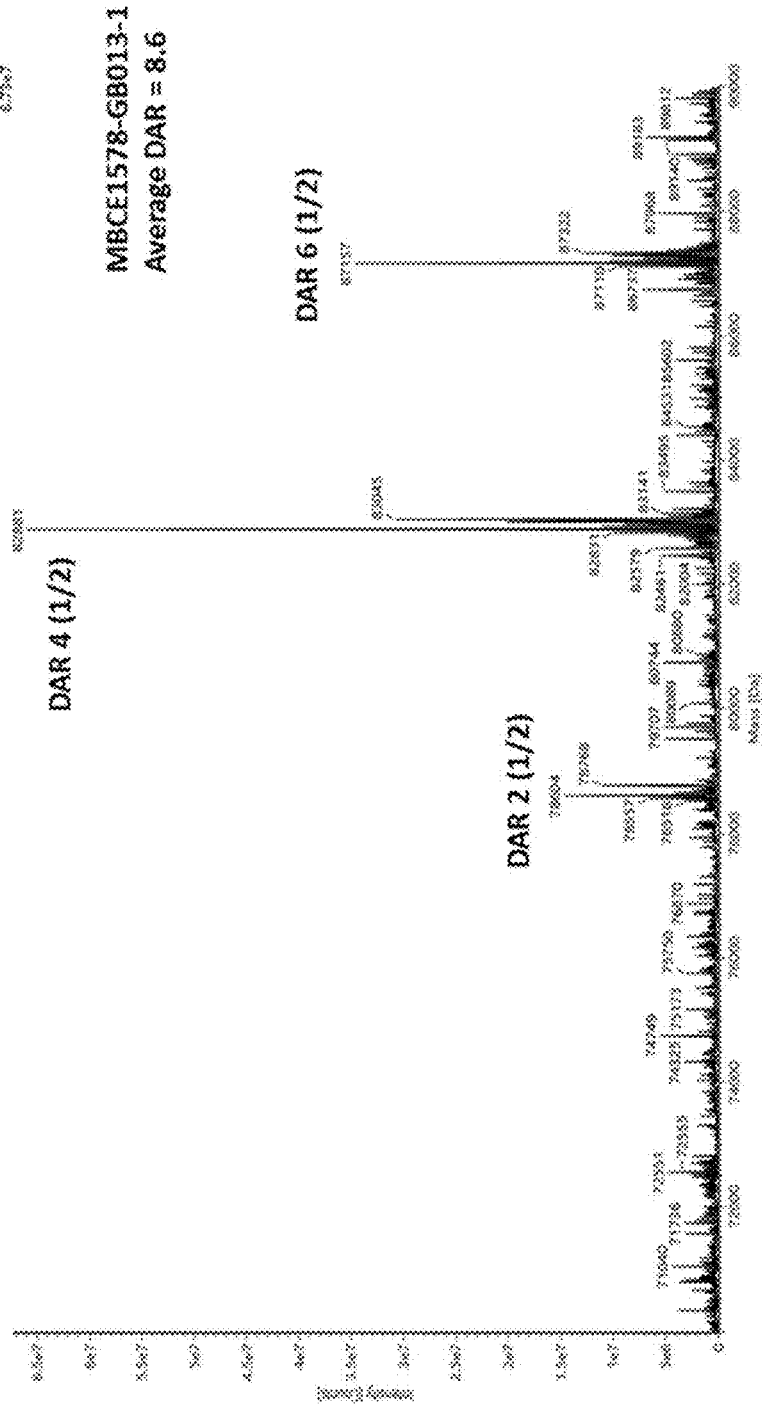
FIG. 50 illustrates a deconvoluted LC-MS spectrum for the VH4Vk3-ThioBridge®-(VCP-SN38)2 ADC (½ mAb conjugate species).
Figure 51:
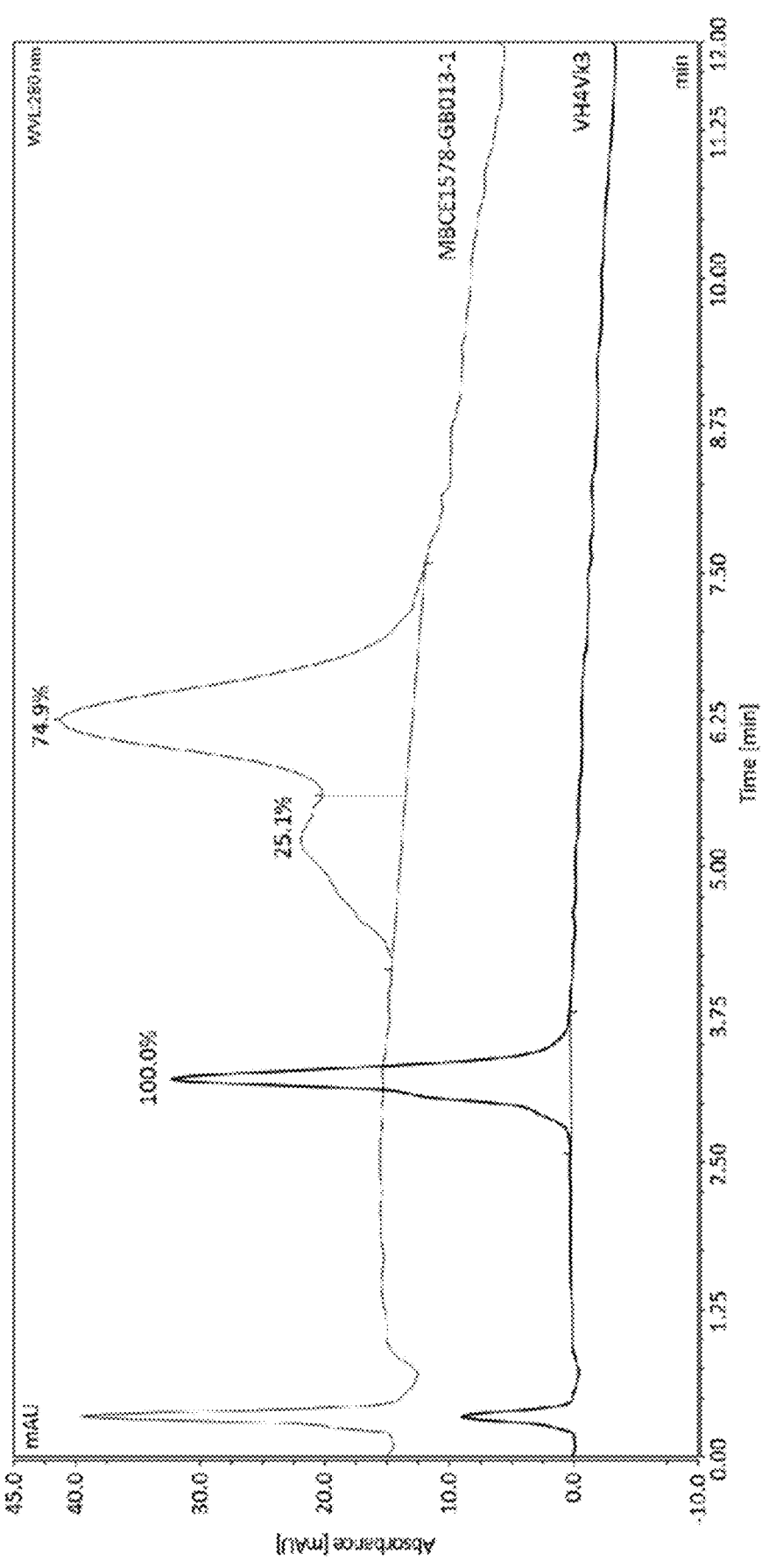
FIG. 51 illustrates a hydrophobic interaction chromatogram ($\lambda$=280 nm) for the VH4Vk3-ThioBridge®-(VCP-SN38)2 ADC (top trace) and VH4Vk3 mAb (bottom trace).
Figure 52:
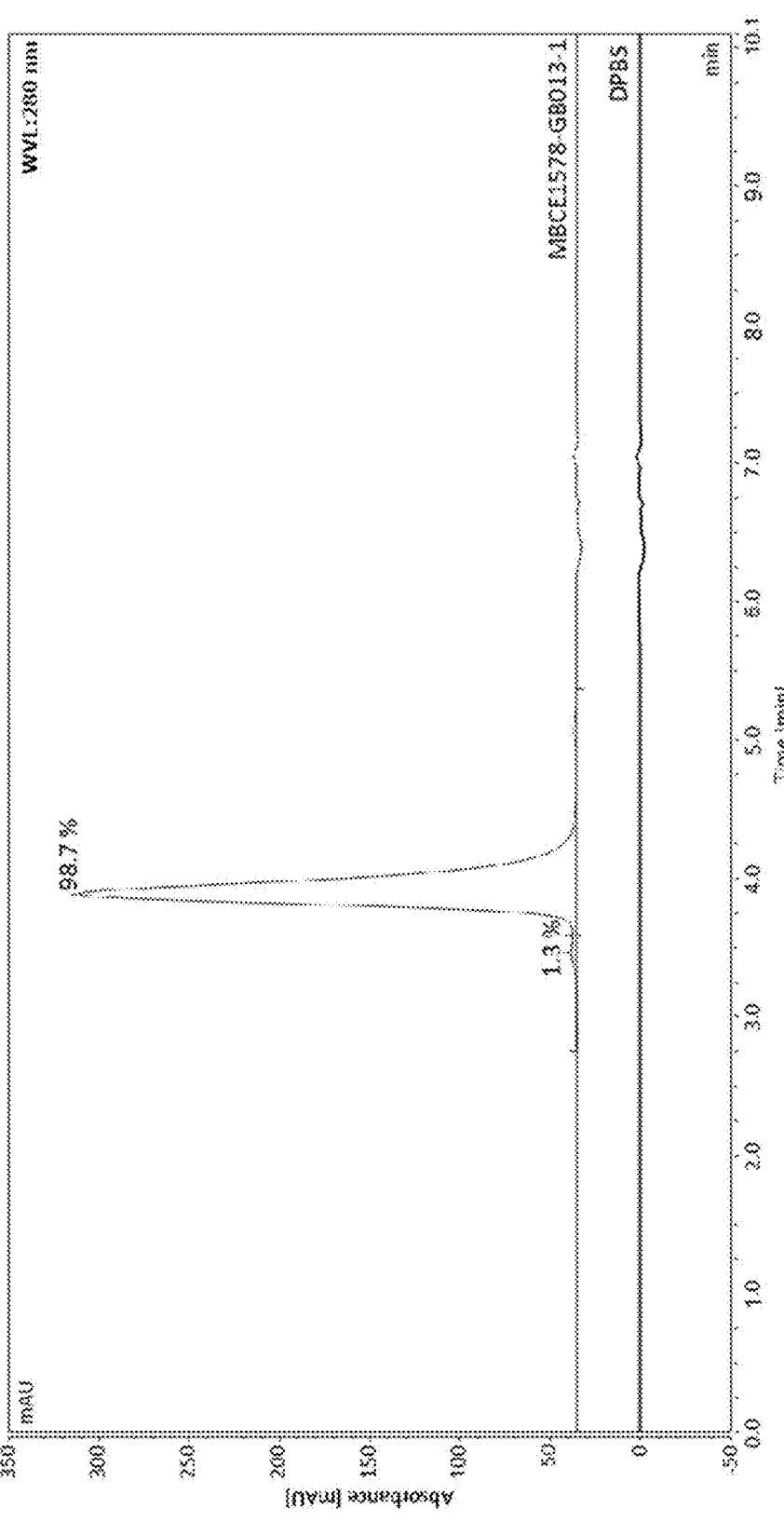
FIG. 52 illustrates a size exclusion chromatogram ($\lambda$=280 nm) for the VH4Vk3-ThioBridge®-(VCP-SN38)2 ADC (top trace) and PBS buffer (bottom trace).
Figure 53:
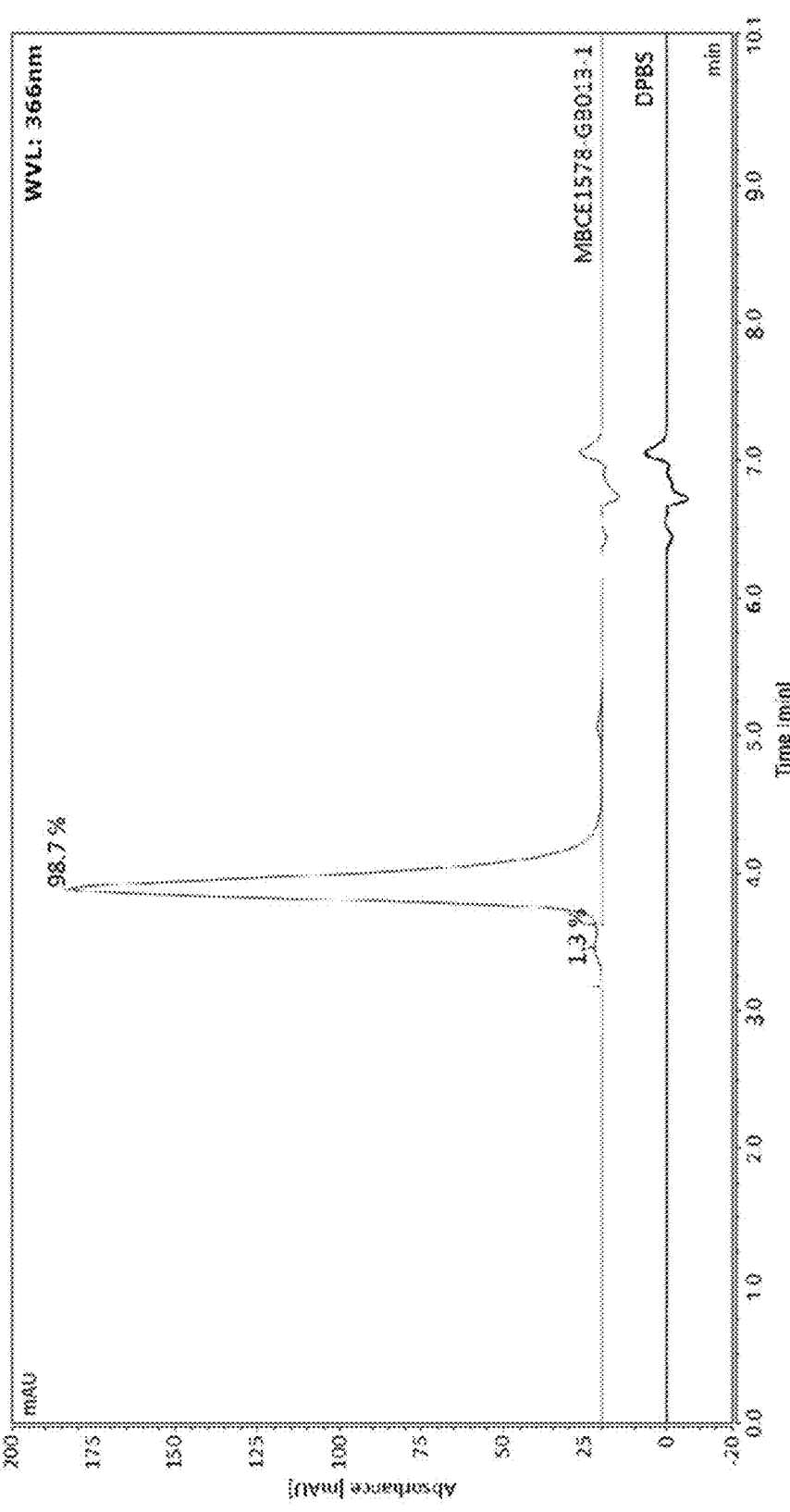
FIG. 53 illustrates a size exclusion chromatogram ($\lambda$=366 nm) for the VH4Vk3-ThioBridge®-(VCP-SN38)2 ADC (top trace) and PBS buffer (bottom trace).
Figure 54:
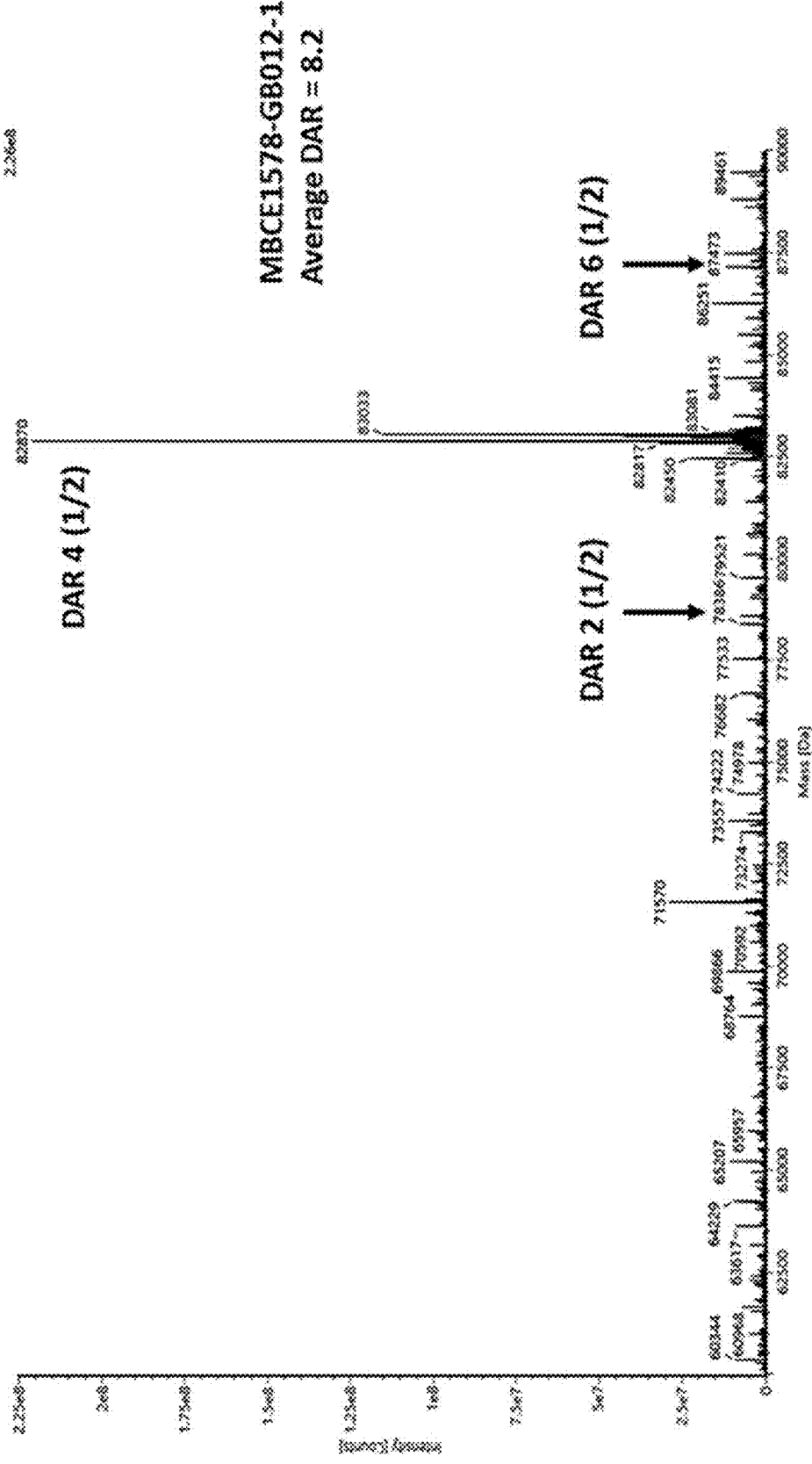
FIG. 54 illustrates a deconvoluted LC-MS spectrum for the VH5Vk3-ThioBridge®-(VCP-SN38)2 ADC (½ mAb conjugate species).
Figure 55:
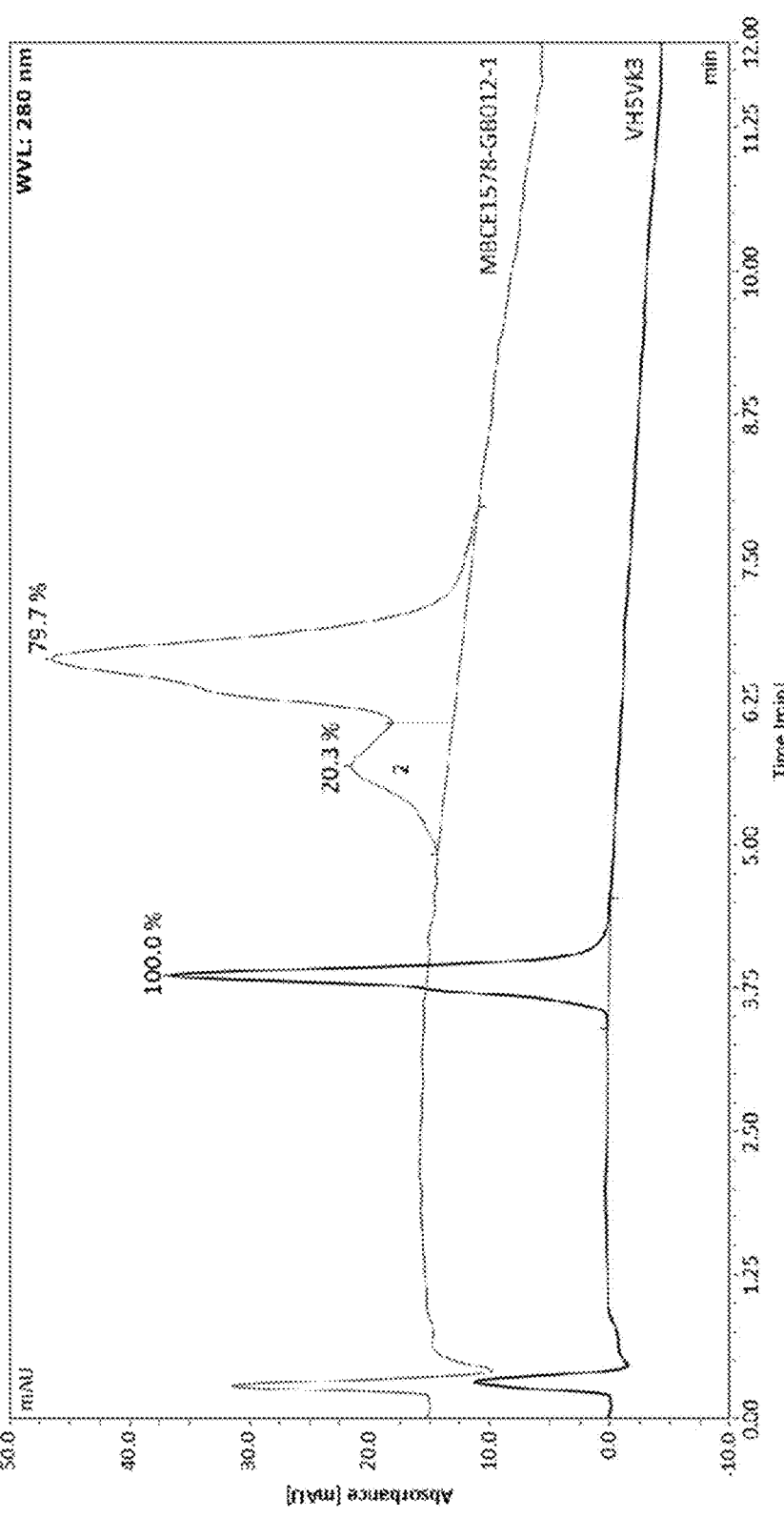
FIG. 55 illustrates a hydrophobic interaction chromatogram ($\lambda$=280 nm) for the VH5Vk3-ThioBridge®-(VCP-SN38)2 ADC (top trace) and VH5Vk3 mAb (bottom trace).
Figure 56:
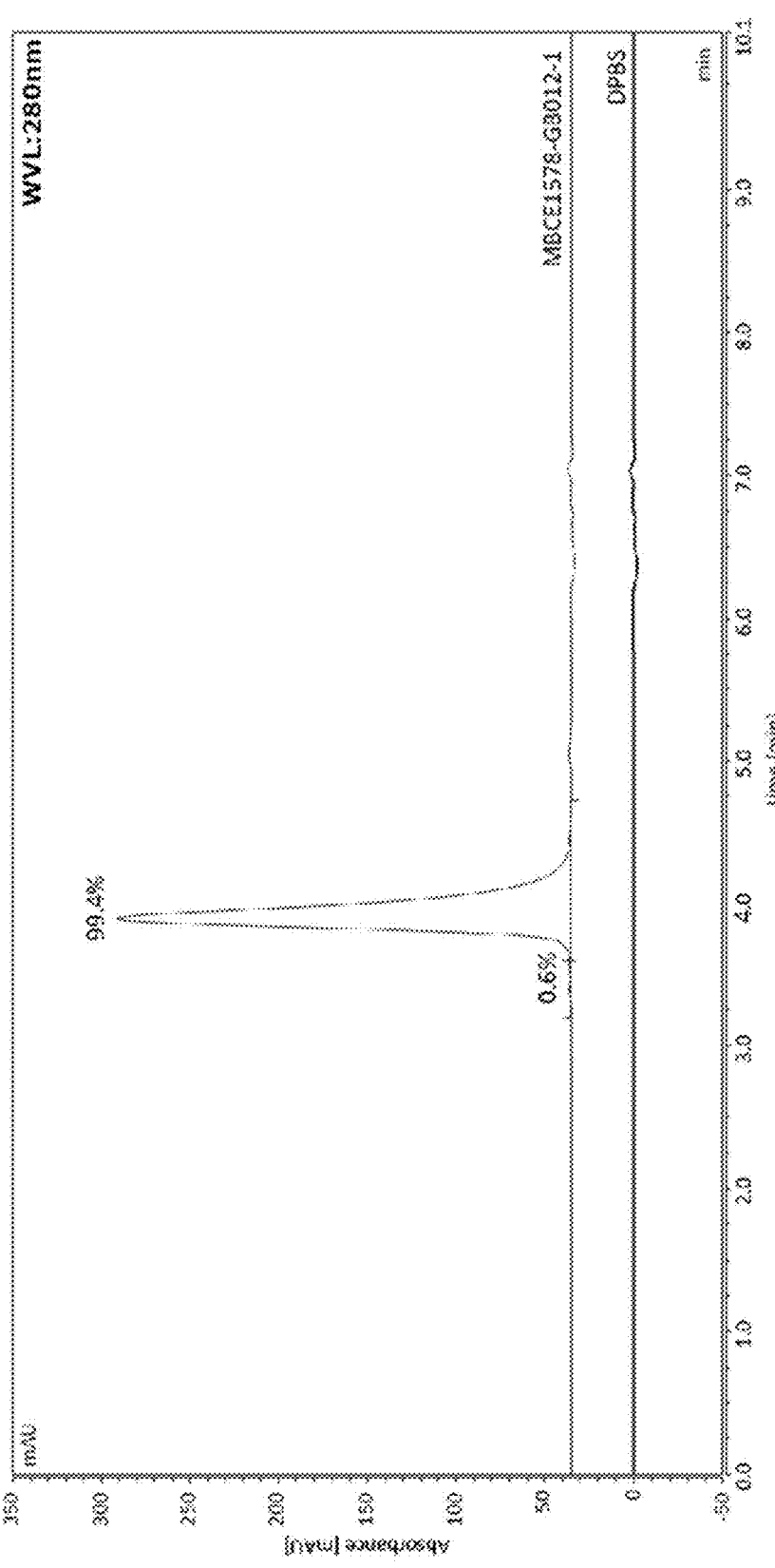
FIG. 56 illustrates a size exclusion chromatogram ($\lambda$=280 nm) for the VH5Vk3-ThioBridge®-(VCP-SN38)2 ADC (top trace) and PBS buffer (bottom trace).
Figure 57:
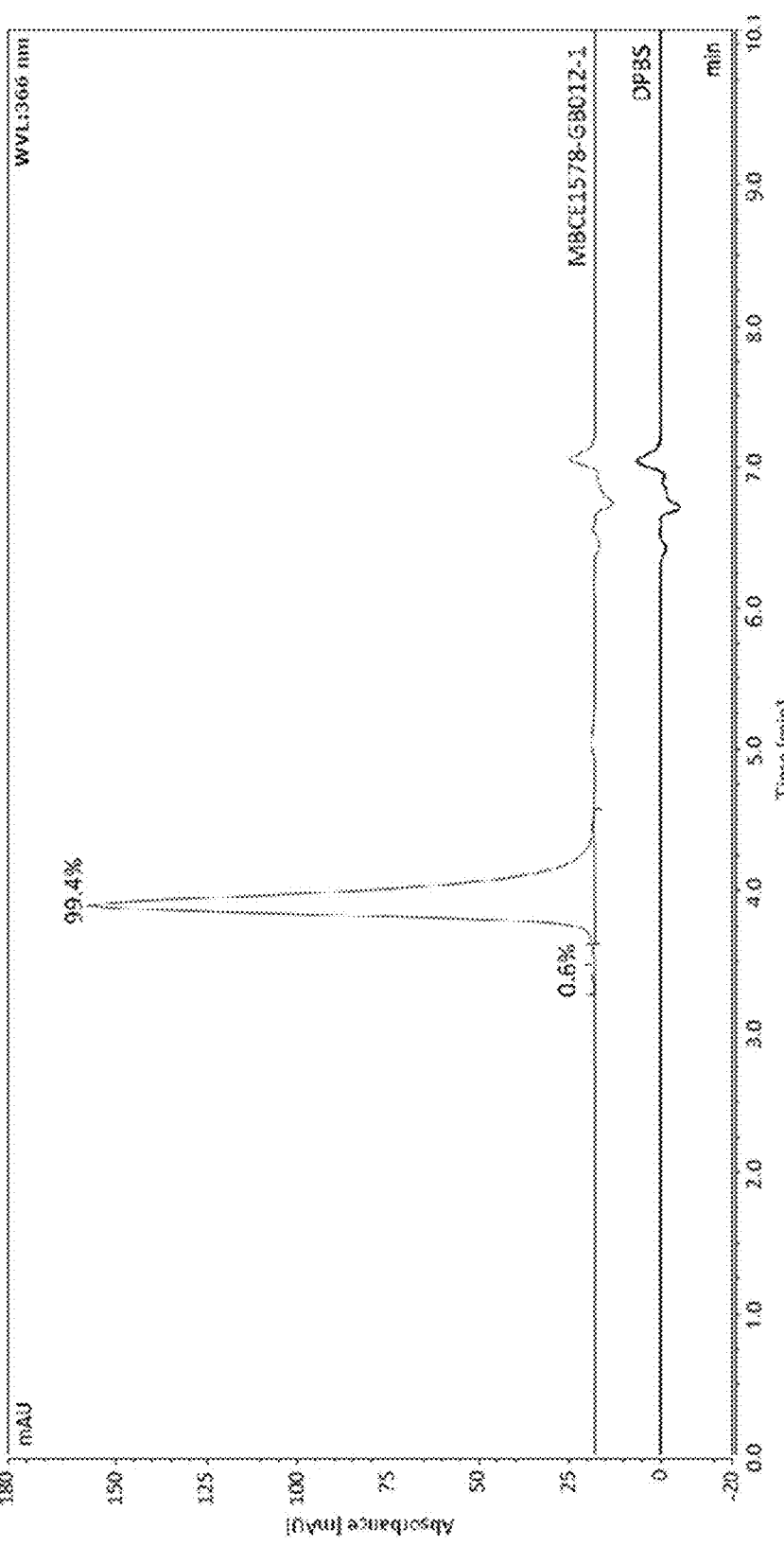
FIG. 57 illustrates a size exclusion chromatogram ($\lambda$=366 nm) for the VH5Vk3-ThioBridge®-(VCP-SN38)2 ADC (top trace) and PBS buffer (bottom trace).

| VH4Vk3-CL2A-SN38 | |
|---|---|
| Analysis | Results |
| Sample Name | VH4Vk3-CL2A-SN38 |
| Batch Code | MBCE1578-CC002-1 |
| Appearance | Clear colorless solution |
| Identity (LC-MS) | MW confirmed |
| | See FIG. 50 for spectra |
| Average DAR (LC-MS) | Average DAR: 8.0 |
| Retention time (HIC) | 4.8 min |
| | See FIG. 51 for chromatogram |
| % Purity (SEC) | 97.1% monomeric |
| | See FIG. 52 for chromatogram |
| % free reagent related species | Not detected |
| | See FIG. 53 for chromatogram |
| Endotoxin (EU/mg) | 0.10 |

TABLE E10.D-continued

| VH4Vk3-CL2A-SN38 | |
|---|---|
| Analysis | Results |
| Concentration (UV) | 3.21 mg/mL |
| Amount (UV) | 56 mg |
| Average MW | 160,495 Da |

For spectral, chromatographic, and hydrophobic interaction analysis, see FIGS. 46-49.

TABLE E10.E

Figure 58:
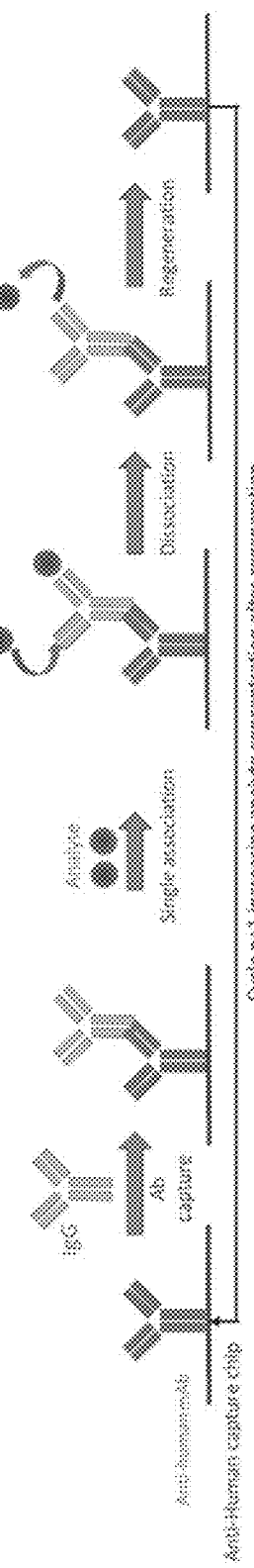
FIG. 58 illustrates a cartoon of the Biacore schematic used to assess the binding of the humanized IgG to EphA5 antigen by multi-cycle kinetic analysis.
Figure 67:
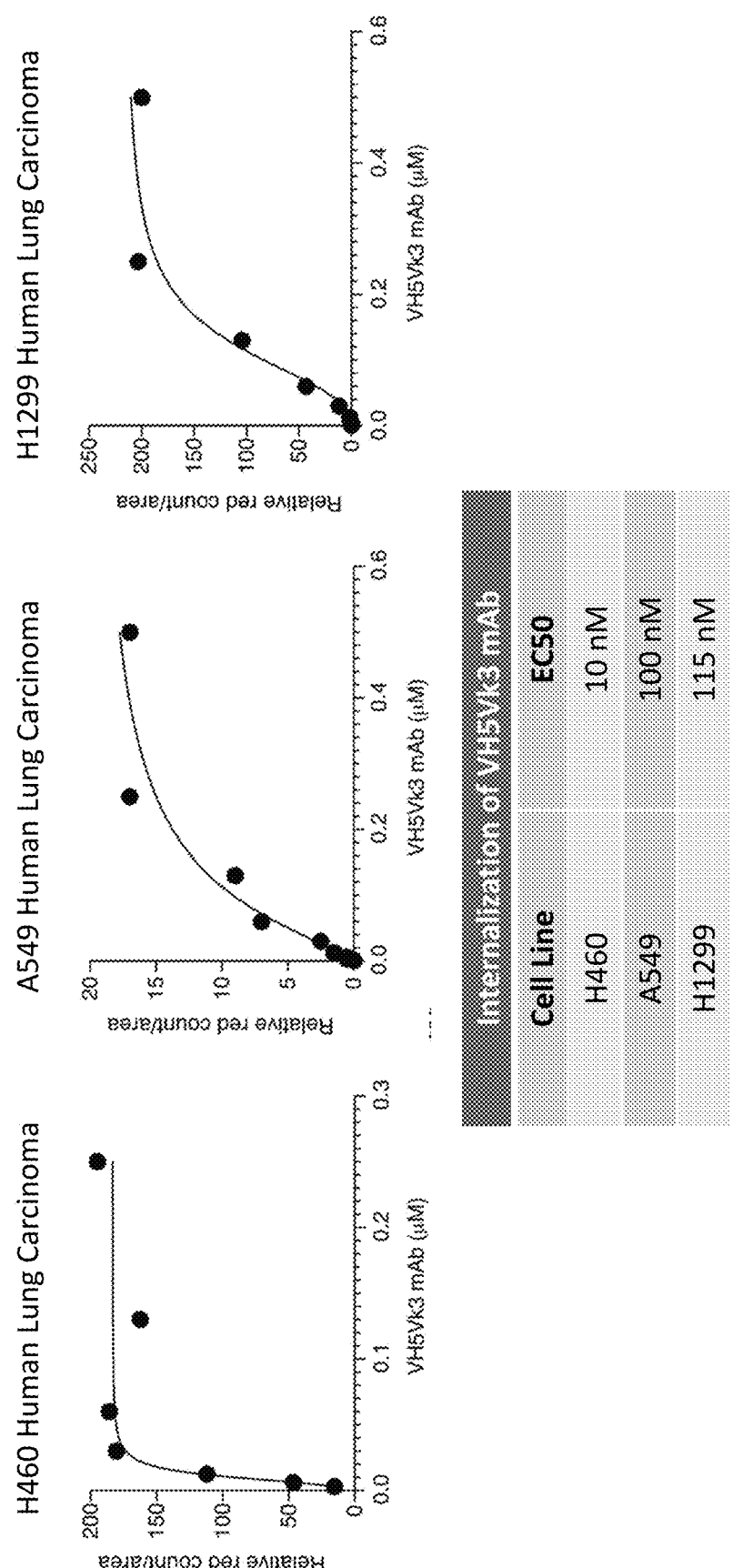
FIG. 67 illustrates the internalization of VH5Vk3 mAb in vitro.

| H4Vk3-ThioBridge ®-(VCP-SN38)$_2$ | |
|---|---|
| Analysis | Results |
| Sample Name | VH4Vk3-ThioBridge ®-(VCP-SN38)2 |
| Batch Code | MBCE1578-GB013-1 |
| Appearance | Clear colorless solution |
| Identity (LC-MS) | MW confirmed |
| | See FIG. 58 for spectra |
| Average DAR (LC-MS) | Average DAR: 8.6 |
| SDS-PAGE | See FIG. 67 for gel |
| Retention time (HIC) | 5.2 and 6.2 min |
| | See FIG. 59 for chromatogram |
| % Purity (SEC) | 98.7% monomeric |
| | See FIG. 60 for chromatogram |
| % free reagent related species | Not detected |
| | See FIG. 61 for chromatogram |
| Endotoxin (EU/mg) | 0.09 |
| Concentration (UV) | 4.70 mg/mL |
| Amount (UV) | 98 mg |
| Average MW | 165,762 Da |

For spectral, chromatographic, and hydrophobic interaction analysis, see FIGS. 50-53.

TABLE E10.F

Figure 64:
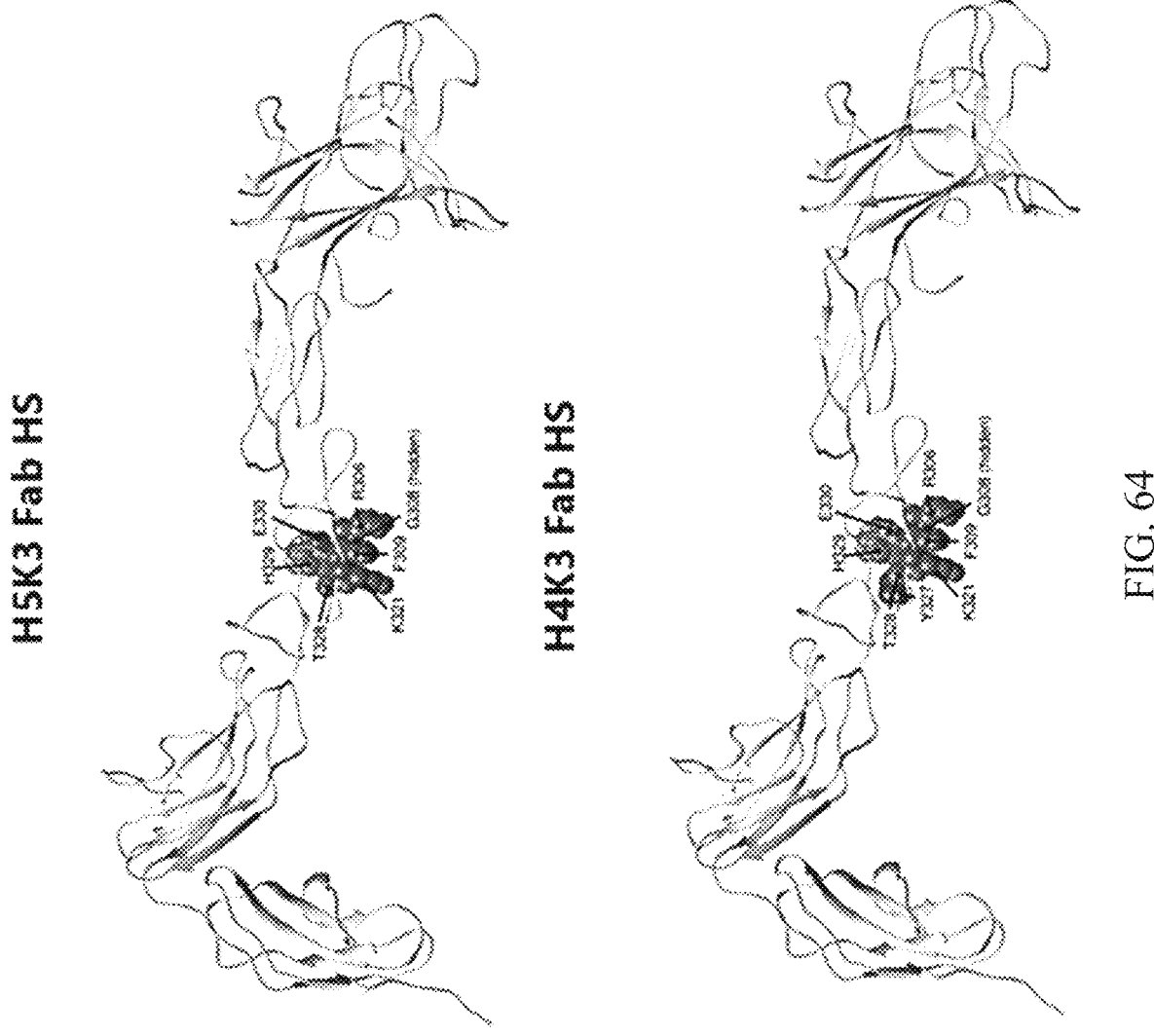
FIG. 64 is a diagram illustrating visualization of primary residues for Ab binding.

| H5Vk3-ThioBridge ®-(VCP-SN38)$_2$ | |
|---|---|
| Analysis | Results |
| Sample Name | VH5Vk3-ThioBridge ®-(VCP-SN38)2 |
| Batch Code | MBCE1578-GB012-1 |
| Appearance | Clear colorless solution |
| Identity (LC-MS) | MW confirmed |
| | See FIG. 62 for spectra |
| Average DAR (LC-MS) | Average DAR: 8.2 |
| SDS-PAGE | See FIG. 67 for gel |
| Retention time (HIC) | 5.7 and 6.6 min |
| | See FIG. 63 for chromatogram |
| % Purity (SEC) | 99.4% monomeric |
| | See FIG. 64 for chromatogram |
| % free reagent related species | Not detected |
| | See FIG. 65 for chromatogram |
| Endotoxin (EU/mg) | 0.05 |
| Concentration (UV) | 4.28 mg/mL |
| Amount (UV) | 141 mg |
| Average MW | 165,740 Da |

For spectral, chromatographic, and hydrophobic interaction analysis, see FIGS. 54-57.

Discussion

Two ADCs were successfully produced by conjugation of either MC-VCP-MMAE or CL2A-SN38 to linker-payload to the VH4Vk3 antibody. The average DAR was 3.9 with MC-VCP-MMAE or 8.0 with CL2A-SN38 as determined by HIC-HPLC. The average DAR of conjugates was 3.6 and 8.0, respectively, as determined by LC-MS. ADCs were successfully produced by conjugation of the ThioBridge®-VCP-MMAE linker-payload to anti-EphA5 VH4Vk3 and VH5Vk3 antibodies. The average DAR was 4.0 for all the conjugates as determined by LC-MS. The average DAR was 4.0 to 4.1 as determined by HIC-HPLC.

ADCs were successfully produced by conjugation of the ThioBridge®-(VCP-SN38)2 linker-payload to anti-EphA5 VH4Vk3 and VH5Vk3 antibodies. The average DAR was in the range of 8.0 to 8.6 for all the conjugates as determined by LC-MS. All ADCs had high monomeric purity as determined by analytical SEC, with monomeric purity in the 98.7% to 99.9% range.

No significant presence of reagent related species could be detected in the ADCs comparing the SEC trace of the samples to the SEC trace of the formulation buffer in the low molecular weight species region at different wavelengths.

LAL assay also confirmed the low levels of endotoxins in all ADC samples (<0.1 EU/mg). LC-MS intact mass analysis performed either with prior reduction for maleimide conjugates or without reduction for ThioBridge® conjugates confirmed the identity of the conjugated species. Expected profiles were observed for the ADCs by SDS-PAGE, with presence of interchain disulfide bridged conjugated species including intact antibody conjugate, fragment species HHL and HH and of 'half-antibody' fragment species HL. High levels (64-73%) of inter heavy-chains bridging were observed for the ThioBridge®-MMAE and -SN38 ADCs.

All ThioBridge® ADCs were isolated following purification by preparative HIC and in moderate yields (33-54% recovery). The MC-VCP-MMAE conjugate was isolated following preparative SEC purification in 78% yield. The CL2A-SN38 conjugate was isolated following desalting and preparative SEC purification in 75% yield.

Example 4: In Vitro and In Vivo Validation of Humanized Antibody and ADE Function Functional cytotoxicity studies were then conducting using the humanized antibodies and the antibody drug conjugates derived in Examples 1-3 of the current disclosure.

In vitro studies were conducted in which three different Eph5A-expressing target cell lines were incubated with various concentrations of VH5Vk3 or VH4Vk3 antibodies after which internalization of bound antibody was calculated. Antibody internalization was performed with the Incucyte® Human Fabfluor-pH Red Antibody Labeling Dye and the naked VH4Vk3 (FIG. 66) and VH5Vk3 (FIG. 67) human monoclonal antibodies in the following cell lines: H460 human lung carcinoma, A549 human lung carcinoma and H1299 human lung carcinoma. These cell lines express variable levels of EphA5 on the cell surface: H460 (+++) >A549 (++)=H1299 (++). Internalization was visualized and quantified using real-time live cell imaging analysis. The Fabfluor-pH Red Antibody Labeling Dye is sensitive to pH and only emits fluorescence once inside lysosomes in low pH conditions. These results confirmed receptor-mediated internalization and trafficking of both human monoclonal antibodies through the lysosomal compartment, an important feature of antibody-drug conjugates.

A series of in vivo studies was then conducted in order to assess the cytotoxicity of the various antibody drug conjugates of the current invention. Cytotoxicity of ADC was tested using the Incucyte® and real time analysis and quantification of confluence cell image mask. In brief, cell confluence is monitored by analyzing the occupied area (% confluence) of cells imaged over time. Confluence of cells is expected to decrease as cells exposed to ADC stop proliferating and die. Data from VH4Vk3-ThioBridge®-VCP-MMAE (FIG. 68), VH4Vk3-ThioBridge®-(VCP-SN-38)2

Figures 4A, 4B:
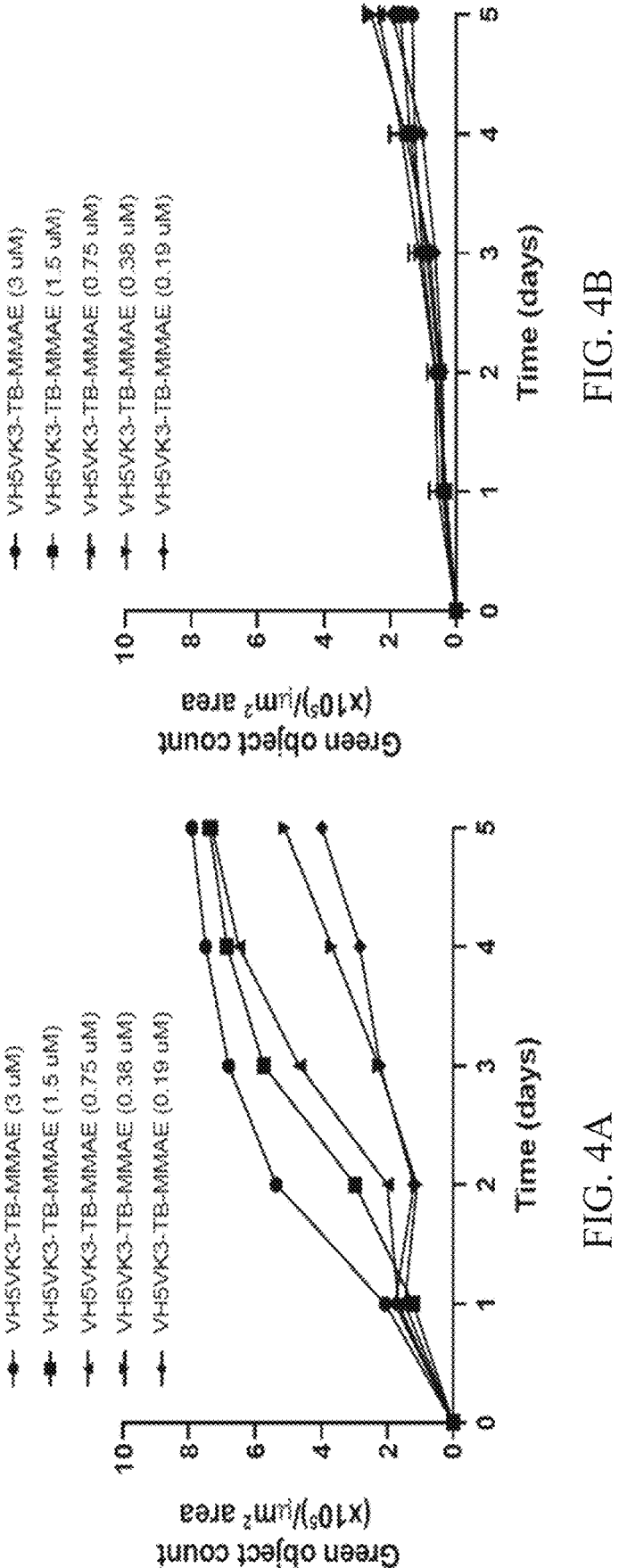
FIGS. 4A-4B illustrate a time-course for the effect of VH5/VK3-ThioBridge®-VCP-MMAE on cell death as measured by Green Object Count.

(FIG. 69), VH5Vk3-ThioBridge®-VCP-MMAE (FIG. 70), and VH5Vk3-ThioBridge®-(VCP-SN-38)2 (FIG. 71) demonstrate increasing amounts of ADC induced cell death which is dependent on the levels of expression of the target EphA5: H522 (++++)>H460 (+++)>A549 (++)=H1299 (++). Additional studies further demonstrated that the VH5Vk3-TB-MMAE ADC was able to kill EPHA5+ cells but not EPHA5− cells in a dose- and time-dependent way (FIGS. 4A and 4B).

Observation of ADC efficacy in vivo was accomplished by using a number of xenograft tumor models. Broadly, Mice bearing tumors of 100 mm³ volume were enrolled in the study, being randomized into 3 experimental groups:

Vehicle (PBS)—mice received intravenous injections of PBS

Cytotoxic agent (MMAE or SN-38, Equimolar)—mice received intravenous injections of an equimolar amount of unconjugated MMAE or SN-38.

VH4Vk3 or VH5Vk3 ADC—mice received intravenous injections of 10 mg/kg of the ADC.

For studies using the VH4Vk3-ThioBridge®-VCP-MMAE and VH4Vk3-ThioBridge®-(VCP-SN-38)2 in a H522-derived Xenograft Model of Human Lung Cancer, treatments were administered weekly for a total of 3 weeks (3 doses total) followed by observation and tumor measurements until the control groups (groups 1 and 2) reached the maximum volume allowed in the study (2500 mm3). Tumor measurements were taken every 48 h with a digital caliper. Tumor growth curves and waterfall charts of progression are illustrated in FIGS. 72, 74, and 76. Full regression was observed for all ADC-treated tumors. The regression was sustained for a total of 50-60 days, which represented the end of the experiment. Concurrently, the body weights of mice enrolled in the study were taken prior to the first treatment dosing and at termination (FIGS. 73, 75, and 77). In each study, no significant changes in body weight were observed.

Figure 79:
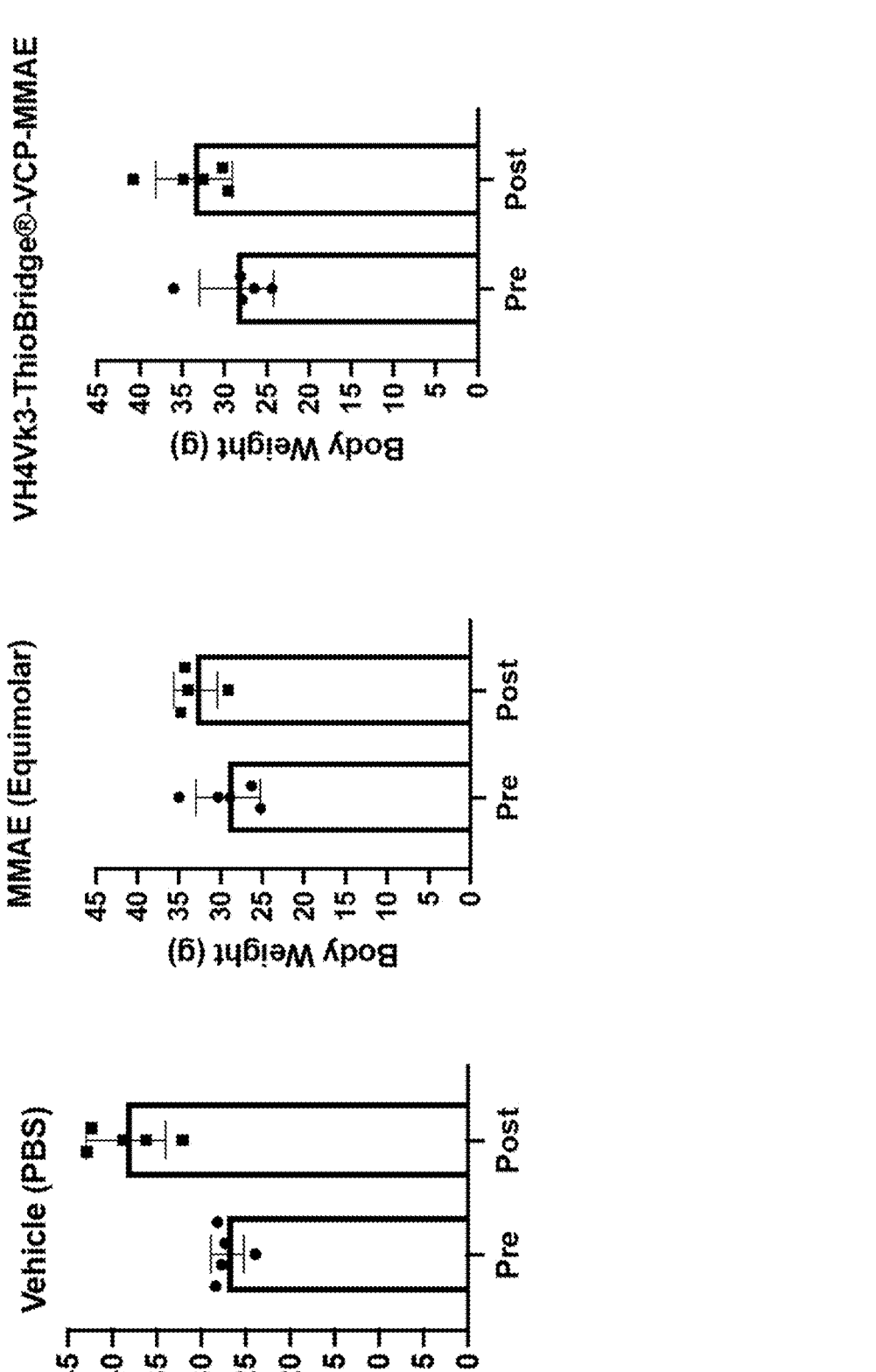
FIG. 79 illustrates body weights of tumor-bearing mice pre- and post-treatment (ref.
Figure 81:
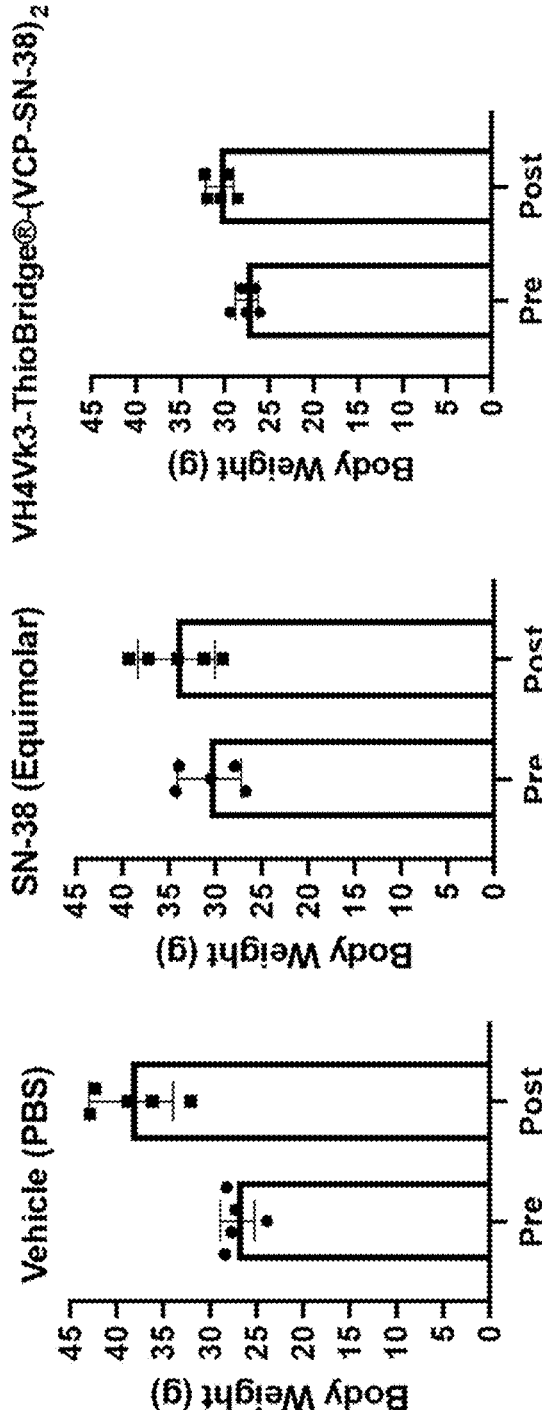
FIG. 81 illustrates body weight of tumor-bearing mice pre- and post-treatment (ref.

Similar studies were performed using an A549 cell line-derived human lung cancer xenograft model. Growth curves and waterfall plots for VH4Vk3-ThioBridge®-VCP-MMAE and VH4Vk3-ThioBridge®-(VCP-SN-38)2 are illustrated in FIGS. 80 and 82. Similar to previous studies, full regression was observed for 4 tumors of the ADC-treated (n=5). One tumor showed partial regression (mouse 4) that was sustained throughout the entirety of the study (total of 32 days). The waterfall chart confirmed both partial and full sustained regressions of tumors treated with the ADC VH4Vk3-ThioBridge®-VCP-MMAE (FIG. 82). For the study using VH4Vk3-ThioBridge®-(VCP-SN-38)2, treatments were administered weekly for the first three weeks (days 1-20). On day 20, mice from group 3 received the first dose of VH4Vk3-ThioBridge®-VCP-MMAE (10 mg/kg). Second and third doses were administered on days 26 and 32 respectively (Treatments are indicated by arrows). Control groups 1 and 2 were terminated on day 32 due to tumor ulcerations. Group 3 was observed until day 38 (FIG. 80). Tumor measurements were taken every 48 h with a digital caliper. For both studies, body weights of mice enrolled in the study taken prior to the first treatment dosing and at termination found no significant changes in body weight were observed in every group (FIGS. 79, 81).

Figure 83:
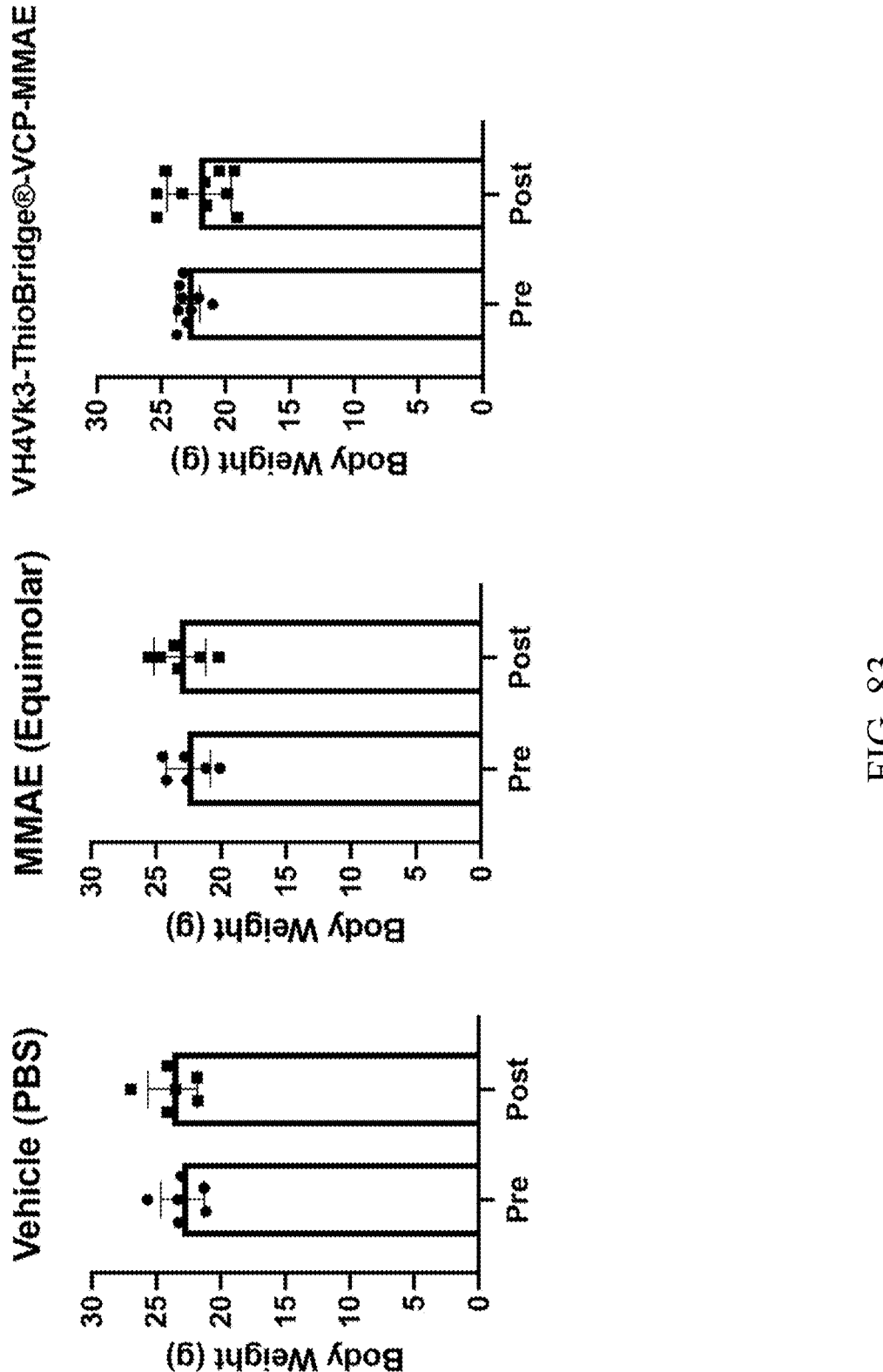
FIG. 83 illustrates body weights of tumor-bearing mice pre- and post-treatment (ref.
Figure 85:
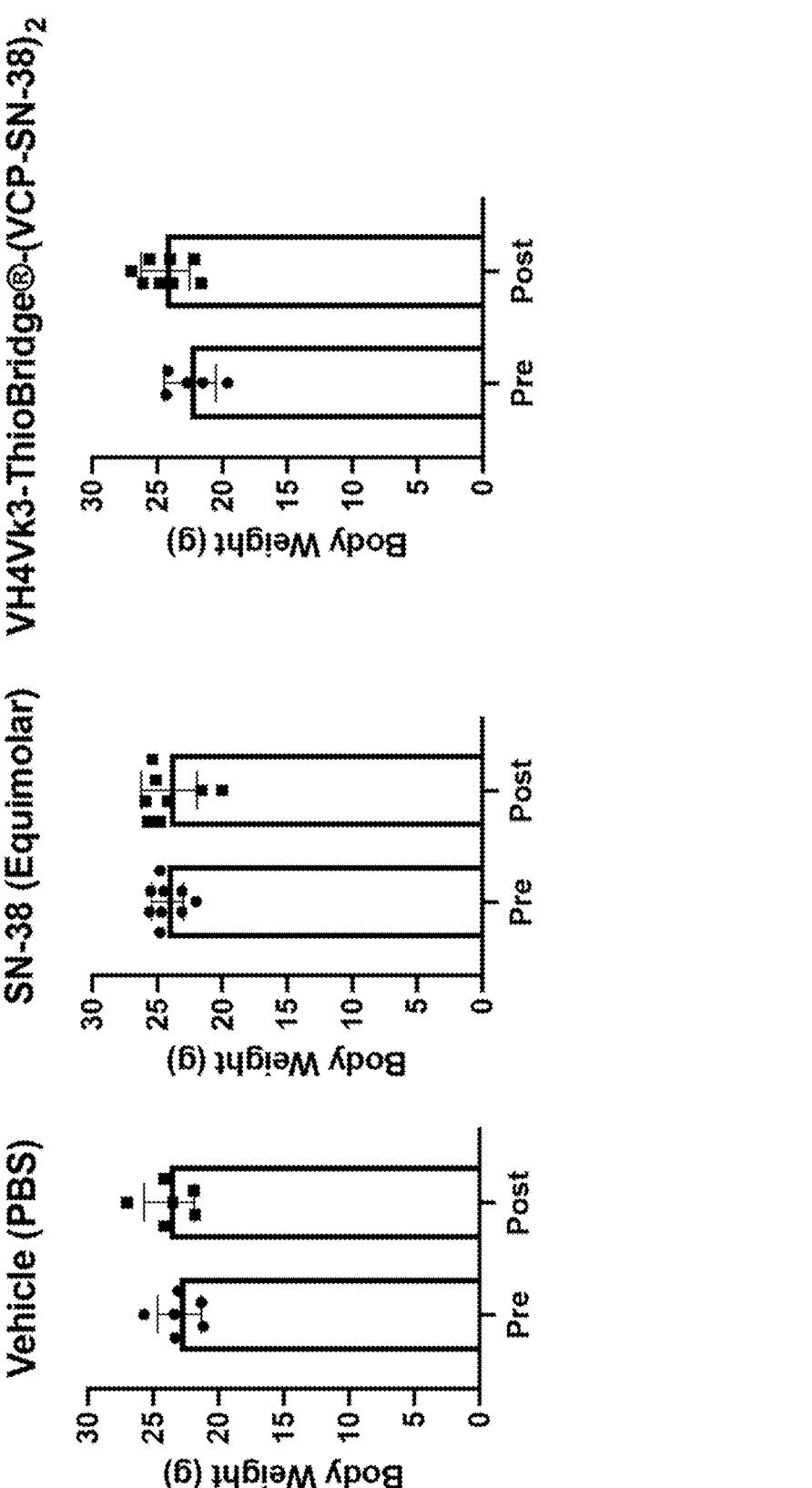
FIG. 85 illustrates body weights of tumor-bearing mice pre- and post-treatment (ref.

Another xenograft model used for similar studies was a H460-derived xenograft model of human lung cancer. For the experiment using VH4Vk3-ThioBridge®-VCP-MMAE, treatments were administered every 5 days for a total of 3 doses followed by observation and tumor measurements until the control groups (groups vehicle and agent alone)

reached the maximum volume allowed in the study (2000 mm3). Tumor measurements were taken every day with a digital caliper. Results found that full regression was observed for 2 tumors (mouse 2 and mouse 8) of group 3 (n=9) (FIG. 82) while no changes in body weight were observed in any group when measured from prior to the first treatment and at termination (FIG. 83). Studies with VH4Vk3-ThioBridge®-(VCP-SN-38)2 were administered every 5 days for a total of 3 doses followed by observation and tumor measurements until the control groups (vehicle and unconjugated cytotoxic agent) reached the maximum volume allowed in the study (2000 mm$^3$) and found that full regression was observed for 1 tumor (mouse 6) of group 3 (n=8) (FIG. 84) with no changes in body weight (FIG. 85).

Figure 87:
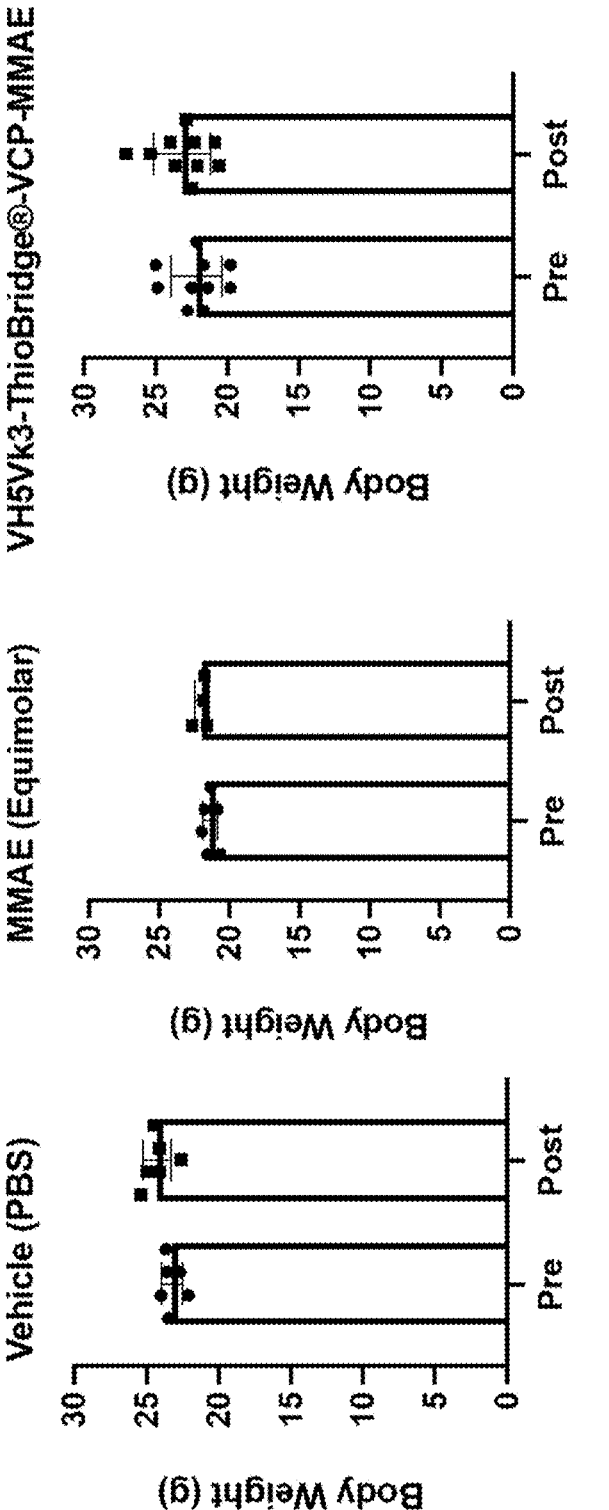
FIG. 87 illustrates body weights of tumor-bearing mice pre- and post-treatment (ref.

Two sets of studies using the VH5Vk3-ThioBridge®-VCP-MMAE ADC in a H522 cell line-based xenograft model of human lung cancer were also performed using a setup and schedule similar to previous studies in the present disclosure. Here treatments were administered weekly for 3 weeks (3 doses total) followed by observation and tumor measurements until the control groups reached the maximum volume allowed in the study (2500 mm$^3$). FIG. 86 shows that full regression was observed for all tumors of group 3 (n=10). The regression was sustained for a total of 60 days. The waterfall chart shows full and sustained regression of all tumors treated with the ADC. Similarly, FIG. 88 shows full regression in all tumors of the experimental group (n=5). The regression was sustained for a total of 50 days. Analysis by waterfall chart shows full and sustained regression of all tumors treated with the ADC. Body weights in both studies showed no significant changes (FIGS. 87 and 89).

Figure 91:
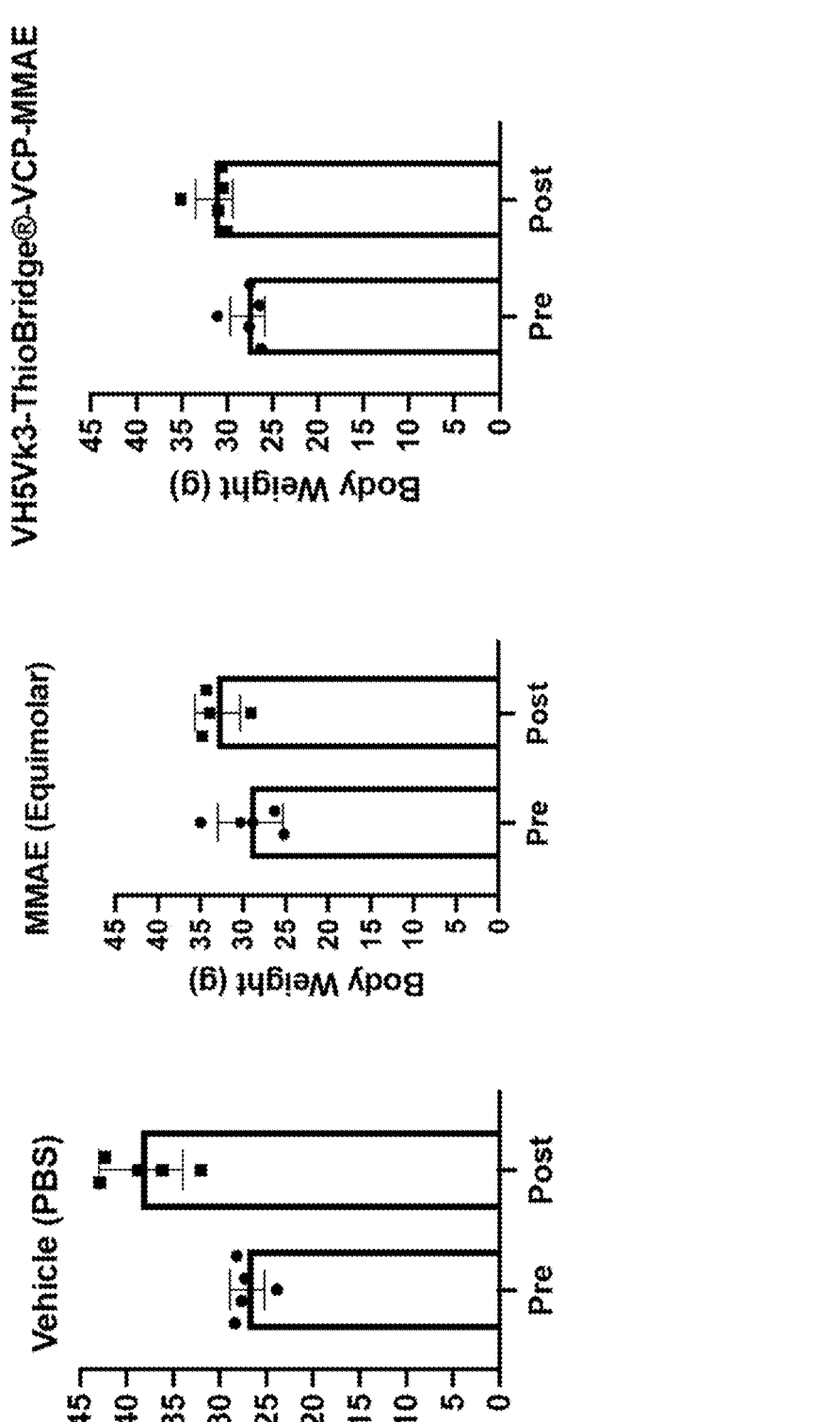
FIG. 91 illustrates body weights of tumor-bearing mice pre- and post-treatment (ref.
Figure 93:
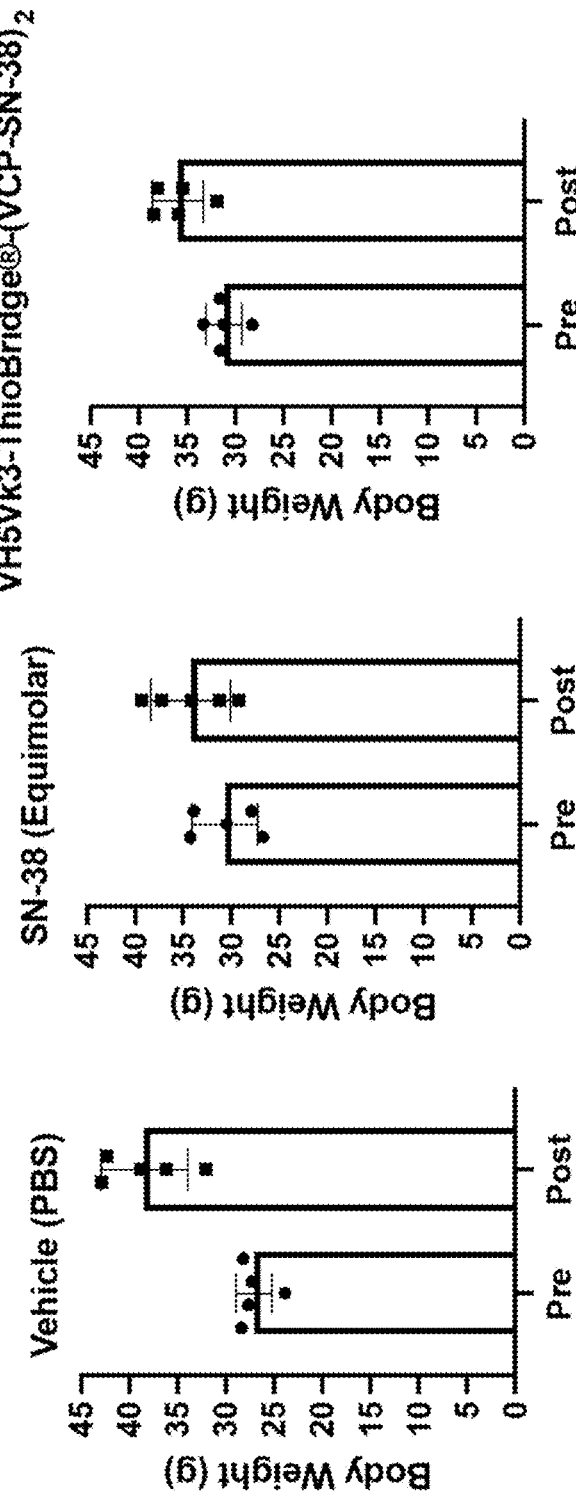
FIG. 93 illustrates body weights of tumor-bearing mice pre- and post-treatment (ref.

A set of studies using the VH5Vk3-ThioBridge®-VCP-MMAE and VH5Vk3-ThioBridge®-(VCP-SN-38)$_2$ ADC were then conducted using a xenograft model using the A549 human lung cancer cell line using a setup and schedule similar to previous studies in the present disclosure. For the MMAE-conjugated ADC, treatments were administered weekly for 3 weeks (3 doses total) followed by observation and tumor measurements until the control groups reached the maximum volume allowed in the study (1200 mm$^3$) or showed signs of ulceration (FIG. 90). Results found full regression of all tumors the experimental group (n=5). Analysis by waterfall chart showed full and sustained regression of 5 tumors treated with the ADC. For animals treated with the SN-38 conjugated ADC, treatments were administered weekly for the first three weeks (days 1-20). On day 20, mice from group 3 received the first dose of VH5Vk3-ThioBridge®-VCP-MMAE (10 mg/kg) (FIG. 92). Second and third doses were administered on days 26 and 32 respectively (Treatments are indicated by arrows). Control groups were terminated on day 32 due to tumor ulcerations. Group 3 was observed until day 38. Partial regressions of tumors treated with the ADC VH5Vk3-ThioBridge®-(VCP-SN-38)2 (10 mg/kg) were observed until day 14, after which tumors progressed steadily until day 20. Treatment of progressing tumors with the ADC VH5Vk3-ThioBridge®-VCP-MMAE resulted in tumor growth inhibition sustained from day 20-38. The waterfall analysis chart shows partial regression of tumors treated with VH5Vk3-ThioBridge®-(VCP-SN-38)2. No significant differences in the body weights of all animals participating in these studies was observed (FIGS. 91 and 93).

Figure 5B:
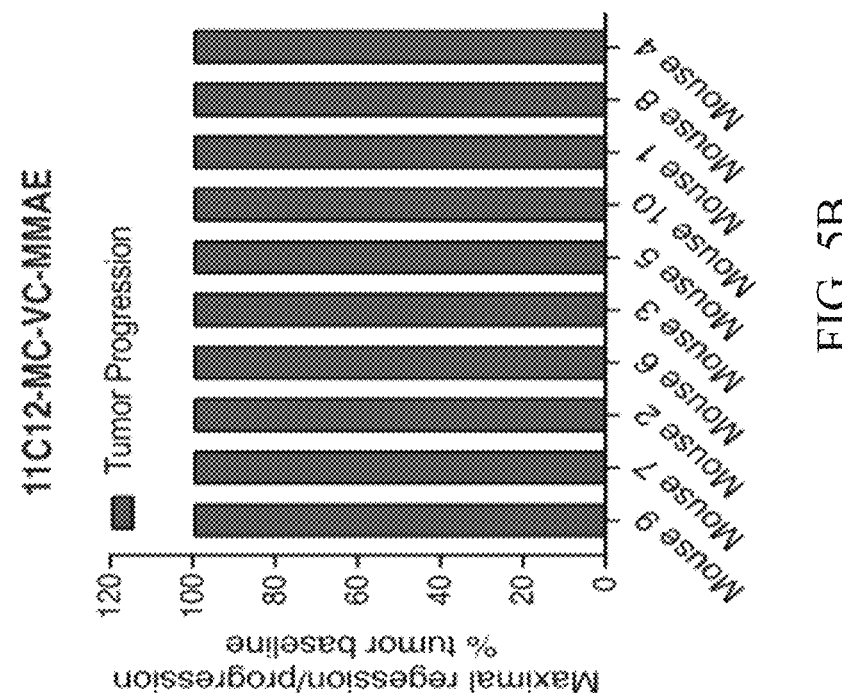
FIGS. 5A-5B illustrate in vivo use of immunoconjugated EphA5 antibodies. Tumor bearing mice were treated with VH5/VK3-ThioBridge®-VCP-MMAE (FIG. 5A) or the murine 11C12 antibody conjugated to the same payload MMAE (FIG. 5B). Maximal tumor regression is shown in green; maximal tumor progression is shown in red.
Figure 5A:
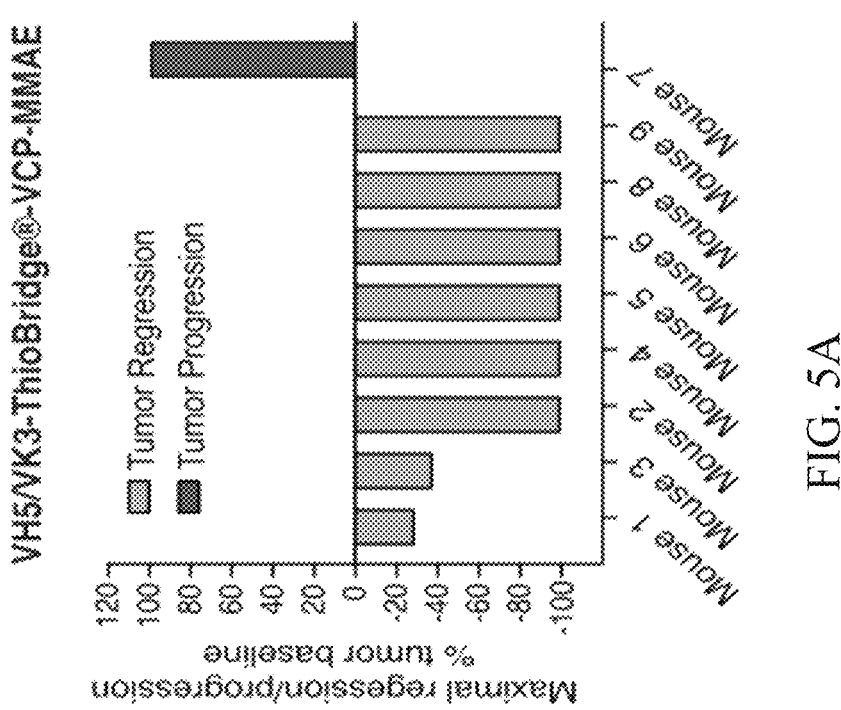
Figure 6:
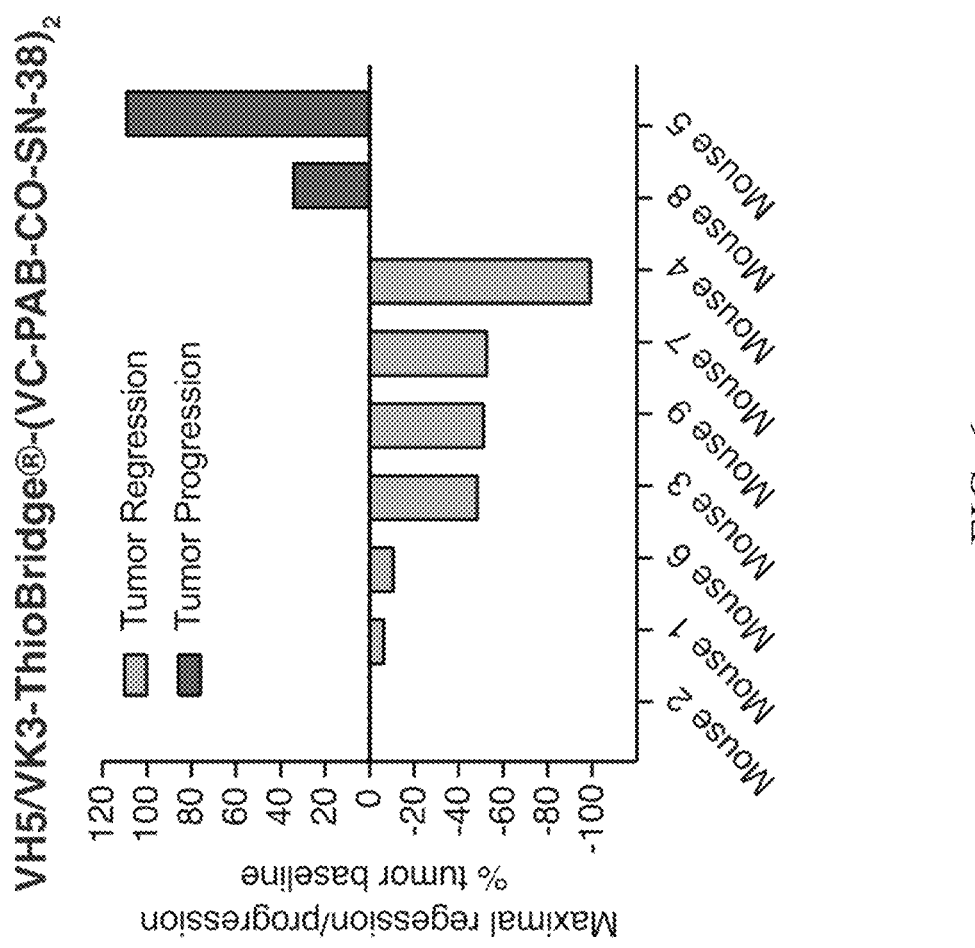
FIG. 6 illustrates the treatment of tumor bearing mice with VH5/VK3-ThioBridge®-(VC-PAB-CO-SN-38)2. Maximal tumor regression is shown for Mice 1-4, 6-7, and 9; maximal tumor progression is shown for Mice 5 and 8.
Figure 94:
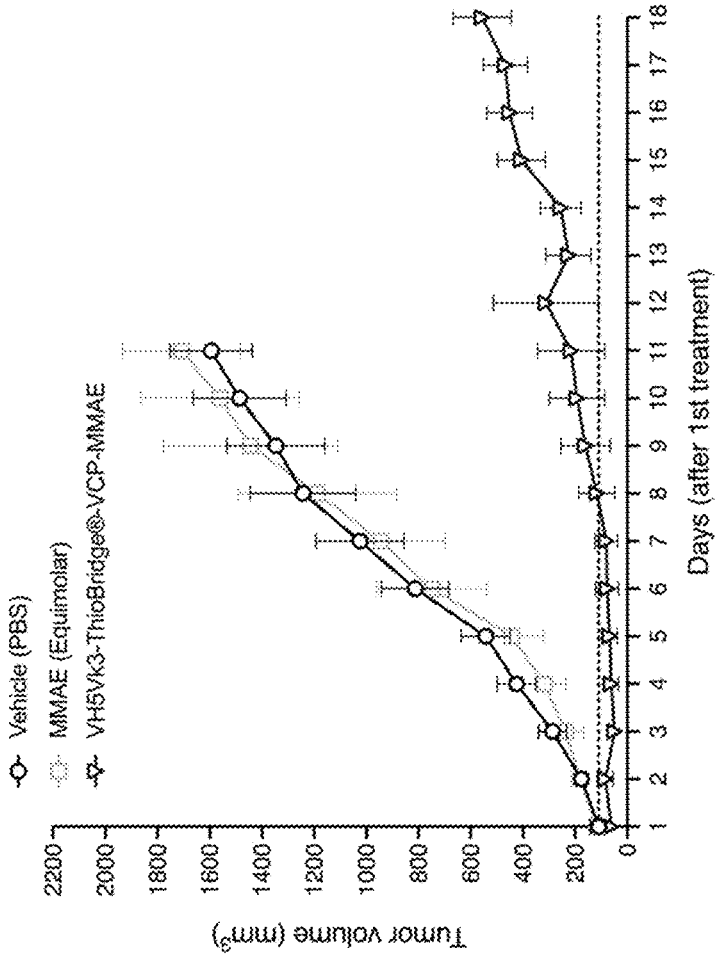
FIG. 94 illustrates the efficacy of VH5Vk3-ThioBridge®-VCP-MMAE in H460-derived xenograft model of human lung cancer. See FIG. 5A for a bar graph analysis.
Figure 95:
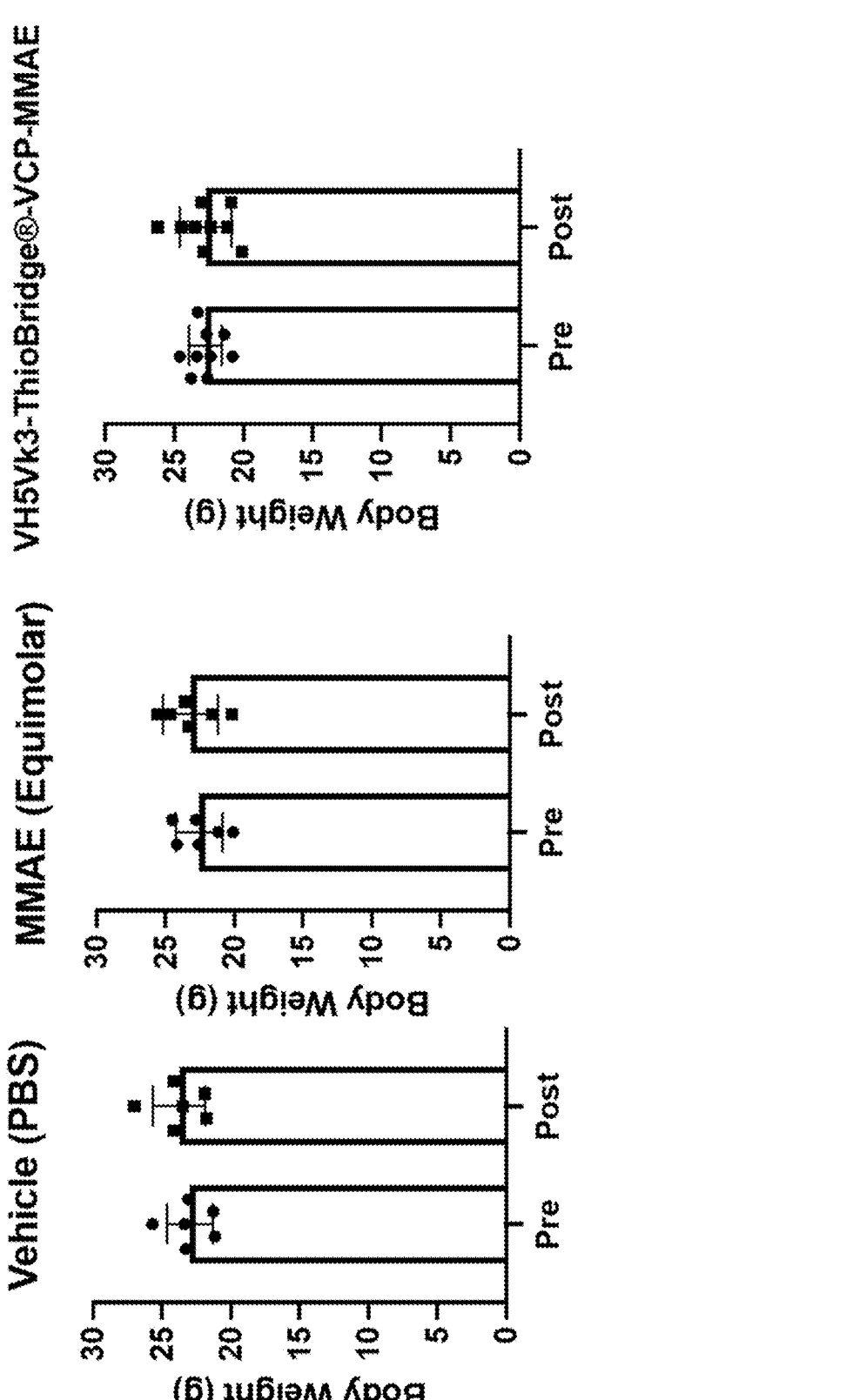
FIG. 95 illustrates body weights of tumor-bearing mice pre- and post-treatment (ref.
Figure 96:
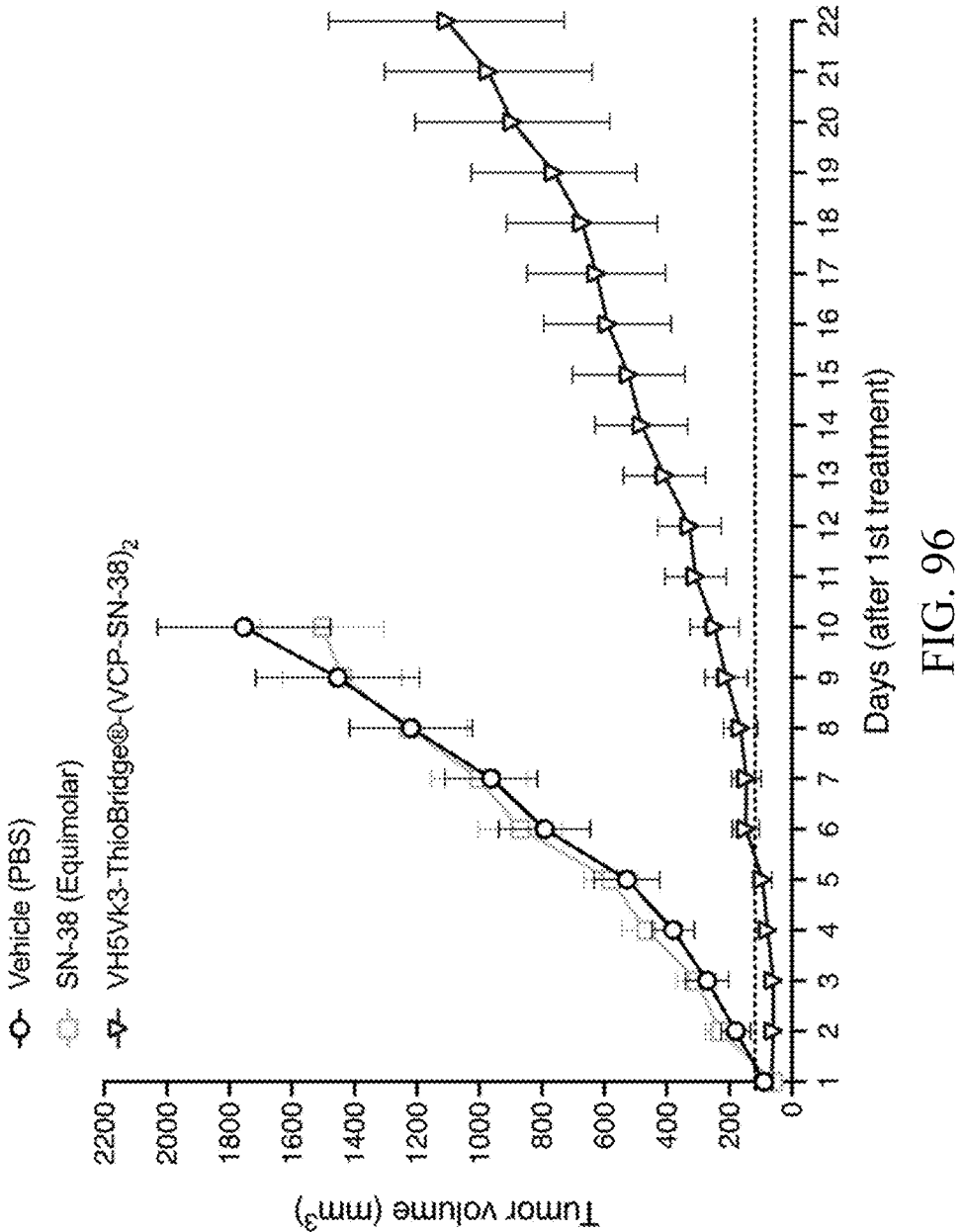
FIG. 96 illustrates the efficacy of VH5Vk3-ThioBridge®-(VCP-SN-38)2 in H460-derived xenograft model of human lung cancer. See FIG. 6 for a bar graph analysis.
Figure 97:
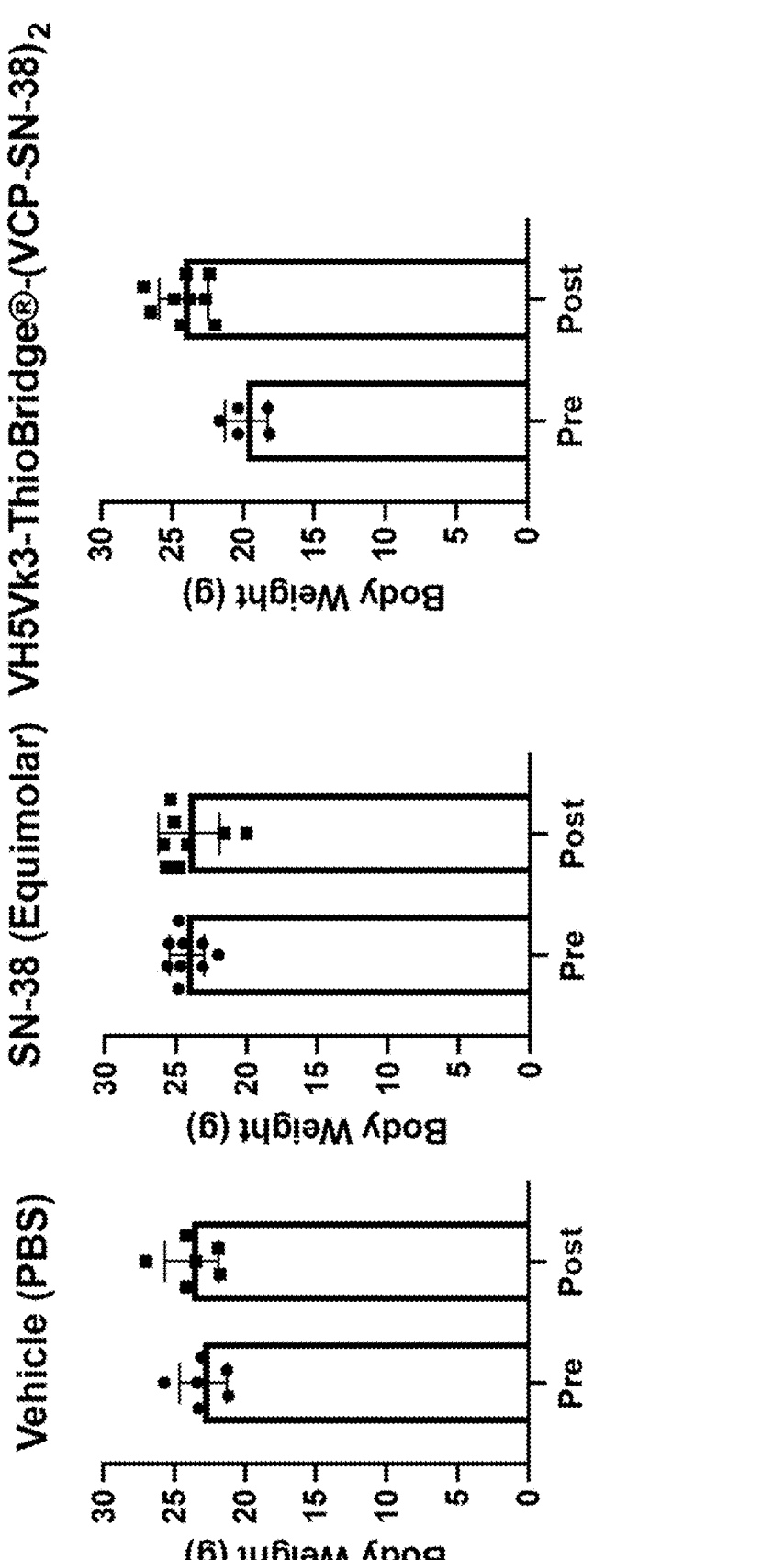
FIG. 97 illustrates body weights of tumor-bearing mice pre- and post-treatment (ref.
Figures 99A, 99B:
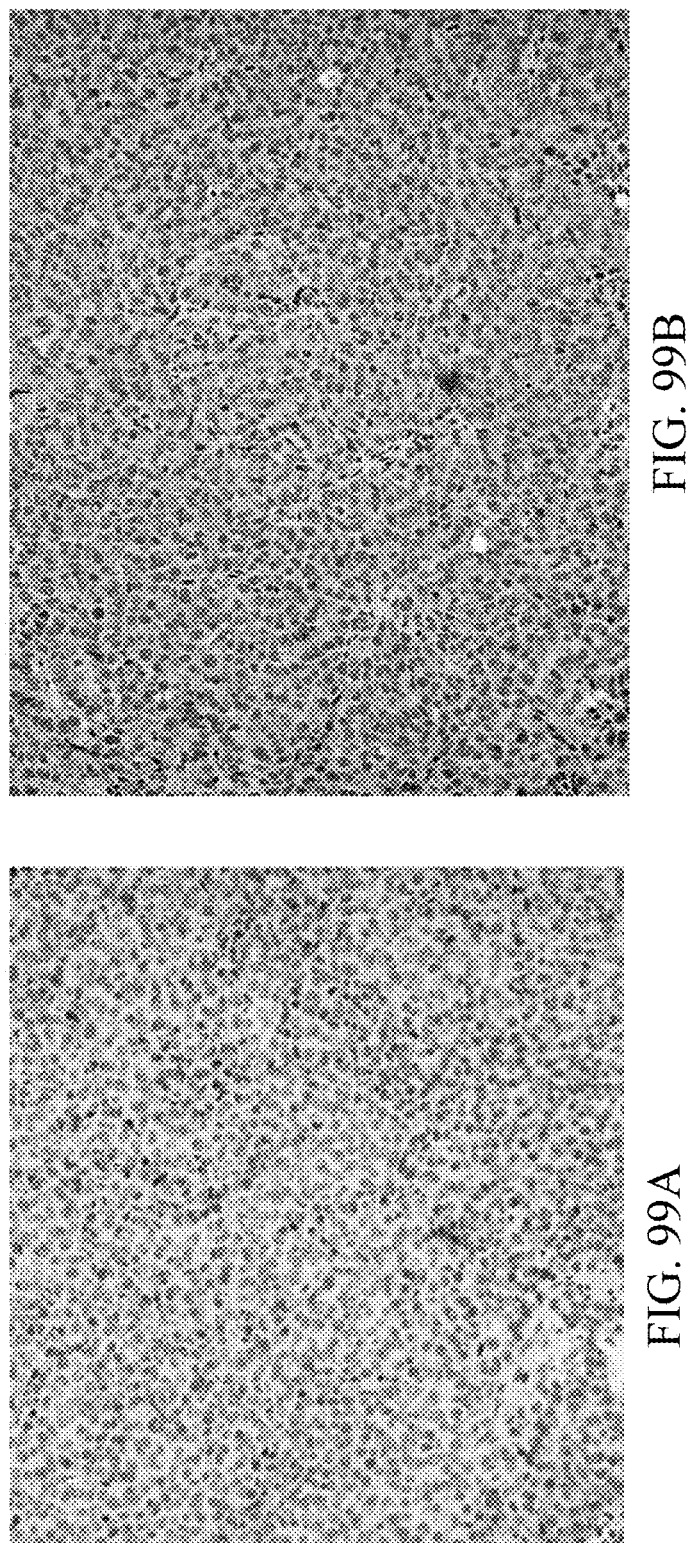
FIGS. 99A-99B illustrate IHC staining of triple negative breast cancer tissue from the TM00096 PDX model using a control IgG antibody (FIG. 99A) and IHC staining of triple negative breast cancer tissue from the TM00096 PDX model using a commercially available antibody that selectively binds to EphA5 (FIG. 99B).

Two studies were then performed using a human lung cancer xenograft mouse model based on the H460 cell line. Here the treatments of tumor-bearing animals with ADC VH5Vk3-ThioBridge®-VCP-MMAE were administered every 5 days for a total of 3 doses followed by observation and tumor measurements until the control groups reached the maximum volume allowed in the study (2000 mm$^3$). FIGS. 94 and 5A demonstrate that partial regression was observed for 8 tumors of group 3 (n=9). For the study utilizing VH5Vk3-ThioBridge®-(VCP-SN-38)$_2$, treatments were administered every 5 days for a total of 3 doses followed by observation and tumor measurements until the control groups reached the maximum volume allowed in the study (2000 mm$^3$). As shown in FIG. 96 and FIG. 6, partial regressions were observed for 7 tumors of the experimental group (n=9). Like previous studies, no significant changes in body weight were observed in all of the groups (FIGS. 95 and 97). For comparison, a study was performed using the anti-human EphA5 receptor mouse antibody 11C12 conjugated to MMAE, which was found to have no effect on tumor growth (FIG. 5B).

Lastly, a study was performed using a patient-derived xenograft model (PDX) of breast cancer. Briefly, tissue from an ER, PR, and HER2 negative (triple-negative) invasive ductal carcinoma breast tumor was xenografted into mice. Tumor-bearing animals were then treated with VH4Vk3-ThioBridge®-VCP-MMAE or VH5Vk3-ThioBridge®-VCP-MMAE or a vehicle control (PBS). After engraftment but prior to treatment, xenograft tissue was evaluated for the expression of EphA5 (FIG. 98, left). Treatment consisted of 5 doses of MMAE-conjugate ADC at 10 mg/kg administered every 7 days. Treatment with both ADCs resulted in little measurable tumor growth, while tumors in control animals rapidly grew to experimental endpoints within 16 days (FIG. 98, right).

Together, and without wishing to be bound by theory, these studies demonstrate the in vitro and in vitro function of the anti-EPHA5 based ADCs of the invention and indicate their clinical utility to treat EPHA5-expressing cancers including lung cancer.

Example 5: In Vivo Anti-Tumor Activity of ADCs Directed to EphA5 in a Patient-Derived Xenograft Model of Triple Negative Breast Cancer Patient-derived tumor xenografts (PDXs), in which tumor fragments are surgically dissected from cancer patients and directly transplanted into immunodeficient mice, have been established as predictive models in translational research. PDX susceptibility to anti-cancer drugs has been closely correlated with clinical data in patients from whom PDX models have been derived, and PDX models often maintain the cellular and histopathological structures of the original tumors. Genetic analysis of tumor cells from PDX models following transplantation has shown preservation of the genomic and gene expression profiles between PDXs and parental patient tumors and sensitivity to standard chemotherapeutics in PDXs closely correlates with clinical data in patients from which the PDXs are derived. Over 500 different PDX models have been characterized for 25 different tumor types in multi-center efforts, which has provided comprehensive information on the correlation between these models and various tumor types. PDX models are thus highly effective in vivo models for predicting the efficacy of anti-cancer therapeutics, especially for solid tumors.

The present studies tested the in vivo anti-tumor activity of two antibody-drug conjugates (ADCs) targeting the novel cell-surface receptor target EphA5 using a PDX model for triple negative breast cancer. EphA5 is an ephrin receptor that belongs to the membrane-bound receptor tyrosine kinases group. The EphA family has been shown to be involved in tumor progression, namely in cell proliferation, invasiveness, and metastasis, and EphA5 in particular has previously been identified as a verified cell-surface target in various cancers including lung cancers. EphA5 had previously been shown to be expressed on the cell surface of breast cancer cells via immunohistochemistry and was confirmed to be highly expressed on the cell surface of the PDX model used in the present studies using IHC.

The four ADCs tested consist of two monoclonal antibodies (VH5Vk3 and VH4Vk3) that selectively bind to human EphA5, a proprietary site-specific conjugation technology, a well-validated linker molecule, and one of two payload toxins as described in more detail herein. These ADCs targeted the tumor cells in the grafted tumor tissue, leading to specific cell death of the cancer cells and regression of the tumors in the treated animals.

Test Animals. The present studies were performed using female NSG™ mice implanted with the PDX model TM00096 (BR085F) purchased from Jackson Laboratories. These mice are extremely immunodeficient and carry two mutations: severe combined immune deficiency (scid) and a complete null allele of the IL2 receptor common gamma chain (IL2rg$^{null}$). The scid mutation is a mutation in the DNA repair complex protein Prkdc and renders the mice B and T cell deficient. The IL2rg$^{null}$ mutation prevents cytokine signaling through multiple receptors, leading to a deficiency in functional NK cells. This severe immunodeficiency allows the implantation of patient derived xenografts (PDX) and growth of human tissue-based tumors in the mice. These tumors have similar characteristics to the human tumors from which they are derived (e.g., gene expression) and are predictive of human response to therapeutic agents. The initial and final diagnosis of the patient from which the model was derived was invasive ductal carcinoma AJCC IIA/Grade 3. The primary site of the tumor was breast, sample for implantation was obtained from the metastatic site (lung). The tumor was not treatment naïve. The patient from which the sample was derived was a 52-year-old white, Hispanic female. The sample was obtained by surgical resection. The host strain of the sample for engraftment was NOD.Cg-Prkdc$^{scid}$ Il2rg$^{tm1Wjl}$/SzJ (aka NSG or NOD Scid gamma).

Mice were housed in specific pathogen- and opportunist-free (SOPF) rooms with controlled temperature (20±2° C.), humidity (50±10%), light/dark cycle (light, 7:00 to 19:00; dark, 19:00 to 7:00), and access to food and water ad libitum at the research animal facilities of the Rutgers Cancer Institute of New Jersey. U.S. Department of Health and Human Services, Public Health Service, and the Office of Laboratory Animal Welfare for Assessment and Accreditation of Laboratory Animal Care, International (AAALAC).

A total of 40 female mice implanted with PDX TM00096 were used in the studies. Mice were received at the study location at 10-12 weeks of age and remained in the study until 18-12 weeks of age on average. Body weights ranged from 20 g to 24 g at the beginning of the studies and 20 g to 26 g at the end of the studies.

Materials. The ADCs used in the present study include four ADCs that use one of two antibodies for conjugation: VH4Vk3 and VH5Vk3. Both selectively bind to EphA5, but VH5Vk3 has one amino acid change in in the CDR2 region of the variable heavy chain resulting in a change from Threonine to Serine in position 190.

I. MMAE-Conjugated ADCs
  A. ADC1ADC1: VH5Vk3-ThioBridge-VCP-MMAE
  B. ADC2 (ADC2): VH4Vk3-ThioBridge-VCP-MMAE
  ADC1 and ADC2 are ADCs prepared using the VH5Vk3 or VH4Vk3 antibodies and the ThioBridge® site-specific conjugation technology utilizing a linker moiety cleavable by lysosomal cathepsins ('Val-Cit-PAB') coupled to the cytotoxic payload MMAE. This linker format is designed with a branched 24-unit PEG polymer to reduce aggregation propensity and improve aqueous solubility (FIG. 33). An average of DAR of 4 was targeted.

All research batches of ADC1 and ADC2 had the appearance of a clear colorless solution with an average DAR of 4 and purity of 95% or higher of monomeric species as determined by size exclusion chromatography (SEC). Endotoxin levels were determined by the EndoSafe®-PTS™ platform (Charles River, Wilmington, MA) aligned with USP <85> and Pharm Eur 2.6.14 that provides quantitative Limulus Amebocyte Lysate (LAL) results. The average molecular weight of ADC1 and ADC2 was 158,000 Da as determined by LC-MS. ADC1 and ADC2 were handled under sterile conditions and stored at −80° C. until use.

(SN-38)$_2$-Conjugated ADCs.
  A. ADC3ADC3: VH5Vk3-ThioBridge®-VCP-(SN-38)$_2$
  B. ADC4ADC4: VH4Vk3-ThioBridge®-VCP-(SN-38)$_2$
  ADC3 and ADC4 are ADCs prepared using the VH5Vk3 or VH4Vk3 antibodies and the ThioBridge® site-specific conjugation technology. A double-loaded structure with moieties cleavable by hydrolysis (carbonate) was used to couple the cytotoxic payload SN-38 to the antibodies (FIG. 33). This linker format was designed with dual branched 24-unit PEG polymers to reduce aggregation propensity and improve aqueous solubility. An average of DAR of 8 was targeted.

All research batches (ADC3 and ADC4) had the appearance of a clear colorless solution with an average DAR of 8 and purity of 95% or higher of monomeric species as determined by size exclusion chromatography (SEC). Endotoxin levels were determined by the EndoSafe®-PTS™ platform (Charles River) aligned with USP <85> and Pharm Eur 2.6.14 that provides quantitative Limulus Amebocyte Lysate (LAL) results. The average molecular weight of ADC3 and ADC4 was 165,000 Da as determined by LC-MS. ADC3 and ADC4 were handled under sterile conditions and stored at −80° C. until use.

Methods

All research batches (ADC3 and ADC4) had the appearance of a clear colorless solution with an average DAR of 8 and purity of 95% or higher of monomeric species as determined by size exclusion chromatography (SEC). Endotoxin levels were determined by the EndoSafe®-PTS™ platform (Charles River) aligned with USP <85> and Pharm Eur 2.6.14 that provides quantitative Limulus Amebocyte Lysate (LAL) results. The average molecular weight of ADC3 and ADC4 was 165,000 Da as determined by LC-MS. ADC3 and ADC4 were handled under sterile conditions and stored at −80° C. until use.

Mice received 5 weekly doses of ADC1 or ADC2, or 4 weekly doses of ADC3 or ADC4 at 10 mg/kg or PBS via tail vein injection. Animals were dosed on days 0, 7, 14, 21 and 28 followed by 2 weeks of observation (day 28-40) without treatment (or until cessation of study). The number of mice used per group averaged n=7-10 with some mice presenting with more than 1 tumor implanted subcutaneously. In those cases, each tumor size was measured and recorded independently. Measurements were performed 2-3 times weekly with the aid of a digital caliper (Fisherbrand™ Traceable™ Digital Carbon Fiber Calipers). Studies lasted an average of 40 days or until maximum allowed tumor volume was reached and/or skin ulceration was noted. All studies included a control group of an equal number of mice to those in the treatment group. Control groups received PBS tail vein injections and were submitted to the same handling procedures as TA treated mice. First treatment was administered when tumors reached 100-150 mm3 volume.

The body weight of the TM00096-bearing mice treated weekly with the TAs or PBS prior to first treatment (pre) and at termination of the respective studies was determined and plotted. Following termination of the studies, any remaining tumors were excised and weighed on a laboratory balance. DNA was extracted from remaining tumors and sequenced to determine the presence of any mutations in the EphA5 epitope potentially caused by the treatment regimen.

Data Analysis

The statistical analysis and graphical plotting of the tumor size and the body weight was performed using GraphPad Prism 9 and Microsoft Excel (Version 16.63.1). The statistical significance of the measured differences between the test and control groups were tested with Student's t-test or analysis of variance (one-way or two-way ANOVA) using GraphPad Prism 9.

Selected Results

Figure 100:
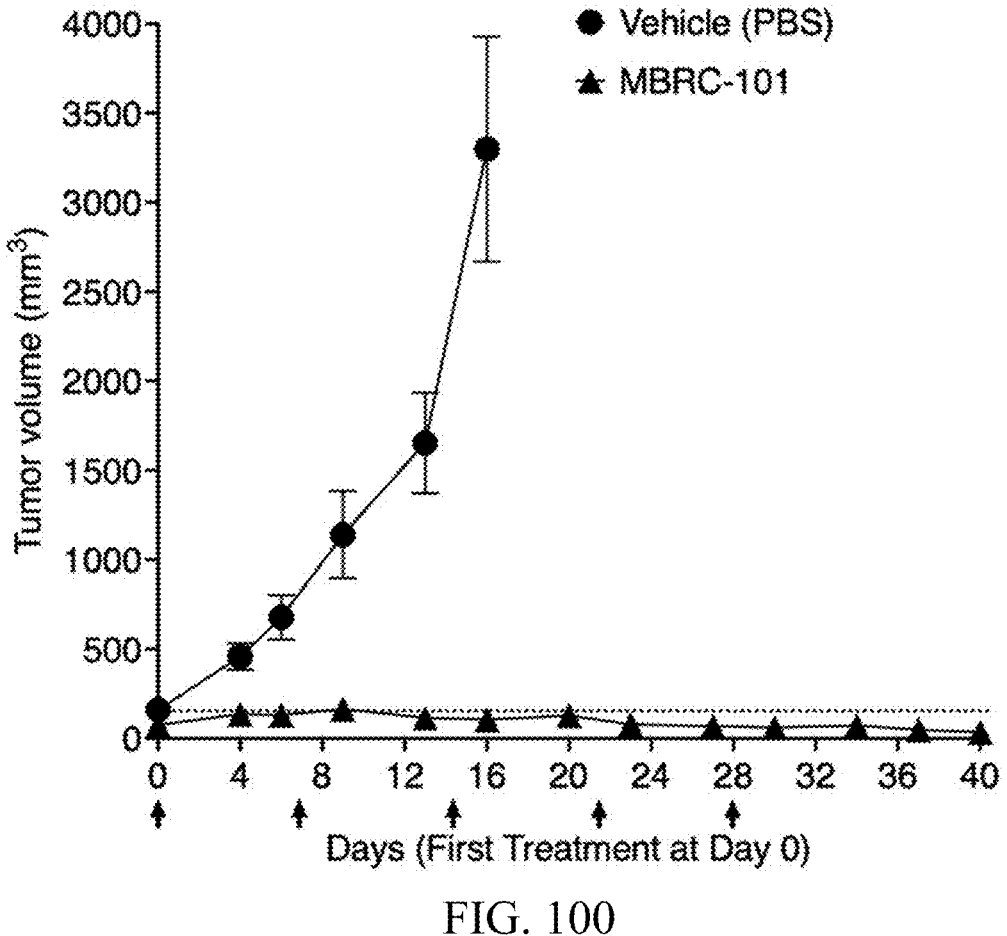
FIG. 100 illustrates tumor volume in mice treated weekly for 5 weeks with ADC1 or PBS (placebo) over a 40-day test period.
Figure 101B:
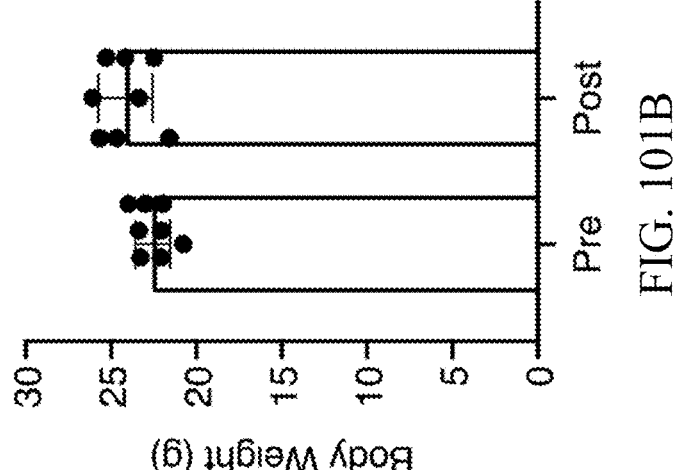
FIGS. 101A-101B illustrate weight of tumors removed from TM00096-bearing mice following treatment with ADC1 or PBS (placebo) (FIG. 101A) and body weight of TM00096-bearing mice before and after treatment with ADC1.
Figure 101A:
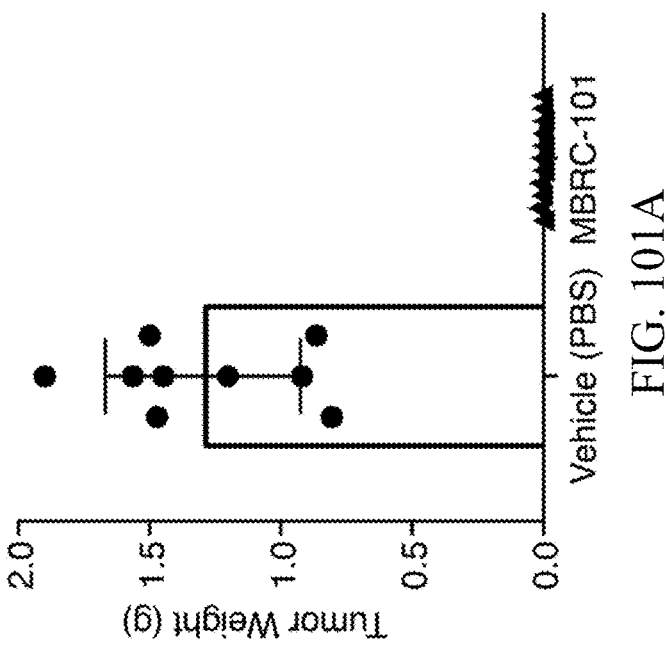

Weekly administration of ADC1 to mice bearing TM00096 tumors over a 5-week period resulted in full and sustained regression of tumors (FIG. 100). From a total of 12 tumors, 4 tumors in the ADC1 treated group regressed completely and tumor weight could not be determined at termination. Eight tumors remained at the end of the study with weights ranging from 0.003 g to 0.019 g (FIG. 101A). As shown in FIG. 101B, there were no significant changes in body weight of mice before and after treatment with both ADC1.

Figure 102:
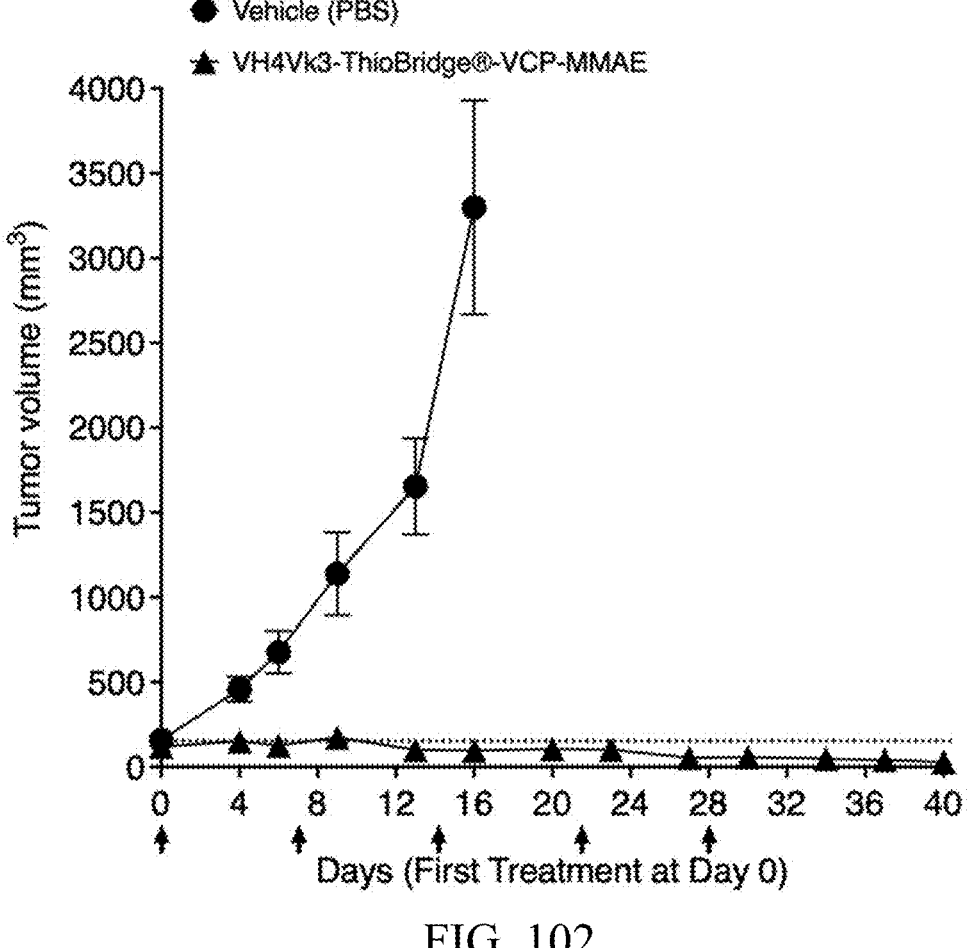
FIG. 102 illustrates tumor volume in mice treated weekly for 5 weeks with ADC2 or PBS (placebo) over a 40-day test period.
Figure 103B:
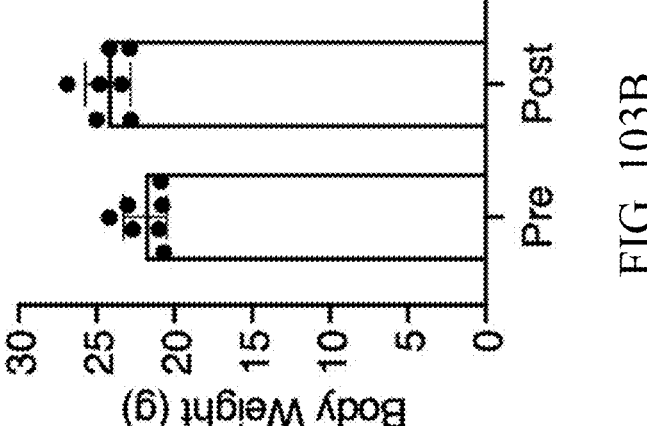
FIGS. 103A-103B illustrate weight of tumors removed from TM00096-bearing mice following treatment with ADC2 or PBS (placebo) (FIG. 103A) and body weight of TM00096-bearing mice before and after treatment with ADC2 (FIG. 103B).
Figure 103A:
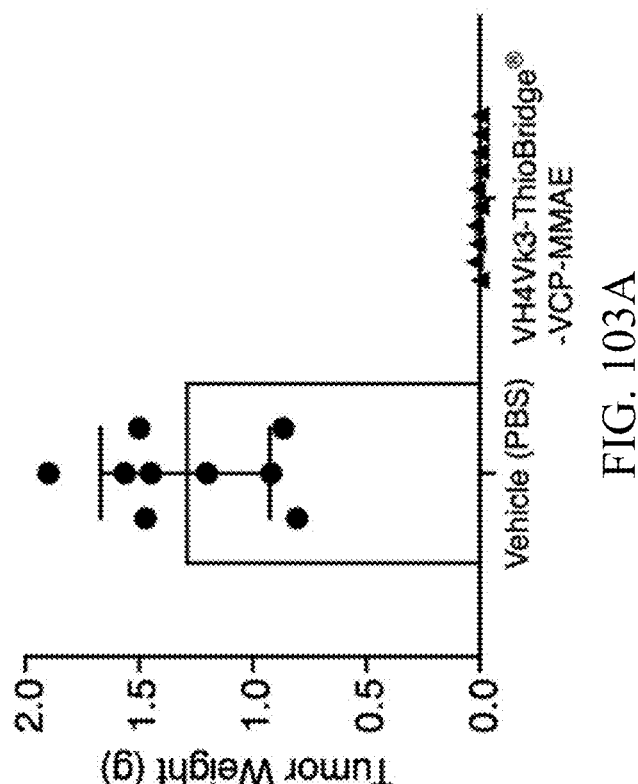

Similarly, weekly administration of ADC2 to mice bearing TM00096 tumors over a 5-week period resulted in full and sustained regression of tumors (FIG. 102). From a total of 10 tumors, 4 tumors in the ADC2 treated group regressed completely and tumor weight could not be determined at termination. Six tumors remained at the end of the study with weights ranging from 0.014 g to 0.025 g (FIG. 103A). As shown in FIG. 103B, there were no significant changes in body weight of mice before and after treatment with ADC2.

Figures 104A, 104B:
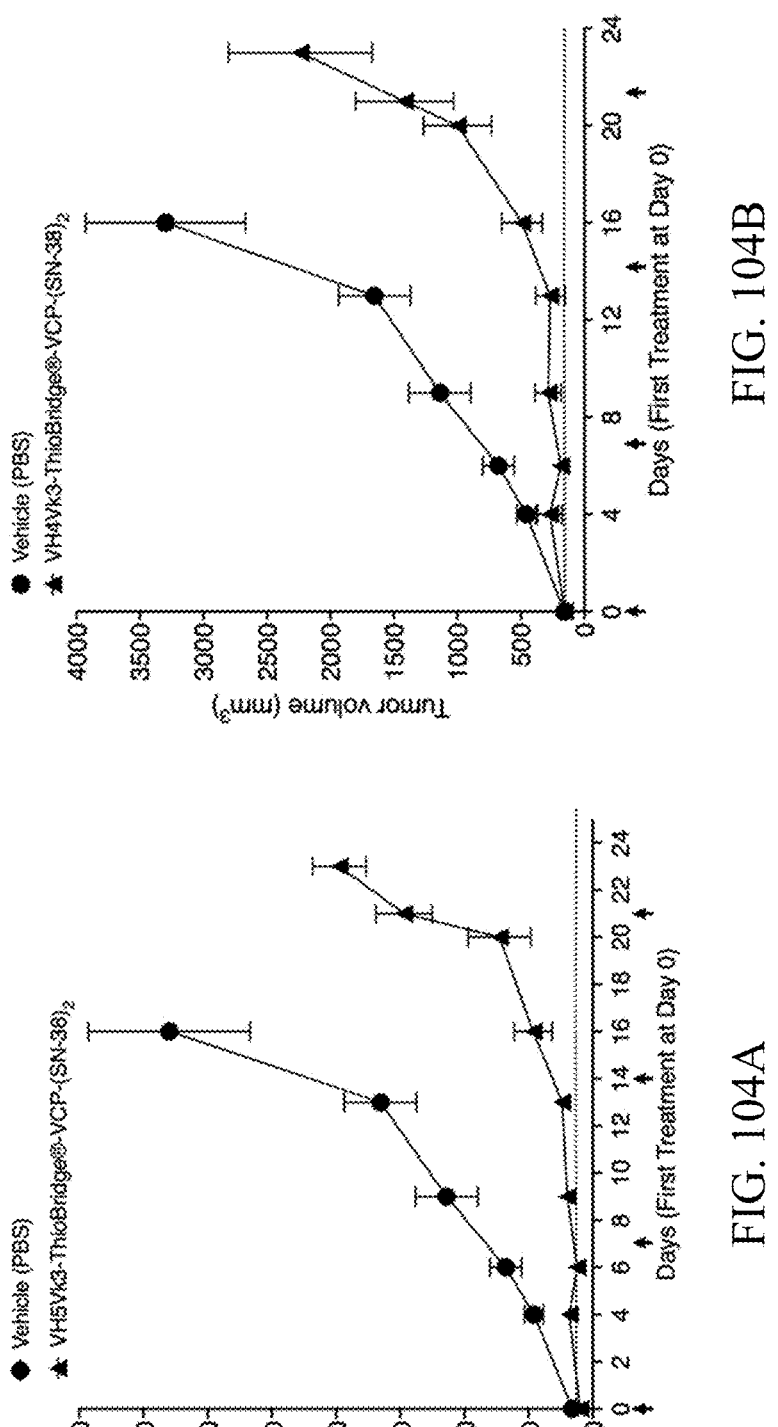
FIGS. 104A-104B illustrate tumor volume in TM00096-bearing mice treated weekly for 4 weeks with ADC3 or PBS (placebo) over a 24-day test period (FIG. 104A) and tumor volume in TM00096-bearing mice treated weekly for 4 weeks with ADC4 or PBS (placebo) over a 24-day test period (FIG. 104B).
Figure 105B:
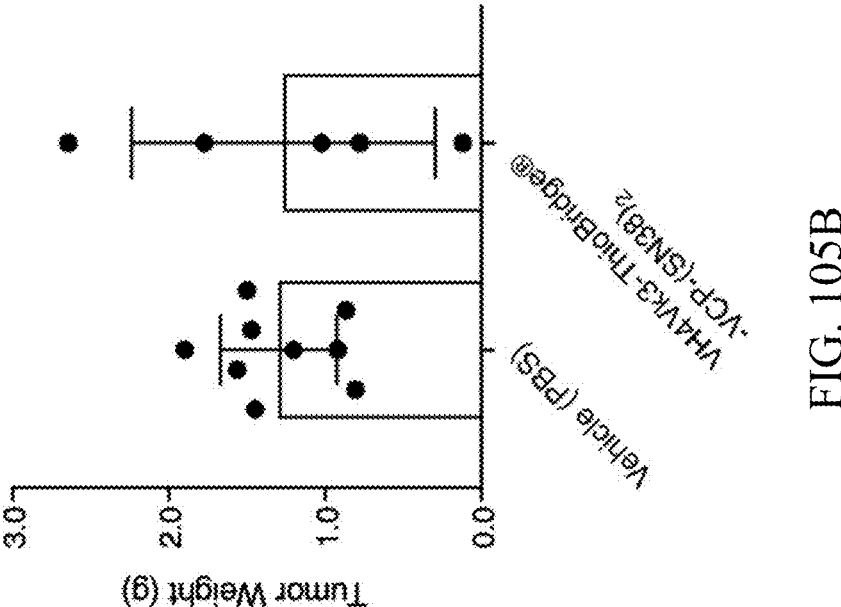
FIGS. 105A-105B illustrate the weight of tumors removed from TM00096-bearing mice following treatment with ADC3 or PBS (placebo) (FIG. 105A) and the weight of tumors removed from TM00096-bearing mice following treatment with ADC4 or PBS (placebo) (FIG. 105B).
Figure 105A:
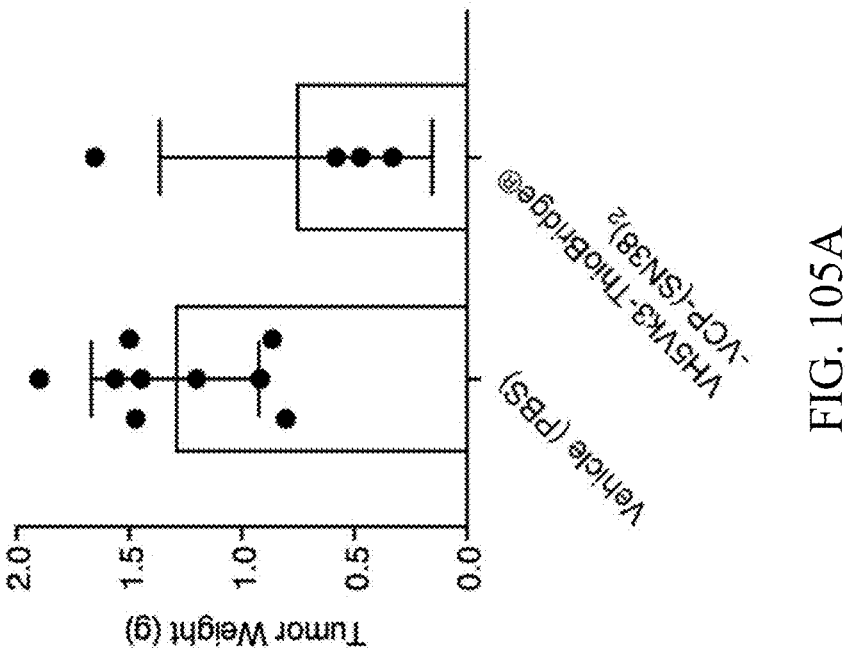
Figure 106B:
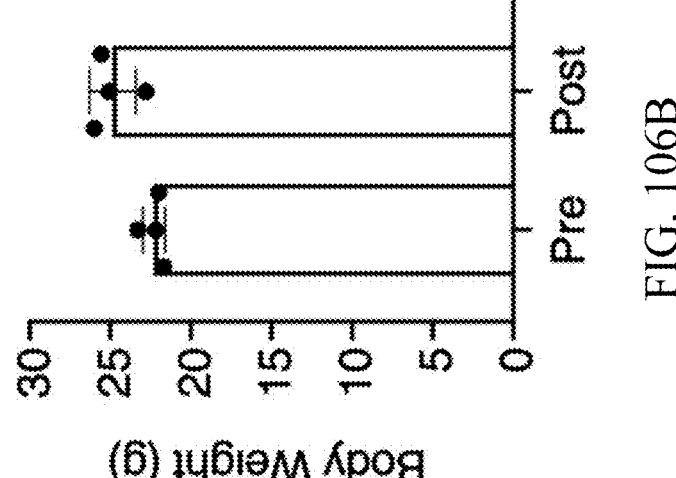
FIGS. 106A-106B illustrate the body weight of TM00096-bearing mice before and after treatment with ADC3 (FIG. 106A) and the body weight of TM00096-bearing mice before and after treatment with ADC4 (FIG. 106B).
Figure 106A:
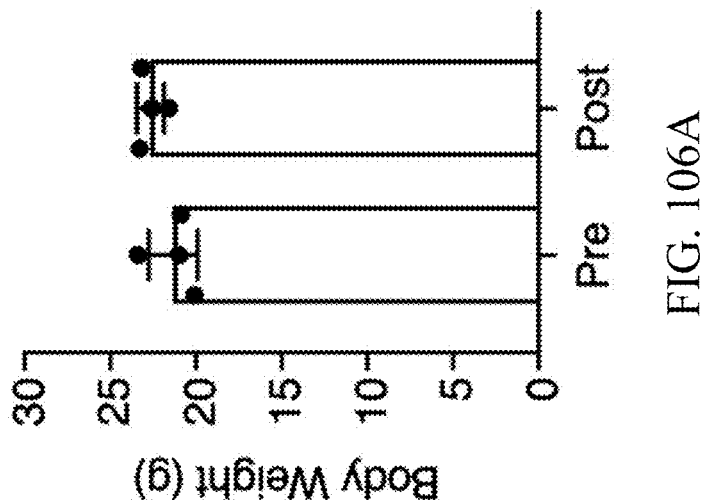
Figures 107A, 107B:
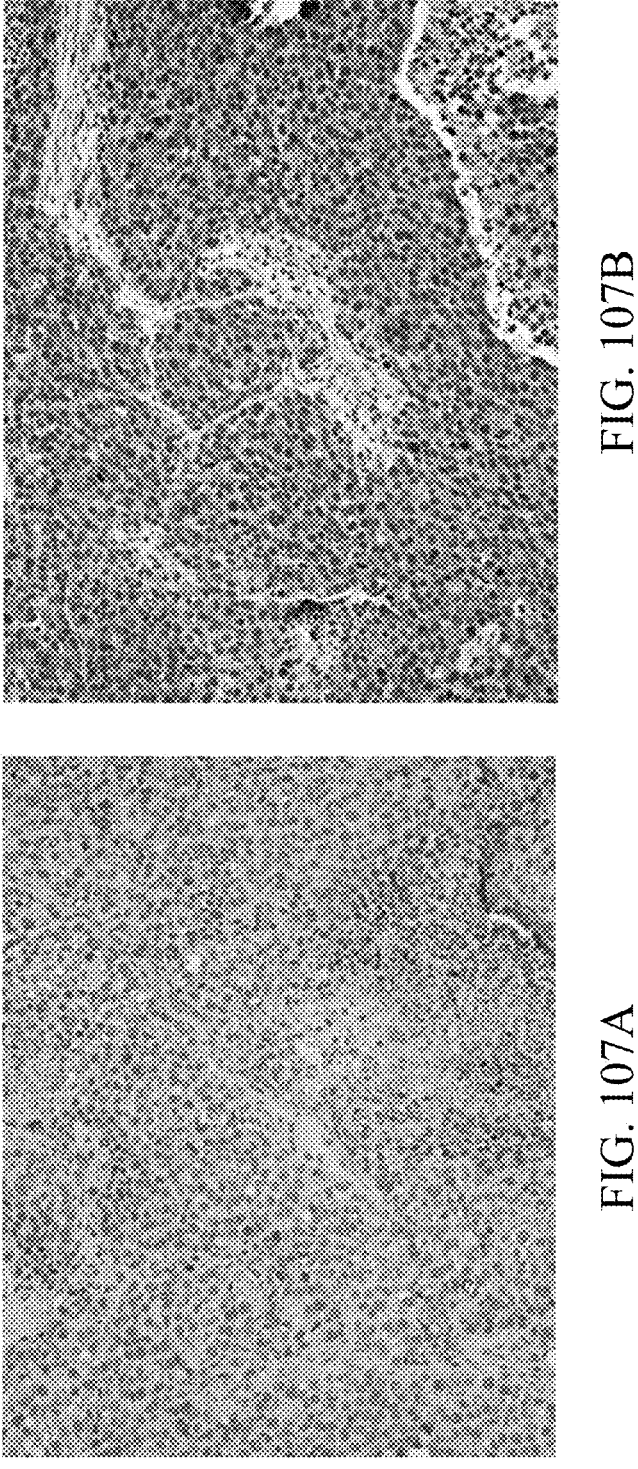
FIGS. 107A-107B illustrate IHC staining of triple negative breast cancer tissue from the TM00098 PDX model using a control IgG antibody (FIG. 107A), and IHC staining of triple negative breast cancer tissue from the TM00098 PDX model using a commercially available antibody that selectively binds to EphA5 (FIG. 107B).
Figure 110A:
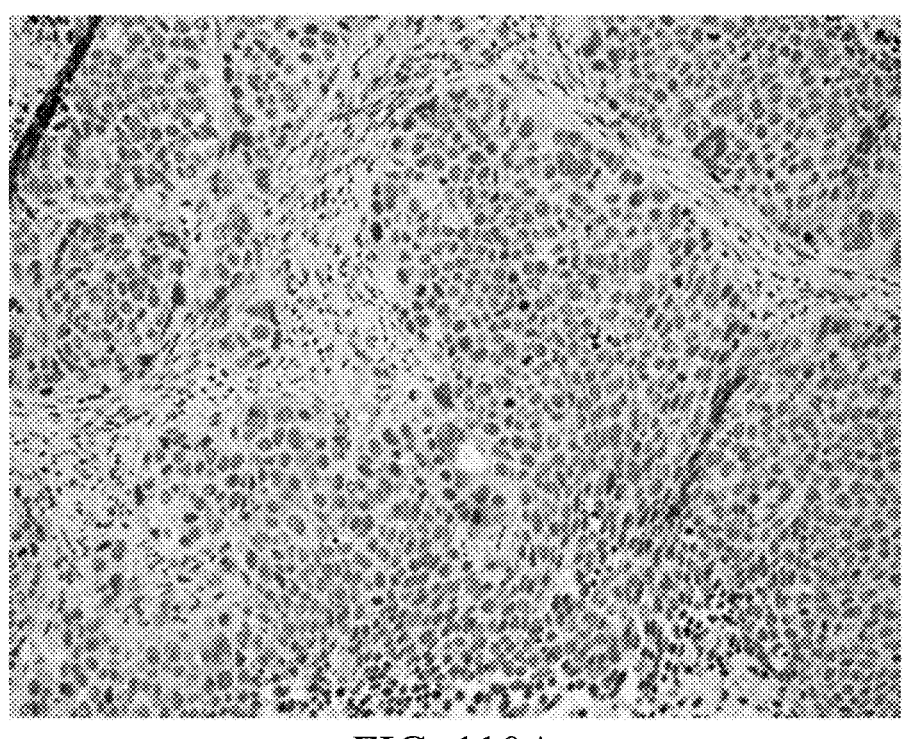
FIGS. 110A-110B illustrate IHC staining of tumor tissue from the TM00188 PDX model using a control IgG antibody (FIG. 110A) and using a commercially available antibody that selectively binds to EphA5 (FIG. 110B).
Figure 110B:
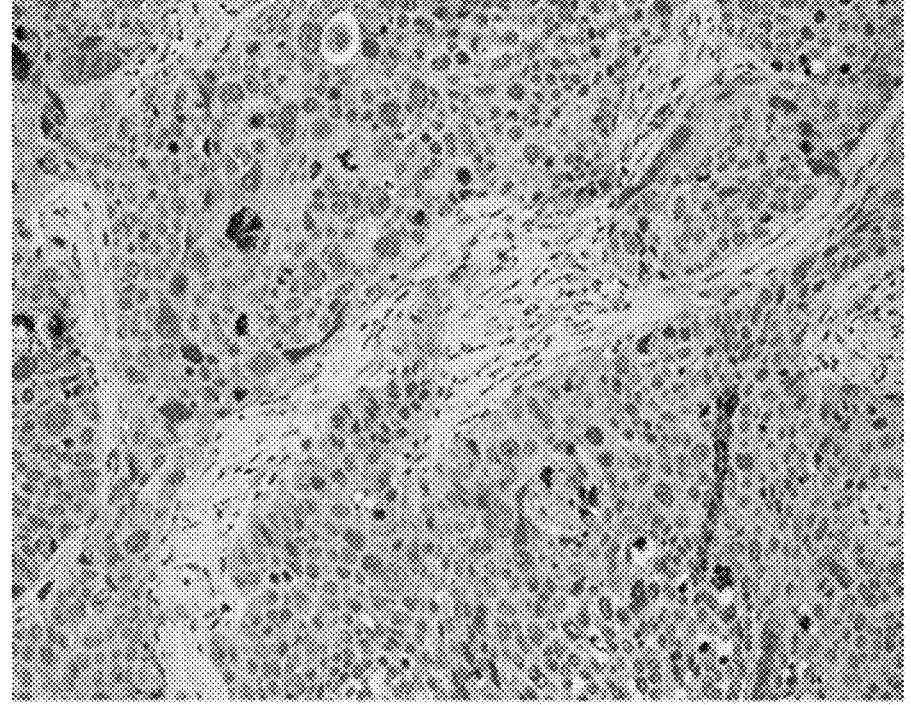

Administration of both ADC3 (FIG. 104A) and ADC4 (FIG. 104B) to the TM00096 PDX mice over a 4-week period resulted in delayed tumor growth followed by rapid re-growth and early termination due to tumor burden. The tumors in the ADC3 treated mice were slightly reduced in weight compared to the PBS control group (FIG. 105A), and the tumors in the ADC4 treated mice showed no significant reduction in weight as compared to placebo (FIG. 105B). As shown in FIGS. 106A and 106B, the treated mice showed no significant changes in body weight before and after treatment.

Triple-negative breast cancer is known to be a heterogeneous disease with aggressive biology and complex tumor evolution. One possibility for the difference in response to ADC3 and ADC4 could be a change in the epitope recognized by the antibody binding portion of the ADCs caused by exposure to the ADCs, which could lead to a reduced anti-tumor activity. To identify the potential for EphA5 mutations in response to TA treatment, the region containing the EphA5 epitope recognized by VH5Vk3 or VH4Vk3 was sequenced in the remaining tumors following the study period. Neither PBS nor TA administration resulted in mutations of the amino acids composing the EphA5 epitope recognized by VH5Vk3 or VH4Vk3 (Tables 1-5).

The critical amino acids (highlighted in bold) for binding of VH5Vk3 to human EphA5 are contained within the region 306_RPGFFKASPHIQSCGKCPPHSYTHE_330 (SEQ ID NO:43), which corresponds to the genomic sequence:

```
                                       (SEQ ID NO: 44)
AGACCTGGGTTCTTCAAAGCCTCACCTCACATCCAGAGCTGCGGCAAAT

GTCCACCTCACAGTTATACCCATGAG
```

The critical amino acids (highlighted in bold) for binding of VH4Vk3 to human EphA5 are contained within the region 306_RPGFFKASPHIQSCGKCPPHSYTHE_330, (SEQ ID NO:43) which corresponds to the same genomic sequence as above.

TABLE 1

Sequencing of Tumors from PBS Treated PDX TM00096 Mice

| Name: | SEQUENCE: |
|---|---|
| VH5Vk EphA5 Epitope | AGACCTGGGTTCTTCAAAGCCTCACCTCACATCCAGAGC TGCGGCAAATGTCCACCTCACAGTTATACCCATGAG (SEQ ID NO: 44) |
| Control Tumor 1 | AGACCTGGGTTCTTCAAAGCCTCACCTCACATCCAGAGC TGCGGCAAATGTCCACCTCACAGTTATACCCATGAG (SEQ ID NO: 44) |
| Control Tumor 2 | AGACCTGGGTTCTTCAAAGCCTCACCTCACATCCAGAGC TGCGGCAAATGTCCACCTCACAGTTATACCCATGAG (SEQ ID NO: 44) |
| Control Tumor 3 | AGACCTGGGTTCTTCAAAGCCTCACCTCACATCCAGAGC TGCGGCAAATGTCCACCTCACAGTTATACCCATGAG (SEQ ID NO: 44) |
| Control Tumor 4 | AGACCTGGGTTCTTCAAAGCCTCACCTCACATCCAGAGC TGCGGCAAATGTCCACCTCACAGTTATACCCATGAG (SEQ ID NO: 44) |
| Control Tumor 5 | AGACCTGGGTTCTTCAAAGCCTCACCTCACATCCAGAGC TGCGGCAAATGTCCACCTCACAGTTATACCCATGAG (SEQ ID NO: 44) |

TABLE 2

Sequencing of Tumors from ADC1 Treated PDX TM00096 Mice

| Name: | SEQUENCE: |
|---|---|
| VH5Vk/ EphA5 Epitope | AGACCTGGGTTCTTCAAAGCCTCACCTCACATCCAGAG CTGCGCCAAATGTCCACCTCACAGTTATACCCATGAG (SEQ ID NO: 44) |
| ADC1 Tumor 1 | AGACCTGGGTTCTTCAAAGCCTCACCTCACATCCAGAG CTGCGGCAAATGTCCACCTCACAGTTATACCCATGAG (SEQ ID NO: 44) |
| ADC1 Tumor 2 | AGACCTGGGTTCTTCAAAGCCTCACCTCACATCCAGAG CTGCGGCAAATGTCCACCTCACAGTTATACCCATGAG (SEQ ID NO: 44) |
| ADC1 Tumor 3 | AGACCTGGGTTCTTCAAAGCCTCACCTCACATCCAGAG CTGCGGCAAATGTCCACCTCACAGTTATACCCATGAG (SEQ ID NO: 44) |
| ADC1 Tumor 4 | AGACCTGGGTTCTTCAAAGCCTCACCTCACATCCAGAG CTGCGGCAAATGTCCACCTCACAGTTATACCCATGAG (SEQ ID NO: 44) |

TABLE 2-continued

Sequencing of Tumors from ADC1
Treated PDX TM00096 Mice

| Name: | SEQUENCE: |
|---|---|
| ADC1 Tumor 5 | AGACCTGGGTTCTTCAAAGCCTCACCTCACATCCAGAG CTGCGGCAAATGTCCACCTCACAGTTATACCCATGAG (SEQ ID NO: 44) |
| ADC1 Tumor 6 | AGACCTGGGTTCTTCAAAGCCTCACCTCACATCCAGAG CTGCGGCAAATGTCCACCTCACAGTTATACCCATGAG (SEQ ID NO: 44) |

TABLE 3

Sequencing of Tumors from ADC2
Treated PDX TM00096 Mice

| Name: | SEQUENCE: |
|---|---|
| VH5Vk EphA5 Epitope | AGACCTGGGTTCTTCAAAGCCTCACCTCACA TCCAGAGCTGCGGCAAATGTCCACCTCACAG TTATACCCATGAG (SEQ ID NO: 44) |
| ADC2 Tumor 1 | AGACCTGGGTTCTTCAAAGCCTCACCTCACA TCCAGAGCTGCGGCAAATGTCCACCTCACAG TTATACCCATGAG (SEQ ID NO: 44) |
| ADC2 Tumor 2 | AGACCTGGGTTCTTCAAAGCCTCACCTCACA TCCAGAGCTGCGGCAAATGTCCACCTCACAG TTATACCCATGAG (SEQ ID NO: 44) |
| ADC2 Tumor 3 | AGACCTGGGTTCTTCAAAGCCTCACCTCACA TCCAGAGCTGCGGCAAATGTCCACCTCACAG TTATACCCATGAG (SEQ ID NO: 44) |
| ADC2 Tumor 4 | AGACCTGGGTTCTTCAAAGCCTCACCTCACA TCCAGAGCTGCGGCAAATGTCCACCTCACAG TTATACCCATGAG (SEQ ID NO: 44) |

TABLE 4

Sequencing of Tumors from ADC3
Treated PDX TM00096 Mice

| Name: | Sequence: |
|---|---|
| VH5Vk EphA5 Epitope | AGACCTGGGTTCTTCAAAGCCTCACCTCACA TCCAGAGCTGCGGCAAATGTCCACCTCACAG TTATACCCATGAG (SEQ ID NO: 44) |
| ADC3 Tumor 1 | AGACCTGGGTTCTTCAAAGCCTCACCTCACA TCCAGAGCTGCGGCAAATGTCCACCTCACAG TTATACCCATGAG (SEQ ID NO: 44) |
| ADC3 Tumor 2 | AGACCTGGGTTCTTCAAAGCCTCACCTCACA TCCAGAGCTGCGGCAAATGTCCACCTCACAG TTATACCCATGAG (SEQ ID NO: 44) |
| ADC3 Tumor 3 | AGACCTGGGTTCTTCAAAGCCTCACCTCACA TCCAGAGCTGCGGCAAATGTCCACCTCACAG TTATACCCATGAG (SEQ ID NO: 44) |
| ADC3 Tumor 4 | AGACCTGGGTTCTTCAAAGCCTCACCTCACA TCCAGAGCTGCGGCAAATGTCCACCTCACAG TTATACCCATGAG (SEQ ID NO: 44) |

TABLE 5

Sequencing of Tumors from ADC4
Treated PDX TM00096 Mice

| Name: | Sequence: |
|---|---|
| VH5Vk EphA5 Epitope | AGACCTGGGTTCTTCAAAGCCTCACCTCACA TCCAGAGCTGCGGCAAATGTCCACCTCACAG TTATACCCATGAG (SEQ ID NO: 44) |
| ADC4 Tumor 1 | AGACCTGGGTTCTTCAAAGCCTCACCTCACA TCCAGAGCTGCGGCAAATGTCCACCTCACAG TTATACCCATGAG (SEQ ID NO: 44) |
| ADC4 Tumor 2 | AGACCTGGGTTCTTCAAAGCCTCACCTCACA TCCAGAGCTGCGGCAAATGTCCACCTCACAG TTATACCCATGAG (SEQ ID NO: 44) |
| ADC4 Tumor 3 | AGACCTGGGTTCTTCAAAGCCTCACCTCACA TCCAGAGCTGCGGCAAATGTCCACCTCACAG TTATACCCATGAG (SEQ ID NO: 44) |
| ADC4 Tumor 4 | AGACCTGGGTTCTTCAAAGCCTCACCTCACA TCCAGAGCTGCGGCAAATGTCCACCTCACAG TTATACCCATGAG (SEQ ID NO: 44) |

Selected Conclusions

ADC1 and ADC2 administration to the TM00096 PDX model of triple negative breast cancer over a five-week period resulted in full and sustained regression of tumors. The treated animals also displayed no significant differences in body weight during the study, suggesting that ADC1 and ADC2 administration did not have an adverse impact on the animals' ability to thrive. Without wishing to be bound by theory, this suggests either ADC1 or ADC2 could be a promising drug candidate for further development for treatment of triple negative breast cancer.

ADC3 and ADC4 show modest in vivo anti-tumor activity in the TM00096 PDX model of triple negative breast cancer, with mildly delayed tumor growth followed by re-growth. The ADC3 and ADC4 treated animals also displayed no significant changes in body weight, suggesting the ADC3 and ADC4 administration did not have an adverse impact on the animals' ability to thrive.

Administration of TAs and placebo did not cause modifications in the EphA5 epitope recognized by VH5Vk3 or VH4Vk3, indicating that the difference in anti-tumor activity of ADC3 and ADC4 was not due to alterations in target epitope display.

Example 6: In Vivo Anti-Tumor Activity of ADCs Directed to EphA5 in a Patient-Derived Xenograft Model of Triple Negative Breast Cancer The objective of this study was to evaluate the therapeutic anti-tumor activity of two ADCs directed to a novel target, EphA5, using a PDX model of triple negative breast cancer. Specifically, the objective of this study was to test the in vivo anti-tumor activity of two ADCs, H5Vk3-MMAE and H5Vk3-(SN-38)2, in a PDX mouse model of triple negative breast cancer that has been shown to express EphA5 at high levels on the cell surface of the tumor cells.

Test Animals

The present studies were performed using female NSG™ mice implanted with the PDX model TM00098 (BR1126F) purchased from Jackson Laboratories. These mice are extremely immunodeficient and carry two mutations: severe combined immune deficiency (scid) and a complete null allele of the IL2 receptor common gamma chain (IL2rgnull). The scid mutation is a mutation in the DNA repair complex protein Prkdc and renders the mice B and T cell deficient. The IL2rgnull mutation prevents cytokine signaling through multiple receptors, leading to a deficiency in functional NK cells. This severe immunodeficiency allows the implantation of PDX and growth of human tissue-based tumors in the mice. These tumors have similar characteristics to the human tumors from which they are derived (e.g., gene expression) and are predictive of human response to therapeutic agents.

The initial and final diagnosis of the tumor from which the TM00098 PDX model was derived was invasive ductal carcinoma, AJCC IA/Grade 3. The primary site of human tumor was breast, and the sample site of the tumor for the PDX model was the primary site of the tumor. The tumor used for the TM00098 PDX model was treatment naïve. The patient from which the sample was derived was a 64-year-old white, non-Hispanic female. The sample was obtained by surgical resection. The host strain of the sample for engraftment was NOD.Cg-Prkdc$^{scid}$ Il2rg$^{tm1Wjl}$/SzJ (aka NSG or NOD Scid gamma).

Test Animal Housing and Care

The mice used in the present study were cared for in compliance with all applicable laws and guidelines, including those from the U.S. Department of Health and Human Services, Public Health Service, and the Office of Laboratory Animal Welfare. The Institutional Animal Care and Use Committee from the Rutgers Cancer Institute of New Jersey approved all animal experiments, and the Rutgers Animal Facility followed guidelines as set forth by the Association for Assessment and Accreditation of Laboratory Animal Care, International (AAALAC).

Mice were housed in specific pathogen and opportunist-free (SOPF) rooms with controlled temperature ($20\pm2°$ C.), humidity ($50\pm10\%$), light/dark cycle (light, 7:00 to 19:00; dark, 19:00 to 7:00), and access to food and water ad libitum at the research animal facilities of the Rutgers Cancer Institute of New Jersey (Newark, NJ). Littermates were randomly assigned to experimental groups.

A total of 40 female mice implanted with PDX TM00098 were used in the studies. Mice were received at the study location at 10-12 weeks of age and remained in the study until 18-12 weeks of age on average. Body weights ranged from 18 g to 25 g at the beginning of the studies and 22 g to 27 g at the end of the studies.

Materials

ADC1: VH5Vk3-ThioBridge-VCP-MMAE

ADC1 is an ADC prepared using the VH5Vk3 antibody conjugated with the ThioBridge® site-specific conjugation technology utilizing a linker moiety cleavable by lysosomal cathepsins ('Val-Cit-PAB') coupled to the cytotoxic payload MMAE. This linker format is designed with a branched 24-unit PEG polymer to reduce aggregation propensity and improve aqueous solubility (FIG. 33). An average of DAR of 4 was targeted.

All research batches of ADC1 had the appearance of a clear colorless solution with an average DAR of 4 and purity of 95% or higher of monomeric species as determined by size exclusion chromatography (SEC). Endotoxin levels were determined by the EndoSafe®-PTS™ platform (Charles River, Wilmington, MA) aligned with USP <85> and Pharm Eur 2.6.14 that provides quantitative Limulus Amebocyte Lysate (LAL) results. The average molecular weight of ADC1 was 158,000 Da as determined by LC-MS. ADC1 was handled under sterile conditions and stored at $-80°$ C. until use.

ADC2 VH5Vk3-ThioBridge®-VCP-(SN-38)$_2$

ADC2 is an ADC prepared using the VH5Vk3 antibody conjugated with the ThioBridge® site-specific conjugation technology and a double-loaded structure with moieties cleavable by hydrolysis (carbonate) to couple the cytotoxic payload SN-38 to the antibody (FIG. 33). This linker format was designed with dual branched 24-unit PEG polymers to reduce aggregation propensity and improve aqueous solubility. An average of DAR of 8 was targeted.

All research batches had the appearance of a clear colorless solution with an average DAR of 8 and purity of 95% or higher of monomeric species as determined by size exclusion chromatography (SEC). Endotoxin levels were determined by the EndoSafe®-PTS™ platform (Charles River) aligned with USP <85> and Pharm Eur 2.6.14 that provides quantitative Limulus Amebocyte Lysate (LAL) results. The average molecular weight of ADC2 was 165,000 Da as determined by LC-MS. ADC2 were handled under sterile conditions and stored at $-80°$ C. until use.

Methods.

The selection of the PDX model was based on EPHA5 gene expression levels (Jackson Laboratory database) and protein expression by immunohistochemistry (IHC) (in-house; IHC staining shown below). PDX models showing moderate to high EphA5 expression and with a favorable growth curve were considered for anti-tumor activity studies. We also analyzed response/resistance to common drugs such as cisplatin, docetaxel and doxorubicin. Models resistant to multiple drugs were eliminated from the selection, and models naïve to treatment were prioritized. Based on these criteria, the TM00098 PDX model was selected for the present study.

Mice received 5 weekly doses of ADC1 or ADC2 at 10 mg/kg or PBS via tail vein injection. Animals were dosed on days 0, 7, 14, 21 and 28 and observed the tumors from day 28-50 without treatment to observe sustained regression and/or delay in tumor regrowth. The number of mice used per group averaged n=7-10 with some mice presenting with more than 1 tumor implanted subcutaneously. In those cases, each tumor size was measured and recorded independently. Measurements were performed 2-3 times weekly with the aid of a digital caliper (Fisherbrand™ Traceable™ Digital Carbon Fiber Calipers). Studies lasted an average of 50 days or until maximum allowed tumor volume was reached (2,000 mm3) and/or skin ulceration was noted. All studies included a control group of an equal number of mice to those in the treatment group. Control groups received PBS tail vein injections and were submitted to the same handling procedures as ADC1 and ADC2 treated mice. Arrows indicate days of treatment. First treatment was administered when tumors reached 100-150 mm3 volume.

The body weight of the TM00098-bearing mice treated weekly for 5 weeks with ADC1, ADC2 or PBS prior to first treatment (pre) and at termination (50 days post treatment) was determined and plotted. Following termination of the studies (50 days), any remaining tumors were excised and weighed on a laboratory balance. DNA was extracted from remaining tumors and sequenced to determine the presence of any mutations in the EphA5 epitope caused by the treatment regimen.

Data Analysis

The statistical analysis and graphical plotting of the tumor size and the body weight was performed using GraphPad Prism 9 and Microsoft Excel (Version 16.63.1). The statistical significance of the measured differences between the test and control groups were tested for s with Student's t-test or analysis of variance (one-way or two-way ANOVA) using GraphPad Prism 9.

Selected Results

Weekly administration of ADC1 to mice bearing TM00098 tumors over a 5-week period resulted in full and sustained regression of tumors (FIG. 108A). The tumors in the ADC1 treated mice were completely regressed and tumor weight could not be determined at study termination (FIG. 108B). DNA extraction from tumors was not possible due to the absence of tumors at the end of the study. As shown in FIG. 108C, there were no significant changes in body weight of mice before and after treatment with both ADC1 and placebo.

Administration of ADC2 to mice bearing TM00098 tumors over a 5-week period resulted in a statistically significant response, with initial regression observed in some tumors followed by stasis or delayed tumor growth (FIG. 109A). The tumors in the ADC2 treated mice were significantly reduced in weight compared to the PBS control group (FIG. 109B). As shown in FIG. 109C, there were no significant changes in body weight of mice before and after treatment with both ADC1 and placebo.

Triple-negative breast cancer is known to be a heterogeneous disease with aggressive biology and complex tumor evolution. One possibility for the difference in response to TA 1 and ADC2 could be a change in the epitope recognized by the antibody binding portion of the ADCs caused by exposure to the ADCs, which could lead to a reduced anti-tumor activity of ADC2. To identify the potential for EphA5 mutations in response to TA treatment, the region containing the EphA5 epitope recognized by VH5Vk3 was sequenced in the remaining tumors following the study period. Neither PBS nor ADC2 administration resulted mutations of the amino acids composing the EphA5 epitope recognized by VH5Vk3 (Tables 1 and 2); insufficient tumor remained for determination of epitope mutations following administration of ADC1.

The EphA5 epitope for binding of VH5Vk3 (critical amino acids for binding in bold):

```
                                    (SEQ ID NO: 43)
         ephA5_RPGFFKASPHIQSCGKCPPHSYTHE
```

Which Corresponds to the Genomic Sequence:

```
                                    (SEQ ID NO: 44)
AGACCTGGGTTCTTCAAAGCCTCACCTCACATCCAGAGCTGCGGCAAATG

TCCACCTCACAGTTATACCCATGAG
```

TABLE 1

Epitope sequencing of Tumors from TM00098-bearing mice treated with PBS (SEQ ID NO: 44)

| | |
|---|---|
| VH5Vk EphA5 Epitope | Agacctgggttcttcaaagcctcacctcacatccagagctgeggcaaatgtccacctcacagttatacccatgag (SEQ ID NO: 44) |
| Control Tumor 1 | Agacctgggttcttcaaagcctcacctcacatccagagctgeggcaaatgtccacctcacagttatacccatgag (SEQ ID NO: 44) |
| Control Tumor 2 | Agacctgggttcttcaaagcctcacctcacatccagagctgeggcaaatgtccacctcacagttatacccatgag (SEQ ID NO: 44) |
| Control Tumor 3 | Agacctgggttcttcaaagcctcacctcacatccagagctgeggcaaatgtccacctcacagttatacccatgag (SEQ ID NO: 44) |
| Control Tumor 4 | Agacctgggttcttcaaagcctcacctcacatccagagctgcggcaaatgtccacctcacagttatacccatgag (SEQ ID NO: 44) |
| Control Tumor 5 | Agacctgggttcttcaaagcctcacctcacatccagagctgeggcaaatgtccacctcacagttatacccatgag (SEQ ID NO: 44) |
| Control Tumor 6 | Agacctgggttcttcaaagcctcacctcacatccagagctgcggcaaatgtccacctcacagttatacccatgag (SEQ ID NO: 44) |

TABLE 2

Epitope sequencing of Tumors from TM00098-bearing mice treated with ADC2

| | |
|---|---|
| VH5Vk EphA5 Epitope | Agacctgggttcttcaaagcctcacctcacatccagagctgeggcaaatgtccacctcacagttatacccatgag (SEQ ID NO: 44) |
| ADC2 Tumor 1 | Agacctgggttcttcaaagcctcacctcacatccagagctgcggcaaatgtccacctcacagttatacccatgag (SEQ ID NO: 44) |
| ADC2 Tumor 2 | Agacctgggttcttcaaagcctcacctcacatccagagctgeggcaaatgtccacctcacagttatacccatgag (SEQ ID NO: 44) |
| ADC2 Tumor 3 | Agacctgggttcttcaaagcctcacctcacatccagagctgcggcaaatgtccacctcacagttatacccatgag (SEQ ID NO: 44) |
| ADC2 Tumor 4 | Agacctgggttcttcaaagcctcacctcacatccagagctgeggcaaatgtccacctcacagttatacccatgag (SEQ ID NO: 44) |

TABLE 2-continued

| Epitope sequencing of Tumors from TM00098-bearing mice treated with ADC2 |
| --- |

ADC2      Agacctgggttcttcaaagcctcacctcacatccagagctgeggcaaatgtccacctcacagttatacccatgag
Tumor 5  (SEQ ID NO: 44)

ADC2      Agacctgggttcttcaaagcctcacctcacatccagagctgeggcaaatgtccacctcacagttatacccatgag
Tumor 6  (SEQ ID NO: 44)

ADC2      Agacctgggttcttcaaagcctcacctcacatccagagctgcggcaaatgtccacctcacagttatacccatgag
Tumor 7  (SEQ ID NO: 44)

Selected Conclusions

ADC1 administration to mice bearing the TM00098 PDX model of triple negative breast cancer over a five-week period resulted in full and sustained regression of tumors, to the extent that no tumors remained to be excised or further evaluated after the 50-day study period. Animals treated with ADC1 or placebo did not show significant changes in body weight during the study, suggesting the ADC1 administration did not have an adverse impact on the animals' ability to thrive. Without wishing to be bound by theory, this suggests ADC1 is a promising drug candidate for further development for treatment of triple negative breast cancer.

Treatment of mice bearing TM00098 PDX model of triple negative breast cancer with ADC2 resulted in statistically significant regression of tumor size and delayed tumor growth that was sustained overtime. Similarly, animals treated with ADC2 or placebo did not show significant changes in body weight during the study period, suggesting that ADC2 administration did not have an adverse impact on the animals' ability to thrive. Therefore, ADC2 may also be a promising drug candidate for further development for treatment of triple negative breast cancer, although ADC2 was less efficacious than ADC1.

The treatment of 10 mg/Kg weekly for 5 doses was well tolerated for both ADC1 and ADC2, and no toxicity or weight loss was observed in the treated animals as compared to untreated animals or animals receiving PBS (placebo).

Administration of ADC2 and placebo did not cause modifications in the EphA5 epitope recognized by VH5Vk3, indicating that the difference in anti-tumor activity of ADC1 and ADC2 was not due to alterations in target epitope display.

Example 7: In Vivo Anti-Tumor Activity of ADCs Directed to EphA5 in a Patient-Derived Xenograft Model of Lung Squamous Cell Carcinoma (Study RS-003

The objective of this study was to evaluate the therapeutic anti-tumor activity of two ADCs directed to a novel target, EphA5, using a PDX model of lung squamous cell carcinoma. Specifically, the objective of this study was to test the in vivo anti-tumor activity of two ADCs, VH5Vk3-MMAE and VH5Vk3-(SN-38)2, in a PDX mouse model of lung squamous cell carcinoma that has been shown to express EphA5 at high levels on the cell surface of the tumor cells.

Test Animals

The present studies were performed using female NSG™ mice implanted with the PDX model TM00188 (LG0520F) purchased from Jackson Laboratories. These mice are extremely immunodeficient and carry two mutations: severe combined immune deficiency (scid) and a complete null allele of the IL2 receptor common gamma chain (IL2rg$^{null}$). The scid mutation is a mutation in the DNA repair complex protein Prkdc and renders the mice B and T cell deficient. The IL2rg$^{null}$ mutation prevents cytokine signaling through multiple receptors, leading to a deficiency in functional NK cells. This severe immunodeficiency allows the implantation of PDX and growth of human tissue-based tumors in the mice. These tumors have similar characteristics to the human tumors from which they are derived (e.g., gene expression) and are predictive of human response to therapeutic agents.

The initial and final diagnosis of the patient from which the model was derived was lung squamous cell carcinoma, AJCC IA/Grade 3. The primary site of human tumor was lung, and the sample site of the tumor for the PDX model was the primary site of the tumor. The tumor used for the TM00188 PDX model was treatment naïve. The patient from which the sample was derived was a 67-year-old white, non-Hispanic male former smoker. The sample was obtained by surgical resection. The host strain of the sample for engraftment was NOD.Cg-Prkdc$^{scid}$ Il2rg$^{wm1Wjl}$/SzJ (aka NSG or NOD Scid gamma).

Test Animal Housing and Care

Mice were housed in specific pathogen- and opportunist-free (SOPF) rooms with controlled temperature ($20\pm2°$ C.), humidity ($50\pm10\%$), light/dark cycle (light, 7:00 to 19:00; dark, 19:00 to 7:00), and access to food and water ad libitum at the research animal facilities of the Rutgers Cancer Institute of New Jersey. The mice used in the present study were cared for in compliance with all applicable laws and guidelines, including those from the U.S. Department of Health and Human Services, Public Health Service, and the Office of Laboratory Animal Welfare The Institutional Animal Care and Use Committee from the Rutgers Cancer Institute of New Jersey approved all animal experiments, and the Rutgers Animal Facility followed guidelines as set forth by the Association for Assessment and Accreditation of Laboratory Animal Care, International (AAALAC).

Mice were housed in specific pathogen and opportunist-free (SOPF) rooms with controlled temperature ($20\pm2°$ C.), humidity ($50\pm10\%$), light/dark cycle (light, 7:00 to 19:00; dark, 19:00 to 7:00), and access to food and water ad libitum at the research animal facilities of the Rutgers Cancer Institute of New Jersey (Newark, NJ). Littermates were randomly assigned to experimental groups.

A total of 40 female mice implanted with PDX TM00098 were used in the studies. Mice were received at the study location at 10-12 weeks of age and remained in the study until 18-12 weeks of age on average. Body weights ranged from 19 g to 24 g at the beginning of the studies and 19 g to 25 g at the end of the studies.

Materials

ADC1: VH5Vk3-ThioBridge-VCP-MMAE

ADC1 is an ADC prepared using the VH5Vk3 antibody and the ThioBridge® site-specific conjugation technology utilizing a linker moiety cleavable by lysosomal cathepsins ('Val-Cit-PAB') coupled to the cytotoxic payload MMAE. This linker format is designed with a branched 24-unit PEG polymer to reduce aggregation propensity and improve aqueous solubility (FIG. 33). An average of DAR of 4 was targeted. All research batches of ADC1 had the appearance of a clear colorless solution with an average DAR of 4 and purity of 95% or higher of monomeric species as determined by size exclusion chromatography (SEC). Endotoxin levels were determined by the EndoSafe®-PTS™ platform (Charles River, Wilmington, MA) aligned with USP <85> and Pharm Eur 2.6.14 that provides quantitative Limulus Amebocyte Lysate (LAL) results. The average molecular weight of ADC1 was 158,000 Da as determined by LC-MS. ADC1 was handled under sterile conditions and stored at −80° C. until use.

ADC2 VH5Vk3-ThioBridge®-VCP-(SN-38)$_2$

ADC2 is an ADC prepared using the VH5Vk3 antibody and the ThioBridge® site-specific conjugation technology. A double-loaded structure with moieties cleavable by hydrolysis (carbonate) was used to couple the cytotoxic payload SN-38 to the antibody (FIG. 33). This linker format was designed with dual branched 24-unit PEG polymers to reduce aggregation propensity and improve aqueous solubility. An average of DAR of 8 was targeted.

All research batches had the appearance of a clear colorless solution with an average DAR of 8 and purity of 95% or higher of monomeric species as determined by size exclusion chromatography (SEC). Endotoxin levels were determined by the EndoSafe®-PTS™ platform (Charles River) aligned with USP <85> and Pharm Eur 2.6.14 that provides quantitative Limulus Amebocyte Lysate (LAL) results. The average molecular weight of ADC2 was 165,000 Da as determined by LC-MS. ADC2 were handled under sterile conditions and stored at −80° C. until use.

Methods

The selection of the PDX model was based on EPHA5 gene expression levels (Jackson Laboratory database) and protein expression by immunohistochemistry (IHC) (in-house; IHC staining shown below). PDX models showing moderate to high EphA5 expression, with a favorable growth curve and deemed responsive to common drugs such as cisplatin, docetaxel and doxorubicin were considered for anti-tumor activity studies. Models resistant to multiple drugs were eliminated from the selection, and models naïve to treatment were prioritized. Based on these criteria, the TM00188 PDX model was selected for the present study.

Mice received 5 weekly doses of ADC1 or ADC2 at 10 mg/kg or PBS via tail vein injection. Animals were dosed on days 0, 7, 14, 21 and 28 followed by 3 weeks of observation (day 28-50) without treatment. The number of mice used per group averaged n=10 with some mice presenting with more than 1 tumor implanted subcutaneously. In those cases, each tumor size was measured and recorded independently. Measurements were performed 2-3 times weekly with the aid of a digital caliper (Fisherbrand™ Traceable™ Digital Carbon Fiber Calipers). Studies lasted on average 50 days or until maximum allowed tumor volume was reached and/or skin ulceration was noted. All studies included a control group of an equal number of mice to those in the treatment group. Control groups received PBS tail vein injections and were submitted to the same handling procedures as ADC1 and ADC2 treated mice. First treatment was administered when tumors reached 100-150 mm$^3$ volume.

The body weight of the TM00188-bearing mice enrolled in the studies were measured prior to the first treatment (pre) and at termination (50 days post first treatment). Following termination of the studies, any remaining tumors were excised and weighed on a laboratory balance. DNA was extracted from remaining tumors and sequenced to determine the presence of any mutations in the EphA5 epitope potentially caused by the treatment regimen.

Data Analysis

The statistical analysis and graphical plotting of the tumor size and the body weight was performed using GraphPad Prism 9 and Microsoft Excel (Version 16.63.1). The statistical significance of the measured differences between the test and control groups were tested with Student's t-test or analysis of variance (one-way or two-way ANOVA) using GraphPad Prism 9.

Selected Results

Figure 111A:
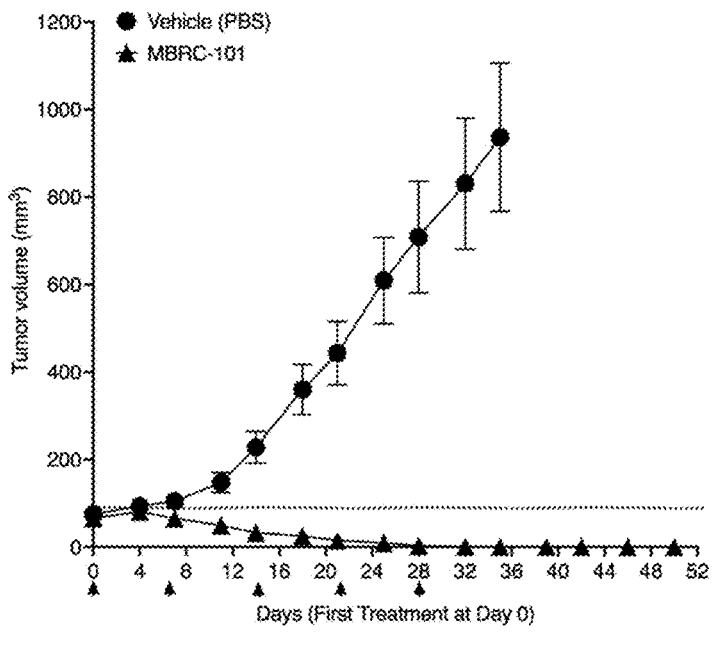
FIGS. 111A-111C illustrate tumor volume in mice treated weekly for 5 weeks with ADC1 or PBS (placebo) over 50-day test period (FIG. 111A), weight of tumors removed from TM0188-bearing mice following treatment with ADC1 or PBS (placebo) (FIG. 111B), and body weight of TM0188-bearing mice before and after treatment with ADC1 (FIG. 111C).
Figures 111B, 111C:
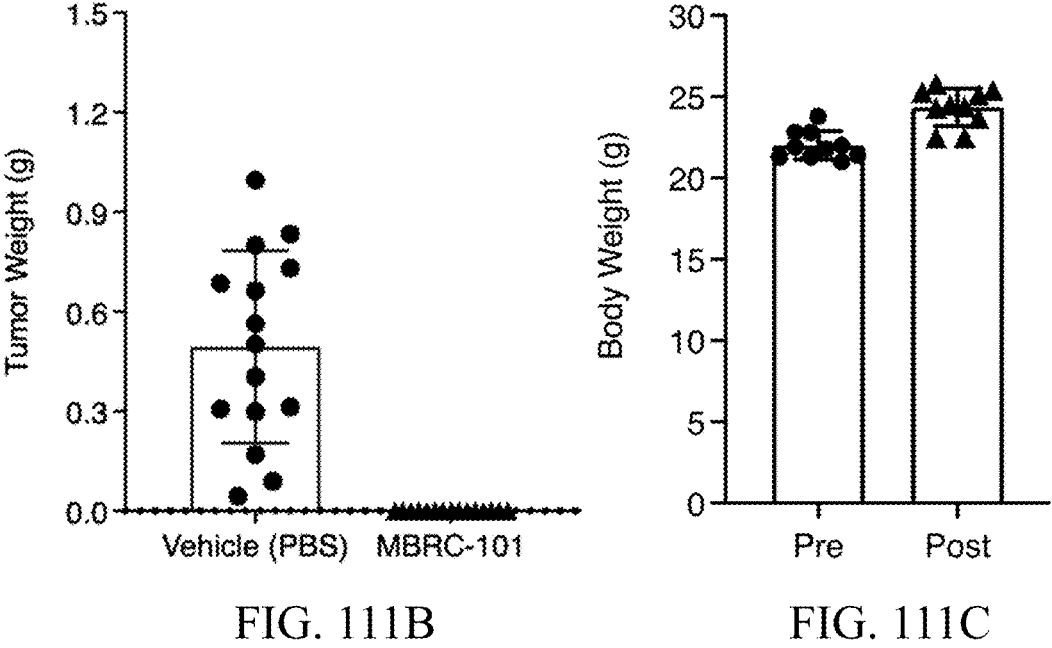
Figure 113A:
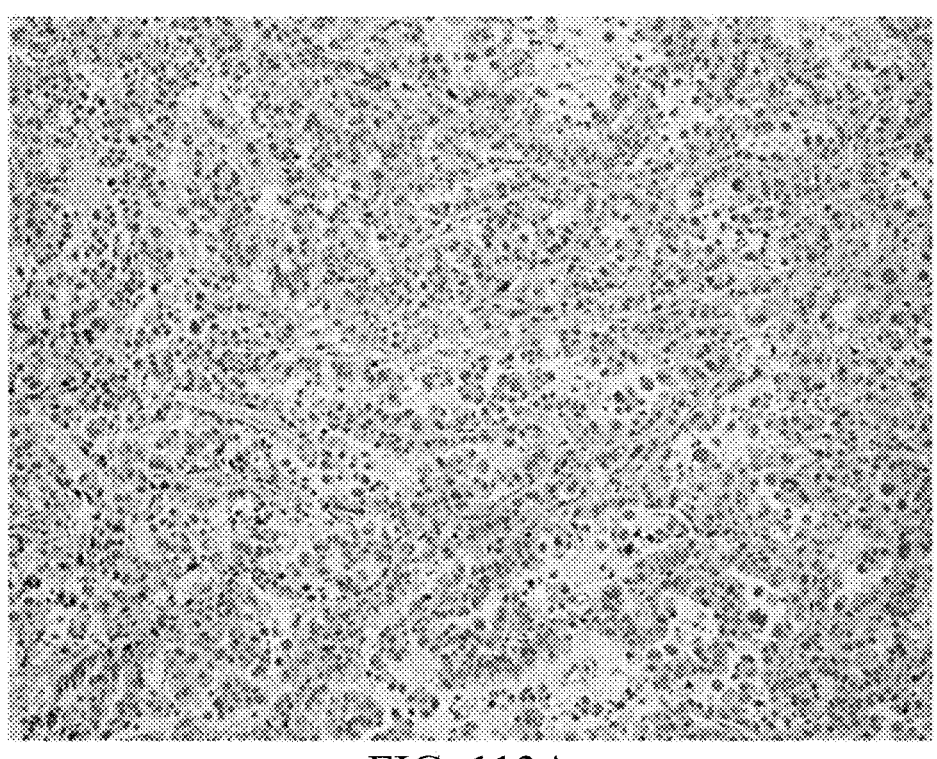
FIGS. 113A-113B illustrate IHC staining of tumor tissue from the TM00219 PDX model using a control IgG antibody (FIG. 113A), and a commercially available antibody that selectively binds to EphA5 (FIG. 113B).
Figure 113B:
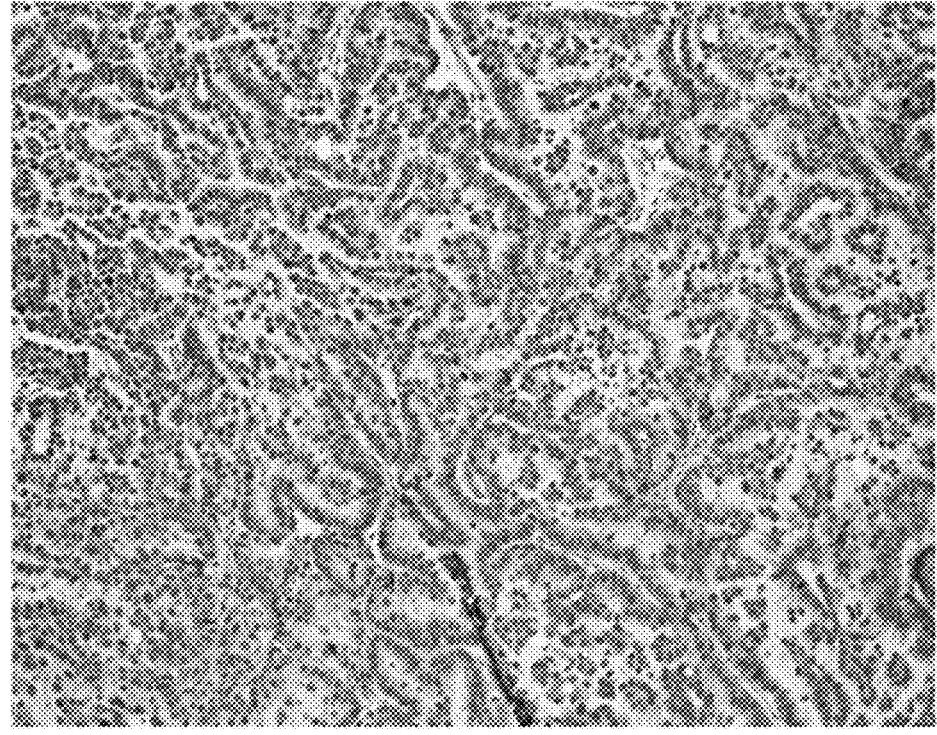

Weekly administration of ADC1 to mice bearing TM00188 tumors over a 5-week period resulted in complete and sustained regression of all tumors (n=16) (FIG. 111A), tumor weight could not be determined at study termination (FIG. 111B). DNA extraction was not possible due to the absence of tumor tissue at the end of the study. As shown in FIG. 111C, there were no significant changes in body weight of mice before and after treatment with both ADC1.

Administration of ADC2 to mice bearing TM00188 tumors over a 5-week period resulted in no response, with all treated tumors progressing overtime. Study was terminated early due to tumor burden in both control and ADC2 treated groups (FIG. 112A). There were no differences in tumor weight between control and ADC2 groups (FIG. 112B). As shown in FIG. 112C, no changes in body weight of mice were observed before and after treatment with ADC2.

Lung squamous cell carcinoma is known to be a heterogeneous disease with aggressive biology and complex tumor evolution. One possibility for the difference in response to ADC1 and ADC2 could be a change in the epitope recognized by the antibody binding portion of the ADCs caused by exposure to the ADCs, which could lead to a reduced anti-tumor activity of ADC2. To identify the potential for EphA5 mutations in response to TA treatment, the region containing the EphA5 epitope recognized by VH5 Vk3 was sequenced in the remaining tumors following the study period. Neither PBS nor ADC2 administration resulted in mutations of the amino acids composing the EphA5 epitope recognized by VH5Vk3 (Tables 1 and 2); insufficient tumor remained for determination of epitope mutations following administration of ADC1.

The critical amino acids (highlighted in bold) for binding of VH5Vk3 to human EphA5 are contained within the region 306_RPGFFKASPHIQSCGKCPPHSYTHE_330 (SEQ ID NO:43), which corresponds to the genomic sequence:

(SEQ ID NO: 44)

AGACCTGGGTTCTTCAAAGCCTCACCTCACATCCAGAGCTGCGGCAAATG

TCCACCTCACAGTTATACCCATGAG

TABLE 1

| Epitope sequencing of Tumors from TM00188-bearing mice treated with PBS |
| --- |

| VH5Vk EphA5 Epitope | Agacctgggttcttcaaagcctcacctcacatccagagctgcggcaaatgtccacctcacagttatacccatgag (SEQ ID NO: 44) |
| --- | --- |
| Control Tumor 1 | Agacctgggttcttcaaagcctcacctcacatccagagctgcggcaaatgtccacctcacagttatacccatgag (SEQ ID NO: 44) |
| Control Tumor 2 | Agacctgggttcttcaaagcctcacctcacatccagagctgcggcaaatgtccacctcacagttatacccatgag (SEQ ID NO: 44) |
| Control Tumor 3 | Agacctgggttcttcaaagcctcacctcacatccagagctgcggcaaatgtccacctcacagttatacccatgag (SEQ ID NO: 44) |
| Control Tumor 4 | Agacctgggttcttcaaagcctcacctcacatccagagctgcggcaaatgtccacctcacagttatacccatgag (SEQ ID NO: 44) |
| Control Tumor 5 | Agacctgggttcttcaaagcctcacctcacatccagagctgcggcaaatgtccacctcacagttatacccatgag (SEQ ID NO: 44) |
| Control Tumor 6 | Agacctgggttcttcaaagcctcacctcacatccagagctgcggcaaatgtccacctcacagttatacccatgag (SEQ ID NO: 44) |
| Control Tumor 7 | Agacctgggttcttcaaagcctcacctcacatccagagctgcggcaaatgtccacctcacagttatacccatgag (SEQ ID NO: 44) |
| Control Tumor 8 | Agacctgggttcttcaaagcctcacctcacatccagagctgcggcaaatgtccacctcacagttatacccatgag (SEQ ID NO: 44) |
| Control Tumor 9 | Agacctgggttcttcaaagcctcacctcacatccagagctgcggcaaatgtccacctcacagttatacccatgag (SEQ ID NO: 44) |

TABLE 2

| Epitope sequencing of Tumors from TM00188-bearing mice treated with ADC2 |
| --- |

| VH5Vk EphA5 Epitope | Agacctgggttcttcaaagcctcacctcacatccagagctgcggcaaatgtccacctcacagttatacccatgag (SEQ ID NO: 44) |
| --- | --- |
| ADC2 Tumor 1 | Agacctgggttcttcaaagcctcacctcacatccagagctgcggcaaatgtccacctcacagttatacccatgag (SEQ ID NO: 44) |
| ADC2 Tumor 2 | Agacctgggttcttcaaagcctcacctcacatccagagctgcggcaaatgtccacctcacagttatacccatgag (SEQ ID NO: 44) |
| ADC2 Tumor 3 | Agacctgggttcttcaaagcctcacctcacatccagagctgcggcaaatgtccacctcacagttatacccatgag (SEQ ID NO: 44) |
| ADC2 Tumor 4 | Agacctgggttcttcaaagcctcacctcacatccagagctgcggcaaatgtccacctcacagttatacccatgag (SEQ ID NO: 44) |
| ADC2 Tumor 5 | Agacctgggttcttcaaagcctcacctcacatccagagctgcggcaaatgtccacctcacagttatacccatgag (SEQ ID NO: 44) |
| ADC2 Tumor 6 | Agacctgggttcttcaaagcctcacctcacatccagagctgcggcaaatgtccacctcacagttatacccatgag (SEQ ID NO: 44) |
| ADC2 Tumor 7 | Agacctgggttcttcaaagcctcacctcacatccagagctgcggcaaatgtccacctcacagttatacccatgag (SEQ ID NO: 44) |
| ADC2 Tumor 8 | Agacctgggttcttcaaagcctcacctcacatccagagctgcggcaaatgtccacctcacagttatacccatgag (SEQ ID NO: 44) |
| ADC2 Tumor 9 | Agacctgggttcttcaaagcctcacctcacatccagagctgcggcaaatgtccacctcacagttatacccatgag (SEQ ID NO: 44) |

Selected Conclusions

ADC1 administration to mice bearing the TM00188 PDX model of lung squamous cell carcinoma over a five-week period resulted in full and sustained regression of tumors, to the extent that no tumor tissue remained to be excised or further evaluated after the 50-day study period. Animals treated with ADC1 or placebo did not show significant changes in body weight during the study, suggesting the ADC1 administration did not have an adverse impact on the animals' ability to thrive. This suggests ADC1 is a promising drug candidate for further development for treatment of lung squamous cell carcinoma.

Treatment of mice bearing TM00188 PDX model of lung squamous cell carcinoma with ADC2 resulted in no response to treatment with all treated tumors progressing overtime. Early termination was necessary due to tumor burden. Animals treated with ADC2 did not show significant changes in body weight during the study period, suggesting that ADC2 administration did not have an adverse impact on the animals' ability to thrive.

Example 8: In Vivo Anti-tumor Activity of ADCs Directed to EphA5 in a Patient-Derived Xenograft Model of Lung Adenocarcinoma The objective of this study was to evaluate the therapeutic anti-tumor activity of two ADCs directed to a novel target, EphA5, using a PDX model of lung adenocarcinoma. Specifically, the objective of this study was to test the in vivo anti-tumor activity of two ADCs, VH5Vk3-MMAE and VH5Vk3-(SN-38)2, in a PDX mouse model of lung adenocarcinoma that has been shown to express EphA5 at medium to high levels on the cell surface of the tumor cells.

Test Animals

The present studies were performed using female NSG™ mice purchased from Jackson Laboratories, reference number TM00219 (LG1049F). These mice are extremely immunodeficient and carry two mutations: severe combined immune deficiency (scid) and a complete null allele of the IL2 receptor common gamma chain (IL2rg$^{null}$). The scid mutation is a mutation in the DNA repair complex protein Prkdc and renders the mice B and T cell deficient. The IL2rg$^{null}$ mutation prevents cytokine signaling through multiple receptors, leading to a deficiency in functional NK cells. This severe immunodeficiency allows the implantation of patient derived xenografts (PDX) and growth of human tissue-based tumors in the mice. These tumors have similar characteristics to the human tumors from which they are derived (e.g., gene expression) and are predictive of human response to therapeutic agents.

The initial and final diagnosis of the patient from which the model was derived was lung adenocarcinoma, AJCC IV/Grade:1. The primary site of the tumor was lung, and sample collection was performed from the metastatic site (lymph node). The tumor was not treatment naïve. The patient from which the sample was derived was a 59-year-old white, non-Hispanic female former smoker. The sample was obtained by fine needle aspirate. The host strain of the sample for engraftment was NOD.Cg-Prkdc$^{scid}$ Il2rg$^{tm1Wjl}$/ SzJ (aka NSG or NOD Scid gamma).

Test Animal Housing and Care

Mice were housed in specific pathogen- and opportunist-free (SOPF) rooms with controlled temperature (20±2° C.), humidity (50±10%), light/dark cycle (light, 7:00 to 19:00; dark, 19:00 to 7:00), and access to food and water ad libitum at the research animal facilities of the Rutgers Cancer Institute of New Jersey. The mice used in the present study were cared for in compliance with all applicable laws and guidelines, including those from the U.S. Department of Health and Human Services, Public Health Service, and the Office of Laboratory Animal Welfare The Institutional Animal Care and Use Committee from the Rutgers Cancer Institute of New Jersey approved all animal experiments, and the Rutgers Animal Facility followed guidelines as set forth by the Association for Assessment and Accreditation of Laboratory Animal Care, International (AAALAC).

Mice were housed in specific pathogen and opportunist-free (SOPF) rooms with controlled temperature (20±2° C.), humidity (50±10%), light/dark cycle (light, 7:00 to 19:00;

dark, 19:00 to 7:00), and access to food and water ad libitum at the research animal facilities of the Rutgers Cancer Institute of New Jersey (Newark, NJ). Littermates were randomly assigned to experimental groups.

A total of 40 female mice implanted with PDX TM00219 were used in the studies. Mice were received at the study location at 10-12 weeks of age and remained in the study until 18-12 weeks of age on average. Body weights ranged from 17 g to 24 g at the beginning of the studies and 18 g to 24 g at the end of the studies.

Materials

ADC1: VH5Vk3-ThioBridge-VCP-MMAE

ADC1 is an ADC prepared using the VH5Vk3 antibody and the ThioBridge® site-specific conjugation technology utilizing a linker moiety cleavable by lysosomal cathepsins ('Val-Cit-PAB') coupled to the cytotoxic payload MMAE. This linker format is designed with a branched 24-unit PEG polymer to reduce aggregation propensity and improve aqueous solubility (FIG. 33). An average of DAR of 4 was targeted.

All research batches of ADC1 had the appearance of a clear colorless solution with an average DAR of 4 and purity of 95% or higher of monomeric species as determined by size exclusion chromatography (SEC). Endotoxin levels were determined by the EndoSafe®-PTS™ platform (Charles River, Wilmington, MA) aligned with USP <85> and Pharm Eur 2.6.14 that provides quantitative Limulus Amebocyte Lysate (LAL) results. The average molecular weight of ADC1 was 158,000 Da as determined by LC-MS. ADC1 was handled under sterile conditions and stored at −80° C. until use.

ADC2 VH5Vk3-ThioBridge®-VCP-(SN-38)$_2$

ADC2 is an ADC prepared using the VH5Vk3 antibody and the ThioBridge® site-specific conjugation technology. A double-loaded structure with moieties cleavable by hydrolysis (carbonate) was used to couple the cytotoxic payload SN-38 to the antibody (FIG. 33). This linker format was designed with dual branched 24-unit PEG polymers to reduce aggregation propensity and improve aqueous solubility. An average of DAR of 8 was targeted.

All research batches had the appearance of a clear colorless solution with an average DAR of 8 and purity of 95% or higher of monomeric species as determined by size exclusion chromatography (SEC). Endotoxin levels were determined by the EndoSafe®-PTS™ platform (Charles River) aligned with USP <85> and Pharm Eur 2.6.14 that provides quantitative Limulus Amebocyte Lysate (LAL) results. The average molecular weight of ADC2 was 165,000 Da as determined by LC-MS. ADC2 were handled under sterile conditions and stored at −80° C. until use.

Methods

The selection of the PDX model was based on EPHA5 gene expression levels (Jackson Laboratory database) and protein expression by immunohistochemistry (IHC) (in-house; IHC staining shown below). PDX models showing moderate to high EphA5 expression, with a favorable growth curve and deemed responsive to common drugs such as cisplatin, docetaxel and doxorubicin were considered for anti-tumor activity studies. Models resistant to multiple drugs were eliminated from the selection, and models naïve to treatment were prioritized. Based on these criteria, the TM00188 PDX model was selected for the present study.

Mice received 5 weekly doses of ADC1 or ADC2 at 10 mg/kg or PBS via tail vein injection. Animals were dosed on days 0, 7, 14, 21 and 28 followed by 3 weeks of observation (day 28-50) without treatment. The number of mice used per group averaged n=8 with some mice presenting with more than 1 tumor implanted subcutaneously. In those cases, each tumor size was measured and recorded independently. Measurements were performed 2-3 times weekly with the aid of a digital caliper (Fisherbrand™ Traceable™ Digital Carbon Fiber Calipers). Studies lasted on average 50 days or until maximum allowed tumor volume was reached and/or skin ulceration was noted. All studies included a control group of an equal number of mice to those in the treatment group. Control groups received PBS tail vein injections and were submitted to the same handling procedures as ADC1 and ADC2 treated mice. First treatment was administered when tumors reached 100-150 mm³ volume.

The body weight of the TM00219-bearing mice enrolled in the studies were measured prior to the first treatment (pre) and at termination (50 days post first treatment). Following termination of the studies, any remaining tumors were excised and weighed on a laboratory balance. DNA was extracted from remaining tumors and sequenced to determine the presence of any mutations in the EphA5 epitope potentially caused by the treatment regimen.

Data Analysis

The statistical analysis and graphical plotting of the tumor size and the body weight was performed using GraphPad Prism 9 and Microsoft Excel (Version 16.63.1). The statistical significance of the measured differences between the test and control groups were tested with Student's t-test or analysis of variance (one-way or two-way ANOVA) using GraphPad Prism 9.

Selected Results

Figure 114A:
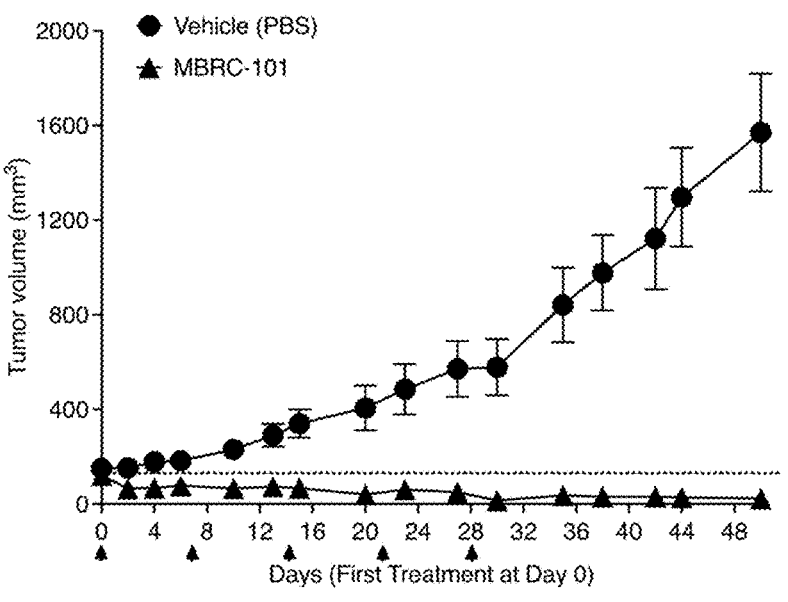
FIGS. 114A-114C illustrate tumor volume in mice treated weekly for 5 weeks with ADC1 or PBS (placebo) over 50-day test period (FIG. 114A), weight of tumors removed from TM00219-bearing mice following treatment with ADC1 or PBS (placebo) (FIG. 114B), and body weight of TM000219-bearing mice before and after treatment with ADC1 (FIG. 114C).
Figures 114B, 114C:
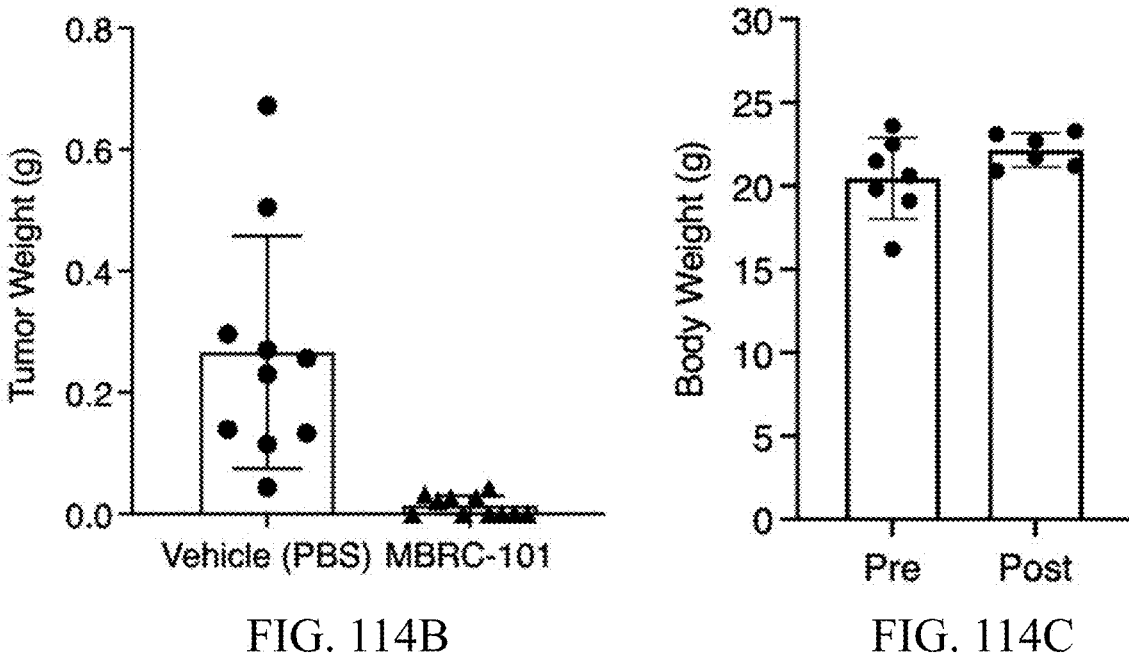

Weekly administration of ADC1 to mice bearing TM00219 tumors over a 5-week period resulted in full and sustained regression of tumors (FIG. 114A). From a total of 11 tumors, 6 tumors in the ADC1 treated group regressed completely and tumor volume could not be determined at study termination. Five tumors remained at the end of the study (FIG. 114B). As shown in FIG. 114C, there were no significant changes in body weight of mice before and after treatment with ADC1.

Figure 115A:
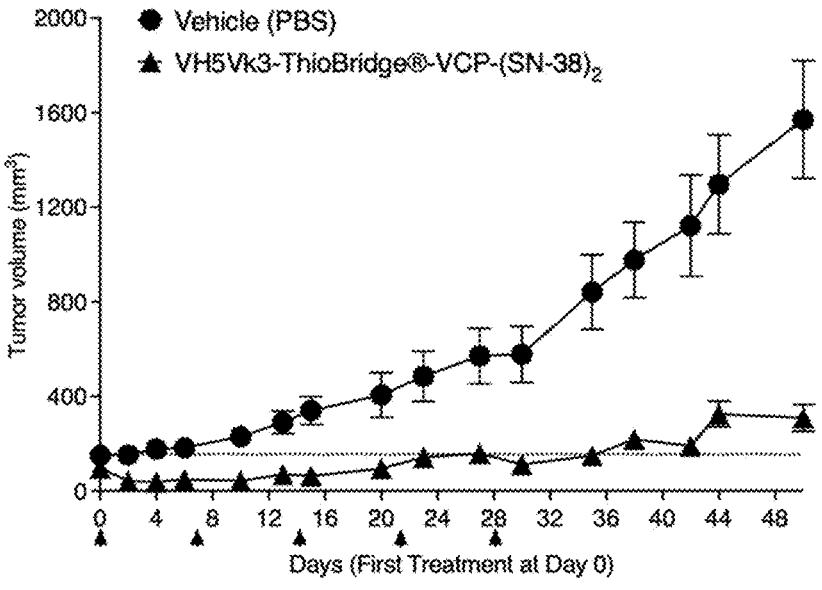
FIGS. 115A-115C illustrate tumor volume in TM000219-bearing mice treated weekly for weeks with ADC2 or PBS (placebo) over 50-day test period (FIG. 115A), weight of tumors removed from TM000219-bearing mice following treatment with ADC2 or PBS (placebo) (FIG. 115B), and body weight TM000219-bearing mice before and after treatment with ADC2 (FIG. 115C).
Figures 115B, 115C:
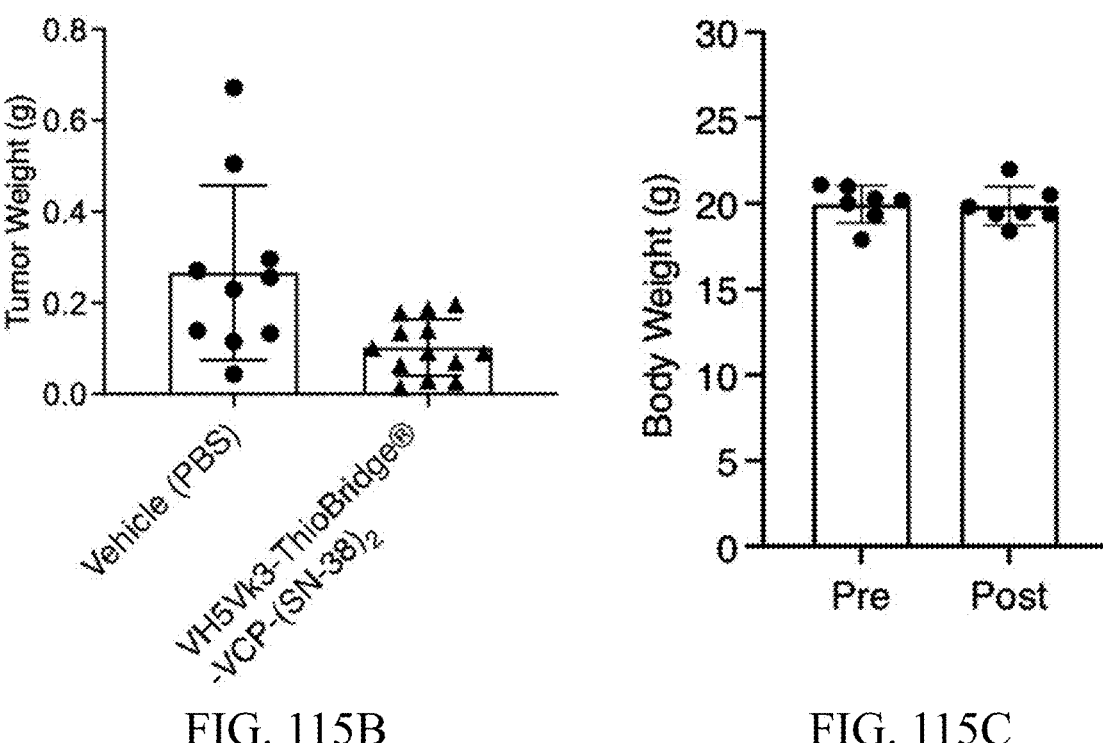
Figure 116A:
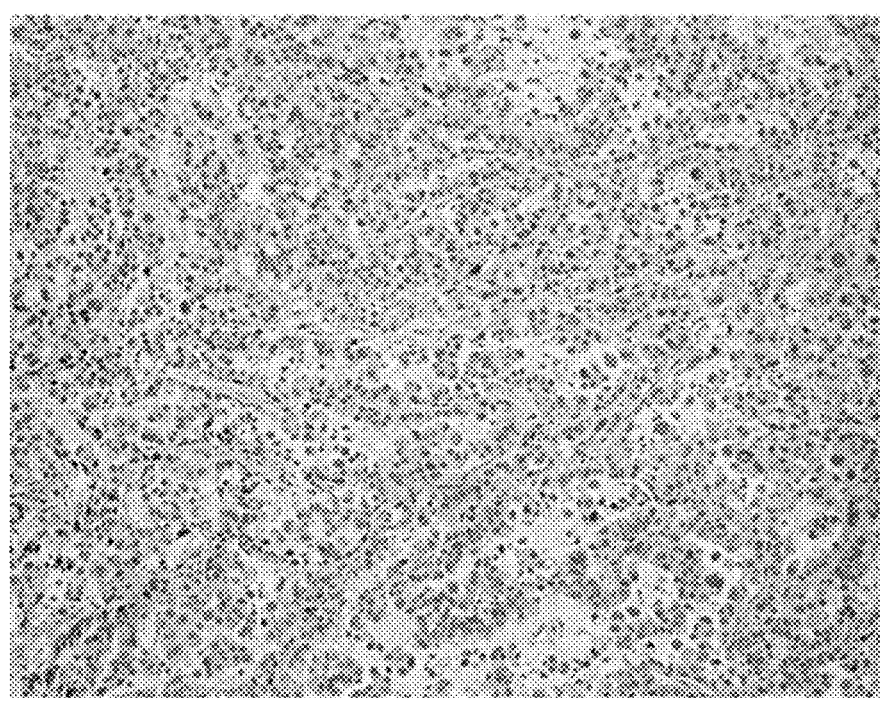
FIGS. 116A-116B illustrate IHC staining of tumor tissue from the TM00226 PDX model using a control IgG antibody (FIG. 116A) and a commercially available antibody that selectively binds to EphA5 (FIG. 116B)
Figure 116B:
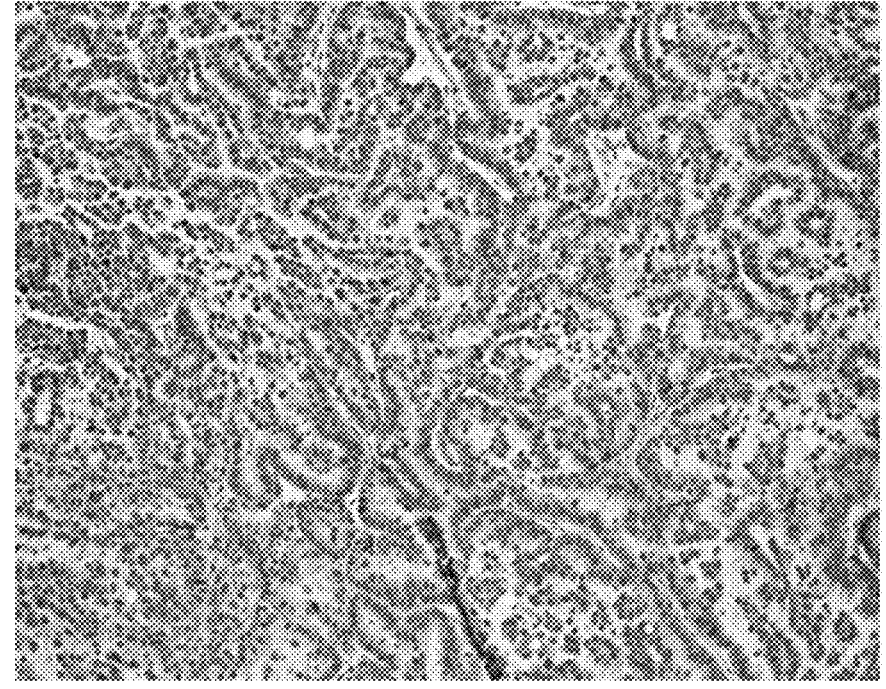

Administration of ADC2 to the TM00219 PDX mice over a 5-week period resulted in good response, with initial regression observed in some tumors followed by stasis or delayed tumor growth (FIG. 115A). The tumors in the ADC2 treated mice were reduced in weight compared to the PBS control group (FIG. 115B). As shown in FIG. 115C, the treated mice showed no changes in body weight before and after treatment.

Lung adenocarcinoma is known to be a heterogeneous disease with aggressive biology and complex tumor evolution. One possibility for the difference in response to ADC1 and ADC2 could be a change in the epitope recognized by the antibody binding portion of the ADCs caused by exposure to the ADCs, which could lead to a reduced anti-tumor activity of ADC2. To identify the potential for EphA5 mutations in response to TA treatment, the region containing the EphA5 epitope recognized by VH5Vk3 was sequenced in the remaining tumors following the study period. Neither PBS nor ADC1 or ADC2 administration resulted in mutations of the amino acids composing the EphA5 epitope recognized by VH5Vk3 (Tables 1-3).

The critical amino acids (highlighted in bold) for binding of VH5Vk3 to human EphA5 are contained within the region 306_RPGFFKASPHIQSCGKCPPHSYTHE_330 (SEQ ID NO:43), which corresponds to the genomic sequence:

```
                                     (SEQ ID NO: 44)
AGACCTGGGTTCTTCAAAGCCTCACCTCACATCCAGAGCTGCGGCAAATG

TCCACCTCACAGTTATACCCATGAG
```

TABLE 1

| Sequencing of Tumors from PBS Treated PDX TM00219 Mice | |
|---|---|
| VH5Vk<br>EphA5<br>Epitope | AGACCTGGGTTCTTCAAAGCCTCACCTCACATCCAGAGCTGCGGCAAATG<br>TCCACCTCACAGTTATACCCATGAG (SEQ ID NO: 44) |
| Control<br>Tumor 1 | AGACCTGGGTTCTTCAAAGCCTCACCTCACATCCAGAGCTGCGGCAAATG<br>TCCACCTCACAGTTATACCCATGAG (SEQ ID NO: 44) |
| Control<br>Tumor 2 | AGACCTGGGTTCTTCAAAGCCTCACCTCACATCCAGAGCTGCGGCAAATG<br>TCCACCTCACAGTTATACCCATGAG (SEQ ID NO: 44) |
| Control<br>Tumor 3 | AGACCTGGGTTCTTCAAAGCCTCACCTCACATCCAGAGCTGCGGCAAATG<br>TCCACCTCACAGTTATACCCATGAG (SEQ ID NO: 44) |
| Control<br>Tumor 4 | AGACCTGGGTTCTTCAAAGCCTCACCTCACATCCAGAGCTGCGGCAAATG<br>TCCACCTCACAGTTATACCCATGAG (SEQ ID NO: 44) |
| Control<br>Tumor 5 | AGACCTGGGTTCTTCAAAGCCTCACCTCACATCCAGAGCTGCGGCAAATG<br>TCCACCTCACAGTTATACCCATGAG (SEQ ID NO: 44) |
| Control<br>Tumor 6 | AGACCTGGGTTCTTCAAAGCCTCACCTCACATCCAGAGCTGCGGCAAATG<br>TCCACCTCACAGTTATACCCATGAG (SEQ ID NO: 44) |
| Control<br>Tumor 7 | AGACCTGGGTTCTTCAAAGCCTCACCTCACATCCAGAGCTGCGGCAAATG<br>TCCACCTCACAGTTATACCCATGAG (SEQ ID NO: 44) |
| Control<br>Tumor 8 | AGACCTGGGTTCTTCAAAGCCTCACCTCACATCCAGAGCTGCGGCAAATG<br>TCCACCTCACAGTTATACCCATGAG (SEQ ID NO: 44) |

TABLE 2

Sequencing of Tumors from ADC1 Treated PDX TM00219 Mice

| | |
|---|---|
| VH5Vk EphA5 Epitope | AGACCTGGGTTCTTCAAAGCCTCACCTCACATCCAGAGCTGCGGCAAATG TCCACCTCACAGTTATACCCATGAG (SEQ ID NO: 44) |
| ADC1 Tumor 1 | AGACCTGGGTTCTTCAAAGCCTCACCTCACATCCAGAGCTGCGGCAAATG TCCACCTCACAGTTATACCCATGAG (SEQ ID NO: 44) |
| ADC1 Tumor 2 | AGACCTGGGTTCTTCAAAGCCTCACCTCACATCCAGAGCTGCGGCAAATG TCCACCTCACAGTTATACCCATGAG (SEQ ID NO: 44) |
| ADC1 Tumor 3 | AGACCTGGGTTCTTCAAAGCCTCACCTCACATCCAGAGCTGCGGCAAATG TCCACCTCACAGTTATACCCATGAG (SEQ ID NO: 44) |
| ADC1 Tumor 4 | AGACCTGGGTTCTTCAAAGCCTCACCTCACATCCAGAGCTGCGGCAAATG TCCACCTCACAGTTATACCCATGAG (SEQ ID NO: 44) |
| ADC1 Tumor 5 | AGACCTGGGTTCTTCAAAGCCTCACCTCACATCCAGAGCTGCGGCAAATG TCCACCTCACAGTTATACCCATGAG (SEQ ID NO: 44) |

TABLE 3

Sequencing of Tumors from ADC2 Treated PDX TM00219 Mice

| | |
|---|---|
| VH5Vk EphA5 Epitope | AGACCTGGGTTCTTCAAAGCCTCACCTCACATCCAGAGCTGCGGCAAATG TCCACCTCACAGTTATACCCATGAG (SEQ ID NO: 44) |
| ADC2 Tumor 1 | AGACCTGGGTTCTTCAAAGCCTCACCTCACATCCAGAGCTGCGGCAAATG TCCACCTCACAGTTATACCCATGAG (SEQ ID NO: 44) |
| ADC2 Tumor 2 | AGACCTGGGTTCTTCAAAGCCTCACCTCACATCCAGAGCTGCGGCAAATG TCCACCTCACAGTTATACCCATGAG (SEQ ID NO: 44) |
| ADC2 Tumor 3 | AGACCTGGGTTCTTCAAAGCCTCACCTCACATCCAGAGCTGCGGCAAATG TCCACCTCACAGTTATACCCATGAG (SEQ ID NO: 44) |
| ADC2 Tumor 4 | AGACCTGGGTTCTTCAAAGCCTCACCTCACATCCAGAGCTGCGGCAAATG TCCACCTCACAGTTATACCCATGAG (SEQ ID NO: 44) |
| ADC2 Tumor 5 | AGACCTGGGTTCTTCAAAGCCTCACCTCACATCCAGAGCTGCGGCAAATG TCCACCTCACAGTTATACCCATGAG (SEQ ID NO: 44) |
| ADC2 Tumor 6 | AGACCTGGGTTCTTCAAAGCCTCACCTCACATCCAGAGCTGCGGCAAATG TCCACCTCACAGTTATACCCATGAG (SEQ ID NO: 44) |
| ADC2 Tumor 7 | AGACCTGGGTTCTTCAAAGCCTCACCTCACATCCAGAGCTGCGGCAAATG TCCACCTCACAGTTATACCCATGAG (SEQ ID NO: 44) |

Selected Comments

The ADCs show in vivo efficacy in the treatment of tumors in the TM00219 PDX model of lung adenocarcinoma, with ADC1 administration resulting in full and sustained regression of tumors following a 5 weekly administration regime, and ADC2 showing initial regression of tumor size that was sustained overtime, or delayed tumor growth. This suggests either ADC1 or ADC2 may be promising drug candidates for further development for treatment of lung adenocarcinoma, although ADC2 was not as efficacious as ADC1. Treatment of mice bearing TM00219 with ADC1 or ADC2 or placebo did not show significant changes in body weight during the study period, suggesting that administration of any of these did not have an adverse impact on the animals' ability to thrive.

Administration of ADC1, ADC2 and placebo did not result in any modification in the VH5Vk3 epitope of EphA5 following treatment, indicating the difference in response from ADC1 and ADC2 was not due to any alterations in the EphA5 epitope.

Example 9: In Vivo Anti-Tumor Activity of ADCs Directed to EphA5 in a Patient-Derived Xenograft Model of Lung Adenocarcinoma The objective of this study was to evaluate the therapeutic anti-tumor activity of two ADCs directed to a novel target, EphA5, using a PDX model of lung adenocarcinoma. Specifically, the objective of this study was to test the in vivo anti-tumor activity of two ADCs, VH5Vk3-MMAE and VH5Vk3-(SN-38)2, in a PDX mouse model of lung adenocarcinoma that has been shown to express EphA5 on the cell surface of the tumor cells.

Test Animals

The present studies were performed using female NSG™ mice implanted with the PDX model TM00226 (LG1179F) purchased from Jackson Laboratories. These mice are extremely immunodeficient and carry two mutations: severe combined immune deficiency (scid) and a complete null allele of the IL2 receptor common gamma chain (IL2rg$^{null}$). The scid mutation is a mutation in the DNA repair complex protein Prkdc and renders the mice B and T cell deficient. The IL2rg$^{null}$ mutation prevents cytokine signaling through multiple receptors, leading to a deficiency in functional NK cells. This severe immunodeficiency allows the implantation of PDX and growth of human tissue-based tumors in the mice. These tumors have similar characteristics to the human tumors from which they are derived (e.g., gene expression) and are predictive of human response to therapeutic agents.

The initial and final diagnosis of the patient from which the model was derived was lung adenocarcinoma, AJCC IB/Grade 3. The primary site of human tumor was lung, and the sample site of the tumor for the PDX model was the primary site of the tumor. The tumor used for the TM00226 PDX model was treatment naïve. The patient from which the sample was derived was a 49-year-old white, non-Hispanic female smoker. The sample was obtained by surgical resection. The host strain of the sample for engraftment was NOD.Cg-Prkdc$^{scid}$ Il2rg$^{tm1Wjl}$/SzJ (aka NSG or NOD Scid gamma).

Test Animal Housing and Care

Mice were housed in specific pathogen- and opportunist-free (SOPF) rooms with controlled temperature (20±2° C.), humidity (50±10%), light/dark cycle (light, 7:00 to 19:00; dark, 19:00 to 7:00), and access to food and water ad libitum at the research animal facilities of the Rutgers Cancer Institute of New Jersey. The mice used in the present study were cared for in compliance with all applicable laws and guidelines, including those from the U.S. Department of Health and Human Services, Public Health Service, and the Office of Laboratory Animal Welfare The Institutional Animal Care and Use Committee from the Rutgers Cancer Institute of New Jersey approved all animal experiments, and the Rutgers Animal Facility followed guidelines as set forth by the Association for Assessment and Accreditation of Laboratory Animal Care, International (AAALAC).

Mice were housed in specific pathogen and opportunist-free (SOPF) rooms with controlled temperature (20±2° C.), humidity (50±10%), light/dark cycle (light, 7:00 to 19:00; dark, 19:00 to 7:00), and access to food and water ad libitum at the research animal facilities of the Rutgers Cancer Institute of New Jersey (Newark, NJ). Littermates were randomly assigned to experimental groups.

A total of 40 female mice implanted with PDX TM00226 were used in the studies. Mice were received at the study location at 10-12 weeks of age and remained in the study until 18-12 weeks of age on average. Body weights ranged from 22 g to 28 g at the beginning of the studies and 22 g to 28 g at the end of the studies.

Materials

ADC1: VH5Vk3-ThioBridge-VCP-MMAE

ADC1 is an ADC prepared using the VH5Vk3 antibody and the ThioBridge® site-specific conjugation technology utilizing a linker moiety cleavable by lysosomal cathepsins ('Val-Cit-PAB') coupled to the cytotoxic payload MMAE. This linker format is designed with a branched 24-unit PEG polymer to reduce aggregation propensity and improve aqueous solubility (FIG. 33). An average of DAR of 4 was targeted.

All research batches of ADC1 had the appearance of a clear colorless solution with an average DAR of 4 and purity of 95% or higher of monomeric species as determined by size exclusion chromatography (SEC). Endotoxin levels were determined by the EndoSafe®-PTS™ platform (Charles River, Wilmington, MA) aligned with USP <85> and Pharm Eur 2.6.14 that provides quantitative Limulus Amebocyte Lysate (LAL) results. The average molecular weight of ADC1 was 158,000 Da as determined by LC-MS. ADC1 was handled under sterile conditions and stored at −80° C. until use.

ADC2 VH5Vk3-ThioBridge®-VCP-(SN-38)$_2$

ADC2 is an ADC prepared using the VH5Vk3 antibody and the ThioBridge® site-specific conjugation technology. A double-loaded structure with moieties cleavable by hydrolysis (carbonate) was used to couple the cytotoxic payload SN-38 to the antibody (FIG. 33). This linker format was designed with dual branched 24-unit PEG polymers to reduce aggregation propensity and improve aqueous solubility. An average of DAR of 8 was targeted.

All research batches had the appearance of a clear colorless solution with an average DAR of 8 and purity of 95% or higher of monomeric species as determined by size exclusion chromatography (SEC). Endotoxin levels were determined by the EndoSafe®-PTS™ platform (Charles River) aligned with USP <85> and Pharm Eur 2.6.14 that provides quantitative Limulus Amebocyte Lysate (LAL) results. The average molecular weight of ADC2 was 165,000 Da as determined by LC-MS. ADC2 were handled under sterile conditions and stored at −80° C. until use.

Methods

The selection of the PDX model was based on EPHA5 gene expression levels (Jackson Laboratory database) and protein expression by immunohistochemistry (IHC) (in-house; IHC staining shown below). PDX models showing moderate to high EphA5 expression, with a favorable growth curve and deemed responsive to common drugs such as cisplatin, docetaxel and doxorubicin were considered for anti-tumor activity studies. Models resistant to multiple drugs were eliminated from the selection, and models naïve to treatment were prioritized. Based on these criteria, the TM00226 PDX model was selected for the present study.

Mice received 5 weekly doses of ADC1 or ADC2 at 10 mg/kg or PBS via tail vein injection. Animals were dosed on days 0, 7, 14, 21 and 28 followed by 3 weeks of observation (day 28-50) without treatment. The number of mice used per group averaged n=7 with some mice presenting with more than 1 tumor implanted subcutaneously. In those cases, each tumor size was measured and recorded independently. Measurements were performed 2-3 times weekly with the aid of a digital caliper (Fisherbrand™ Traceable™ Digital Carbon Fiber Calipers). Studies lasted on average 50 days or until maximum allowed tumor volume was reached and/or skin ulceration was noted. All studies included a control group of an equal number of mice to those in the treatment group. Control groups received PBS tail vein injections and were submitted to the same handling procedures as ADC1 and ADC2 treated mice. First treatment was administered when tumors reached 100-150 mm³ volume.

The body weights of the TM00226-bearing mice enrolled in the studies were measured prior to the first treatment (pre) and at termination. Following termination of the studies, any remaining tumors were excised and weighed on a laboratory balance.

Data Analysis

The statistical analysis and graphical plotting of the tumor sizes and the body weights was performed using GraphPad Prism 9 and Microsoft Excel (Version 16.63.1). The statistical significance of the measured differences between the test and control groups were tested with Student's t-test or analysis of variance (one-way or two-way ANOVA) using GraphPad Prism 9.

Selected Results

Weekly administration of ADC1 to mice bearing TM00226 tumors over a 5-week period resulted in sustained regression of tumors (n=8) (FIG. 117A). From a total of 8 tumors, 1 tumor in the ADC1 treated group regressed completely and tumor volume could not be determined at study termination. Seven tumors remained at the end of the study with weights ranging from 0.001 g to 0.019 g (FIG. 117B). DNA extraction was not possible due to the absence of tumor tissue at the end of the study. As shown in FIG. 117C, there were no significant changes in body weight of mice before and after treatment with both ADC1.

Administration of ADC2 to mice bearing TM00226 tumors over a 5-week period resulted in initial tumor regression followed by re-growth after week 4 (FIG. 118A). At the end of the study, tumors treated with ADC2 were smaller in size compared to tumors treated with placebo (FIG. 118B). As shown in FIG. 118C, no changes in body weights of mice were observed before and after treatment with ADC2.

Selected Conclusions

ADC1 administration to mice bearing the TM00226 PDX model of lung adenocarcinoma over a five-week period resulted in sustained regression of tumors during the 50-day study period. Animals treated with ADC1 or placebo did not show significant changes in body weight during the study, suggesting the ADC1 administration did not have an adverse impact on the animals' ability to thrive. This suggests ADC1 is a promising drug candidate for further development for treatment of lung adenocarcinoma.

Treatment of mice bearing TM00266 PDX model of lung adenocarcinoma with ADC2 resulted in initial regression of tumors followed by re-growth after week 4. Animals treated with ADC2 did not show significant changes in body weights during the study period, suggesting that ADC2 administration did not have an adverse impact on the animals' ability to thrive.

Enumerated Embodiments

The following enumerated embodiments are provided, the numbering of which is not to be construed as designating levels of importance.

Embodiment 1 provides an antibody or antigen-binding fragment thereof that specifically binds to an epitope of human EPH Receptor A5, wherein the antibody or antigen-binding fragment comprises:

a. a heavy chain variable region comprising three heavy chain complementarity-determining regions (HCDRs), wherein HCDR1 comprises the amino acid sequence set forth in SEQ ID NO:16, HCDR2 comprises the amino acid sequence selected from the group consisting of SEQ ID NOs:17-19, and HCDR3 comprises the amino acid sequence set forth in SEQ ID NO:20; and b. a light chain variable region comprises three light chain complementarity-determining regions (LCDRs), wherein LCDR1 comprises the amino acid sequence selected from the group consisting of SEQ ID NOs:21 and 22, LCDR2 comprises the amino acid sequence set forth in SEQ ID NO:23, and LCDR3 comprises the amino acid sequence set forth in SEQ ID NO:24.

Embodiment 2 provides the antibody or antigen-binding fragment of Embodiment 1, wherein the antibody or antigen-binding fragment further comprises:

a. a heavy chain comprising a heavy chain variable region comprising an amino acid sequence having at least 85% sequence identity to SEQ ID NO:1; and b. a light chain comprising a light chain variable region comprising an amino acid sequence having at least 85% sequence identity to SEQ ID NO:8;

Embodiment 3 provides the antibody or antigen-binding fragment of Embodiment 1 or 2, wherein:

a. the heavy chain variable region comprises a HCDR1 comprising the amino acid sequence set forth in SEQ ID NO:16, a HCDR2 comprising the amino acid sequence set forth in SEQ ID NO:17, and a HCDR3 comprising the amino acid sequence set forth in SEQ ID NO:20; and the light chain variable region comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24;

b. the heavy chain variable region comprises a HCDR1 comprising the amino acid sequence set forth in SEQ ID NO:16, a HCDR2 comprising the amino acid sequence set forth in SEQ ID NO:18, and a HCDR3 comprising the amino acid sequence set forth in SEQ ID NO:20; and the light chain variable region comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24;

c. the heavy chain variable region comprises a HCDR1 comprising the amino acid sequence set forth in SEQ ID NO:16, a HCDR2 comprising the amino acid sequence set forth in SEQ ID NO:19, and a HCDR3 comprising the amino acid sequence set forth in SEQ ID NO:20; and the light chain variable region comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24;

d. the heavy chain variable region comprises a HCDR1 comprising the amino acid sequence set forth in SEQ ID NO:16, a HCDR2 comprising the amino acid sequence set forth in SEQ ID NO:17, and a HCDR3 comprising the amino acid sequence set forth in SEQ ID NO:20; and the light chain variable region comprises a LCDR1 comprising the amino acid sequence set forth in SEQ ID NO:22, a LCDR2 comprising the amino acid sequence set forth in SEQ ID NO:23, and a LCDR3 comprising the amino acid sequence set forth in SEQ ID NO:24;

e. the heavy chain variable region comprises a HCDR1 comprising the amino acid sequence set forth in SEQ ID NO:16, a HCDR2 comprising the amino acid sequence set forth in SEQ ID NO:18, and a HCDR3 comprising the amino acid sequence set forth in SEQ ID NO:20; and the light chain variable region comprises a LCDR1 comprising the amino acid sequence set forth in SEQ ID NO:22, a LCDR2 comprising the amino acid sequence set forth in SEQ ID NO:23, and a LCDR3 comprising the amino acid sequence set forth in SEQ ID NO:24; or f. the heavy chain variable region comprises a HCDR1 comprising the amino acid sequence set forth in SEQ ID NO:16, a HCDR2 comprising the amino acid sequence set forth in SEQ ID NO:19, and a HCDR3 comprising the amino acid sequence set forth in SEQ ID NO:20; and the light chain variable region comprises a LCDR1 comprising the amino acid sequence set forth in SEQ ID NO:22, a LCDR2 comprising the amino acid sequence set forth in SEQ ID NO:23, and a LCDR3 comprising the amino acid sequence set forth in SEQ ID NO:24.

Embodiment 4 provides the antibody or antigen-binding fragment thereof of any one of Embodiments 1-3, wherein the amino acid sequence of the heavy chain variable region has at least 85%, 90%, 91%, 92%, 93%, 94%, 95%, 96%, 97%, 98%, or 99% sequence identity to the amino acid sequence selected from the group consisting of SEQ ID NOs:2-7.

Embodiment 5 provides the antibody or antigen-binding fragment thereof of any one of Embodiments 1-4, wherein the heavy chain variable region comprises the amino acid sequence selected from the group consisting of SEQ ID NOs:2-7.

Embodiment 6 provides the antibody or antigen-binding fragment thereof of any one of Embodiments 1-5, wherein the heavy chain variable region consists of the amino acid sequence selected from the group consisting of SEQ ID NOs:2-7.

Embodiment 7 provides the antibody or antigen-binding fragment thereof of any one of Embodiments 1-6, wherein the heavy chain variable region is encoded by a nucleic acid sequence selected from the group consisting of SEQ ID NOs:26-31.

Embodiment 8 provides the antibody or antigen-binding fragment thereof of any one of Embodiments 1-7, wherein the amino acid sequence of the light chain variable region has at least 85%, 90%, 95%, 96%, 97%, 98%, or 99% sequence identity to the amino acid sequence selected from the group consisting of SEQ ID NOs:9-13.

Embodiment 9 provides the antibody or antigen-binding fragment thereof of any one of Embodiments 1-3 and 8, wherein the light chain variable region comprises the amino acid sequence selected from the group consisting of SEQ ID NOs:9-13.

Embodiment 10 provides the antibody or antigen-binding fragment thereof of any one of Embodiments 1-3 and 8-9, wherein the light chain variable region consists of the amino acid sequence selected from the group consisting of SEQ ID NOs:9-13.

Embodiment 11 provides the antibody or antigen-binding fragment thereof of any one of Embodiments 1-3 and 8-9, wherein the light chain variable region is encoded by a nucleic acid sequence selected from the group consisting of SEQ ID NOs:33-37.

Embodiment 12 provides the antibody or antigen binding fragment thereof of any one of Embodiments 1-11, wherein:

a. the heavy chain variable region is set forth in SEQ ID NO:2 and the light chain variable region is set forth in SEQ ID NO:9;

b. the heavy chain variable region is set forth in SEQ ID NO:2 and the light chain variable region is set forth in SEQ ID NO:10;

c. the heavy chain variable region is set forth in SEQ ID NO:2 and the light chain variable region is set forth in SEQ ID NO:11;

d. the heavy chain variable region is set forth in SEQ ID NO:2 and the light chain variable region is set forth in SEQ ID NO:12;

e. the heavy chain variable region is set forth in SEQ ID NO:2 and the light chain variable region is set forth in SEQ ID NO:13;

f. the heavy chain variable region is set forth in SEQ ID NO:3 and the light chain variable region is set forth in SEQ ID NO:9;

g. the heavy chain variable region is set forth in SEQ ID NO:3 and the light chain variable region is set forth in SEQ ID NO:10;

h. the heavy chain variable region is set forth in SEQ ID NO:3 and the light chain variable region is set forth in SEQ ID NO:11;

i. the heavy chain variable region is set forth in SEQ ID NO:3 and the light chain variable region is set forth in SEQ ID NO:12;

j. the heavy chain variable region is set forth in SEQ ID NO:3 and the light chain variable region is set forth in SEQ ID NO:13;

k. the heavy chain variable region is set forth in SEQ ID NO:4 and the light chain variable region is set forth in SEQ ID NO:9;

l. the heavy chain variable region is set forth in SEQ ID NO:4 and the light chain variable region is set forth in SEQ ID NO:10;

m. the heavy chain variable region is set forth in SEQ ID NO:4 and the light chain variable region is set forth in SEQ ID NO:11;

n. the heavy chain variable region is set forth in SEQ ID NO:4 and the light chain variable region is set forth in SEQ ID NO:12;

o. the heavy chain variable region is set forth in SEQ ID NO:4 and the light chain variable region is set forth in SEQ ID NO:13;

p. the heavy chain variable region is set forth in SEQ ID NO:5 and the light chain variable region is set forth in SEQ ID NO:9;

q. the heavy chain variable region is set forth in SEQ ID NO:5 and the light chain variable region is set forth in SEQ ID NO:10;

r. the heavy chain variable region is set forth in SEQ ID NO:5 and the light chain variable region is set forth in SEQ ID NO:11;

s. the heavy chain variable region is set forth in SEQ ID NO:5 and the light chain variable region is set forth in SEQ ID NO:12;

t. the heavy chain variable region is set forth in SEQ ID NO:5 and the light chain variable region is set forth in SEQ ID NO:13;

u. the heavy chain variable region is set forth in SEQ ID NO:6 and the light chain variable region is set forth in SEQ ID NO:9;

v. the heavy chain variable region is set forth in SEQ ID NO:6 and the light chain variable region is set forth in SEQ ID NO:10;

w. the heavy chain variable region is set forth in SEQ ID NO:6 and the light chain variable region is set forth in SEQ ID NO:11;

x. the heavy chain variable region is set forth in SEQ ID NO:6 and the light chain variable region is set forth in SEQ ID NO:12;

y. the heavy chain variable region is set forth in SEQ ID NO:6 and the light chain variable region is set forth in SEQ ID NO:13;

z. the heavy chain variable region is set forth in SEQ ID NO:7 and the light chain variable region is set forth in SEQ ID NO:9;

aa. the heavy chain variable region is set forth in SEQ ID NO:7 and the light chain variable region is set forth in SEQ ID NO:10;

bb. the heavy chain variable region is set forth in SEQ ID NO:7 and the light chain variable region is set forth in SEQ ID NO:11;

cc. the heavy chain variable region is set forth in SEQ ID NO:7 and the light chain variable region is set forth in SEQ ID NO:12; or dd. the heavy chain variable region is set forth in SEQ ID NO:7 and the light chain variable region is set forth in SEQ ID NO:13.

Embodiment 13 provides the antibody or antigen binding fragment thereof of any one of Embodiments 1-11, wherein:

a. the heavy chain variable region comprises a sequence that has at least 90% sequence identity to the sequence set forth in SEQ ID NO:2 and the light chain variable region comprises a sequence that has at least 90% sequence identity to the sequence set forth in SEQ ID NO:9;

b. the heavy chain variable region comprises a sequence that has at least 90% sequence identity to the sequence set forth in SEQ ID NO:2 and the light chain variable region comprises a sequence that has at least 90% sequence identity to the sequence set forth in SEQ ID NO:10;

c. the heavy chain variable region comprises a sequence that has at least 90% sequence identity to the sequence set forth in SEQ ID NO:2 and the light chain variable region comprises a sequence that has at least 90% sequence identity to the sequence set forth in SEQ ID NO:11;

d. the heavy chain variable region comprises a sequence that has at least 90% sequence identity to the sequence set forth in SEQ ID NO:2 and the light chain variable region comprises a sequence that has at least 90% sequence identity to the sequence set forth in SEQ ID NO:12;

e. the heavy chain variable region comprises a sequence that has at least 90% sequence identity to the sequence set forth in SEQ ID NO:2 and the light chain variable region comprises a sequence that has at least 90% sequence identity to the sequence set forth in SEQ ID NO:13;

f. the heavy chain variable region comprises a sequence that has at least 90% sequence identity to the sequence set forth in SEQ ID NO:3 and the light chain variable region comprises a sequence that has at least 90% sequence identity to the sequence set forth in SEQ ID NO:9;

g. the heavy chain variable region comprises a sequence that has at least 90% sequence identity to the sequence set forth in SEQ ID NO:3 and the light chain variable region comprises a sequence that has at least 90% sequence identity to the sequence set forth in SEQ ID NO:10;

h. the heavy chain variable region comprises a sequence that has at least 90% sequence identity to the sequence set forth in SEQ ID NO:3 and the light chain variable region comprises a sequence that has at least 90% sequence identity to the sequence set forth in SEQ ID NO:11;

i. the heavy chain variable region comprises a sequence that has at least 90% sequence identity to the sequence set forth in SEQ ID NO:3 and the light chain variable region comprises a sequence that has at least 90% sequence identity to the sequence set forth in SEQ ID NO:12;

j. the heavy chain variable region comprises a sequence that has at least 90% sequence identity to the sequence set forth in SEQ ID NO:3 and the light chain variable region comprises a sequence that has at least 90% sequence identity to the sequence forth in SEQ ID NO:13;

k. the heavy chain variable region comprises a sequence that has at least 90% sequence identity to the sequence set forth in SEQ ID NO:4 and the light chain variable region comprises a sequence that has at least 90% sequence identity to the sequence set forth in SEQ ID NO:9;

l. the heavy chain variable region comprises a sequence that has at least 90% sequence identity to the sequence set forth in SEQ ID NO:4 and the light chain variable region comprises a sequence that has at least 90% sequence identity to the sequence set forth in SEQ ID NO:10;

m. the heavy chain variable region comprises a sequence that has at least 90% sequence identity to the sequence set forth in SEQ ID NO:4 and the light chain variable region comprises a sequence that has at least 90% sequence identity to the sequence set forth in SEQ ID NO:11;

n. the heavy chain variable region comprises a sequence that has at least 90% sequence identity to the sequence set forth in SEQ ID NO:4 and the light chain variable region comprises a sequence that has at least 90% sequence identity to the sequence set forth in SEQ ID NO:12;

o. the heavy chain variable region comprises a sequence that has at least 90% sequence identity to the sequence set forth in SEQ ID NO:4 and the light chain variable region comprises a sequence that has at least 90% sequence identity to the sequence set forth in SEQ ID NO:13;

p. the heavy chain variable region comprises a sequence that has at least 90% sequence identity to the sequence set forth in SEQ ID NO:5 and the light chain variable region comprises a sequence that has at least 90% sequence identity to the sequence set forth in SEQ ID NO:9;

q. the heavy chain variable region comprises a sequence that has at least 90% sequence identity to the sequence set forth in SEQ ID NO:5 and the light chain variable region comprises a sequence that has at least 90% sequence identity to the sequence set forth in SEQ ID NO:10;

r. the heavy chain variable region comprises a sequence that has at least 90% sequence identity to the sequence set forth in SEQ ID NO:5 and the light chain variable region comprises a sequence that has at least 90% sequence identity to the sequence set forth in SEQ ID NO:11;

s. the heavy chain variable region comprises a sequence that has at least 90% sequence identity to the sequence set forth in SEQ ID NO:5 and the light chain variable region comprises a sequence that has at least 90% sequence identity to the sequence set forth in SEQ ID NO:12;

t. the heavy chain variable region comprises a sequence that has at least 90% sequence identity to the sequence set forth in SEQ ID NO:5 and the light chain variable region comprises a sequence that has at least 90% sequence identity to the sequence set forth in SEQ ID NO:13;

u. the heavy chain variable region comprises a sequence that has at least 90% sequence identity to the sequence set forth in SEQ ID NO:6 and the light chain variable region comprises a sequence that has at least 90% sequence identity to the sequence set forth in SEQ ID NO:9;

v. the heavy chain variable region comprises a sequence that has at least 90% sequence identity to the sequence set forth in SEQ ID NO:6 and the light chain variable region comprises a sequence that has at least 90% sequence identity to the sequence set forth in SEQ ID NO:10;

w. the heavy chain variable region comprises a sequence that has at least 90% sequence identity to the sequence set forth in SEQ ID NO:6 and the light chain variable region comprises a sequence that has at least 90% sequence identity to the sequence set forth in SEQ ID NO:11;

x. the heavy chain variable region comprises a sequence that has at least 90% sequence identity to the sequence set forth in SEQ ID NO:6 and the light chain variable region comprises a sequence that has at least 90% sequence identity to the sequence set forth in SEQ ID NO:12;

y. the heavy chain variable region comprises a sequence that has at least 90% sequence identity to the sequence set forth in SEQ ID NO:6 and the light chain variable region comprises a sequence that has at least 90% sequence identity to the sequence set forth in SEQ ID NO:13;

z. the heavy chain variable region comprises a sequence that has at least 90% sequence identity to the sequence set forth in SEQ ID NO:7 and the light chain variable region comprises a sequence that has at least 90% sequence identity to the sequence set forth in SEQ ID NO:9;

aa. the heavy chain variable region comprises a sequence that has at least 90% sequence identity to the sequence set forth in SEQ ID NO:7 and the light chain variable region comprises a sequence that has at least 90% sequence identity to the sequence set forth in SEQ ID NO:10;

bb. the heavy chain variable region comprises a sequence that has at least 90% sequence identity to the sequence set forth in SEQ ID NO:7 and the light chain variable region comprises a sequence that has at least 90% sequence identity to the sequence set forth in SEQ ID NO:11;

cc. the heavy chain variable region comprises a sequence that has at least 90% sequence identity to the sequence set forth in SEQ ID NO:7 and the light chain variable region comprises a sequence that has at least 90% sequence identity to the sequence set forth in SEQ ID NO:12; or dd. the heavy chain variable region comprises a sequence that has at least 90% sequence identity to the sequence set forth in SEQ ID NO:7 and the light chain variable region comprises a sequence that has at least 90% sequence identity to the sequence set forth in SEQ ID NO:13.

Embodiment 14 provides an antibody or antigen-binding fragment thereof that specifically binds to an epitope of human EPH Receptor A5, wherein the antibody or antigen-binding fragment comprises:

a. a heavy chain comprising a heavy chain variable region comprising a heavy chain complementarity-determining region 1 (HCDR1) comprising the sequence set forth in SEQ ID NO:16, a HCDR2 comprising the sequence set forth in SEQ ID NO:18, a HCDR3 set forth in SEQ ID NO:20; and b. a light chain comprising a light chain variable region comprising a light chain complementarity determining region 1 (LCDR1) comprising the sequence set forth in SEQ ID NO:21, a LCDR2 comprising the sequence set forth in SEQ ID NO:23, and an LCDR3 comprising the sequence set forth in SEQ ID NO:24.

Embodiment 15 provides an antibody or antigen-binding fragment thereof that specifically binds to an epitope of human EPH Receptor A5, wherein the antibody or antigen-binding fragment comprises:

a. a heavy chain comprising a heavy chain variable region comprising a heavy chain complementarity-determining region 1 (HCDR1) comprising the sequence set forth in SEQ ID NO:16, a HCDR2 comprising the sequence set forth in SEQ ID NO:19, a HCDR3 set forth in SEQ ID NO:20; and b. a light chain comprising a light chain variable region comprising a light chain complementarity determining region 1 (LCDR1) comprising the sequence set forth in SEQ ID NO:21, an LCDR2 comprising the sequence set forth in SEQ ID NO:23, and an LCDR3 comprising the sequence set forth in SEQ ID NO:24.

Embodiment 16 provides an antibody or antigen-binding fragment thereof that specifically binds to an epitope of human EPH Receptor A5, wherein the antibody or antigen-binding fragment comprises:

a. a heavy chain comprising a heavy chain variable region comprising a heavy chain complementarity-determining region 1 (HCDR1) comprising the sequence set forth in SEQ ID NO:16, a HCDR2 comprising the sequence set forth in SEQ ID NO:17, a HCDR3 set forth in SEQ ID NO:20; and b. a light chain comprising a light chain variable region comprising a complementarity determining region 1 (LCDR1) comprising the sequence set forth in SEQ ID NO:22, an LCDR2 comprising the sequence set forth in SEQ ID NO:23, and an LCDR3 comprising the sequence set forth in SEQ ID NO:24.

Embodiment 17 provides an antibody or antigen-binding fragment thereof that specifically binds to an epitope of human EPH Receptor A5, wherein the antibody or antigen-binding fragment comprises:

a. a heavy chain comprising a heavy chain variable region comprising a heavy chain complementarity-determining region 1 (HCDR1) comprising the sequence set forth in SEQ ID NO:16, a HCDR2 comprising the sequence set forth in SEQ ID NO:18, a HCDR3 set forth in SEQ ID NO:20; and b. a light chain comprising a light chain variable region comprising a light chain complementarity determining region 1 (LCDR1) comprising the sequence set forth in SEQ ID NO:22, LCDR2 comprising the sequence set forth in SEQ ID NO:23, and an LCDR3 comprising the sequence set forth in SEQ ID NO:24.

Embodiment 18 provides an antibody or antigen-binding fragment thereof comprising:

a. a heavy chain comprising a heavy chain variable region comprising the amino acid sequence set forth in SEQ ID NO:5; and b. a light chain comprising a light chain variable region comprising the amino acid sequence set forth in SEQ ID NO:11.

Embodiment 19 provides an antibody or antigen-binding fragment thereof comprising:

a. a heavy chain comprising a heavy chain variable region comprising the amino acid sequence set forth in SEQ ID NO:6; and b. a light chain comprising a light chain variable region comprising the amino acid sequence set forth in SEQ ID NO:11.

Embodiment 20 provides the antibody or antigen-binding fragment thereof of any one of Embodiments 1-19, wherein the antibody or antigen-binding fragment thereof is selected from the group consisting of a full-length antibody, a Fab, and a single-chain variable fragment (scFv).

Embodiment 21 provides the antibody or antigen-binding fragment thereof of any one of Embodiments 1-20, wherein the antibody or antigen-binding fragment thereof is a full-length antibody.

Embodiment 22 provides the antibody or antigen-binding fragment thereof of any one of Embodiments 1-21, wherein the antibody is humanized.

Embodiment 23 provides the antibody or antigen-binding fragment thereof of any one of Embodiments 1-22, wherein the heavy chain further comprises a constant domain of a human immunoglobulin heavy chain and the light chain further comprises a constant domain of a human light chain.

Embodiment 24 provides the antibody or antigen-binding fragment thereof of Embodiment 23, wherein the constant domain of a human immunoglobulin heavy chain is from a IgG1 heavy chain.

Embodiment 25 provides the antibody or antigen-binding fragment thereof of Embodiment 23 or 24 wherein the constant domain of a human immunoglobulin heavy chain comprises the amino acid sequence set forth in SEQ ID NO:14.

Embodiment 26 provides the antibody of Embodiment 23, wherein the constant domain of a human light chain is from a human kappa light chain.

Embodiment 27 provides the antibody or antigen-binding fragment thereof of Embodiment 23 or Embodiment 26, wherein the constant domain of a human light chain comprises the amino acid sequence set forth in SEQ ID NO:15.

Embodiment 28 provides an antibody or antigen-binding fragment thereof that specifically binds to an epitope of human EPH Receptor A5, wherein the antibody or antigen-binding fragment comprises:

a. a heavy chain comprising at least 85%, 90%, 91%, 92%, 93%, 94%, 95%, 96%, 97%, 98%, or 99% sequence identity to the amino acid sequence set forth in SEQ ID NO:38; and b. a light chain comprising at least 85%, 90%, 91%, 92%, 93%, 94%, 95%, 96%, 97%, 98%, or 99% sequence identity to the amino acid sequence set forth in SEQ ID NOs:40.

Embodiment 29 provides the antibody or antigen-binding fragment of Embodiment 28, wherein:

a. the variable region of the heavy chain comprises a HCDR1 comprising the amino acid sequence set forth in SEQ ID NO:16, a HCDR2 comprising the amino acid sequence set forth in SEQ ID NO:17, and a HCDR3 comprising the amino acid sequence set forth in SEQ ID NO:20; and b. the variable region of the light chain comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24.

Embodiment 30 provides the antibody or antigen-binding fragment thereof of any of Embodiments 1-29, wherein the heavy chain is set forth in SEQ ID NO:38 and the light chain is set forth in SEQ ID NO:40.

Embodiment 31 provides an antibody or antigen-binding fragment thereof that specifically binds to an epitope of human EPH Receptor A5, wherein the antibody or antigen-binding fragment comprises:

a. a heavy chain comprising at least 85%, 90%, 91%, 92%, 93%, 94%, 95%, 96%, 97%, 98%, or 99% sequence identity to the amino acid sequence set forth in SEQ ID NO:39; and b. a light chain comprising at least 85%, 90%, 91%, 92%, 93%, 94%, 95%, 96%, 97%, 98%, or 99% sequence identity to the amino acid sequence set forth in SEQ ID NO:40.

Embodiment 32 provides the antibody or antigen-binding fragment of Embodiment 31, wherein:

a. the variable region of the heavy chain comprises a HCDR1 comprising the amino acid sequence set forth in SEQ ID NO:16, a HCDR2 comprising the amino acid sequence set forth in SEQ ID NO:18, and a HCDR3 comprising the amino acid sequence set forth in SEQ ID NO:20; and b. the variable region of the light chain comprises a LCDR1 comprising the amino acid sequence set forth in SEQ ID NO:21, a LCDR2 comprising the amino acid sequence set forth in SEQ ID NO:23, and a LCDR3 comprising the amino acid sequence set forth in SEQ ID NO:24.

Embodiment 33 provides the antibody or antigen-binding fragment thereof of any of Embodiments 1-27, 31, and 32, wherein the heavy chain is set forth in SEQ ID NO:39 and the light chain is set forth in SEQ ID NO:40.

Embodiment 34 provides the antibody or antigen-binding fragment thereof of any one of Embodiments 1-33, wherein the dissociation constant ($K_D$) for binding to human EpHA5 is less than $1.25 \times 10^{-9}$ M.

Embodiment 35 provides the antibody or antigen-binding fragment thereof of any one of Embodiments 1-34, wherein the dissociation constant ($K_D$) for binding to human EpHA5 is between $8 \times 10^{-10}$ M and $1.1 \times 10^{-9}$ M.

Embodiment 36 provides the antibody or antigen-binding fragment thereof of any one of Embodiments 1-35, wherein the antibody or antigen-binding fragment has a dissociation constant ($K_D$) for binding to human EpHA5 that is within 2-fold better than a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

Embodiment 37 provides the antibody or antigen-binding fragment thereof of any one of Embodiments 1-36, wherein the dissociation constant ($K_D$) for binding to human EpHA5 is more than 1.2 fold better than a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

Embodiment 38 provides the antibody or antigen-binding fragment thereof of any one of Embodiments 34-37, wherein the dissociation constant ($K_D$) is determined by Biacore.

Embodiment 39 provides the antibody or antigen-binding fragment thereof of any one of Embodiments 1-38, which exhibits increased thermal stability compared to a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

Embodiment 40 provides the antibody or antigen-binding fragment thereof of any one of Embodiments 1-39, wherein the antibody or antigen-binding fragment has a melting temperature profile with a Tm1 that is increased greater than or about 5° C. compared to a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

Embodiment 41 provides the antibody or antigen-binding fragment thereof of any one of Embodiments 1-40, wherein the antibody or antigen-binding fragment has a melting temperature profile with a Tm1 that is increased greater than or about 10° C. compared to a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

Embodiment 42 provides the antibody or antigen-binding fragment of Embodiment 40 or 41, wherein the Tm1 of the thermal unfolding curve of the antibody or antigen-binding fragment is greater than 60° C.

Embodiment 43 provides the antibody or antigen-binding fragment thereof of any one of Embodiments 40-42, wherein Tm1 of the antibody or antigen-binding fragment is between about 60° C. and about 70° C.

Embodiment 44 provides the antibody or antigen-binding fragment thereof of any one of Embodiments 40-43, wherein the Tm1 of the antibody or antigen-binding fragment is about 64° C., about 65° C., about 66° C., about 67° C., about 68° C., or about 69° C.

Embodiment 45 provides the antibody or antigen-binding fragment thereof of any one of Embodiments 40-44, wherein the melting temperature profile is monophasic.

Embodiment 46 provides the antibody or antigen-binding fragment thereof of any one of Embodiments 1-45, wherein onset temperature of aggregation (Tagg) of the antibody or antigen-binding fragment is increased greater than about 1° C., greater than about 2° C., greater than about 3° C., greater than about 4° C. or greater than about 5° C. compared to a reference antibody, wherein the reference antibody is 11C12 or an antibody comprising a variable heavy chain set forth in SEQ ID NO:1 and a variable light chain set forth in SEQ ID NO:8.

Embodiment 47 provides the antibody or antigen-binding fragment thereof of any of Embodiments 1-46, wherein onset temperature of aggregation (Tagg) of the antibody or antigen-binding fragment is greater than about 67° C.

Embodiment 48 provides the antibody or antigen-binding fragment thereof of any of Embodiments 1-47, wherein onset temperature of aggregation (Tagg) of the antibody or antigen-binding fragment is between about 67° C. and about 71° C.

Embodiment 49 provides the antibody or antigen-binding fragment thereof of any of Embodiments 1-48, wherein the Tagg of the antibody or antigen-binding fragment is about 67° C., about 68° C., about 69° C., about 70° C., or about 71° C.

Embodiment 50 provides the antibody or antigen-binding fragment thereof of any one of Embodiments 1-49, wherein the antibody or antigen-binding fragment binds to cell surface human EphA5.

Embodiment 51 provides the antibody or antigen-binding fragment thereof of any one of Embodiments 1-50, wherein the antibody or fragment binds human EphA5 expressed on the surface of cells, optionally an H460 cell line, with an EC50 that is increased compared to a reference antibody, wherein the reference antibody is 11C12 or an antibody comprising a variable heavy chain set forth in SEQ ID NO:1 and a variable light chain set forth in SEQ ID NO:8, optionally wherein the reference antibody is of the same form.

Embodiment 52 provides the antibody or antigen-binding fragment thereof of any one of Embodiments 1-51, wherein the antibody or fragment binds human EphA5 expressed on the surface of cells, optionally an H460 cell line, with an EC50 of less than or equal to 0.020 µg/mL optionally wherein the EC50 is determined by flow cytometry.

Embodiment 53 provides the antibody or antigen-binding fragment thereof of any one of Embodiments 1-52, wherein the antibody or fragment binds human EphA5 expressed on the surface of cells, optionally an H460 cell line, with an EC50 of between about 0.010 µg/mL and 0.020 µg/mL, optionally wherein the EC50 is determined by flow cytometry.

Embodiment 54 provides the antibody or antigen-binding fragment thereof of any one of Embodiments 1-53, wherein the antibody or fragment binds human EphA5 expressed on the surface of cells, optionally an H460 cell line, with an EC50 of about 0.015 µg/mL, about 0.016 µg/mL, about 0.017 µg/mL, about 0.018 µg/mL, about 0.019 µg/mL, or about 0.020 µg/mL, optionally wherein the EC50 is determined by flow cytometry.

Embodiment 55 provides the antibody or antigen-binding fragment thereof of any one of Embodiments 1-54, wherein the antibody or antigen-binding fragment is internalized by human EphA5-expressing cells.

Embodiment 56 provides a nucleic acid encoding the heavy chain of the antibody or antigen-binding fragment thereof of any one of Embodiments 1-55.

Embodiment 57 provides a nucleic acid encoding the light chain of the antibody or antigen-binding fragment thereof of any one of Embodiments 1-55.

Embodiment 58 provides a nucleic acid encoding the heavy chain and the light chain of the antibody or antigen-binding fragment thereof of any one of Embodiments 1-55.

Embodiment 59 provides a vector comprising the nucleic acid of any one of Embodiments 56-58.

Embodiment 60 provides the vector of Embodiment 59, wherein the vector is an expression vector.

Embodiment 61 provides a vector comprising a nucleic acid encoding the heavy chain and a nucleic acid encoding the light chain, wherein the heavy chain and light chain is of the antibody or antigen-binding fragment thereof of any one of Embodiments 1-58.

Embodiment 62 provides the vector of Embodiment 61, which is a bicistronic vector.

Embodiment 63 provides a vector system comprising a first vector comprising a first nucleic acid encoding a heavy chain and a second vector comprising a second nucleic acid encoding a light chain, wherein the heavy chain and the light chain is of the antibody or antigen-binding fragment thereof of any one of Embodiments 1-58.

Embodiment 64 provides the vector system of Embodiment 63, wherein the first vector and the second vector are each an expression vector.

Embodiment 65 provides a host cell comprising the vector of any one of Embodiments 61-62 or the vector system of any one of Embodiments 63-64.

Embodiment 66 provides the host cell of Embodiment 65, which is a mammalian cell.

Embodiment 67 provides a method of producing an antibody, the method comprising introducing a vector of any one of Embodiments 61-62 and/or a vector system of any one of Embodiments 63-64 into a host cell, culturing the host cell under conditions for expression of an antibody or antigen binding fragment from the host cell, and isolating or purifying the antibody or antigen-binding fragment.

Embodiment 68 provides the method of Embodiment 67, wherein the host cell is a mammalian cell.

Embodiment 69 provides an immunoconjugate having the formula Ab-(L-D), wherein:

Ab is the antibody or antigen-binding fragment thereof of any one of Embodiments 1-55;

L is a linker; and

D is a cytotoxic drug.

Embodiment 70 provides the immunoconjugate of Embodiment 69, wherein the linker is a cleavable linker.

Embodiment 71 provides the immunoconjugate of Embodiment 69 or Embodiment 70, wherein the linker is a cathepsin-cleavable linker.

Embodiment 72 provides the immunoconjugate of Embodiment 71, wherein the cathepsin-cleavable linker comprises a valine-citruline (Val-Cit).

Embodiment 73 provides the immunoconjugate of any one of Embodiments 68-72, wherein the linker is MC-VCP, having the structure:

Embodiment 74 provides the immunoconjugate of any one of Embodiments 69-72, wherein the linker comprises the structure:

or

-continued

Embodiment 75 provides the immunoconjugate of any one of Embodiments 68-74, wherein the linker is a pH cleavable linker.

Embodiment 76 provides the immunoconjugate of any one of Embodiments 69-79 and 75, wherein the linker is CL2A, having the structure:

Embodiment 77 provides the immunoconjugate of any one of Embodiments 69-76, wherein the cytotoxic drug is an auristatin.

Embodiment 78 provides the immunoconjugate of Embodiment 77, wherein the auristatin is monomethyl auristatin E (MMAE) having the structure:

Embodiment 79 provides the immunoconjugate of any one of Embodiments 69-73, 77, and 78, wherein the L-D comprises the structure:

Embodiment 80 provides the immunoconjugate of any one of Embodiments 69-72, 74, 77, and 78, wherein the L-D comprises the structure:

Embodiment 81 provides an immunoconjugate having the formula Ab-(L-D), wherein:

Ab is an antibody that specifically binds to an epitope of human EPH Receptor A5 (EphA5) comprising the heavy chain set forth in SEQ ID NO:38 and the light chain set forth in SEQ ID NO:40; and the L-D comprises the structure:

Embodiment 82 provides an immunoconjugate having the formula Ab-(L-D), wherein:

Ab is an antibody that specifically binds to an epitope of human EPH Receptor A5 (EphA5) comprising the heavy chain set forth in SEQ ID NO:39 and the light chain set forth in SEQ ID NO:40; and the L-D comprises the structure:

Embodiment 83 provides the immunoconjugate of any one of Embodiments 69-76, wherein the cytotoxic drug is SN38, having the structure:

Embodiment 84 provides the immunoconjugate of any one of Embodiments 69, 70, 75, 76, and 83 wherein the L-D comprises the structure:

Embodiment 85 provides the immunoconjugate of any one of Embodiments 69-72, 74 and 83, wherein the L-D comprises the structure:

Embodiment 86 provides the immunoconjugate of any one of Embodiments 69-85, wherein the drug to antibody ratio is about 4.

Embodiment 87 provides the immunoconjugate of any one of Embodiments 69-85, wherein the drug to antibody ratio is about 8.

Embodiment 88 provides a pharmaceutical composition comprising the antibody or antigen-binding fragment thereof of any one of Embodiments 1-55 and a pharmaceutically acceptable carrier.

Embodiment 89 provides a pharmaceutical composition comprising the immunoconjugate of any one of Embodiments 69-87 and a pharmaceutically acceptable carrier.

Embodiment 90 provides the antibody or antigen-binding fragment thereof of any one of Embodiments 1-55 for use in the treatment, amelioration, and/or prevention of cancer in a subject in need thereof, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 91 provides the immunoconjugate of any one of Embodiments 69-78 for use in the treatment, amelioration, and/or prevention of cancer in a subject in need thereof, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 92 provides the pharmaceutical composition of Embodiment 88 for the use in treating, ameliorating, and/or preventing cancer in a subject in need thereof, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 93 provides the pharmaceutical composition of Embodiment 89 for use in treating, ameliorating, and/or preventing cancer in a subject in need thereof, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 94 provides the antibody or antigen-binding fragment thereof of any one of Embodiments 1-55 for use in inducing tumor regression in a subject, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 95 provides the immunoconjugate of any one of Embodiment 67-85 for use in inducing tumor regression in a subject in need thereof, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 96 provides the pharmaceutical composition of Embodiment 86 for use in inducing tumor regression in a subject in need thereof, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 97 provides the pharmaceutical composition of Embodiment 87 for use in inducing tumor regression in a subject in need thereof, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 98 provides a method of treating, ameliorating, and/or preventing cancer in a subject in need thereof, the method comprising administering to the subject a therapeutically effective amount of the antibody or antigen-binding fragment thereof of any one of Embodiments 1-55, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 99 provides a method of treating, ameliorating, and/or preventing cancer in a subject in need thereof, the method comprising administering to the subject a therapeutically effective amount of the immunoconjugate of any one of Embodiments 69-87, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 100 provides a method of treating, ameliorating, and/or preventing cancer in a subject in need thereof, the method comprising administering to the subject a therapeutically effective amount of the pharmaceutical composition of Embodiment 88, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 101 provides a method of treating, ameliorating, and/or preventing cancer in a subject in need thereof, the method comprising administering to the subject a therapeutically effective amount of the pharmaceutical composition of Embodiment 89, wherein the cancer is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 102 provides a method of inducing tumor regression in a subject in need thereof, the method comprising administering to the subject a therapeutically effective amount of the antibody or antigen-binding fragment thereof of any one of Embodiments 1-53, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 103 provides a method of inducing tumor regression in a subject in need thereof, the method comprising administering to the subject a therapeutically effective amount of the immunoconjugate of any one of Embodiment 67-85, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 104 provides a method of inducing tumor regression in a subject in need thereof, the method comprising administering to the subject a therapeutically effective amount of the pharmaceutical composition of Embodiment 86 wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Embodiment 105 provides a method of inducing tumor regression in a subject in need thereof, the method comprising administering to the subject a therapeutically effective amount of the pharmaceutical composition of Embodiment 87, wherein the tumor is a cancer, wherein the tumor is associated with expression of EPH Receptor A5, wherein the EPH Receptor A5 is expressed on the cancer cells, and wherein the cancer is selected from the group consisting of lung cancer, breast cancer, esophageal cancer, gastric cancer, and ovarian cancer.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An immunoconjugate having the formula Ab-(L-D), wherein:

(a) Ab is an antibody comprising a heavy chain (HC) variable region and a light chain (LC) variable region, wherein the heavy chain variable region comprises three heavy chain complementarity-determining regions (HCDRs), wherein:

(i) HCDR1 comprises the amino acid sequence set forth in SEQ ID NO: 16, (ii) HCDR2 comprises the amino acid sequence set forth in SEQ ID NO: 17, and (iii) HCDR3 comprises the amino acid sequence set forth in SEQ ID NO: 20; and wherein the light chain variable region comprises three light chain complementarity-determining regions (LCDRs), wherein (iv) LCDR1 comprises the amino acid sequence set forth in SEQ ID NO 21, (v) LCDR2 comprises the amino acid sequence set forth in SEQ ID NO: 23, and (vi) LCDR3 comprises the amino acid sequence set forth in SEQ ID NO: 24, (b) L is a linker; and (c) D is a cytotoxic drug.

2. The immunoconjugate of claim 1, wherein the linker is a cleavable linker.

3. The immunoconjugate of claim 2, wherein the linker is a cathepsin-cleavable linker.

4. The immunoconjugate of claim 3, wherein the cathepsin-cleavable linker comprises a valine-citruline (Val-Cit).

5. The immunoconjugate of claim 2, wherein the linker is MC-VCP, having the structure:

6. The immunoconjugate of claim 2, wherein the linker comprises the structure:

or

-continued

7. The immunoconjugate of claim 1, wherein the linker is a pH cleavable linker.

8. The immunoconjugate of claim 7, wherein the linker is CL2A, having the structure:

9. The immunoconjugate of claim 1, wherein the cytotoxic drug is an auristatin.

10. The immunoconjugate of claim 9, wherein the auristatin is monomethyl auristatin E (MMAE) having the structure:

11. The immunoconjugate of claim 1, wherein the cyto-toxic drug is SN38, having the structure:

12. The immunoconjugate of claim 1, wherein the L-D comprises the structure:

13. The immunoconjugate of claim 1, wherein the L-D comprises the structure:

14. The immunoconjugate of claim 1, wherein the L-D comprises the structure:

15. The immunoconjugate of claim 1, wherein the L-D comprises the structure:

16. An immunoconjugate having the formula Ab-(L-D), wherein:

(a) Ab is an antibody comprising a heavy chain (HC) variable region and a light chain (LC) variable region, wherein the heavy chain variable region comprises three heavy chain complementarity-determining regions (HCDRs), wherein:

(i) HCDR1 comprises the amino acid sequence set forth in SEQ ID NO: 16, (ii) HCDR2 comprises the amino acid sequence set forth in SEQ ID NO: 17, and (iii) HCDR3 comprises the amino acid sequence set forth in SEQ ID NO: 20; and wherein the light chain variable region comprises three light chain complementarity-determining regions (LCDRs), wherein (iv) LCDR1 comprises the amino acid sequence set forth in SEQ ID NO: 22, (v) LCDR2 comprises the amino acid sequence set
forth in SEQ ID NO: 23, and (vi) LCDR3 comprises the amino acid sequence set
forth in SEQ ID NO: 24, (b) L is a linker; and (c) D is a cytotoxic drug.

17. The immunoconjugate of claim 16, wherein the linker
is a cleavable linker.

18. The immunoconjugate of claim 17, wherein the linker
is a cathepsin-cleavable linker.

19. The immunoconjugate of claim 18, wherein the cathe-
psin-cleavable linker comprises a valine-citruline (Val-Cit).

20. The immunoconjugate of claim 17, wherein the linker
is MC-VCP, having the structure:

21. The immunoconjugate of claim 17, wherein the linker
comprises the structure:

or

-continued

22. The immunoconjugate of claim 16, wherein the linker is a pH cleavable linker.

23. The immunoconjugate of claim 22, wherein the linker is CL2A, having the structure:

24. The immunoconjugate of claim 16, wherein the cytotoxic drug is an auristatin.

25. The immunoconjugate of claim 24, wherein the auristatin is monomethyl auristatin E (MMAE) having the structure:

26. The immunoconjugate of claim 16, wherein the cytotoxic drug is SN38, having the structure:

27. The immunoconjugate of claim 16, wherein the L-D comprises the structure:

28. The immunoconjugate of claim 16, wherein the L-D comprises the structure:

29. The immunoconjugate of claim 16, wherein the L-D comprises the structure:

30. The immunoconjugate of claim 16, wherein the L-D comprises the structure:

31. An immunoconjugate having the formula Ab-(L-D), wherein:

(a) Ab is an antibody having a heavy chain variable region and a light chain variable region, wherein the heavy chain variable region comprises three heavy chain complementarity-determining regions (HCDRs), wherein:

(i) HCDR1 comprises the amino acid sequence set forth in SEQ ID NO: 16, (ii) HCDR2 comprises the amino acid sequence set forth in SEQ ID NO: 18, and (iii) HCDR3 comprises the amino acid sequence set forth in SEQ ID NO: 20; and wherein the light chain variable region comprises three light chain complementarity-determining regions (LCDRs), wherein (iv) LCDR1 comprises the amino acid sequence set forth in SEQ ID NO: 21, (v) LCDR2 comprises the amino acid sequence set forth in SEQ ID NO: 23, and (vi) LCDR3 comprises the amino acid sequence set forth in SEQ ID NO: 24, (b) L is a linker; and (c) D is a cytotoxic drug.

32. The immunoconjugate of claim 31, wherein the linker is a cleavable linker.

33. The immunoconjugate of claim 32, wherein the linker is a cathepsin-cleavable linker.

34. The immunoconjugate of claim 33, wherein the cathepsin-cleavable linker comprises a valine-citruline (Val-Cit).

35. The immunoconjugate of claim 32, wherein the linker is MC-VCP, having the structure:

36. The immunoconjugate of claim 32, wherein the linker comprises the structure:

or

-continued

37. The immunoconjugate of claim 31, wherein the linker is a pH cleavable linker.

38. The immunoconjugate of claim 37, wherein the linker is CL2A, having the structure:

39. The immunoconjugate of claim 31, wherein the cytotoxic drug is an auristatin.

40. The immunoconjugate of claim 39, wherein the auristatin is monomethyl auristatin E (MMAE) having the structure:

41. The immunoconjugate of claim 31, wherein the cytotoxic drug is SN38, having the structure:

42. The immunoconjugate of claim 31, wherein the L-D comprises the structure:

43. The immunoconjugate of claim 31, wherein the L-D comprises the structure:

44. The immunoconjugate of claim 31, wherein the L-D comprises the structure:

45. The immunoconjugate of claim 31, wherein the L-D comprises the structure:

46. An immunoconjugate having the formula Ab-(L-D), wherein:

(a) Ab is an antibody comprising a heavy chain variable region and a light chain variable region, wherein the heavy chain variable region comprises three heavy chain complementarity-determining regions (HCDRs), wherein:

(i) HCDR1 comprises the amino acid sequence set forth in SEQ IID NO: 16, (ii) HCDR2 comprises the amino acid sequence set forth in SEQ IID NO: 18, and (iii) HCDR3 comprises the amino acid sequence set forth in SEQ IID NO: 20; and wherein the light chain variable region comprises three light chain complementarity-determining regions (LCDRs), wherein (iv) LCDR1 comprises the amino acid sequence set forth in SEQ ID NO: 22, (v) LCDR2 comprises the amino acid sequence set forth in SEQ ID NO: 23, and (vi) LCDR3 comprises the amino acid sequence set forth in SEQ ID NO: 24, (b) L is a linker; and (c) D is a cytotoxic drug.

47. The immunoconjugate of claim 46, wherein the linker is a cleavable linker.

48. The immunoconjugate of claim 47, wherein the linker is a cathepsin-cleavable linker.

49. The immunoconjugate of claim 48, wherein the cathepsin-cleavable linker comprises a valine-citruline (Val-Cit).

50. The immunoconjugate of claim 47, wherein the linker is MC-VCP, having the structure:

51. The immunoconjugate of claim 47, wherein the linker comprises the structure:

or

-continued

52. The immunoconjugate of claim 46, wherein the linker is a pH cleavable linker.

53. The immunoconjugate of claim 52, wherein the linker is CL2A, having the structure:

54. The immunoconjugate of claim 46, wherein the cytotoxic drug is an auristatin.

55. The immunoconjugate of claim 54, wherein the auristatin is monomethyl auristatin E (MMAE) having the structure:

56. The immunoconjugate of claim 46, wherein the cytotoxic drug is SN38, having the structure:

57. The immunoconjugate of claim 46, wherein the L-D comprises the structure:

58. The immunoconjugate of claim 46, wherein the L-D comprises the structure:

59. The immunoconjugate of claim 46, wherein the L-D comprises the structure:

60. The immunoconjugate of claim 46, wherein the L-D comprises the structure:

61. An immunoconjugate having the formula Ab-(L-D), wherein:

(a) Ab is an antibody which comprises a heavy chain variable region and a light chain variable region, wherein the heavy chain variable region comprises three heavy chain complementarity-determining regions (HCDRs), wherein:

(i) HCDR1 comprises the amino acid sequence set forth in SEQ ID NO: 16, (ii) HCDR2 comprises the amino acid sequence set forth in SEQ ID NO: 19, and (iii) HCDR3 comprises the amino acid sequence set forth in SEQ ID NO: 20; and wherein the light chain variable region comprises three light chain complementarity-determining regions (LCDRs), wherein (iv) LCDR1 comprises the amino acid sequence set forth in SEQ ID NO: 21, (v) LCDR2 comprises the amino acid sequence set forth in SEQ ID NO: 23, and (vi) LCDR3 comprises the amino acid sequence set forth in SEQ ID NO: 24, (b) L is a linker; and (c) D is a cytotoxic drug.

62. The immunoconjugate of claim 61, wherein the linker is a cleavable linker.

63. The immunoconjugate of claim 62, wherein the linker is a cathepsin-cleavable linker.

64. The immunoconjugate of claim 63, wherein the cathepsin-cleavable linker comprises a valine-citruline (Val-Cit).

65. The immunoconjugate of claim 62, wherein the linker is MC-VCP, having the structure:

66. The immunoconjugate of claim 62, wherein the linker comprises the structure:

-continued

67. The immunoconjugate of claim 61, wherein the linker is a pH cleavable linker.

68. The immunoconjugate of claim 67, wherein the linker is CL2A, having the structure:

69. The immunoconjugate of claim 61, wherein the cytotoxic drug is an auristatin.

70. The immunoconjugate of claim 69, wherein the auristatin is monomethyl auristatin E (MMAE) having the structure:

71. The immunoconjugate of claim 61, wherein the cytotoxic drug is SN38, having the structure:

72. The immunoconjugate of claim 61, wherein the L-D comprises the structure:

73. The immunoconjugate of claim 61, wherein the L-D comprises the structure:

74. The immunoconjugate of claim 61, wherein the L-D comprises the structure:

75. The immunoconjugate of claim 61, wherein the L-D comprises the structure:

76. An immunoconjugate having the formula Ab-(L-D), wherein:
    (a) Ab is an antibody comprising a heavy chain variable region and a light chain variable region, wherein the heavy chain variable region comprises three heavy chain complementarity-determining regions (HCDRs), wherein:
        (i) HCDR1 comprises the amino acid sequence set forth in SEQ ID NO: 16,
        (ii) HCDR2 comprises the amino acid sequence set forth in SEQ ID NO: 19, and
        (iii) HCDR3 comprises the amino acid sequence set forth in SEQ ID NO: 20; and wherein the light chain variable region comprises three light chain comple-mentarity-determining regions (LCDRs), wherein
        (iv) LCDR1 comprises the amino acid sequence set forth in SEQ ID NO: 22, (v) LCDR2 comprises the amino acid sequence set forth in SEQ ID NO: 23, and
        (vi) LCDR3 comprises the amino acid sequence set forth in SEQ ID NO: 24,
    (b) L is a linker; and
    (c) D is a cytotoxic drug.

77. The immunoconjugate of claim 76, wherein the linker is a cleavable linker.

78. The immunoconjugate of claim 77, wherein the linker is a cathepsin-cleavable linker.

79. The immunoconjugate of claim 78, wherein the cathe-psin-cleavable linker comprises a valine-citruline (Val-Cit).

80. The immunoconjugate of claim 77, wherein the linker is MC-VCP, having the structure:

81. The immunoconjugate of claim 77, wherein the linker comprises the structure:

-continued

82. The immunoconjugate of claim 76, wherein the linker is a pH cleavable linker.

83. The immunoconjugate of claim 82, wherein the linker is CL2A, having the structure:

84. The immunoconjugate of claim 76, wherein the cytotoxic drug is an auristatin.

85. The immunoconjugate of claim 84, wherein the auristatin is monomethyl auristatin E (MMAE) having the structure:

86. The immunoconjugate of claim 76, wherein the cytotoxic drug is SN38, having the structure:

87. The immunoconjugate of claim 76, wherein the L-D comprises the structure:

88. The immunoconjugate of claim 76, wherein the L-D comprises the structure:

89. The immunoconjugate of claim 76, wherein the L-D comprises the structure:

90. The immunoconjugate of claim 76, wherein the L-D comprises the structure:

91. An immunoconjugate having the formula Ab-(L-D), wherein:

(a) Ab is an antibody comprising the heavy chain set forth in SEQ ID NO: 38 and the light chain set forth in SEQ ID NO: 40; and (b) the L-D comprises the structure:

92. An immunoconjugate having the formula Ab-(L-D), wherein:

(a) Ab is an antibody comprising the heavy chain set forth in SEQ ID NO: 39 and the light chain set forth in SEQ ID NO: 40; and (b) the L-D comprises the structure:

93. A pharmaceutical composition comprising the immunoconjugate of claim 91.

94. A pharmaceutical composition comprising the immunoconjugate of claim 92.

95. The immunoconjugate of claim 1, wherein the antibody heavy chain constant region comprises at least 95% identity to SEQ ID NO: 14.

96. The immunoconjugate of claim 1, wherein the antibody heavy chain constant region comprises at least 99% identity to SEQ ID NO: 14.

97. The immunoconjugate of claim 1, wherein the antibody light chain constant region comprises at least 95% identity to SEQ ID NO: 15.

98. The immunoconjugate of claim 1, wherein the antibody light chain constant region comprises at least 95% identity to SEQ ID NO: 15.

99. The immunoconjugate of claim 1, wherein the antibody heavy chain comprising the HCDR 1, HCDR2, and HCDR3 further comprises an amino acid sequence having at least 95% identity to SEQ ID NO: 38.

100. The immunoconjugate of claim 1, wherein the antibody heavy chain comprises an amino acid sequence at least 99% identity to SEQ ID NO: 38.

101. The immunoconjugate of claim 99 wherein the antibody light chain comprising the LCDR 1, LCDR2, and LCDR3 has an amino acid sequence having at least 95% identity to SEQ ID NO: 40.

102. The immunoconjugate of claim 99, wherein the antibody light chain comprises an amino acid sequence having at least 99% identity to SEQ ID NO: 40.

103. The immunoconjugate of claim 1, wherein the heavy chain variable region comprising the HCDR1, HCDR2, and HCDR3 has an amino acid sequence having at least 99% identity to SEQ ID NO: 5.

104. The immunoconjugate of claim 103, wherein the light chain variable region comprising the HCDR1, HCDR2, and HCDR3 has an amino acid sequence having at least 99% identity to SEQ ID NO: 11.

105. The immunoconjugate of claim 31, wherein the antibody heavy chain constant region comprises at least 95% identity to SEQ ID NO: 14.

106. The immunoconjugate of claim 31, wherein the antibody heavy chain constant region comprises at least 99% identity to SEQ ID NO: 14.

107. The immunoconjugate of claim 31, wherein the antibody light chain constant region comprises at least 95% identity to SEQ ID NO: 15.

108. The immunoconjugate of claim 31, wherein the antibody light chain constant region comprises at least 99% identity to SEQ ID NO: 15.

109. The immunoconjugate of claim 31, wherein the antibody heavy chain comprising the HCDR 1, HCDR2, and HCDR3 further comprises at least 95% identity to SEQ ID NO: 39.

110. The immunoconjugate of claim 31, wherein the antibody heavy chain comprises at least 99% identity to SEQ ID NO: 39.

111. The immunoconjugate of claim 109, wherein the antibody light chain comprising the LCDR 1, LCDR2, and LCDR3 further comprises at least 95% identity to SEQ ID NO: 40.

112. The immunoconjugate of claim 109, wherein the antibody light chain comprises at least 99% identity to SEQ ID NO: 40.

113. The immunoconjugate of claim 31, wherein the antibody heavy chain variable region comprises an amino acid sequence at least 99% identity to SEQ ID NO: 6.

114. The immunoconjugate of claim 113, wherein the antibody light chain variable region comprises an amino acid sequence at least 99% identity to SEQ ID NO: 11.

* * * * *